US008785876B2

(12) United States Patent
Tajima

(10) Patent No.: US 8,785,876 B2
(45) Date of Patent: Jul. 22, 2014

(54) RADIATION IMAGE CAPTURING APPARATUS

(75) Inventor: Hideaki Tajima, Hachioji (JP)

(73) Assignee: Konica Minolta Medical & Graphic, Inc. (JP)

(*) Notice: Subject to any disclaimer, the term of this patent is extended or adjusted under 35 U.S.C. 154(b) by 42 days.

(21) Appl. No.: 13/701,713

(22) PCT Filed: Mar. 2, 2011

(86) PCT No.: PCT/JP2011/054690
§ 371 (c)(1),
(2), (4) Date: Dec. 3, 2012

(87) PCT Pub. No.: WO2011/152093
PCT Pub. Date: Dec. 8, 2011

(65) Prior Publication Data
US 2013/0068961 A1 Mar. 21, 2013

(30) Foreign Application Priority Data

Jun. 3, 2010 (JP) .................................. 2010-127667
Sep. 7, 2010 (JP) .................................. 2010-199629

(51) Int. Cl.
G01J 1/42 (2006.01)
G01T 1/00 (2006.01)
H01L 27/146 (2006.01)
A61B 6/00 (2006.01)

(52) U.S. Cl.
CPC .............. *A61B 6/4233* (2013.01); *A61B 6/4241* (2013.01); *H01L 27/14676* (2013.01)
USPC .................. 250/394; 250/370.09; 250/363.02

(58) Field of Classification Search
CPC ............... A61B 6/4233; A61B 6/4241; H01L 27/14676
USPC ................. 250/394, 370.09, 363.02
See application file for complete search history.

(56) References Cited

U.S. PATENT DOCUMENTS 7,211,803 B1 5/2007 Dhurjaty et al.
2004/0211908 A1* 10/2004 Sato et al. ................ 250/370.09
2010/0104067 A1* 4/2010 Okada ............................ 378/62

FOREIGN PATENT DOCUMENTS

JP 6-342099 A 12/1994
JP 7-72252 A 3/1995

(Continued)

OTHER PUBLICATIONS

International Search Report for International application No. PCT/JP2011/054690, Apr. 12, 2011, with English translation.

(Continued)

*Primary Examiner* — David Porta
*Assistant Examiner* — Abra Fein
(74) *Attorney, Agent, or Firm* — Cantor Colburn LLP

(57) ABSTRACT

A radiation image capturing apparatus is provided with a scanning drive unit which sequentially applies ON voltage to respective scanning lines during a readout process to read out image data from radiation detection elements. From the time before radiation imaging, a controller controls the scanning drive unit to sequentially apply the ON voltage to the respective scanning lines and executes the readout process for the image data from the radiation detection elements. The controller detects start of the radioactive irradiation when the image data exceeds a threshold value, and controls that ON time, during which the ON voltage is applied to the scanning lines from the scanning drive unit during the readout process for the image data before radiation imaging, becomes longer than ON time during a readout process for the image data after finishing the radioactive irradiation.

15 Claims, 70 Drawing Sheets

(56) References Cited

FOREIGN PATENT DOCUMENTS

| | | |
|---|---|---|
| JP | 9-73144 A | 3/1997 |
| JP | 9-107503 A | 4/1997 |
| JP | 9-140691 A | 6/1997 |
| JP | 9-197051 A | 7/1997 |
| JP | 11-155847 A | 6/1999 |
| JP | 2003-126072 A | 5/2003 |
| JP | 2004-344249 A | 12/2004 |
| JP | 2006-58124 A | 3/2006 |
| JP | 2007-151761 A | 6/2007 |
| JP | 2008-595 A | 1/2008 |
| JP | 2008-132216 A | 12/2008 |
| JP | 2009-153984 A | 7/2009 |
| JP | 2009-219538 A | 10/2009 |
| WO | 9325059 A1 | 12/1993 |
| WO | 2009005119 A1 | 1/2009 |

OTHER PUBLICATIONS

International Preliminary Report on Patentability for International Application No. PCT/JP2011/054690 mailed Jan. 8, 2013.

* cited by examiner

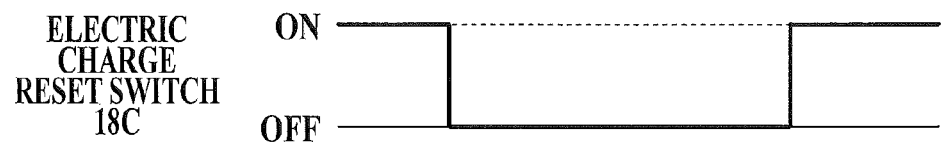
FIG.9
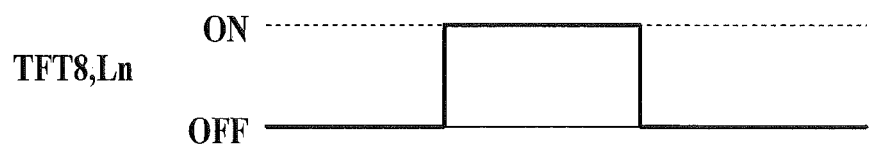
FIG.10
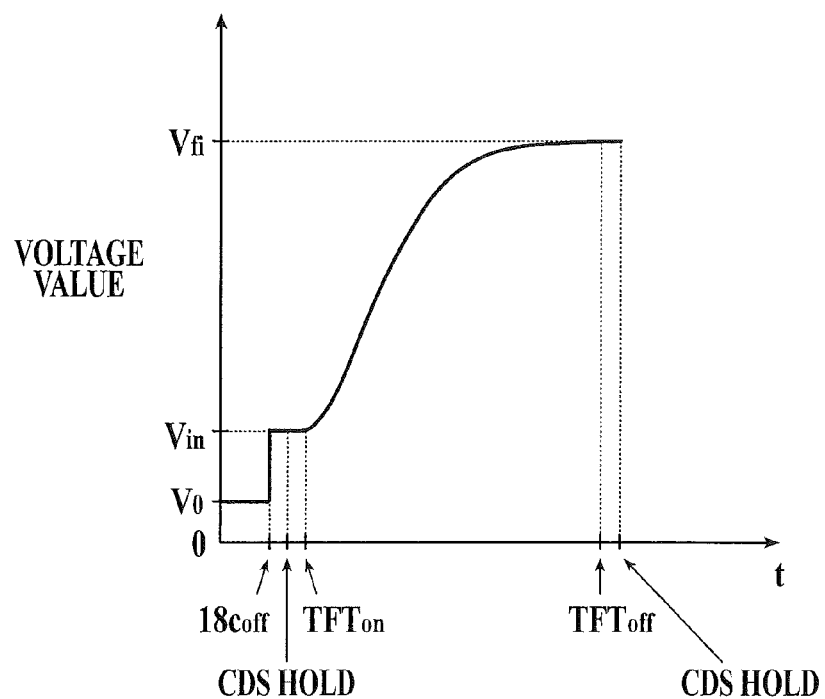

INITIATION OF IRRADIATION

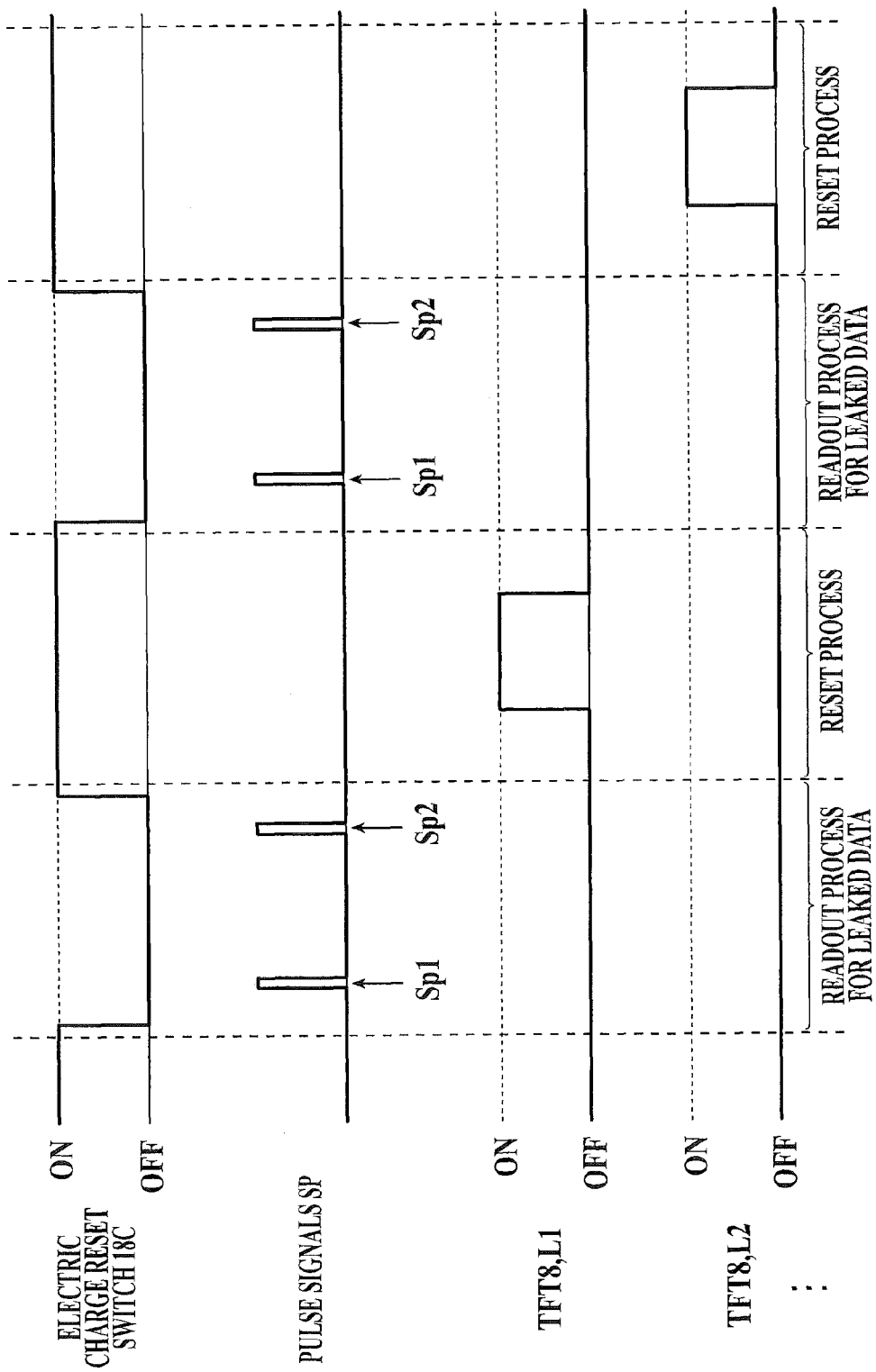

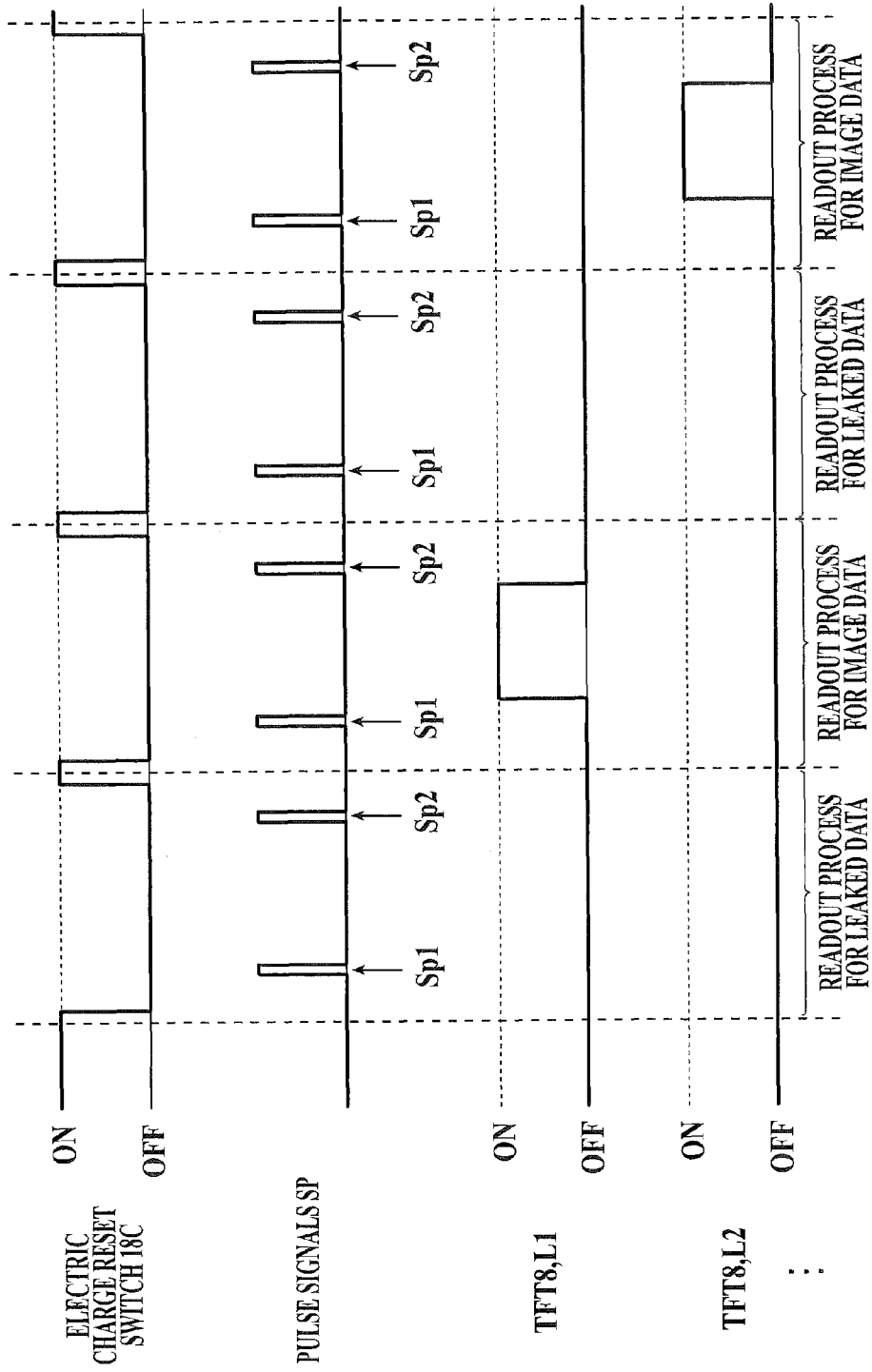

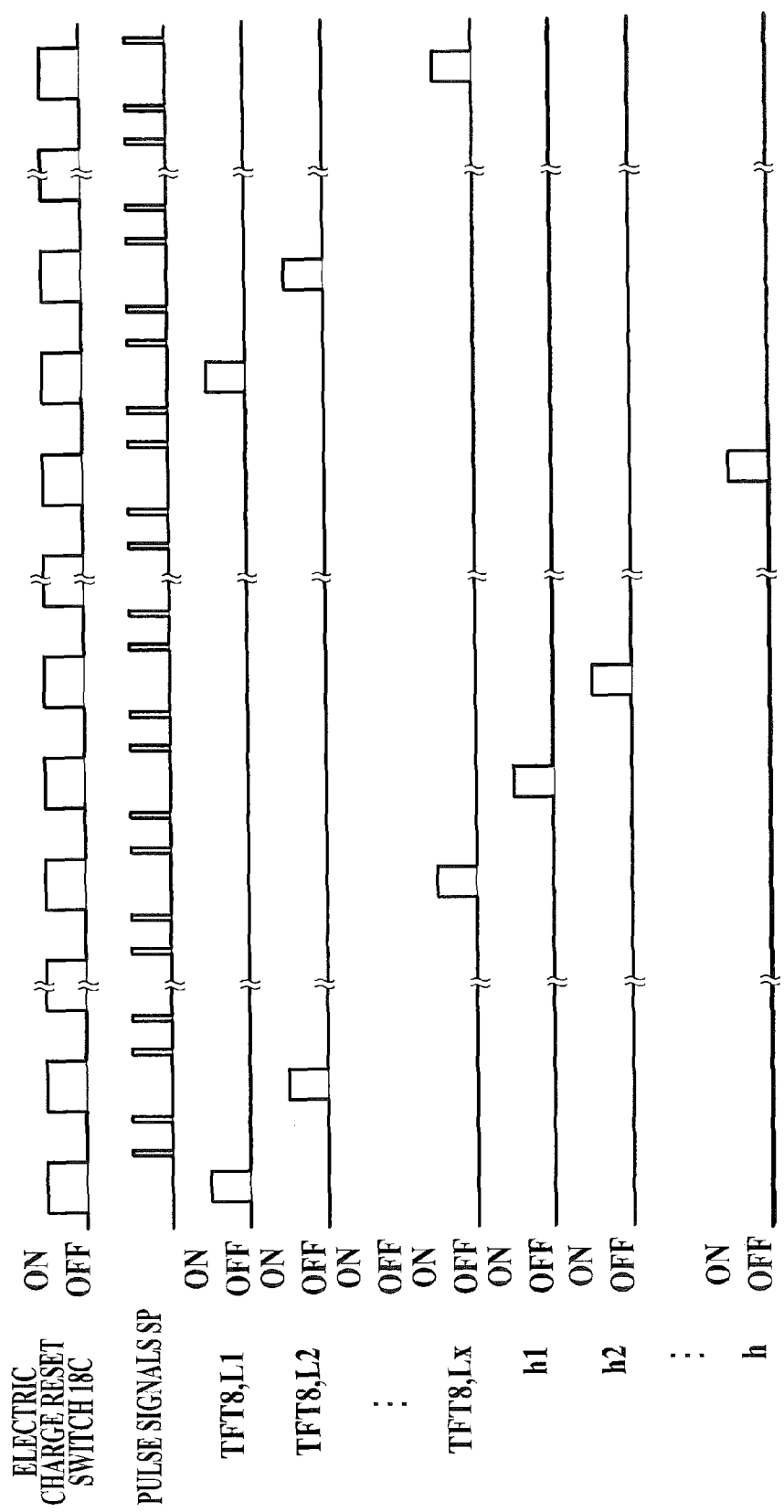

FIRST FRAME          SECOND FRAME

RADIATION IMAGE CAPTURING APPARATUS

CROSS REFERENCE TO RELATED APPLICATIONS

This is a U.S. National Stage of Application No. PCT/JP2011/054690, filed on 2 Mar. 2011. Priority under 35 U.S.C. §119(a) and 35 U.S.C. §365(b) is claimed from Japanese Application Nos. 2010-127667, filed 3 Jun. 2010, and 2010-199629, filed 7 Sep. 2010, the disclosure of which are also incorporated herein by reference.

TECHNICAL FIELD

The present invention relates to a radiation image capturing apparatus, particularly to a radiation image capturing apparatus capable of detecting initiation of radioactive irradiation etc. by the apparatus itself.

BACKGROUND ART

There has been development of various types of radiation image capturing apparatuses including a so-called direct-type radiation image capturing apparatus in which a detection element generates an electric charge according to an irradiation dose of radiation such as X-ray and converts the electric charge into an electric signal, and a so-called indirect-type radioactive imaging device in which, after irradiated radiation is converted by a scintillator or the like into an electromagnetic wave such as visible light having a different wavelength, an photoelectric converting element such as a photodiode generates an electric charge in accordance with the energy of the electromagnetic wave which has been converted and irradiated and then converts the electric charge into an electric signal. It should be noted that a detection element in a direct-type radiation image capturing apparatus and a photoelectric converting element in an indirect-type radiation image capturing apparatus are collectively referred to as radiation detection elements in the present invention.

This type of radiation image capturing apparatus is known as a FPD (flat panel detector) and had been formed integrally with a supporting stand (or a bucky device) (for example, see Patent document 1), but, in recent years, a portable radiation image capturing apparatus, in which radiation detection elements and the like are stored in a housing, has been developed and put into practical use (see Patent documents 2 and 3, for example).

In the above radiation image capturing apparatus, for example as shown in FIGS. 3 and 7 described later, usually, radiation detection elements 7 are arranged on a detecting section P in a two dimensional manner (matrix form) and on each of the radiation detection elements, a switch formed of a thin film transistor 8 (hereinafter referred to as a TFT) is provided. The radiation image capturing apparatus is often configured so that: before radiation image capturing operation, that is, before irradiating the radiation image capturing apparatus with radiation outputted from a radiation generation device, a reset process is executed for discharging an excess electric charge remaining in each of the radiation image capturing apparatus 7, while appropriately controlling an ON/OFF state of the respective TFTs 8.

Then, after the reset process of each of the radiation detection elements 7 is finished, an OFF voltage is applied to the TFTs 8 by a gate driver 15b of scanning drive unit 15 via each of scanning lines 6 to turn all of the TFTs to the OFF state. When the radiation image capturing apparatus is irradiated with the radiation from the radiation generating device in this state, the electric charge of an amount according to a radiation dose are generated and accumulated in each of the radiation detection elements 7.

Thereafter, after an end of the radiation image capturing operation, as shown in FIG. 73, while sequentially switching between each of lines L1 to Lx of the scanning lines 5 to which an ON voltage for signal readout is applied by the gate driver 15b of the scanning drive unit 15, the electric charge accumulated in each of the radiation detection elements 7 is read out therefrom, and the read out electric charge is directed to charge-to-voltage conversion in a reading circuit 17 to be read out as image data.

However, in a case of the above configuration, an interface between the radiation image capturing apparatus and the radiation generation device that irradiate with radiation on the radiation image capturing apparatus needs to be appropriately constructed, so that on the radiation image capturing apparatus side, each of the radiation detection elements 7 is in a state in which the electric charge can be accumulated. The construction between the devices is not always simple. Also, when the device is irradiated with the radiation during the reset process of each of the radiation detection elements 7 on the radiation image capturing apparatus side, the electric charge generated by the irradiation flow out of each of the radiation detection elements 7, causing a problem of reducing conversion efficiency of the electric charge generated by the irradiation, that is, the conversion efficiency to the image data.

For this reason, techniques to detect radioactive irradiation by the radiation image capturing apparatus itself has recently been developed. And as a part of the techniques, the detection of the radioactive irradiation by the radiation image capturing apparatus itself has been developed using the techniques described in Patent documents 4 and 5 for example.

A radiation image capturing apparatus and a readout method of image data are disclosed in Patent documents 4 and 5, in which: while irradiating the radiation image capturing apparatus with the radiation, the lines L1 to Lx of the scanning lines 5, to which the ON voltage is applied from the gate driver 15b of the scanning drive unit 15, are sequentially switched to repeatedly execute the readout process for the image data outputted from the radiation emitting elements 7.

In this case, as shown in FIG. 74, when the ON voltage is sequentially applied to the respective lines L1 to Lx of the scanning lines 5 and a readout period is referred to as one frame, the electric charges generated in the radiation detection elements 7 by radioactive irradiation are read out separately in the readout process in each of the frames. Here, the readout period is a period of reading out the image data from each of the target radiation detection elements 7 for reading out the image data among all the radiation detection elements 7 arranged on the detecting section P.

For this reason, the image data of each of the radiation detection elements 7 is reconstructed as follows. Regarding the frames from the frame in which the radioactive irradiation is initiated to the frame in which the radioactive irradiation is finished, the image data read out in the respective frames before the next frame are added together for each of the radiation detection elements 7.

However, the inventors of the present invention knows that the following problem occurs in the cases of Patent documents 4 and 5, in which the readout process for the image data for each frame is configured to continue after the radioactive irradiation.

In this case, as shown in FIG. 75, the ON voltage is sequentially applied to each of the scanning lines 5 starting from the top and the readout process for image data for each frame is executed. And, for example, it is assumed that the irradiation is finished while the ON voltage is being applied to the scanning lines 5 in a portion ΔT which is a shaded area in FIG. 76. Here, in FIG. 76, the radioactive irradiation is performed on the entire region of the detecting section P and does not mean that the radioactive irradiation is performed only on the portion ΔT defined by the shaded area.

Thereafter, the readout process for the image data is carried on and then the image data for the respective frames is added together as described above, the image data being read out in two or three frames including the present frame. Then, when the image data for each of the radiation detection elements 7 is reconstructed, as shown in FIGS. 77A and 77B, shading unevenness appears in a radiation image p generated based on the reconstructed image data.

Specifically, for example, the radiation image p is generated based on each of the pieces of image data d which has been reconstructed when irradiating the entire region of the detecting section P of the radiation image capturing apparatus with the radiation of the same dose. And with respect to each of the pieces of image data d reconstructed along the extending direction of signal lines 6 (in the vertical arrow direction in FIG. 77A), the image data d of an image region δT becomes larger in value than the image data d in an image region A positioned thereabove and the image data d in an image region B positioned therebelow. Here, the image region δT corresponds to the position of the scanning lines 5 (i.e., shaded area ΔT in FIG. 76) to which the ON voltage is applied while being irradiated with the radiation.

This causes the image region δT to become somewhat darker than the image region A and the image region B. As described above, the problem is known that the shading unevenness in the radiation image p appears even if the radiation image capturing apparatus is irradiated with the radiation evenly.

The problem arises not only when the entire region of the detecting section P of the radiation image capturing apparatus is irradiated evenly with the radiation, but also when the radiation image capturing apparatus is irradiated with the radiation with an object interposed therebetween as in a practical case. Also in the latter case, the shading unevenness appears in the generated radiation image.

The reason is considered as follows, that the image data d in the image region δT becomes larger than the image data d of the image regions A and B.

That is, as shown in FIG. 78, when the image data di is read out from the radiation detection element 7i after the ON voltage is applied to the line Li in one of the scanning lines 5, simultaneously, an electric charge q leaks from other radiation detection elements 7, which are respectively connected to other lines L of the scanning lines 5, by small amounts through the respective TFTs 8. This causes the actual image data di read out as the image data of the radiation detection element 7i to become the image data corresponding to the sum value of an electric charge Q read out from the radiation detection element 7i and electric charges leaked from other radiation detection elements 7 through the respective TFTs 8.

Further, when the readout process is executed while irradiating the radiation image capturing apparatus 1 with the radiation, the radiation irradiating the radiation image capturing apparatus also irradiates the respective TFTs 8 or the irradiated radiation is converted into an electromagnetic wave by a scintillator to cause the electromagnetic wave to irradiate the respective TFTs 8, increasing the amount of the electric charge q leaked from the radiation detection elements 7 through the respective TFTs 8.

For this reason, in this case, the image data di read out as the image data of the radiation detection element 7i shown in FIG. 78 becomes larger by the amount corresponding to the increased amount of the electric charge q leaked from the other radiation detection elements 7 connected to the same signal line 6. Thus, the image data d in the image region δT is considered to become larger than the image data d of the image regions A and B.

In the above case, the radiation image becomes difficult to be seen when the shading unevenness appears on the generated radiation image. And for example, in a case of utilizing the radiation image in a diagnosis and the like in a medical field, a lesion may be overlooked or misjudged if the shading unevenness and the lesion overlap with each other in the radiation image. Also, as in shown in FIG. 77B, the image data d of the image data δT, which has become larger than the image data d of the image regions A and B, is difficult to be corrected.

Therefore, applying the inventions described in Patent documents 4 and 5, a configuration is considered in which: the readout process for the image data is started before initiating the radioactive irradiation onto the radiation image capturing apparatus; and the readout process for the image data d is stopped at the time of initiating the radioactive irradiation, and the readout process for the image data d is not continued while irradiating the radiation image capturing apparatus with the radiation, as described in Patent documents 4 and 5.

In the above configuration, at the time of initiating the radioactive irradiation onto the radiation image capturing apparatus, the image data d read out from each of the radiation detection elements 7 connected to the scanning lines 5, to which the ON voltage is applied by the gate driver 15b of the scanning drive unit 15, becomes significantly larger than the image data d read out from each of the radiation detection elements 7 connected to the scanning lines 5, to which the ON voltage is applied, before the initiation of the radioactive irradiation.

Using the above phenomenon, as shown in Patent document 6 for example, the initiation of the radioactive irradiation can be detected by the radiation image capturing apparatus itself. In the imaging device in Patent document 6, the readout process for the image data is configured to start before initiating the radioactive irradiation onto the radiation image capturing apparatus, and to detect the radioactive irradiation at the time when the readout image data rapidly increases and exceeds a threshold value.

Further, in Patent document 7 for example, among all charge coupled devices (CCDs) as the radiation detection elements, the image data of the CCDs in multiple rows is read out simultaneously to improve the detection efficiency for detecting the radioactive irradiation.

Then, the configuration can be made in which: at the time of detecting that the read out image data rapidly increases and exceeds the threshold value, the application of the ON voltage to each of the scanning lines 5 by the gate driver 15b of the scanning drive unit 15 is stopped, and the readout process for the image data is not executed while irradiating the device with the radiation.

CITATION LIST

Patent document 1: JP-A-09-73144
Patent document 2: JP-A-2006-058124
Patent document 3: JP-A-06-342099
Patent document 4: JP-A-09-140691
Patent document 5: JP-A-07-72252
Patent document 6: JP-A-07-506993
Patent document 7: JP-A-09-107503

SUMMARY OF INVENTION

Technical Problem

Now, in the case of configuring the device as described above, the radioactive irradiation is detected at the time when the ON voltage is applied to one of the scanning lines 5 and the read out image data becomes large. This indicates that at the time, the electric charge is generated by being irradiated with the radiation from each of the radiation detection elements 7 connected to the scanning line 5, to which the ON-voltage is applied, and a part of the electric charge leaks from each of the radiation detection elements 7.

Therefore, for example, among the image data of the respective radiation detection elements 7 read out in the readout process after the end of the radioactive irradiation, the image data read out from each of the radiation detecting devices 7 connected to the above scanning lines 5 is considered unreliable, and is configured to be abandoned.

In this case, as shown in FIG. 79, when the image data on the line Ln of the scanning lines 5 is abandoned for example, a so-called line defect occurs. Thus, for example, using a method of linear interpolation based on each of the pieces of image data read out from each of the radiation detection elements 7 connected to lines Ln−1, Ln+1 adjacent to the line Ln of the scanning lines 5, the abandoned image data is configured to be interpolated.

For example, as mentioned above, in the case of utilizing the radiation image in a diagnosis and the like in a medical field, size or width of the lesion imaged on the radiation image is usually not small enough to be fitted in width of one line defect. Hence, as described above, no problem arises in actual operations, even if the configuration is made in which: the image data is treated as the line defect and is abandoned for each of the radiation detecting devices 7 connected to the scanning lines 5, to which the ON voltage is applied at the time of detecting the radioactive irradiation, and the image data is configured to be interpolated by the neighboring image data.

However, in the case of applying the technique as described above in Patent document 7 to configure the device so that the detection efficiency is improved by applying the ON voltage simultaneously to the plurality of scanning lines 5, for example, as shown in FIG. 80, the line defects occur successively in the plurality of adjacent lines L (lines Ln and Ln+1 in FIG. 80).

Then, in the example of FIG. 80, the sequential line defects are interpolated by the image data of the lines Ln−1, Ln+2 in the adjacent scanning lines 5. This means, even if the lesion is imaged in each of the abandoned image data, because the image data is to be abandoned, there is a risk of lesion information being lost.

The risk occurs especially when the lesion is very small as in early stages of disease. Further, the more a number of scanning lines 5 becomes line defect successively, that is, the more the number of scanning lines 5 is to which the ON voltage is applied simultaneously, the more the lesion information is lost from the image data.

Accordingly, in the case of applying the invention described in Patent document 6 to configure the device so that the radioactive irradiation is detected at the time when the value of the read out image data rapidly increases and exceeds the threshold value, as described above, the configuration to simultaneously apply the ON voltage to the plurality of scanning lines 5 for improving the detection efficiency of the radioactive irradiation is not an appropriate approach.

And in order to improve the detection efficiency of the radioactive irradiation, an approach other than the one described in Patent document 7 needs to be developed.

The present invention is made in light of the above problems. An object of the present invention is to provide a radiation image capturing apparatus which is capable of improving the detection efficiency for detecting initiation of radioactive irradiation by the device itself. Moreover, another object of the present invention is to provide the radiation image capturing apparatus which is capable of: preventing the line defects to occur in the plurality of adjacent scanning lines successively; or reducing the number of the scanning lines in which the line defect occur.

Means for Solving the Problems

In order to solve at least one of the aforementioned problems, a radiation image capturing apparatus according to an embodiment of the present invention includes:

a plurality of scanning lines and a plurality of signal lines arranged to intersect with each other, and a plurality of radiation detection elements that are two-dimensionally aligned in respective regions partitioned by the plurality of scanning lines and the plurality of signal lines;

a scanning drive unit that sequentially applies an ON voltage to each of the scanning lines during a readout process for image data in which the image data is read out from the radiation detection elements;

switch units each connected to each of the scanning lines, discharges electric charges accumulated in the radiation detection elements to the signal lines when the ON voltage is applied thereto through the scanning lines, and accumulates the electric charges in the radiation detection elements when an OFF voltage is applied thereto through the scanning lines;

reading circuits which convert the electric charges discharged to the signal lines from the radiation detection elements into the image data and reads out the image data during the readout process for the image data; and a controller which controls at least the scanning drive unit and the reading circuit and causes the same to execute the readout process for the data from the radiation detection elements, wherein the controller controls to:

before radiation image capturing operation, cause the scanning drive unit to sequentially apply the ON voltage to each of the scanning lines to execute the readout process for the image data from the radiation detection elements, and detect initiation of radioactive irradiation at a time when the read out image data exceeds a threshold value, when the initiation of the radioactive irradiation is detected, cause the scanning drive unit to apply an OFF voltage to all of the scanning lines and turn each of the switch unit to an OFF state to shift to an electric charge accumulation mode, after finishing the radioactive irradiation, cause the scanning drive unit to sequentially apply the ON voltage to each of the scanning lines, and cause the reading circuit to sequentially execute the readout operation to execute the readout process for the image data from each of the radiation detection elements, and make time or period longer during the readout process for the image data before the radiation image capturing operation than the time or period after finishing the radiation image capturing operation, where the time is one from causing the scanning drive unit to apply the ON voltage to the scanning lines until switching an applied voltage to the OFF voltage, and the period is one from causing the scanning drive unit to apply the ON voltage to one scanning line until applying the ON voltage to the next scanning line.

Advantageous Effects of Invention

According to the radiation image capturing apparatus with a method described in the present invention, the readout process is executed for the image data by sequentially applying the ON voltage to each of the scanning lines before initiating the radiation image capturing operation, and the initiation of the radioactive irradiation onto the radiation image capturing apparatus is detected based on the value of the read out image data. Therefore, the radioactive irradiation can be detected by the radiation image capturing apparatus itself.

Then, in doing so, the configuration is adopted in which: the ON time is controlled to be set longer during the readout process for the image data before initiating the radioactive irradiation than the ON time during the readout process for the image data as a final image after the end of the radioactive irradiation. Accordingly, the detection efficiency can be appropriately improved when detecting the initiation of the radioactive irradiation.

The detection efficiency can be improved when detecting the initiation of the radioactive irradiation as described above; therefore, the radioactive irradiation can be detected at the time of actually initiating the irradiation onto the radiation image capturing apparatus with the radiation. This causes the line defect to occur only in one scanning line, appropriately preventing the plurality of line defects to occur in the adjacent scanning lines successively.

Further, even if the initiation of the radioactive irradiation cannot be detected at the time of actually initiating the irradiation with the radiation, because the detection efficiency has been improved, the initiation of the radioactive irradiation is accurately detected based on the image data read out in the immediately following readout process. This can appropriately reduce the number of scanning lines in which the line defect occurs.

As described above, only one scanning line becomes the line defect, or the number of the scanning lines in which the line defect occurs is appropriately reduced. Accordingly, even if the image data is treated as the line defect and is restored using the neighboring image data, for example, the risk of losing the lesion information of a patient, which is imaged in a portion of the line defect, is appropriately avoided. Moreover, the lesion information appears also in the radiation image generated based on the above restored image data; hence the generated radiation image can be appropriately used in the diagnosis and the like in the medical field.

BRIEF DESCRIPTION OF DRAWINGS

FIG. 9 is a timing chart showing ON/OFF timing of an electric charge reset switch, pulse signals, and the TFTs in an image data readout process.

FIG. 10 is a graph showing changes and the like of a voltage value in a correlated double sampling circuit.

FIG. 65 is a timing chart showing ON/OFF timing of the electric charge reset switch, pulse signals, and the TFTs in a case of making a configuration in which the leaked data readout process and a reset process of each radiation detection element are alternately executed before initiating the radiation image capturing operation.

FIG. 66 is a timing chart showing ON/OFF timing of the electric charge reset switch, pulse signals, and the TFTs in a case of making a configuration in which the leaked data readout process and the image data readout process are alternately executed before initiating the radiation image capturing operation.

FIG. 67 is a timing chart explaining application timing to which the ON voltage is applied to the terminals of the respective scanning lines and non-connecting lines in a case of making a configuration in which the leaked data readout process and the reset process of each of the radiation detection elements are executed alternately.

DESCRIPTION OF EMBODIMENTS

Hereinafter, embodiments of the radiation image capturing apparatus according to the present invention will be explained with reference to the drawings.

It should be noted that, although the explanation below is about a case where the radiation image capturing apparatus is a so-called indirect-type radioactive imaging device which is provided with a scintillator and so on, and obtains an electric signal by converting radiation into an electromagnetic wave such as visible light having other wavelength, the present invention is also applicable to a direct-type radiation image capturing apparatus. In addition, although the explanation pertains to a case where the radiation image capturing apparatus is a portable type, the present invention is also applied to a radiation image capturing apparatus which is integrally formed with a supporting stand or the like, which is a so-called dedicated machine.

First Embodiment

Figure 1:
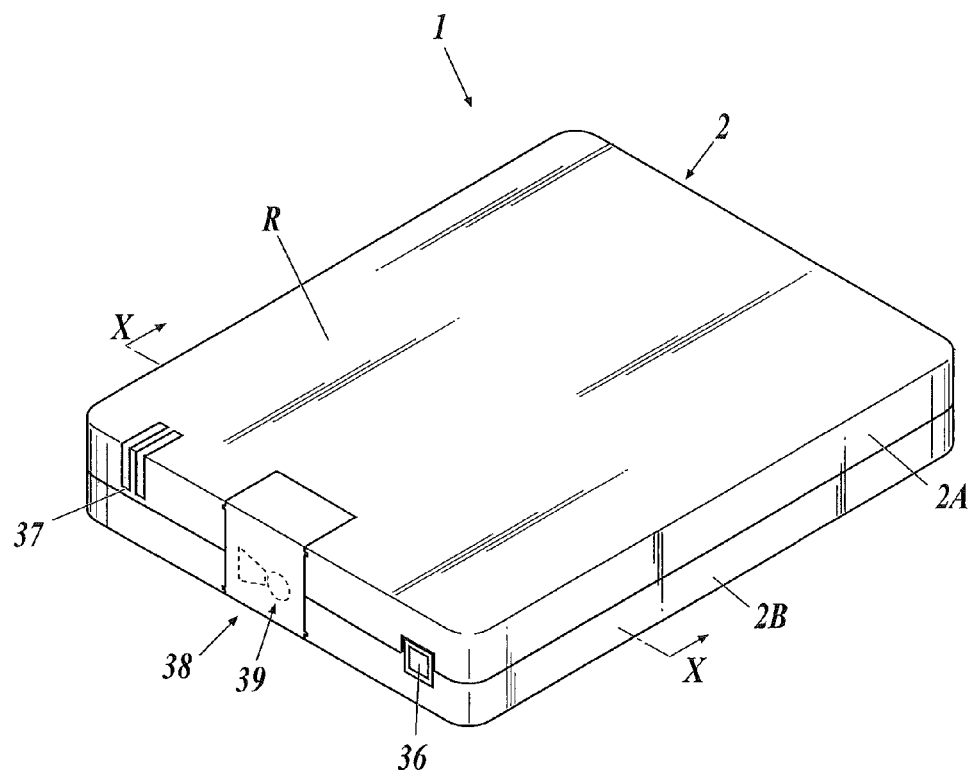
FIG. 1 is a perspective view showing a radiation image capturing apparatus according to respective embodiments.
Figure 2:
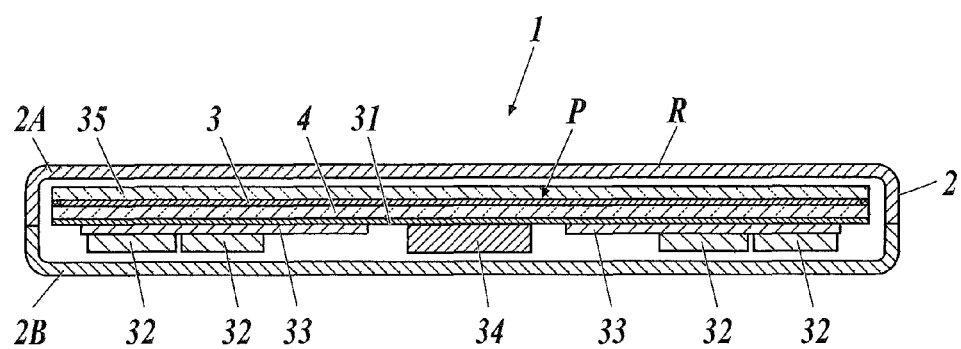
FIG. 2 is a cross-sectional view along a line X-X in FIG. 1.

FIG. 1 is an external perspective view showing a radiation image capturing apparatus according to this embodiment, and FIG. 2 is a cross-sectional view along a line X-X in FIG. 1. The radiation image capturing apparatus 1 according to this embodiment is constructed by storing a scintillator 3, a substrate 4 and so on in a case 2 as illustrated in FIGS. 1 and 2.

In the case 2, at least a radiation entrance face R is formed of a material such as a carbon plate and plastic through which radiation can pass. FIGS. 1 and 2 show a case in which the case 2 has a so-called rectangular lunch-box shape, formed of a front plate 2A and a back plate 2B, but the case 2 may also have a so-called monocoque shape in which the case 2 is formed integrally into a square tube shape.

Further, as illustrated in FIG. 1, a power source switch 36, an indicator 37 configured by LED or the like, a cover member 38 which can be opened and closed for changing a battery 41 (see FIG. 7 described later), and the like are arranged on a side surface part of the case 2. In addition, in this embodiment, an antenna device 39 is embedded in the side surface part of the cover member 38 for wirelessly sending and receiving information such as later-described image data d with an external device such as an image processing computer.

Also, the antenna device 39 is not necessarily installed in the side surface part of the cover member 38, but may be installed at an arbitral position in the radioactive imaging device 1. Further, the number of the antenna device 39 is not limited to one and may be more than one. Moreover, the antenna device 39 may be configured to send and receive image data d and the like with the external device in a wired form such as a cable, and, in such a case, a connecting terminal or the like is provided on the side surface part or the like of the radioactive imaging device 1 for establishing connection by inserting a cable or the like thereinto.

As shown in FIG. 2, in the case 2, a base 31 is located through a non-illustrated thin lead plate or the like on the lower side of the substrate 4. And on the base 31, a PCB substrate 33 on which electronic components 32 and the like are arranged, a buffer member 34, and so on are attached. It should be noted that, in this embodiment, a glass substrate 35 is arranged on the radiation entrance face R of the substrate 4 and the scintillator 3 for protecting the substrate 4 and the scintillator 3.

The scintillator 3 is located to face a later-described detecting section P of the substrate 4. The scintillator 3 is formed mostly of, for example, a fluorescent material, and once radioactive irradiation is received, the one used here as the scintillator 3 converts the radiation into an electromagnetic wave having a wavelength of between 300 and 800 nm, in other words, an electromagnetic wave which is mainly visible light.

Figure 3:
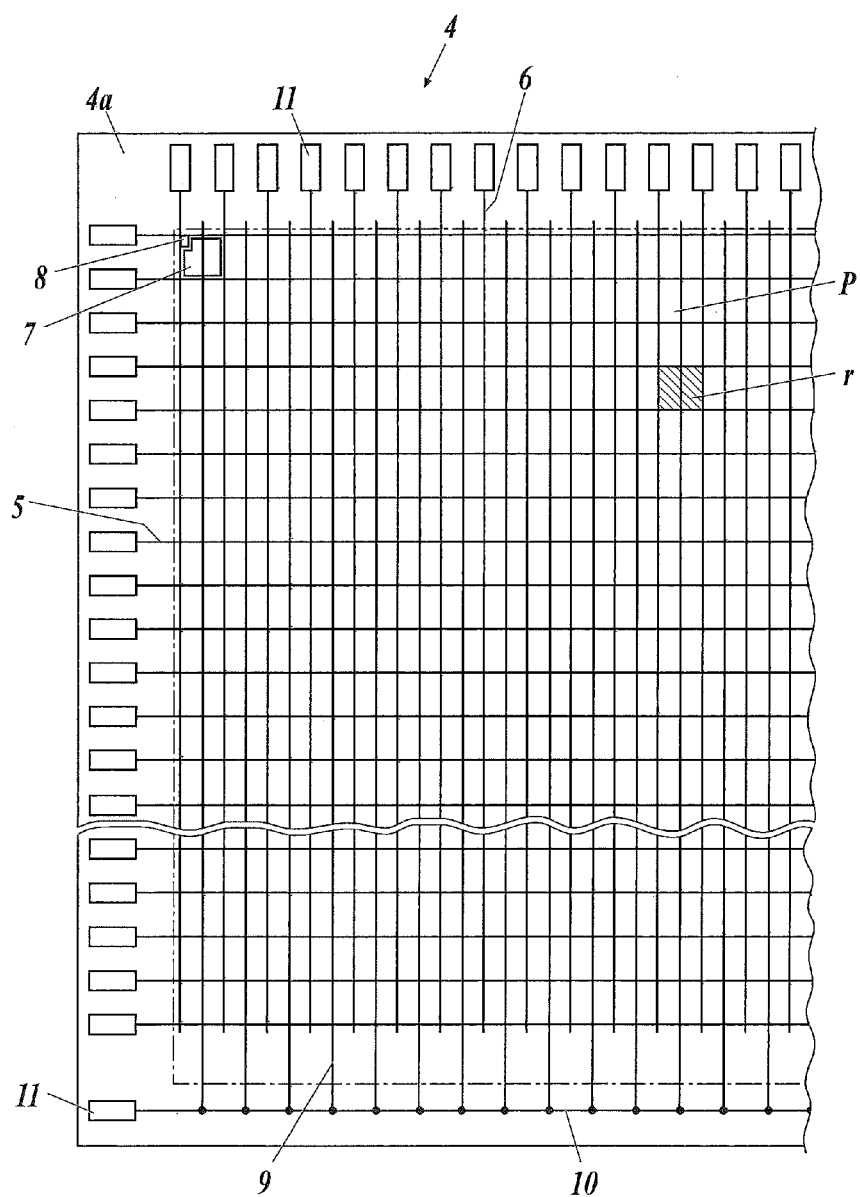
FIG. 3 is a plan view showing a configuration of a substrate of the radiation image capturing apparatus.

The substrate 4 in this embodiment is constructed by a glass substrate, and, as illustrated in FIG. 3, a plurality of scanning lines 5 and a plurality of signal lines 6 are arranged to intersect with each other on a surface 4a of the substrate 4 which faces the scintillator 3. Radiation detection elements 7 are respectively provided in small regions r that are partitioned by the plurality of scanning lines 5 and the plurality of signal lines 6 on the surface 4a of the substrate 4.

According to the foregoing, the entire regions r on which the plurality of radiation detection elements 7 are provided in a two-dimensional arrangement in the respective small regions r partitioned by the scanning lines 5 and the signal lines 6 as describe above, in other words, the region indicated by a dashed line in FIG. 3, is regarded as the detecting section P.

In this embodiment, although photodiodes are used as the radiation detection elements 7, other materials such as phototransistors may be used. As illustrated in the enlarged views of FIGS. 3 and 4, each of the radiation detection elements 7 is connected to a source electrode 8s of a TFT 8 which serves as switch unit. Incidentally, a drain electrode 8d of the TFT 8 is connected to the signal line 6.

Thereafter, the TFT 8 is switched to an ON state when the scanning line 5, to which the TFT 8 is connected, is applied with an ON voltage by later-described scanning drive unit 15, and the gate electrode 8g is applied with the ON voltage via the scanning line 5. Then the TFT 8 causes the signal line 6 to discharge an electric charge accumulated in the radiation detection element 7. Moreover, the TFT 8 is switched to an OFF state when the scanning line 5, to which the TFT 8 is connected, is applied with an OFF voltage and the gate electrode 8g is applied with the OFF voltage via the scanning line 5. And the TFT 8 stops discharging of the electric charge from the radiation detection element 7 to the signal line 6 to hold and accumulate the electric charge in the radiation detection element 7.

Figure 4:
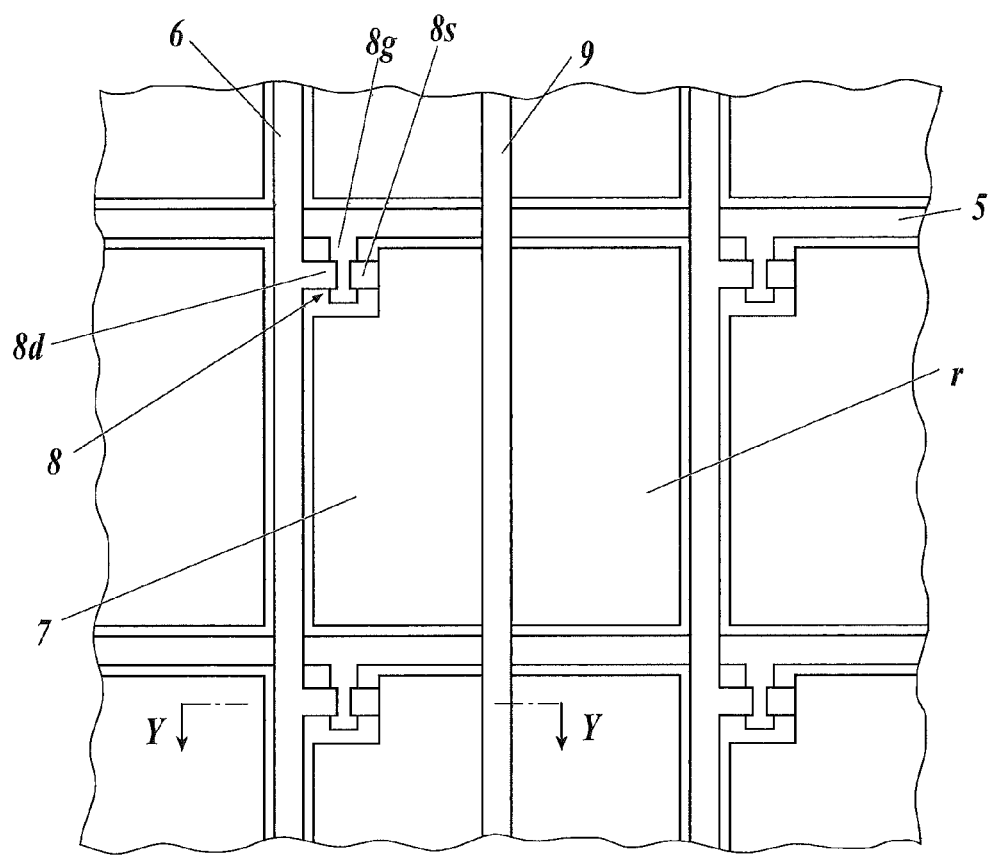
FIG. 4 is an enlarged view showing a configuration of radiation detection elements, TFTs, and so on formed in small regions on the substrate shown in FIG. 3.
Figure 5:
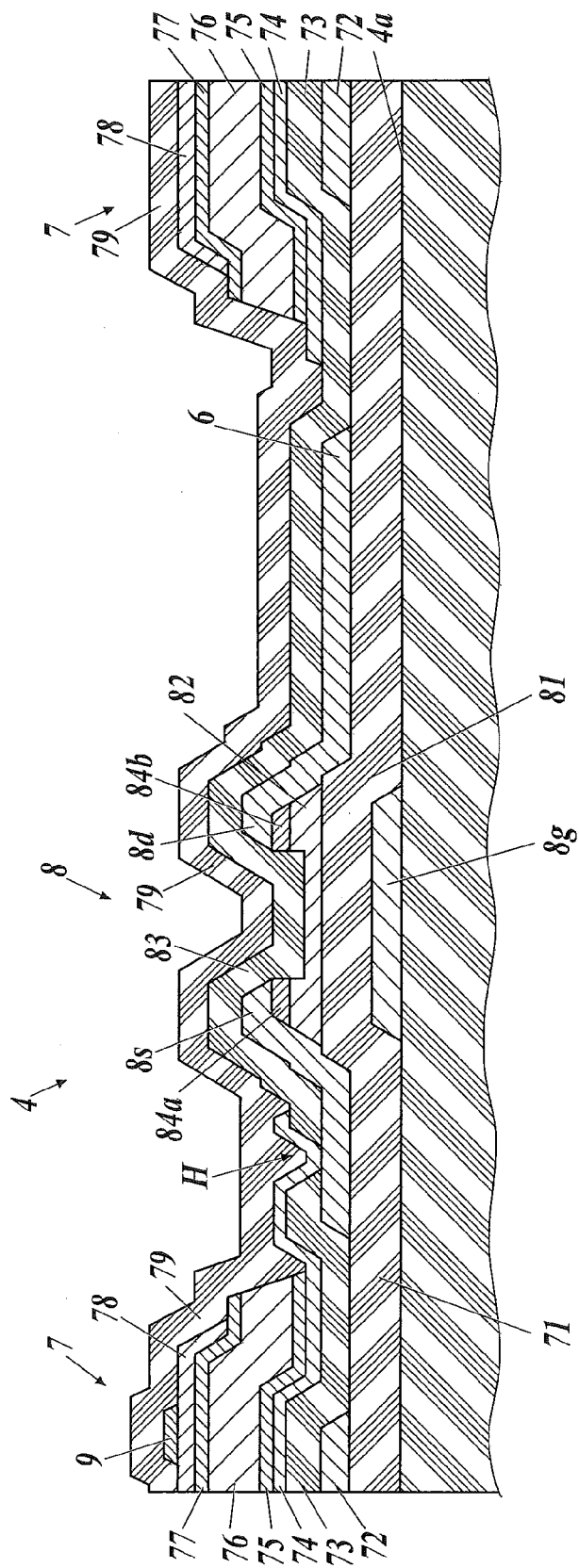
FIG. 5 is a cross-sectional view along the line Y-Y in FIG. 4.

Here, configurations of the radiation detection element 7 and the TFT 8 in this embodiment are briefly explained using the cross-sectional view illustrated in FIG. 5. FIG. 5 is a cross-sectional view along a line Y-Y in FIG. 4.

On the surface 4a of the substrate 4, the gate electrode 8g of the TFT 8, made from Al, Cr, or the like, is formed in a laminated manner integrally with the scanning line 5, and, in an area above the gate electrode 8g on a gate insulating layer 81 made from silicon nitride ($SiN_x$) or the like laminated on the gate electrode 8g and the surface 4a, the source electrode 8s connected to a first electrode 74 of the radiation detection element 7 and a drain electrode 8d integrally formed with the signal line 6 are formed in a laminated manner through a semiconductor layer 82 made from hydrogenated amorphous silicon (a-Si) or the like.

The source electrode 8s and the drain electrode 8d are divided by a first passivation layer 83 made from nitride silicon ($SiN_x$) or the like, and the first passivation layer 83 also covers the both electrodes 8s and 8d from above. Further, ohmic contact layers 84a and 84b formed into n-type by doping VI-group elements into hydrogenated amorphous silicon are laminated respectively between the semiconductor layer 82, and the source electrode 8s and the drain electrode 8d. In this way, the TFT 8 is formed.

In the portion of the radiation detection element 7, Al, Cr or the like is laminated to form an auxiliary electrode 72 on an insulating layer 71 which is formed integrally with the gate insulating layer 81 on the surface 4a of the substrate 4, and the first electrode 74 made from Al, Cr, Mo or the like is laminated on the auxiliary electrode 72 through an insulating layer 73 which is integrally formed with the first passivation layer 83. The first electrode 74 is connected to the source electrode 8a of the TFT 8 through a hole H formed in the first passivation layer 83. Note that the auxiliary electrode 72 may not be necessarily provided.

On the first electrode 74, an n layer 75 formed into the n type by doping VI-group elements into hydrogenated amorphous silicon, an i layer 76 which is a converting layer formed from hydrogenated amorphous silicon, and a p layer 77 formed into the p type by doping III-group elements into hydrogenated amorphous silicon are formed in a laminated manner in this order from the bottom.

Then, at the time of radiation image capturing operation, when radiation irradiating the radiation image capturing apparatus 1 enters from the radiation entrance face R of the case 2, is converted into an electromagnetic wave such as visible light by the scintillator 3, and the converted electromagnetic wave irradiates the device from above in the drawing, the electromagnetic wave reaches the i layer 76 of the radiation detection element 7, and an electron-hole pair is generated in the i layer 76. In this way, the radiation detection element 7 converts an electromagnetic wave emitted from the scintillator 3 into an electric charge (electron-hole pair).

Also, a second electrode 78 which is a transparent electrode made from ITO or the like is formed in a laminated fashion on the p layer 77, and is configured so that the electromagnetic wave irradiation reaches the i layer 76 and the like. In this embodiment, the radiation detection element 7 is formed in the way described above. It should be noted that the lamination order of the p layer 77, the i layer 76, and the n layer 75 may be upside down which is the reverse order. Further, in this embodiment, a case is explained in which, as the radiation detection element 7, a so-called pin-type radiation detection element formed by laminating the p layer 77, the i layer 76, and the n layer 75 in this order as described above is used, but the radiation detection element 7 is not limited thereto.

On the upper surface of the second electrode 78 of the radiation detection element 7, a bias line 9 is connected, which applies a bias voltage to the radiation detection element 7 via the second electrode 78. It should be noted that the second electrode 78 and the bias line 9 of the radiation detection element 7, the first electrode 74 extended to the TFT 8 side, the first passivation layer 83 of the TFT 8, and the like, in other words, the upper surface areas of the radiation detection element 7 and the TFT 8 are coated by a second passivation layer 79 made from silicon nitride ($SiN_x$) from the upper side thereof.

As illustrated in FIGS. 3 and 4, in this embodiment, one bias line 9 is connected to the plurality of radiation detection elements 7 which are respectively arranged in line, and each of the bias lines 9 is provided parallel to each of the signal lines 6. Also, each of the bias lines 9 is bundled to the wire connection 10 at a position on the outer side of the detecting section P of the substrate 4.

Figure 6:
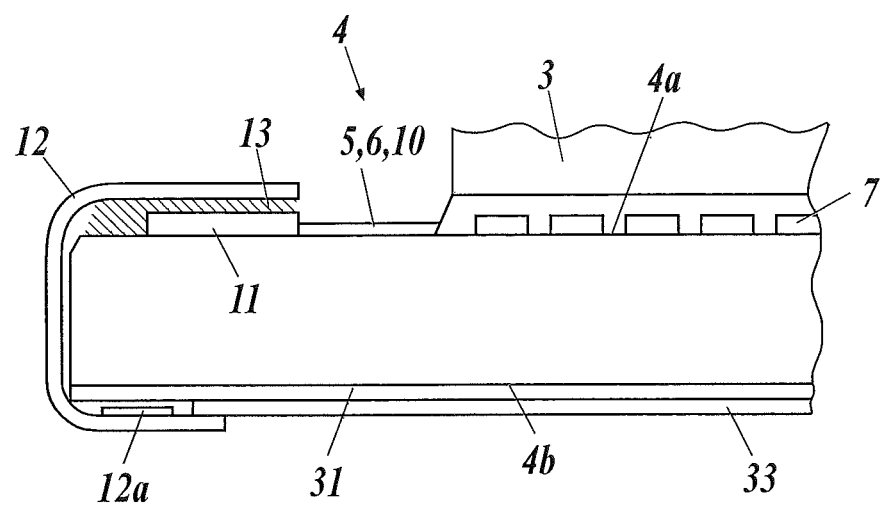
FIG. 6 is a side view explaining the substrate onto which a COF, a PCB substrate, and so on are attached.

In this embodiment, as illustrated in FIG. 3, the scanning lines 5, the signal lines 6, and the wiring connection 10 of the bias line 9 are respectively connected to input/output terminals (or pads) 11 provided near an end edge part of the substrate 4. As illustrated in FIG. 6, a COF (chip on film) 12 is connected to each of the input/output terminals 11 via an anisotropic conductive adhesive material 13 such as an anisotropic conductive film or an anisotropic conductive paste. Here, in the COF, a chip such as a gate IC 12a which configures a gate driver 15b of the later-described scanning drive unit 15 is embedded in a film.

Also, the COF 12 is drawn around to a back surface 4b side of the substrate 4 and is connected to the previously-mentioned PCB substrate 33 on the back surface 4b side. The portion of the substrate 4 in the radioactive imaging device 1 is configured in this way. Note that illustration of the electronic components 32 and so on is omitted in FIG. 6.

Figure 7:
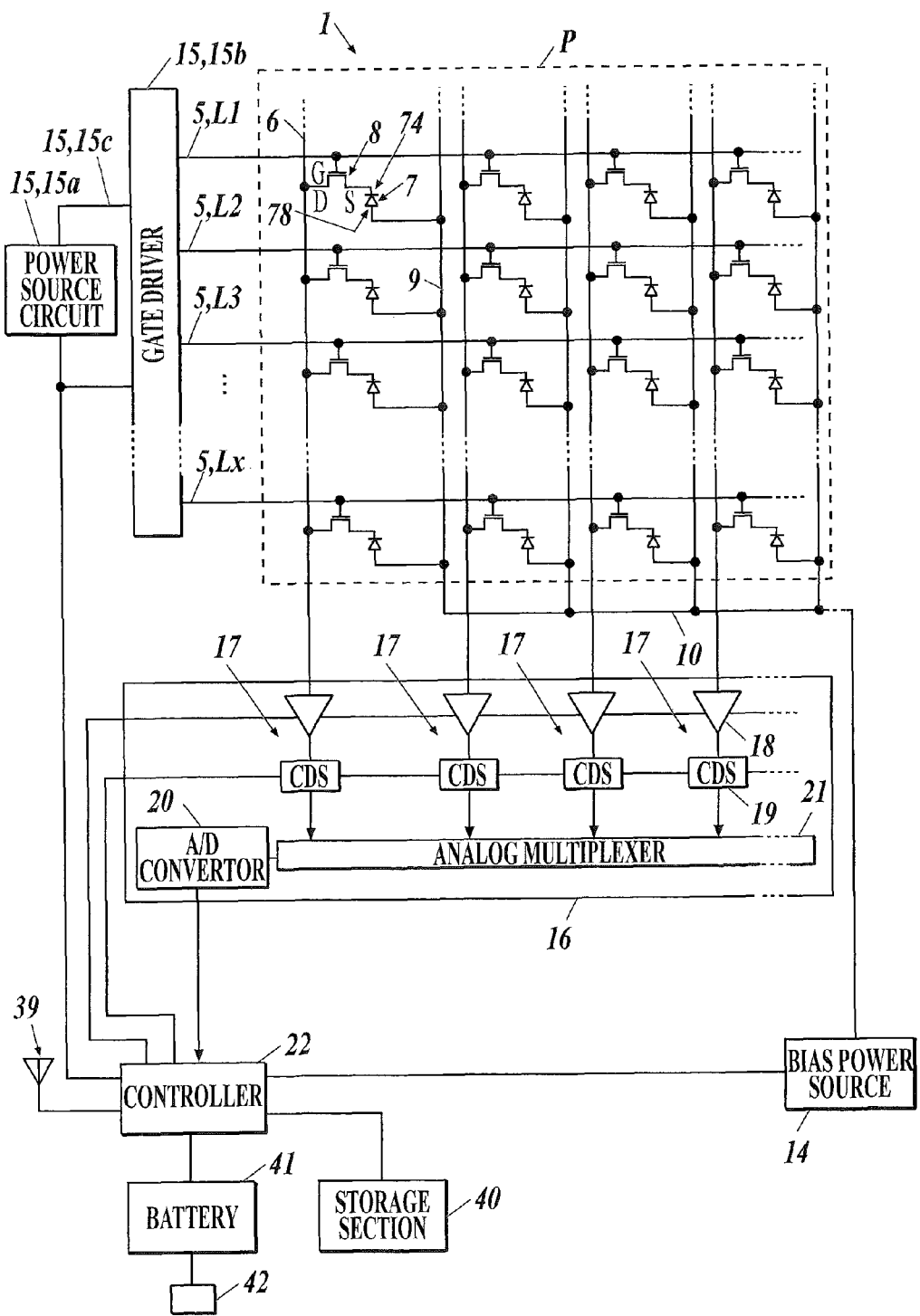
FIG. 7 is a block diagram showing an equivalent circuit of the radiation image capturing apparatus.

Here, the circuit configuration of the radioactive imaging device 1 is described. FIG. 7 is a block diagram showing an equivalent circuit of the radiation image capturing apparatus 1 according to the present embodiment, and FIG. 8 is a block diagram showing an equivalent circuit for one pixel which configures the detecting section P.

As stated previously, in each of the radiation detection elements 7 of the detecting section P of the substrate 4, the bias line 9 is connected to the second electrode 78 thereof, and each of the bias lines 9 is bundled to the wire connection 10 and connected to a bias power source 14. The bias power source 14 is designed to apply a bias voltage to the second electrode 78 of each of the radiation detection elements 7 through the wire connection 10 and each of the bias lines 9. Moreover, the bias power source 14 is connected to controller 22 which is described later, and a bias voltage to be applied to each of the radiation detection elements 7 by the bias power source 14 is controlled by the controller 22.

Figure 8:
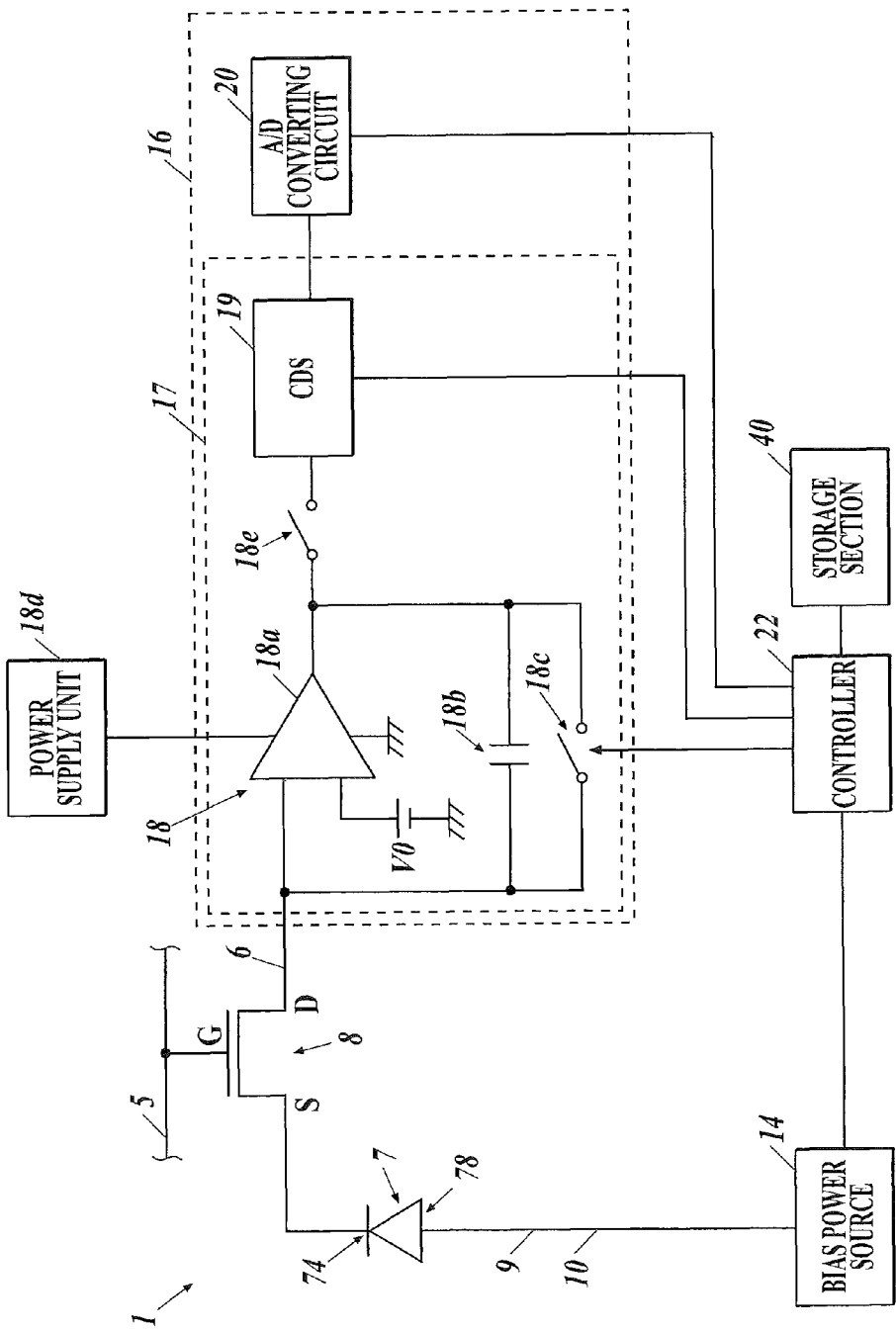
FIG. 8 is a block diagram showing an equivalent circuit for one pixel which configures a detecting section.

As depicted in FIGS. 7 and 8, in this embodiment, as will be noted from the fact that the bias line 9 is connected to the p layer 77 side of the radiation detection element 7 (see FIG. 5) via the second electrode 78, a voltage which is equal to or smaller than a voltage applied to the first electrode 74 side of the radiation detection element 7 (which is so-called reverse bias voltage) is applied as a bias voltage by the bias power source 14 to the second electrode 78 of the radiation detection element 7 through the bias line 9.

The first electrodes 74 of the radiation detection elements 7 are connected to the source electrodes 8s (denoted as S in FIGS. 7 and 8) of the TFTs 8, respectively, and the gate electrodes 8g (denoted as G in FIGS. 7 and 8) of the TFTs 8 are respectively connected to the lines L1 to Lx of the scanning lines 5 extending from the gate driver 15b of the later-described scanning drive unit 15. In addition, the drain electrodes 8d (denoted as D in FIGS. 7 and 8) of the TFTs 8 are connected to the signal lines 6, respectively.

The scanning drive unit 15 is provided with a power source circuit 15a which supplies an ON voltage and an OFF voltage to the gate driver 15b through a wire 15c, and the gate driver 15b which switches a voltage applied to the respective lines L1 to Lx of the scanning lines 5 between the ON voltage and the OFF voltage and switches each of the TFTs 8 between an ON state and an OFF state.

In this embodiment, as describe below, the scanning drive unit 15 sequentially applies the ON voltage to the respective lines L1 to Lx of the scanning lines 5, or keeps applying the OFF voltage to all of the lines L1 to Lx of the scanning line 15 according to instructions from the later-described controller 22.

Further, descriptions are made later, for timing and so on to sequentially apply the respective lines L1 to Lx of the scanning lines 5 by the gate driver 15b of the scanning drive unit 15 at the time of reading out the image data d and the like from each of the radiation detection elements 7.

As illustrated in FIGS. 7 and 8, each of the signal lines 6 is connected to each of the reading circuits 17 formed in each of reading ICs 16. Note that, in this embodiment, one reading circuit 17 is provided for one signal line 6 in the reading IC 16.

The reading circuit 17 includes an amplifier circuit 18, a correlated double sampling circuit 19, and the like. In addition, in the reading IC 16, an analog multiplexer 21 and an A/D converter 20 are further provided. Note that, in FIGS. 7 and 8, the correlated double sampling circuit 19 is stated as CDS. Also, in FIG. 8, the analog multiplexer 21 is omitted.

In this embodiment, the amplifier circuit 18 is configured with a charge amplifier circuit and includes an operational amplifier 18a, as well as a capacitor 18b and an electric charge reset switch 18c which are connected to the operational amplifier 18a in parallel, respectively. Also, a power supply unit 18d for supplying power to the amplifier circuit 18 is connected to the amplifier circuit 18. In addition, a switch 18e, which opens and closes in conjunction with the electric charge reset switch 18c, is provided between the operational amplifier 18a and the correlated double sampling circuit 19.

The signal line 6 is connected to an inverting input terminal on the input side of the operational amplifier 18a of the amplifier circuit 18, and a reference potential $V_0$ is applied to a non-inverting input terminal on the input side of the amplifier circuit 18. Note that the reference potential $V_0$ is set to an appropriate value, and in this embodiment, for example, 0 [V] is applied.

Further, the electric charge reset switch 18c of the amplifier circuit 18 is connected to the controller 22 so that ON/OFF control is executed by the controller 22. And when the electric charge reset switch 18c is turned into the ON state, the switch 18e is simultaneously switched to the OFF state, and when the electric charge reset switch 18c is turned into the OFF state, the switch 18e is switched to the ON state simultaneously.

As illustrated in FIG. 9, in the amplifier circuit 18, during a readout process for the image data d and in a state of the electric charge reset switch 18c being OFF (and the switch 18e being ON), accumulated electric charge is discharged from each of the radiation detection elements 7 to the signal line 6 through each of the TFTs 8 switched to the ON state, the electric charges flow in the signal lines 6, enter the capacitor 18b of the amplifier circuit 18, and are accumulated therein.

At this time, as illustrated in FIG. 7B, electric charges that leak via the TFT 8 from other radiation detecting devices 7 connected to the same signal line 6 also enter the capacitor 18b. Further, FIG. 9 only shows the ON/OFF state of the electric charge reset switch 18c and does not include the ON/OFF state of the switch 18e (refer to FIG. 8); however, as described above, the ON/OFF state of the switch 18e switches simultaneously with the ON/OFF state of the electric charge reset switch 18c. Still further, cases may appear in which only the operation of the electric charge reset switch 18*c* is described in the following, but the same applies also to these cases.

Also, in the amplifier circuit 18, a voltage value according to an amount of the electric charge accumulated in the capacitor 18*b* is outputted from the output side of the operational amplifier 18*a*. This way, the amplifier circuit 18 performs charge-to-voltage conversion by outputting a voltage value in accordance with an electric charge amount outputted from each of the radioactive detection elements 7.

It should be noted that the amplifier circuit 18 may be configured so as to output a current in accordance with the electric charges outputted from the radiation detection elements 7. Further, when resetting the amplifier circuit 18, and the electric charge reset switch 18*c* is turned into the ON state and the switch 18*e* is simultaneously turned into the OFF state, the input side and the output side of the amplifier circuit 18 are short-circuited and the electric charge accumulated in the capacitor 18*b* is discharged. Thereafter, the discharged electric charge passes through inside of the operational amplifier 18*a* from the output terminal side of the operational amplifier 18*a*, and exits from the non-inverting input terminal to be earthed or is flown out into the power supply unit 18*d*, thus resetting the amplifier circuit 18.

The correlated double sampling circuit (CDS) 19 is connected to the output side of the amplifier circuit 18. In this embodiment, the correlated double sampling circuit 19 has a sample-and-hold function, and ON/OFF control of this sample-and-hold function of the correlated double sampling circuit 19 is conducted by a pulse signal transmitted from the controller 22.

Namely, for example, during the readout process for the image data d, the electric charge reset switch 18*c* of the amplifier circuit 18 of each of the reading circuits 7 is first controlled to become the OFF state. At this time, the moment the electric charge reset switch 18*c* is turned into the OFF state, a so-called kTC noise is generated, and an electric charge caused by the kTC noise is accumulated in the capacitor 18*b* of the amplifier circuit 18.

Therefore, as shown in FIG. 10, a voltage value outputted from the amplifier circuit 18 is changed from the aforementioned reference voltage $V_0$ to a voltage value Vin by an amount of the electric charge caused by the kTC noise, at the moment when the electric charge reset switch 18*c* is turned into the OFF state (expressed as "18*c* off" in FIG. 10). At this stage, the controller 22 transmits a first pulse signal Sp1 to the correlated double sampling circuit 19 as shown in FIG. 9 to hold the voltage value Vin which is outputted from the amplifier circuit 18 at that point (expressed as "CDS hold" on the left side in FIG. 10).

Thereafter, as shown in FIG. 9, when the gate driver 15*b* of the scanning drive unit 15 applies an ON voltage to one of the scanning lines 5 (for example, a line Ln of the scanning lines 5) so that the TFTs 8 in which the gate electrodes 8*g* thereof are connected to the scanning line 5 are turned into the ON state (see FIG. 9; expressed as "TFT on" in FIG. 10), the accumulated electric charges are flown into the capacitor 18*b* of the amplifier 18 through each of the signal lines 6 from each of the radiation detection elements 7 to which these TFTs 8 are connected, and, as shown in FIG. 10, a voltage value, which is outputted from the amplifier circuit 18 in accordance with the amount of the electric charge accumulated in the capacitor 18, increases.

Then, as shown in FIG. 9, after a predetermined period of time has elapsed, the controller 22 switches the ON voltage applied by the gate driver 15*b* to the scanning line 5 into the OFF voltage so that the TFTs 8 in which the gate electrodes 8*g* thereof are connected to the scanning line 5 is turned to the OFF state (expressed as "TFT off" in FIG. 10). At this stage, the controller 22 transmits a second pulse signal Sp2 to each of the correlated double sampling circuits 19 to hold a voltage value Vfi which is outputted from the amplifier circuit 18 at that point (expressed as "CDS hold" on the right side in FIG. 10).

Once the voltage value Vfi is held due to the second pulse signal Sp2, the correlated double sampling circuit 19 calculates a difference of the voltage values Vfi-Vin, and outputs the calculated difference Vfi-Vin to the downstream side as image data d in an analog value.

The image data d of each of the radiation detection elements 7 outputted from the correlated double sampling circuit 19 is transmitted to the analog multiplexer 21, and is transmitted sequentially from the analog multiplexer 21 to the A/D converter 20. Then, the image data d in an analog value is converted into image data d in a digital value sequentially in the A/D converter 20, outputted to and sequentially stored in a storage section 40.

The controller 22 is configured by a computer in which a non-illustrated CPU (central processing unit), a ROM (read only memory), a RAM (random access memory), an input/output interface and the like are connected to a bus, a FPGA (field programmable gate array) and the like. The controller 22 may also be constructed by a designated control circuit. Also, the controller 22 is designed to control operations and the like of respective members of the radiation image capturing apparatus 1. In addition, as illustrated in FIG. 7 and so on, the storage section 40 configured by DRAM (dynamic RAM) or the like is connected to the controller 22.

Further, in this embodiment, the aforementioned antenna device 39 is connected to the controller 22, and, in addition, the battery 41 for supplying power to each of the members including the detecting section P, the scanning drive unit 15, the reading circuit 17, the storage section 40, and the bias power source 14, is connected to the controller 22. Moreover, a connecting terminal 42 is attached to the battery 41 for charging the battery 41 by supplying power to the battery 41 from non-illustrated charging equipment.

As stated previously, the controller 22 is designed to control operations of respective functional parts of the radiation image capturing apparatus 1, such as control of the bias power source 14 in order to set or change a bias voltage which is applied by the bias power source 14 to each of the radiation detection elements 7.

Hereinafter, each of configurations and the like in this embodiment and an operation of the radiation image capturing apparatus 1 according to this embodiment are described.

In this invention, the readout process for the image data d is executed before initiating the radiation image capturing operation in which the radiation image capturing apparatus 1 is irradiated with the radiation. Further, after finishing the readout process of the radiation image capturing apparatus 1, the readout process for the image data d as a so-called final image is executed.

In the following, the image data d read out after finishing the radioactive irradiation is called image data D, to be easily distinguished from the image data d read out before initiating the radiation image capturing operation. Also, the readout process after finishing the radioactive irradiation is called the readout process after the end of the radiation image capturing operation, to be easily distinguished from the readout process before the initiation of the radiation image capturing operation. Accordingly, the image data d before the initiation of the radiation image capturing operation, and the image data D after the end of the radiation image capturing operation, are read out in the respective readout processes.

[Model Configuration]

Here, before describing each of the configurations and the like in this embodiment, a configuration is described which is a target for comparison to each of the configurations of this embodiment. In below, the configuration is abbreviated as Model Configuration.

Figure 73:
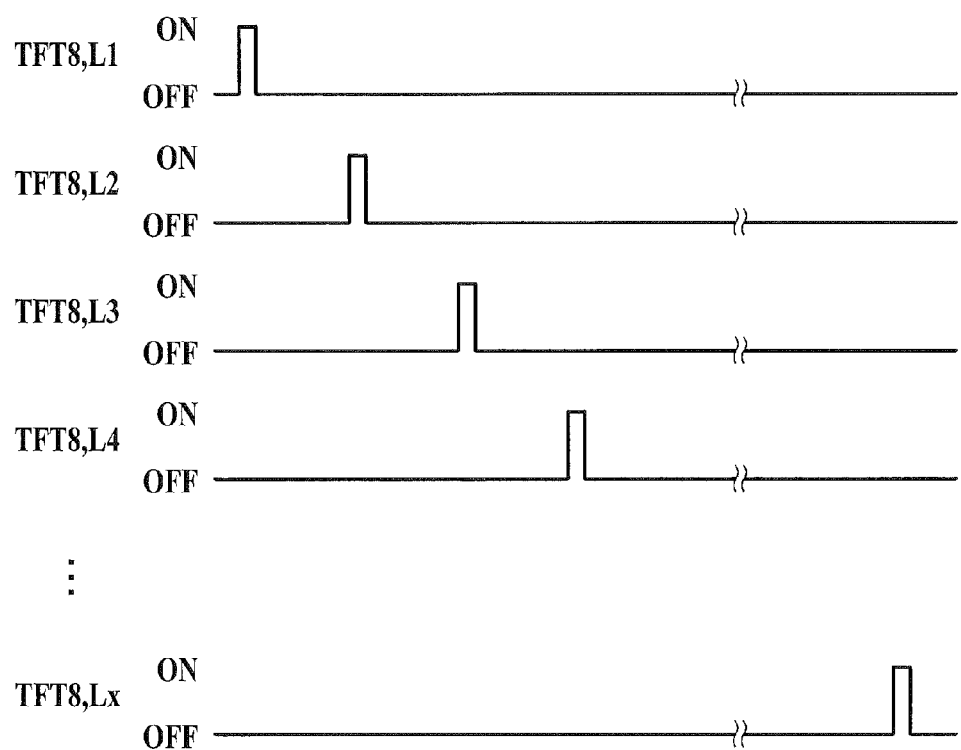
FIG. 73 is a timing chart showing timing of switching between the ON voltage and the OFF voltage, the voltage being applied to each scanning line in the readout process for normal image data.

In Model Configuration, as illustrated in FIG. 73, the readout process for the image data d is executed by sequentially applying the ON voltage to the respective lines L1 to Lx of the scanning line 5 by the gate driver 15b of the scanning drive unit 15 from the time before initiating the radiation image capturing operation. A value of the image data d is then monitored, and for example, as shown in FIG. 73, at the time when the value of the read out image data d increases and exceeds the predetermined threshold value dth (time t1 in FIG. 11), the radiation image capturing apparatus is configured to detect that the irradiation with the radiation on the radiation image capturing apparatus is initiated.

Figure 12:
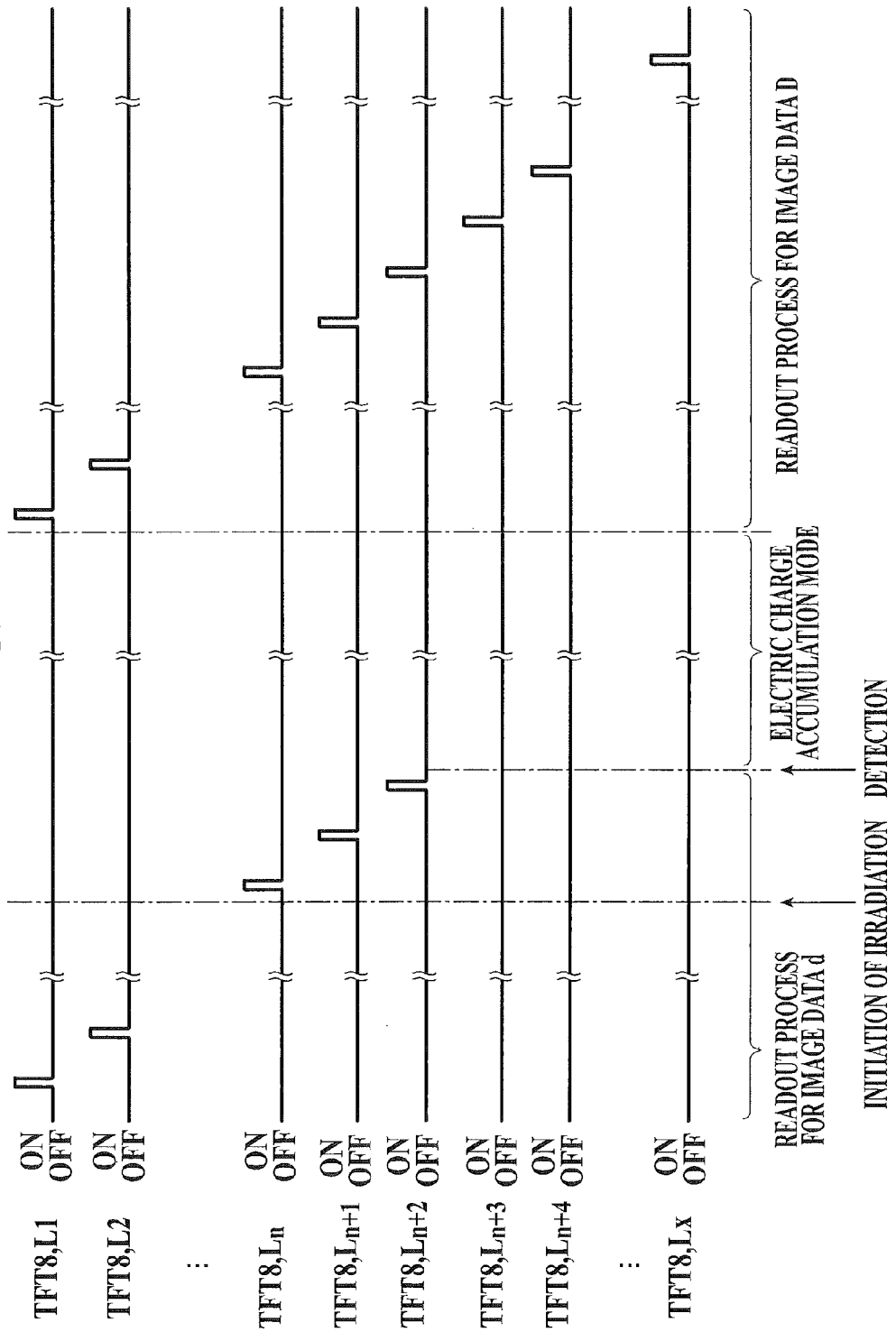
FIG. 12 is a timing chart showing application timing of ON voltage to each scanning line in the readout process for the image data before and after initiating the radiation image capturing operation of a model configuration.

Thereafter, as shown in FIG. 12, for example, when the ON voltage is applied to the line Ln of the scanning line 5 and the initiation of the radioactive irradiation is detected based on the image data d read out from each of the radiation detection elements 7 connected to the line Ln of the scanning line 5, the application of the ON voltage from the scanning drive unit 15 to the respective lines L1 to Lx of the scanning lines 5 is stopped, to switch the voltage applied to the respective lines L1 to Lx of the scanning lines 5 to the OFF voltage. Then, the process proceeds to an electric charge accumulation mode in which an electric charge generated in each of the radiation detecting devices 7 by the radioactive irradiation are accumulated therein.

After the end of irradiation onto the radiation image capturing apparatus with the radiation, the readout process for the image data D after the end of the radiation image capturing operation is executed, the ON voltage is applied to the respective lines L1 to Lx of the scanning lines 5 from the scanning drive unit 15, and the image data ID is read out from each of the radiation detection elements 7.

In Model Configuration, in both cases of the readout process for the image data d before the initiation of the radiation image capturing operation, and also in the readout process for the image data D after the end of the radiation image capturing operation, as illustrated in FIG. 12, the readout process is executed by applying the ON voltage from the scanning drive unit 15 to the respective lines L1 to Lx of the scanning lines 5.

On this occasion, in the readout process for the image data d before the initiation of the radiation image capturing operation, a time period between a time after turning each of the TFTs 8 to the ON state by applying the ON voltage to the respective lines L1 to Lx of the scanning lines 5 from the scanning drive unit 15, and a time of turning each of the TFTs 8 to the OFF state by switching the applied voltage to the OFF voltage, that is, a time in which the TFTs 8 are turned to the ON state in FIG. 9 (a time between "TFT on" and "TFT off" in FIG. 10. Hereinafter referred to as ON time) is set equal to the case in the readout process for the image data D as the final image after the end of the radiation image capturing operation.

Moreover, in this case, a transmission interval of pulse signals Sp1 and Sp2 transmitted to the correlated double sampling circuit 19 indicated in FIG. 9, and timing of ON/OFF operation of the electric charge reset switch 18c of the amplifier circuit 18, are set equal in the case in the readout process for the image data d before the initiation of the radiation image capturing operation and in the case in the readout process for the image data D after the end of the radiation image capturing operation.

However, in the configuration in Model Configuration, detection efficiency to detect the initiation of the radioactive irradiation does not necessarily improve. This is the same as in the case in the previously described Patent document 6, and a configuration to improve the detection efficiency is required.

[Regarding Improvement of Detection Efficiency of Initiation of Radioactive Irradiation, and the Like]

A description is made below of the respective configurations and the like according to this embodiment for improving the detection efficiency in the event of detecting that the radioactive irradiation is initiated.

[Configuration 1]

Figure 13:
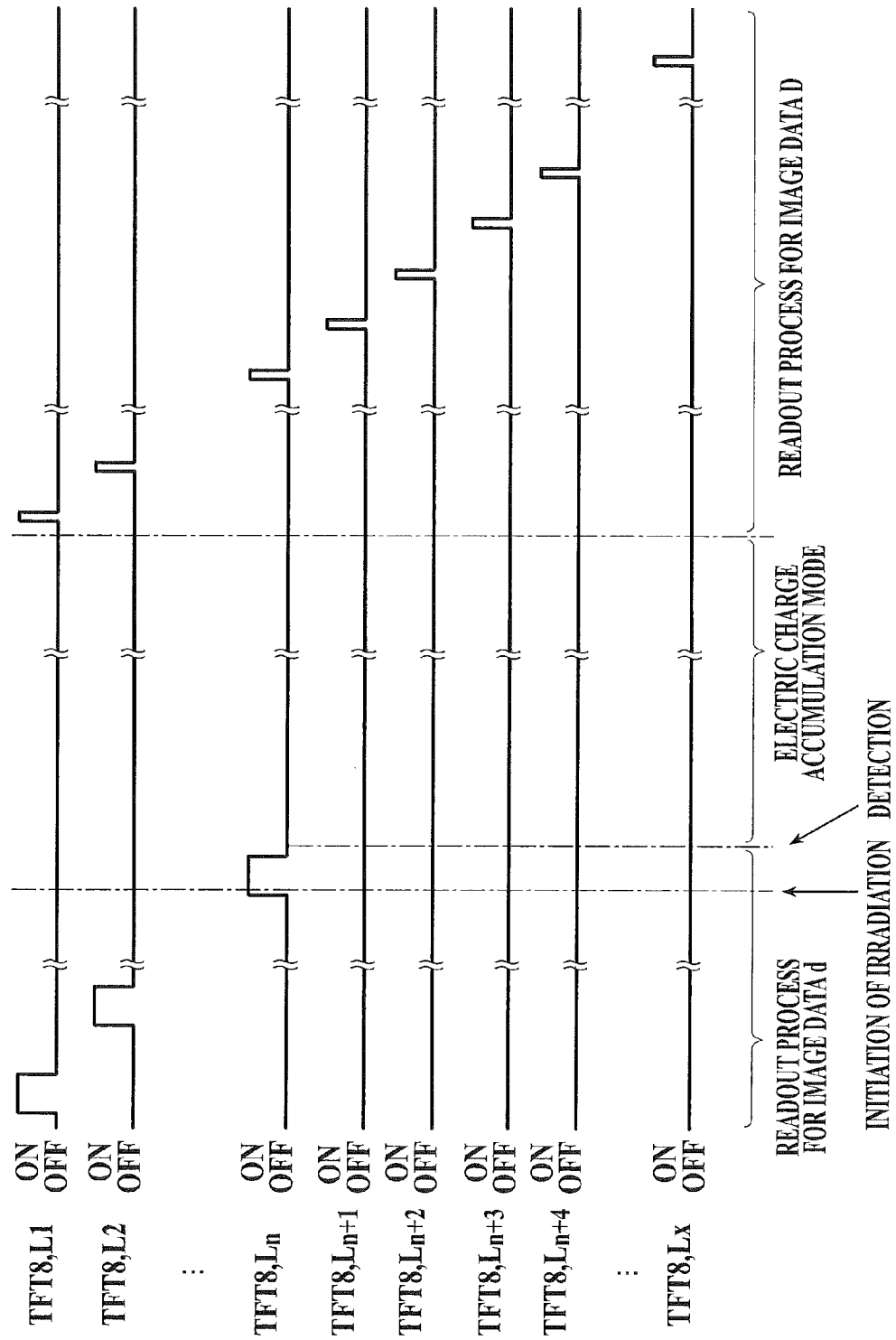
FIG. 13 is a timing chart showing application timing the ON voltage to each scanning line in Configuration 1 in which ON time in the readout process before initiating the radiation image capturing operation is made longer.

As one of the reasons why the detection efficiency is not always increased with the above-described model configuration, there is mentioned the fact that the ON time of each of the TFTs 8 in the readout process for the image data d before the radiation image capturing operation is short. Accordingly, for example as shown in FIG. 13, it is possible to adopt a configuration so that the ON time of the TFT 8 in the event of the readout process for the image data d before the radiation image capturing operation can be longer than the ON time in the event of the readout process for the image data D after the radiation image capturing operation.

As mentioned above, the image data d to be read out in the readout process before the radiation image capturing operation is the data for use in detecting the initiation of the radioactive irradiation. Accordingly, the image data d just needs to be the one that enables the detection that the radioactive irradiation is initiated by seeing a value of the image data d, that is, by determining whether or not the value of the image data d exceeds the threshold value dth. Therefore, it is not always necessary that the readout process for the image data d be performed under the same conditions as those for the image data D to be read out as a final image after the radiation image capturing operation.

That is to say, it is not necessary to perform the readout process for the image data d before the radiation image capturing operation at the same ON time and transmission timing as those of the ON time of the TFT 8 and the transmission timing (refer to FIG. 9) of the pulse signals Sp1 and Sp2 in the readout process for the image data D after the radiation image capturing operation.

Moreover, in the readout process for the image data D after the radiation image capturing operation, which is to be performed in a state where the radioactive irradiation onto the radiation image capturing apparatus 1 is ended and the electric charge generated by the radioactive irradiation in each of the radiation detection elements 7 is accumulated, as shown in FIG. 10, even if the ON time (a time from "TFTon" to "TFToff" in FIG. 10) of the TFT 8 is lengthened, the value Vfi of the voltage to be outputted from the amplifier circuit 18 does not become very large. Therefore, if the ON time of the TFT 8 is sufficiently long, then the value of the image data D to be read out hardly changes even if the ON time of the TFT 8 is lengthened.

As opposed to this, when the ON time of the TFT 8 in the readout process for the image data d before the radiation image capturing operation is lengthened, then in the image data d to be read out while the radiation is being irradiated after the radioactive irradiation is initiated, the electric charges continue to be generated by the radioactive irradiation in each of the radiation detection elements 7 also during the ON time of the TFT 8. Therefore, the longer the ON time of the TFT 8 becomes, the greater the value of the image data d becomes.

Figure 78:
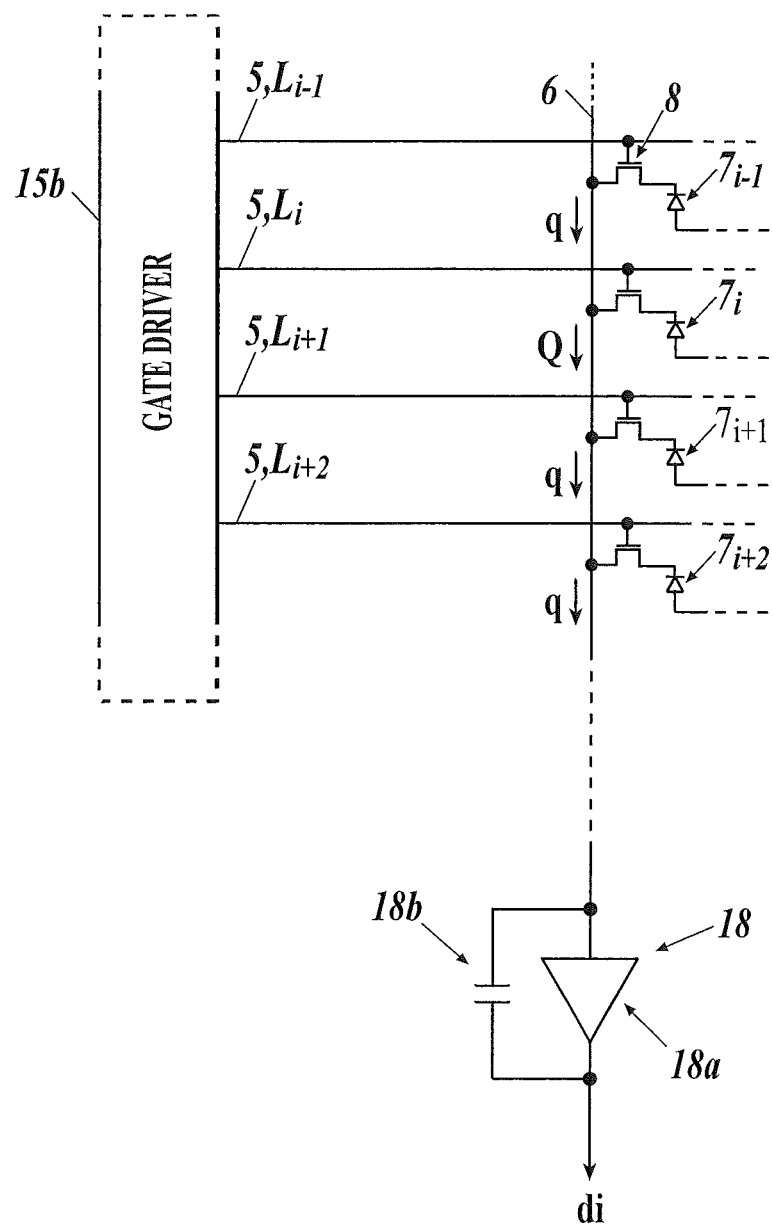
FIG. 78 is a view explaining that the sum value of the electric charge read out from the radiation detection element and the electric charge leaked from other radiation detection elements is read out as the image data.

Moreover, as described by using FIG. 78, when the radiation is irradiated, with regard to the radiation detection element 7 (the radiation detection element 7*i* in FIG. 78) that is reading out the image data d during the radioactive irradiation, the amount of the electric charges q, which leak through the TFTs 8 from other radiation detection elements 7 connected to the same signal line 6, also increase as described above. Then, the amount of the respective electric charges q which leak from the other radiation detection elements 7 and flow into the capacitor 18*b* of the amplifier circuit 18, increase as the ON time of the TFT 8 becomes longer. Therefore, also in this point, the greater the value of the image data d becomes, as the longer the ON time of the TFT 8 becomes.

Therefore, as in this Configuration 1, the above configuration is adopted so that the ON time of the TFT 8 in the event of the readout process for the image data d before the radiation image capturing operation can be longer than the ON time in the event of the readout process for the image data D after the radiation image capturing operation, whereby the size of the image data d itself, which is to be read out in the single readout process for the image data d, is becomes greater than in the case of the model configuration, thus making it possible to enhance the detection efficiency in the event of detecting that the radioactive irradiation onto the radiation image capturing apparatus 1 is initiated.

Note that the detection efficiency in the event of detecting that the radioactive irradiation is initiated is enhanced as described above, whereby it is made possible to reduce the number of scanning lines 5 in which the line defects occur. A description is made later of this matter.

[Configuration 2]

Moreover, as described above, talking from a viewpoint of enhancing the detection efficiency by increasing the value of the image data d itself to be read out in the single readout process for the image data d, the method described in Patent document 7 is also a process for increasing the value of the image data d itself.

Figure 80:
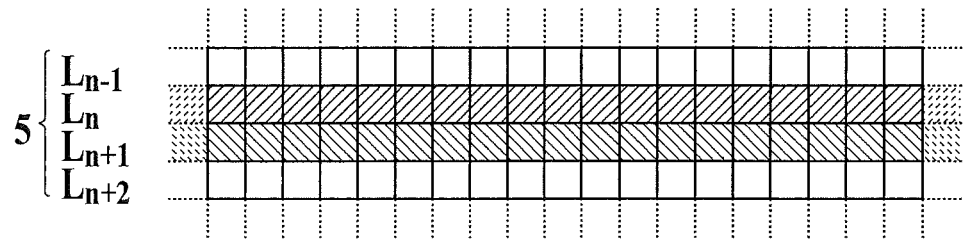
FIG. 80 is a view explaining a state in which the line defects successively occur in the plurality of adjacent scanning lines.

However, though the technology described in Patent document 7 is applied, and the detection efficiency of the radioactive irradiation is enhanced by simultaneously applying an ON voltage to the plurality of adjacent scanning lines 5, the line defects continuously appear on a plurality of adjacent lines L of the scanning lines 5 as shown in FIG. 80 if such a configuration is adopted.

Accordingly, in the event of the readout process for the image data d before the radiation image capturing operation, a configuration is adopted so as to perform the readout process by simultaneously applying the ON voltage to the plurality of scanning lines 5, which are not adjacent to one another on the detecting section P, from the scanning drive unit 15, whereby it is made possible to enhance the detection efficiency by increasing the value of the image data d itself to be read out in the single readout process for the image data d.

Figure 14:
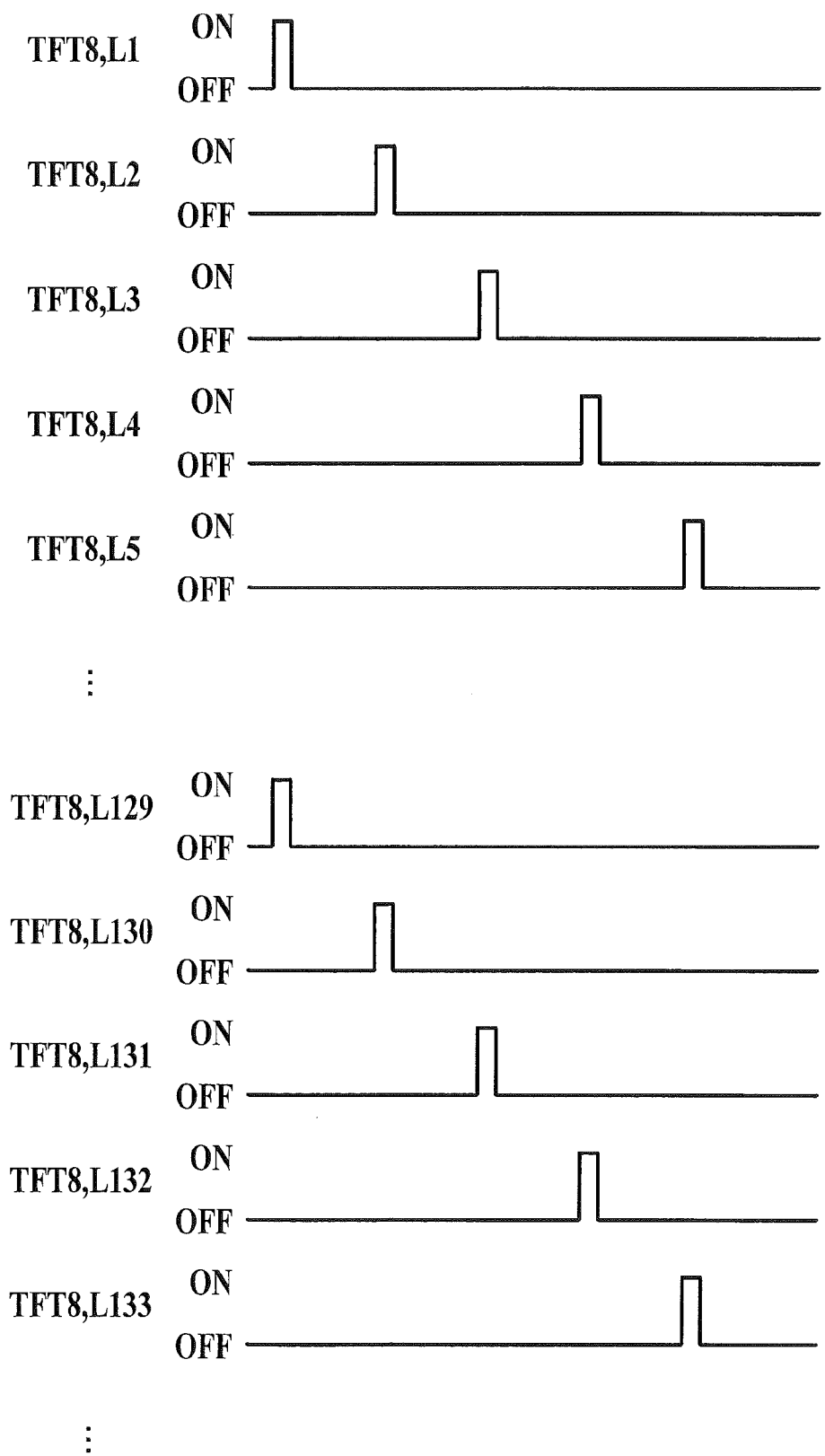
FIG. 14 is a timing chart showing an example in a case of executing the readout process by simultaneously applying the ON voltage to the plurality of scanning lines in the readout process for the image data before initiating the radiating imaging.

Specifically, for example, in a case where 128 scanning lines 5 are connected to the respective terminals of the respective gate ICs 12*a* which compose the gate driver 15*b* of the scanning drive unit 15, for example as shown in FIG. 14, a configuration can be adopted as follows. The ON voltage is simultaneously applied to the respective scanning lines 5 connected to first terminals of the respective gate ICs 12*a*, and the readout processes for the image data d are performed simultaneously, and at next timing, the ON voltage is simultaneously applied to the respective scanning lines 5 connected to second terminals of the respective gate ICs 12*a*, and the readout processes are performed.

If this configuration is adopted, for example, in the case where the gate driver 15*b* of the scanning drive unit 15 is composed of eight pieces of the respective gate ICs 12*a*, then the value of the image data d itself to be read out in the single readout process for the image data d becomes eight times larger. Therefore, it is made possible to enhance the detection efficiency by increasing the value of the image data d itself to be read out in the single readout process for the image data d.

Moreover, the configuration is adopted so as to perform the readout process by simultaneously applying the ON voltage to the plurality of scanning lines 5 which are not adjacent to one another on the detecting section P, whereby, even if a plurality of the scanning lines 5 occur which cause the line defects, the continuous occurrence of the line defects on the plurality of adjacent lines L of the scanning lines 5 is surely suppressed. Moreover, the configuration is adopted so as to simultaneously perform the readout processes for the image data d by simultaneously applying the ON voltage to the plurality of scanning lines L of the scanning lines 5, whereby a time required for the readout process for one frame is shortened, and it is made possible to further reduce extra electric charges such as dark electric charges to be accumulated in the respective radiation detection elements 7 connected to the respective scanning lines 5.

Note that, also in the case of lengthening the ON time of the TFT 8 in the event of the readout process for the image data d before the radiation image capturing operation as described in [Configuration 1], it is possible to adopt the configuration so as to perform the readout process for the image data d by simultaneously applying the ON voltage to the plurality of lines L of the scanning lines 5 in a similar way.

[Configuration 3]

Figure 11:
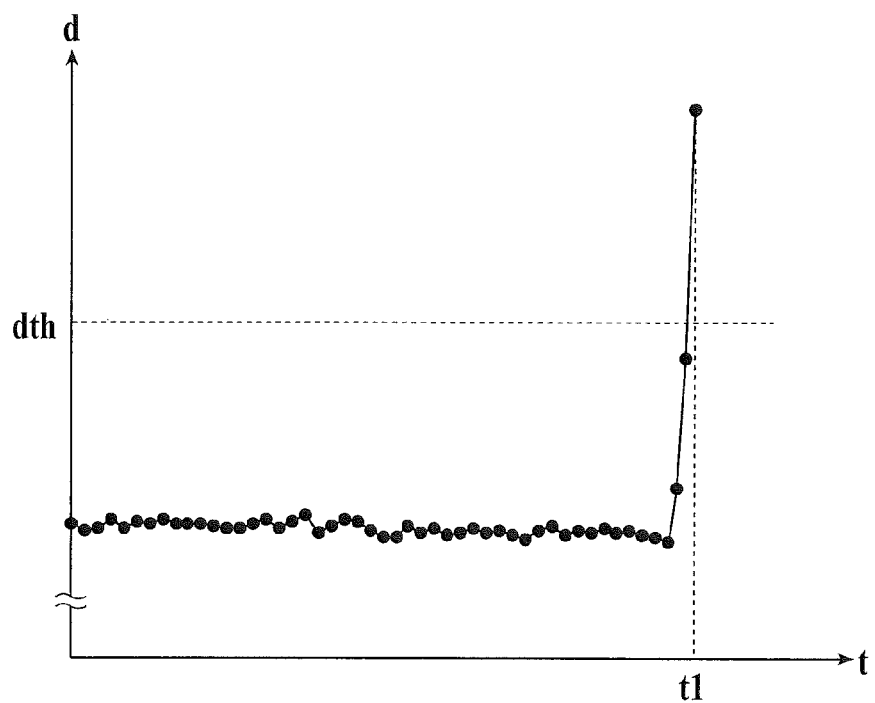
FIG. 11 is a graph showing that an image data value read out in the readout process becomes large after initiating radioactive irradiation compared to an image data value before initiating the radiation image capturing operation.

In the above-described model configuration, if the image data d read out by the readout process for the image data d, which is repeatedly performed before the radiation image capturing operation, is plotted in a time series, then the value of the image data d increases as shown in FIG. 11 when the radiation image capturing apparatus 1 is irradiated with the radiation.

Then, in this case, a configuration can be adopted as follows. The threshold value dth is preset as shown in FIG. 11, the readout process for the image data d is performed as described above, and at the point of time (refer to the time t1 in FIG. 11) when the read out image data d exceeds the threshold value dth, it is detected that the radioactive irradiation is initiated.

Accordingly, also in this embodiment, a configuration can be adopted as follows. From before the radiation image capturing operation, the controller 22 sequentially applies the ON voltage from the scan drive means 15 to the respective lines L1 to Lx of the scanning lines 5 to repeatedly perform the readout process for the image data d, for example, as shown in FIG. 12 or FIG. 13, and at the point of time when the value of the read out image data d exceeds the threshold value dth, it is detected that the radioactive irradiation is initiated.

Note that, as shown in FIG. 7 and the like, the image data d are individually outputted from the respective reading circuits 17 every time the ON voltage is sequentially applied to the respective lines L1 to Lx of the scanning lines 5. Then, since one reading circuit 17 is provided for each of the signal lines 6 provided by the number from thousands to tens of thousands on the detecting section P, several thousand to several ten thousand pieces of the image data d are outputted from each of the reading circuits 17 by the single readout process for the image data d.

Then, if a configuration is adopted so as to perform a determination as to whether or not each of the several thousand to several ten thousand pieces of the image data d exceeds the threshold value dth, then a load of a determination process becomes extremely large. Accordingly, for example, it is possible to adopt a configuration so as to extract a maximum value dmax from among these respective pieces of image data d to be read out for each readout process for the image data d, and to determine whether or not the maximum value dmax of the image data d exceeds the threshold value dth.

If the configuration is adopted as described above, then for example, in a case where only a narrow range of the detecting section P of the radiation image capturing apparatus 1 is irradiated with the radiation (that is to say, in the case where the radioactive irradiation is performed while the irradiation field is being narrowed), the image data d does not increase in a portion onto which the radioactive irradiation is performed, and meanwhile, in a portion onto which the radioactive irradiation is performed, the image data d increases, and accordingly, the maximum value dmax of the image data d increases. Therefore, it is determined whether or not the maximum value dmax of the image data d exceeds the threshold value dth, whereby it is made possible to surely detect the initiation of the radioactive irradiation.

However, among the radiation detection elements 7, there is a radiation detection element 7 from which image data d with an extraordinarily large value is read out. Moreover, though depending on the performance of each reading circuit 17, there is also a case where noise generated in the reading circuit 17 is large. In this case, though the radiation is not irradiated onto the radiation image capturing apparatus 1, in some case, the image data d with the extraordinarily large value or the image data d on which the noise is superimposed exceeds the threshold value dth, and there is a risk that it may be erroneously detected that the radioactive irradiation is initiated.

Therefore, in the above case, for example, with regard to the radiation detection element 7 from which the extraordinary image data is read out, it is possible to adopt a configuration so as to prestore information of the extraordinary radiation detection element 7, and to exclude the image data d, which is read out from the extraordinary radiation detection element 7, from objects of the above-described determination for the initiation of the radioactive irradiation.

Moreover, for example, in the event of applying the ON voltage to the scanning line 5 to which the extraordinary radiation detection element 7 is connected, it is also possible to adopt a configuration so as to lower the voltage value of the ON voltage to be applied to the scanning line 5 concerned, and to thereby prevent the image data d with the extraordinarily large value from the extraordinary radiation detection element 7.

Furthermore, for example, it is also possible to adopt a configuration so as to calculate statistic values such as average values and total values of the image data d for each of the reading ICs 16 in which a predetermined number of the reading circuits 17 are provided, and to adopt a configuration so as to extract a maximum value from among the average values concerned or the total values concerned, and to compare the maximum value concerned and the threshold value dth with each other.

If the configuration is adopted as described above, then since the reading circuits 17 of which number is large such as 128 and 256 are usually formed in each of the reading ICs 16, the image data d with the extraordinarily large value is, so to speak, diluted in the course of being averaged with other image data d with normal values or being totalized therewith to calculate the total value, and the calculated average value or total value does not become a very extraordinarily large value. Therefore, if the threshold value dth is preset at an appropriate value, then it is made possible to prevent the radioactive irradiation from being erroneously detected even if the image data d with the extraordinarily large value is read out.

Moreover, if the configuration is adopted so as to calculate the average value or total value of the image data d as described above, then the noises to be individually generated in the respective reading circuits 17 are cancelled out with one another in the event of calculating the average value or total value of the image data d, and accordingly, it is made possible to reduce an influence of the noises to be generated in the reading circuits 17 on the image data d.

As described above, the configuration is adopted so as to extract the maximum value dmax from among the image data d to be readout in the readout process before the radiation image capturing operation, or to extract the maximum value from among the average values or total values of the image data d, and to thereby detect that the radioactive irradiation is initiated by comparing the maximum value concerned and the threshold value dth with each other, whereby it is made possible to enhance the detection efficiency in the event of detecting that the radioactive irradiation onto the radiation image capturing apparatus 1 is initiated.

Moreover, in place of adopting the configuration as described above so as to extract the maximum value of the individual image data d, or to calculate the average value or total value of the image data d in each of the reading ICs 16, to extract the maximum value from thereamong, and to compare the maximum value concerned with the threshold value dth, it is also possible to adopt a configuration so as to calculate an average value or total value of all the pieces of image data d read out by the respective reading circuits 17 in the event of the single readout process for the image data d, and to compare the average value or the total value with the threshold value dth. If the configuration is adopted as described above, the process for extracting the maximum value becomes unnecessary.

Note that the average value and total value of the image data d or the like are different from each other only in whether or not to perform a process for dividing the total value by a total number of pieces of the image data d or the like, and are the same process in the meaning of adding up the image data d or the like. Hence, also in the case below in which only the average value or the total value is described, it is possible to appropriately adopt a configuration so as to use the total value in place of the average value, and to use the average value in place of the total value.

Moreover, as the statistic values of the image data d for each of the reading ICs 16, besides the average value and total value of the image data d as described above, a variety of values are usable, for example, such as a median and mode of the image data d in each of the reading ICs 16, or a weighting average value thereof, a mean square value thereof, a root of the mean square, and the like. Then, a description is made below of the case of mainly using the average value as the statistic value; however, it is also possible to adopt a configuration so as to use, in place of the average value, the above-described respective statistic values other than the average value.

[Configuration 4]

Meanwhile, in the case where a radiation with a usual dose is irradiated onto the radiation image capturing apparatus 1, the image data d to be read out in the readout process is increased relatively obviously than the image data d read out at a stage where the radiation is not irradiated. Accordingly, it is easy to detect the initiation of the radioactive irradiation. However, for example, in the case where a radiation with an extremely low dose rate (that is, a dose per unit time) is irradiated onto the radiation image capturing apparatus 1 as in the Schuller projection for the auditory organ, there is also a case where the increase of the image data d is not obvious.

Accordingly, in this Configuration 4, a description is made of a configuration for enhancing the detection efficiency even in the case where the radiation with an extremely low dose rate is irradiated onto the radiation image capturing apparatus 1 as described above, and for surely detecting the initiation of the radioactive irradiation.

In the case where the radiation with an extremely low dose rate is irradiated onto the radiation image capturing apparatus 1 as described above, a ratio of the image data d and the noise to be superimposed thereonto, that is, an S/N ratio of the image data d becomes an important subject. While a variety of the noises are superimposed on the image data d, for example, mentioned as main noises can be noise generated in the voltage of the bias power source 14 (refer to FIG. 7), and the noise derived from the power source circuit 15*a* of the scanning drive unit 15.

The bias power source 14 is connected to the respective radiation detection elements 7 through the wire connection 10 and the respective bias lines 9, and a bias voltage Vbias on which the noise generated in the bias power source 14 is superimposed is applied to the respective radiation detection elements 7.

Each of the radiation detection elements 7 is in a state where the i layer 76 (refer to FIG. 5) or the like is interposed between the first electrode 74 and the second electrode 78, forms a type of a capacitor-like structure, and accordingly, has a parasitic capacity C. Then, in each of the radiation detection elements 7, basically, electric charge Q represented by $Q=C \cdot (V_0-Vbias)$ is accumulated, and the electric charge Q fluctuate by the noise of the bias voltage Vbias.

That is to say, the electric charge noise caused by the fluctuation of the bias voltage Vbias is superimposed on the electric charge Q accumulated in each of the radiation detection elements 7. The bias power source 14 is connected to all the radiation detection elements 7 through the bias lines 9 and the like, and accordingly, the noise of the bias voltage Vbias simultaneously travels through all the radiation detection elements 7, and the electric charge noise caused by the noise of the bias voltage Vbias is simultaneously superimposed on all the radiation detection elements 7.

Therefore, the ON voltage is applied to certain lines L of the scanning lines L, and on the image data d to be read out from the respective radiation detection elements 7 connected to the lines L concerned of the scanning lines 5, the same noise caused by the noise of the bias voltage Vbias is superimposed.

Moreover, the ON voltage supplied from the power source circuit 15*a* (refer to FIG. 7) of the scanning drive unit 15 is applied to the scanning lines 5 through the gate driver 15*b*, and is applied to the gate electrodes 8*g* of the respective TFTs 8. In that event, the noise of the ON voltage, which is generated in the one power source circuit 15*a*, is transmitted to the scanning lines 5 to which the ON voltage is applied, and is transmitted through the scanning lines 5 instantaneously to the respective TFTs 8 connected thereto.

Therefore, the noise generated on the power source circuit 15*a* is simultaneously transmitted to all the TFTs 8 connected to the scanning lines 5 to which the ON voltage is applied, and is superimposed on the image data d, which is to be read out, in the event of, the readout process for the image data d.

As described above, in the case where the ON voltage is applied to the certain lines L of the scanning lines 5, and the readout process for the image data d is executed, then the same noise caused by the noise of the bias voltage Vbias or the noise of the power source circuit 15*a* is superimposed on the image data d to be read out from the respective radiation detection elements 7 connected to the lines L concerned of the scanning lines 5.

As described above, the noise of the bias voltage Vbias and the noise generated in the power source circuit 15*a* of the scanning drive unit 15 are simultaneously superimposed on all the radiation detection elements 7. Therefore, on the image data d read out at the same timing, that is, on the image data d read out from the respective radiation detection elements 7 connected to the certain lines L of the scanning lines 5 in the case where the ON voltage is applied to the lines L concerned and the readout process is executed, the same noise component is superimposed. Moreover, every time when the scanning lines 5 to which the ON voltage is applied are switched, the noise component to be superimposed on the respective pieces of image data d is increased and decreased in the same way.

Accordingly, for example, a configuration is adopted as follows by using these characteristics, whereby it is made possible to enhance the detection efficiency by improving the S/N ratio of the image data d. Note that, though a description is made below of the case of using an average value dave of the respective pieces of image data d in each of the reading ICs 16, it is as mentioned above that the individual image data d and the statistic value such as the total value of the respective pieces of image data d for each of the reading ICs 16 may be used in place of the average value dave.

[Configuration 4-1]

Figure 15:
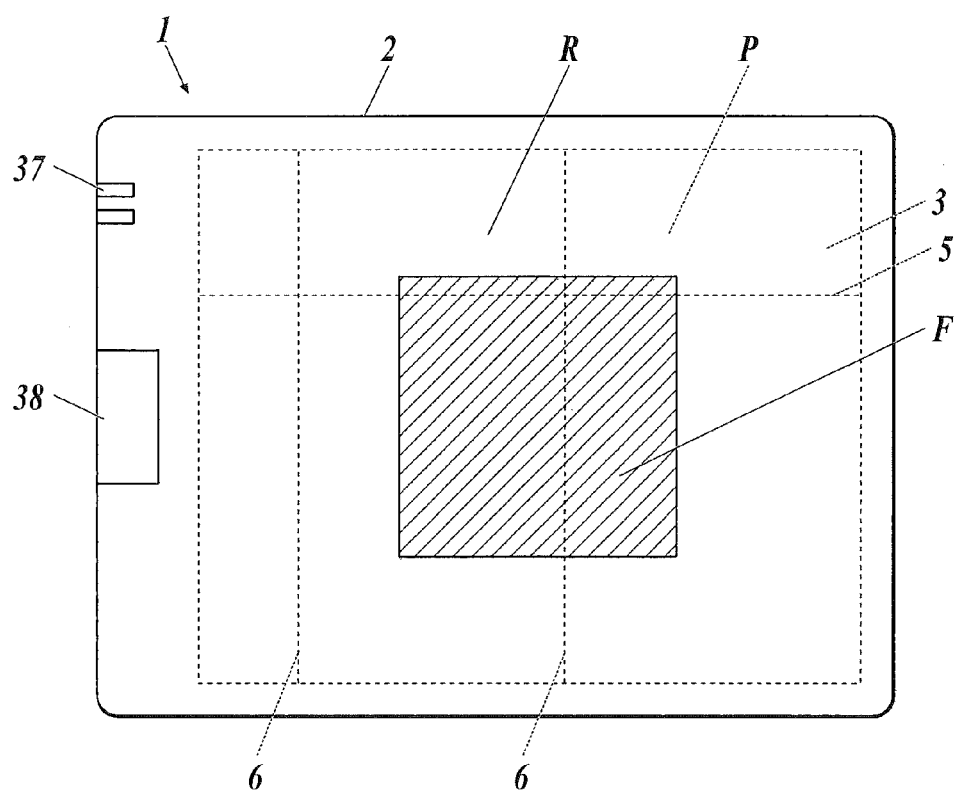
FIG. 15 is a view showing an example of an irradiation position of a radiation with an irradiation field being narrowed on a scintillator and the detecting section.

As mentioned above, in the event of irradiating the radiation onto the radiation image capturing apparatus 1, in the case of viewing the radiation image capturing apparatus 1 from the radiation entrance face R (refer to FIG. 1 and FIG. 2) thereof, sometimes, the radioactive irradiation is not made onto the entire region of the scintillator 3 or detecting section P of the radiation image capturing apparatus 1 but, as shown in FIG. 15, is made onto a part of the scintillator 3 or the detecting section P while the irradiation field F is being narrowed. In particular, in the case of irradiating with the radiation with a low dose rate onto the radiation image capturing apparatus 1, frequently, the irradiation with the radiation is performed while the irradiation field F thereof is being narrowed.

Note that, in FIG. 15, it is defined that each of the scanning lines 5 is wired so as to be extended in the lateral direction of FIG. 15, and that each of the signal lines 6 is wired so as to be extended in the longitudinal direction thereof.

In the case where the radioactive irradiation is performed as described above, when the radiation image capturing apparatus 1 is irradiated with the radiation, then in the respective radiation detection elements 7 provided at positions on the detecting section P, which correspond to the irradiation field F of the radiation, that is, at positions which the electromagnetic wave can enter, the electromagnetic wave being converted from the irradiated radiation by the scintillator 3, the electric charges are generated in insides of the radiation detection elements 7 concerned by such irradiation with the radiation, and the value of the image data d to be read out increases.

However, even if the radiation image capturing apparatus 1 is irradiated with the radiation, then in the respective radiation detection elements 7 provided at positions other than the positions on the detecting section P, which correspond to the irradiation field F of the radiation, that is, at positions on the detecting section P, which the electromagnetic wave from the scintillator 3 does not enter, the electromagnetic wave converted by the scintillator 3 does not enter the radiation detection elements 7 concerned, and accordingly, the image data d does not increase.

Then, as mentioned above, also to the radiation detection elements 7 and the TFTs 8, which are located at any positions, the noises generated in the bias power source 14 and the power source circuit 15 of the scanning drive unit 15 are simultaneously transmitted through the bias lines 9 and the respective lines L1 to Lx of the scanning lines 5. Therefore, the same noise is superimposed on the image data d to be read out from the respective radiation detection elements 7.

Accordingly, by using this, it is possible to adopt a configuration as follows. By the controller 22, calculated is a difference Δd obtained by subtracting the image data d, which is read out from the respective radiation detection elements 7 provided at the positions on the detection part P, into which the electromagnetic wave irradiated from the scintillator 3 does not enter (that is, the positions other than the positions on the detecting section P, which correspond to the irradiation field F of the radiation), from the image data d, which is read out from the respective radiation detection elements 7 at the positions on the detecting section P, into which the electromagnetic wave irradiated from the scintillator 3 can enter (that is, the positions on the detecting section P, which correspond to the irradiation field F of the radiation). Then, at the point of time when the calculated difference Δd exceeds a threshold value Δdth set for the difference Δd concerned, it is detected that the radioactive irradiation is initiated.

Note that, in this case, it is premised that, as described above, the radioactive irradiation is performed while narrowing the irradiation field F so that the radiation concerned can be irradiated not onto the entire region of the scintillator 3 or detecting section P of the radiation image capturing apparatus 1 but onto a part of the scintillator 3 or the detecting section P.

However, in this case, the irradiation field F of the radiation to be irradiated onto the radiation image capturing apparatus 1 is usually set at the most suitable position on the radiation entrance face R for each imaging and for the sake of imaging convenience. Therefore, though the irradiation field F is sometimes set in the vicinity of the center of the radiation entrance face R as shown in FIG. 15, the irradiation field F is also sometimes set at a position corresponding to the vicinity of a peripheral edge portion of the scintillator 3 or the detecting section P. Accordingly, the radiation detection elements 7, into which the electromagnetic wave from the scintillator 3 does not enter, cannot be specified in advance.

Accordingly, for example, by the controller 22, a maximum value dmax and a minimum value dmin are extracted from the respective pieces of image data d read out for each of the reading circuits 17. That is to say, the maximum value dmax and the minimum value dmin are extracted from all the pieces of image data d individually read out from all the radiation detection elements 7 connected to one scanning line 5 to which the ON voltage is applied in the single readout process. Then, it is possible to adopt a configuration so as to calculate a difference Δd obtained by subtracting the extracted minimum value dmin from the extracted maximum value dmax, and to detect that the radioactive irradiation is initiated at the point of time when the calculated difference Δd exceeds a threshold value Δdth set for the difference Δd concerned.

Moreover, also in this case, on the respective pieces of image data d read out for each of the reading circuits 17, in usual, amounts of offsets caused by readout characteristics of the respective reading circuits 17 are individually superimposed. Therefore, when the pieces of the image data d with respect to the same electric charge Q are read out in the respective reading circuits 17, the respective pieces of image data d differ from one another by the respective amounts of offsets.

Therefore, for example, every time of performing the readout process for the image data d, a moving average of the image data d extracted in each of the readout processes in previous round of which number of times is a predetermined number, for example, such as five times and ten times, each of the readout processes in the previous round including a readout process immediately before the readout process concerned, is calculated for each of the reading circuits 17. Then, this moving average is subtracted from the image data d read out in the readout process performed in a current round, and a value obtained by this subtraction is taken as the image data d read out in the reading circuits 17 in the readout process performed in the current round.

Then, as described above, from the respective pieces of image data d calculated by subtracting the moving average individually from the respective pieces of image data d read out for each of the reading circuits 17, the maximum value dmax and the minimum value dmin are extracted, and the difference Δd obtained by subtracting the minimum value dmin from the maximum value dmax is calculated. Then, it is possible to adopt a configuration so as to detect that the radioactive irradiation is initiated at the point of time when the calculated difference Δd exceeds the threshold value Δth set for the difference Δd concerned.

If the configuration is adopted as described above, then, before the radioactive irradiation onto the radiation image capturing apparatus 1, with regard to the image data d calculated by subtracting the moving average from the image data d read out in the respective reading circuits 17, the amounts of offsets in each of the reading circuits 17 are cancelled with one another, and a value thereof outputted from any reading circuit 17 becomes a value substantially approximate to zero. Accordingly, the difference Δd obtained by subtracting the minimum value dmin from the maximum value dmax becomes a value approximate to zero.

However, for example, as shown in FIG. 15, in the case where the radiation image capturing apparatus 1 is irradiated with the radiation, then as mentioned above, in the respective radiation detection elements 7 arranged at the positions on the detecting section P, which correspond to the irradiation field F of the radiation, the value of the image data d to be readout by the radioactive irradiation is increased, and meanwhile, in the respective radiation detection elements 7 arranged at the positions other than the positions on the detecting section P, which correspond to the irradiation field F of the radiation, the value of the image data d is not increased.

Therefore, during a period from when the radioactive irradiation is actually initiated to when it is detected that the radioactive irradiation is initiated, the difference Δd obtained by subtracting the minimum value dmin of the image data d from the maximum value dmax thereof, the image data d being calculated by subtracting the moving average from the image data d read out in the respective reading circuits 17, becomes a positive value significantly different from zero. Therefore, the threshold value Δdth is preset at a suitable value for this difference Δd, whereby it is made possible to surely detect at least the initiation of the radioactive irradiation.

Figure 16:
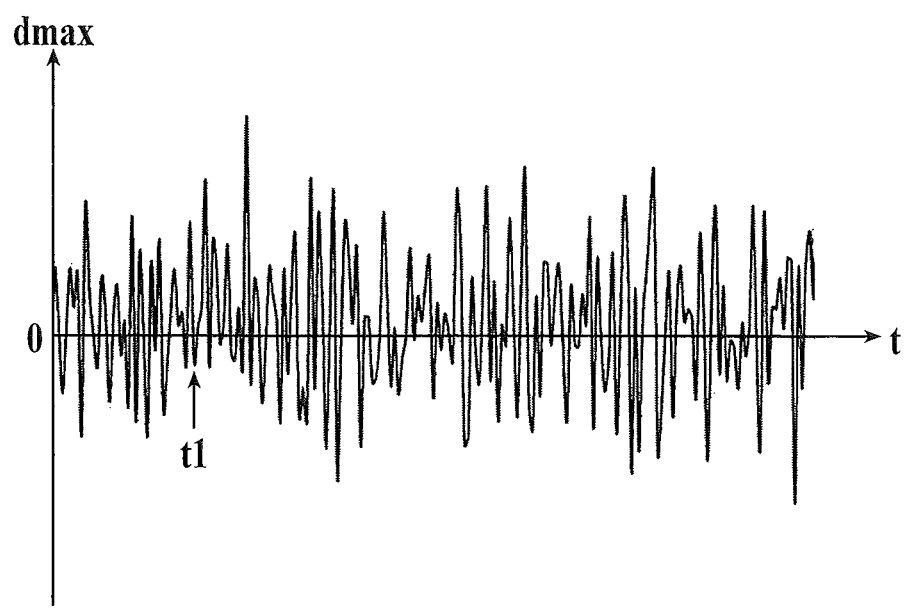
FIG. 16 is a graph showing an example of the maximum value of the image data read out from a reading IC in a case of irradiating the radiation image capturing apparatus with a very weak radiation.

For example, FIG. 16 is a graph showing the maximum value dmax of the image data d to be read out from a certain reading IC 16 in the case where the radiation image capturing apparatus is irradiated with an extremely weak radiation. In FIG. 16, the image data d increases and decreases by the noises generated in the bias power source 14 and the power source circuit 15 of the scanning drive unit 15. Then, though the radioactive irradiation is initiated at the time t1 in actual, an amount of the increase of the image data d by the radioactive irradiation is buried in the noise, and the initiation of the radioactive irradiation cannot be detected.

Figure 17:
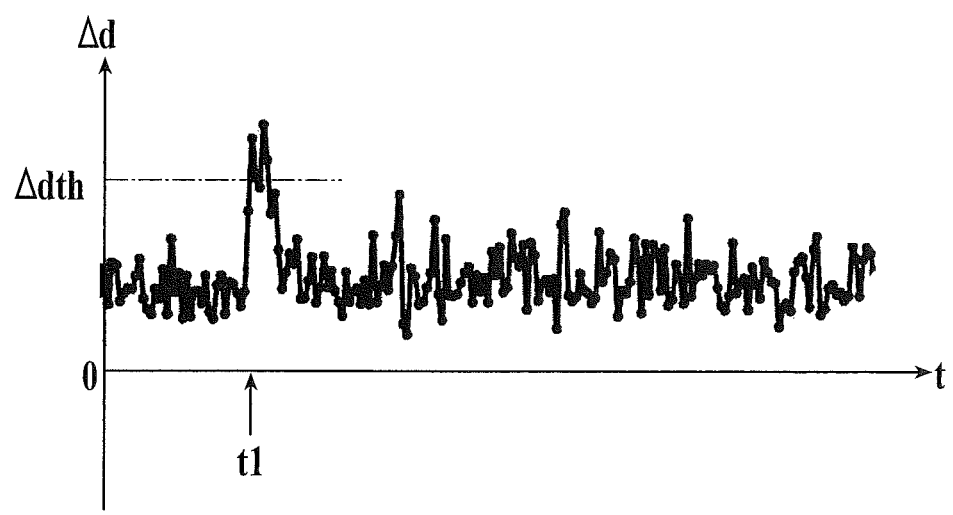
FIG. 17 is a graph showing, by enlarging, a difference between maximum and minimum values extracted from image data calculated by deducing a moving average from the image data read out from the reading IC.

However, as described above, when the maximum value dmax and the minimum value dmin are extracted from the image data d calculated by subtracting the moving average from the image data d, and the difference Δd obtained by subtracting the minimum value dmin from the maximum value dmax is calculated, then as enlargedly shown in FIG. 17, the calculated difference Δd certainly rises at the time t1, and exceeds the threshold value Δdth, and it can be detected that the radioactive irradiation is initiated at that point of time.

As described above, a configuration is adopted so as to calculate the difference Δd, whereby it is made possible to remove the noise component, which is superimposed on the image data d and is derived from the bias power source 14 and the power source circuit 15a, and it is made possible to improve the S/N ratio of the image data d and to thereby enhance the detection efficiency in the event of detecting that the radioactive irradiation is initiated.

Then, a configuration is adopted so as to set the threshold value Δdth, and to detect that the radioactive irradiation is initiated based on the calculated difference Δd, whereby it is made possible to accurately detect the initiation of the radioactive irradiation.

Note that, as mentioned above, the difference Δd shown in FIG. 17 is the difference Δd in the case where the radiation image capturing apparatus 1 is irradiated with the radiation with an extremely low dose, and also for the difference Δd as described above, such a result as shown in FIG. 17 is obtained. Therefore, needless to say, in the case where the radiation image capturing apparatus 1 is irradiated with a usual radiation with a higher dose rate, the difference Δd rises more clearly.

Moreover, in both of the cases where the dose rate of the radiation with which the radiation image capturing apparatus 1 is irradiated is high and where the dose rate is low, sometimes, the entire region of the radiation entrance face R (refer to FIG. 1 and the like) is irradiated with the radiation without narrowing the irradiation field F. In this case, the initiation of the radiation detection cannot be detected by the processing method of this [Configuration 4-1].

However, meanwhile, if the processing method of [Configuration 4-1] is adopted, for example, even in the case where the radiation with such a feeble dose rate of the radiation with which the appropriate detection of the initiation and end of the radioactive irradiation cannot always be performed in accordance with the configurations described above in [Configuration 1] to [Configuration 3], then as shown in FIG. 17, it is made possible to surely detect the initiation and end of the radioactive irradiation.

Accordingly, in the actual radiation image capturing apparatus 1, it is possible to adopt configurations in which [Configuration 1] to [Configuration 3], which are described above, and this [Configuration 4-1] are combined. Moreover, it is possible to adopt a configuration as follows. The configuration shown in the description of any of the above [Configuration 1] to [Configuration 3] and the above-described [Configuration 4-1] are used in combination, and the initiation of the radioactive irradiation is detected at the point of time when it is detected that the radioactive irradiation is initiated in either of the configurations between both of the configurations as well as in the case where the initiation of the radioactive irradiation is detected simultaneously in these configurations.

Figure 18:
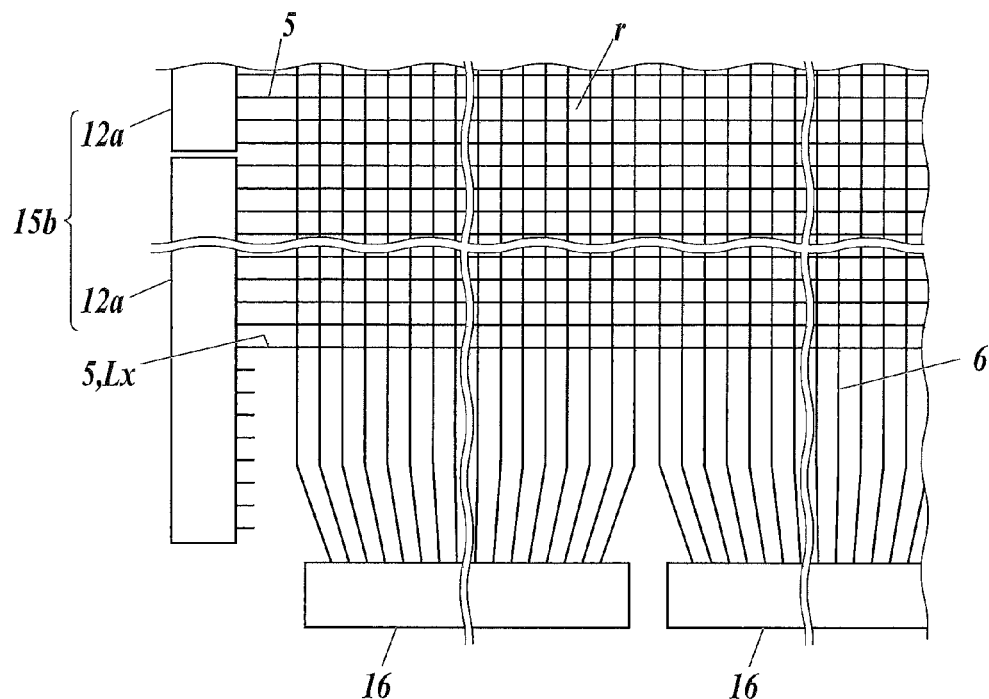
FIG. 18 is a block diagram showing each of the reading ICs to which plurality of signal lines are connected and in which plurality of reading circuits are formed.

Incidentally, as mentioned above, in each of the reading ICs 16, the respective reading circuits 17 of which number is predetermined, for example, such as 128 and 256 are formed as shown in FIG. 18. Then, for example, in the case where 128 pieces of the reading circuits 17 are formed in one reading IC 16, and 1,024 lines of the signal lines 6 are wired therein, at least eight pieces of the reading ICs 16 are provided.

Then, as described above, in the case where the radiation image capturing apparatus 1 is irradiated with the radiation in a state where the irradiation field F (refer to FIG. 15) is narrowed, for example, it is conceived that, among the eight pieces of the reading ICs 16, there is a reading IC 16 in which the respective radiation detection elements 7 connected to the reading ICs 16 through the respective signal lines 6 become the respective radiation detection elements 7 provided at the positions other than the positions on the detecting section P, which correspond to the above-described irradiation field F of the radiation, that is, the positions on the detecting section P, into which the electromagnetic wave from the scintillator 3 does not enter.

That is to say, by the fact that the irradiation field F of the radiation is narrowed, it is conceived that, though the radiation image capturing apparatus 1 is irradiated with the radiation, there is a reading IC 16 in which the radiation does not reach all the radiation detection elements 7 connected to a certain reading IC 16 (in this embodiment, into which the electromagnetic wave converted from the radiation in the scintillator 3 does not enter).

Therefore, in place of adopting the configuration as described above so as to extract the maximum value and the minimum value from among the respective pieces of image data d calculated by subtracting the moving average individually from the respective pieces of image data d read out for each of the reading circuits 17, it is also possible to adopt a configuration so as to calculate average values of the respective pieces of image data d in each of the reading ICs 16, the image data d being calculated by subtracting the moving averages individually from the respective pieces of image data d read out for each of the reading circuits 17, and to extract a maximum value and a minimum value from among the average values in each of the reading ICs 16.

If the configuration is adopted as described above, then the number of reading ICs 16 is eight in the above-described example, accordingly, the number of average values in each of the reading ICs 16 also becomes eight, and it is made possible to easily perform an extraction process for the maximum value and the minimum value.

Meanwhile, in the actual radiation image capturing apparatus 1, the signal lines 6 and the reading circuits 17 exist by the number from thousands to tens of thousands, and in any of the above-described cases, for all thereof, the moving averages must be individually calculated, the moving averages must be individually subtracted from the respective pieces of image data d read out for each of the reading circuits 17, and there is a possibility that it may take a time to perform these processes.

Then, in the case where it takes a time to perform the above-described processes as described above, the determination as to whether or not the radioactive irradiation is initiated, which is performed for each of the readout processes for the image data d, or the like takes too long, and as will be described later, there is a possibility that there is a risk that the line defects may continuously occur on the plurality of adjacent scanning lines 5.

Accordingly, it is possible to adopt a configuration as follows. In place of individually subtracting the moving average from the respective pieces of image data d read out for each of the reading circuits 17, by using the structure as shown in FIG. 18, in which the respective reading circuits 17 of which number is predetermined, for example, such as 128 and 256 are formed in each of the reading ICs 16, for example, the average values of 128 pieces of the image data d in each of the reading ICs 16, the image data d being outputted from the respective reading circuits 17 for one reading IC 16 are first calculated in the single readout process.

If the configuration is adopted as described above, then the number of average values of the respective pieces of image data d in each of the reading ICs 16 in the single readout process becomes eight which is equal to the number of reading ICs 16 in the case of the above-described example.

Then, it is possible to adopt a configuration as follows. For the average values of the image data d for each of these eight reading ICs 16, the moving average is individually calculated, the moving average is individually subtracted from the respective average values, and the respective averages values from which the moving average is subtracted are compared with one another, the maximum value and the minimum value are extracted from among the compared average values, the difference Δd obtained by subtracting the minimum value from the maximum value is calculated, and at the point of time when the calculated difference Δd exceeds the threshold value Δdth, it is detected that the radioactive irradiation is initiated.

If the configuration is adopted as described above, then as described above, it is made possible to enhance the detection efficiency, and to surely detect the initiation and end of the radioactive irradiation. In addition, for the 1,024 pieces of the image data d to be read out in the respective reading circuits 17 in the single readout process, it is not necessary to calculate the moving average, and it becomes sufficient if the moving average is calculated for the averages values of the image data d for each of the eight reading ICs 16.

Therefore, it is made possible to rapidly perform a series of the respective processes, which are: the calculation of the moving average; the subtraction of the moving average from the average values of the image data d; the extraction of the maximum value and the minimum value; the calculation of the difference Δd; and the comparison between the difference Δd and the threshold value Δdth, and it is made possible to rapidly perform the determination as to whether or not the radioactive irradiation is initiated, which is performed for each of the readout processes for the image data d, or the like.

Moreover, if the configuration is adopted so as to calculate the average values of the respective pieces of image data d for each of the reading ICs 16 as described above, then the electric noises to be generated for each of the large number of reading circuits 17 in the reading IC 16 are cancelled with one another in the event of calculating the average values of the image data d. Accordingly, there is also an advantage that it is made possible to reduce an influence of the electric noises to be generated in the respective reading circuits 17 on the image data d and on the moving average thereof.

[Configuration 4-2]

Figure 19:
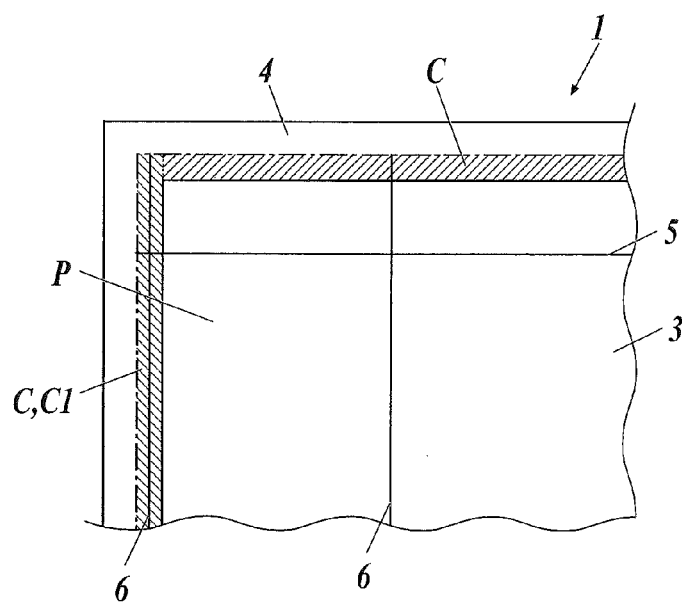
FIG. 19 is a view seen from an incident plane side of the radiation and the view explaining positions on the detecting section in which an electromagnetic wave irradiation from the scintillator can enter and cannot enter.

Meanwhile, depending on the radiation image capturing apparatus 1, there is a case where the scintillator 3 is formed to be smaller than the detecting section P provided on the substrate 4 from the beginning as schematically shown in FIG. 19. Note that, also in FIG. 19, it is defined that each of the scanning lines 5 is wired so as to be extended in the lateral direction of FIG. 19, and that each of the signal lines 6 is wired so as to be extended in the longitudinal direction thereof.

Then, in the case where a configuration is adopted as described above, then in the respective radiation detection elements 7 provided at positions on the detecting section P, which are located immediately under the scintillator 3, that is, at positions into which the electromagnetic wave obtained by converting the irradiated radiation in the scintillator 3 can enter, the image data d rises when the radiation image capturing apparatus 1 is irradiated with the radiation.

However, in the respective radiation detection elements 7 provided at positions other than the positions on the detecting section P, which are located immediately under the scintillator 3, that is, at positions on the detecting section P, into which the electromagnetic wave from the scintillator 3 does not enter (refer to a position C shown to be hatched in FIG. 19), even if the radiation image capturing apparatus 1 is irradiated with the radiation, the electromagnetic wave does not enter the radiation detection elements 7, and accordingly, the image data d does not rise.

Then, as mentioned above, in any of the TFTs 8 connected to the radiation detection elements 7 at any positions, the noises generated in the bias power source 14 and the power source circuit 15a are simultaneously transmitted to the respective radiation detection elements 7 and the respective TFTs 8 through the bias lines 9 and the scanning lines 5. Therefore, the noises generated in the bias power source 14 and the like are superimposed on the respective pieces of image data d to be read out.

Accordingly, by using this, it is possible to adopt a configuration as follows. By the controller 22, calculated is a difference Δd obtained by subtracting the image data d, which is read out from the respective radiation detection elements 7 provided at the positions on the detection part P, into which the electromagnetic wave irradiated from the scintillator 3 does not enter (that is, the positions other than the positions located immediately under the scintillator 3), from the image data d, which is read out from the respective radiation detection elements 7 at the positions on the detecting section P, into which the electromagnetic wave irradiated from the scintillator 3 can enter (that is, the positions located immediately under the scintillator 3). Then, in a similar way to the above, it is detected that the radioactive irradiation is initiated at the point of time when the calculated difference Δd exceeds the threshold value Δdth.

Note that, in the case of calculating the difference Δd by adopting the configuration as described, it is also possible to adopt a configuration as follows. As the latter image data d read out from the respective radiation detection elements 7 provided at the positions on the detecting section P, into which the electromagnetic wave irradiated from the scintillator 3 does not enter (that is, the positions other than the positions located immediately under the scintillator 3), for example, one piece of the image data d among the image data d read out from the respective radiation detection elements 7 at the above-described position C is selected and used. Moreover, it is also possible to adopt a configuration so as to calculate an average value of these image data d and to use the calculated average value as the latter image data d.

As described above, in the case where the radiation image capturing apparatus 1 is configured as shown in FIG. 19, the configuration is adopted so as to calculate the difference Δd by performing the respective processes as described above, whereby it is made possible to remove at least the nose component, which is superimposed on the image data d and is derived from the bias power source 14 and the like, and it is made possible to improve the S/N ratio of the image data d.

Then, a configuration is adopted so as to set the threshold value Δdth, and to detect that the radioactive irradiation is initiated based on the calculated difference Δd, whereby it is made possible to surely detect the initiation of the radioactive irradiation.

Note that, also in the case of this [Configuration 4-2], the amounts of offsets caused by the readout characteristics of the respective reading circuits 17 are individually superimposed on the respective pieces of image data d read out for each of the reading circuits 17. Therefore, in a similar way to the above-described [Configuration 4-1], it is preferable that such processes as follows be performed. Every time of performing the readout process for the image data d, the moving averages of the image data d, which are read out from the respective radiation detection elements 7 at the position C, and are read out in the respective readout processes in the previous round of which number of times is predetermined, the readout processes in the previous round including the readout process immediately before the readout process concerned, is calculated for each of the reading circuits 17. Moreover, the moving average is subtracted from the image data d read out in the readout process performed this time, and a value obtained this subtraction is taken as the image data d read out in the reading circuits 17 concerned in the readout process performed this time.

Moreover, in this case, it is accurately determined whether the configuration is adopted so as to always perform the process for taking, as the image data d, the value obtained by subtracting the moving average from the image data d read out in the respective reading circuits 17 or the configuration is adopted so as to perform the process concerned only in the case where the dose rate of the radiation to be irradiated is extremely low.

[Configuration 5]

Moreover, as the configuration of enhancing the detection efficiency by improving the S/N ratio of the image data d, it is also possible to adopt a configuration as follows. The capacity of the capacitor 18b of the amplifier circuit 18 composed of the above-mentioned charge amplifier circuit is made variable in advance, and in the event of the readout process for the image data d before the radiation image capturing operation, the capacity cf of the capacitor 18b of the amplifier circuit 18 is varied so as to be smaller than a capacity thereof in the event of the readout process for the image data D after the radiation image capturing operation.

As mentioned above, the amplifier circuit 18 outputs the voltage value corresponding to the electric charges Q discharged from the radiation detection elements 7 and flown and accumulated in the capacitor 18b. The capacity cf of the capacitor 18b is varied so as to be small, whereby, in accordance with the relationship of V=Q/cf, the voltage value V to be outputted from the amplifier circuit 18 can be increased even in the case where the same amount of the electric charge Q are accumulated in the capacitor 18b.

In this event, with regard to the noise component superimposed from the beginning on the electric charges Q discharged from the radiation detection elements 7, that is, for example, the noise component derived from the bias power source 14 and the like as described above, by the fact that the voltage value V to be outputted from the amplifier circuit 18 increases, the noise component concerned also increases, and this does not contribute to the improvement of the S/N ratio. However, with regard to at least the noise component to be generated in the reading circuit 17 including the amplifier circuit 18, the noise component concerned does not increase even if the voltage value V increases.

However, in this case, with regard to at least the noise component to be generated in the reading circuit 17 including the amplifier circuit 18, it is made possible to improve the S/N ratio, and it is made possible, by improving the S/N ratio, to enhance the detection efficiency in the event of detecting that the radioactive irradiation is initiated.

Note that, if the capacity cf of the capacitor 18b is reduced too much, then the capacitor 18b becomes prone to be saturated with the electric charges q discharged from the respective radiation detection elements 7. When the capacitor 18b is saturated, the readout at the next time and after in the reading circuit 17 including the capacitor 18b concerned is adversely affected in some case. Therefore, the capacity cf of the capacitor 18b is adjusted so as to be lowered to an appropriate value. Moreover, in the event of the readout process for the image data D, which is to be performed after the radiation image capturing operation, the capacity cf of the capacitor 18b is returned to a usual predetermined capacity.

Figure 20:
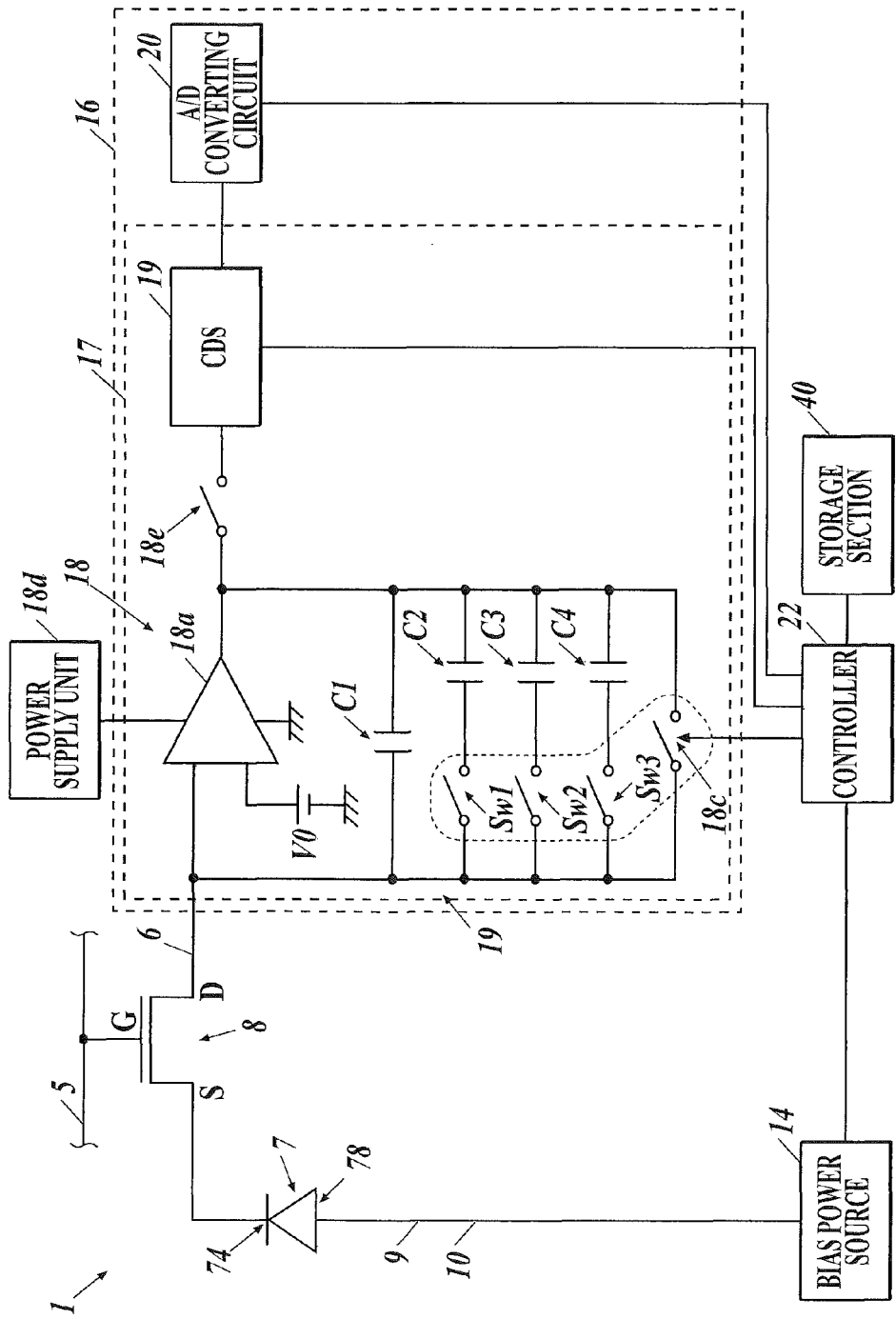
FIG. 20 is a block diagram showing an equivalent circuit for one pixel which configures the detecting section in a case of configuring a capacitor in an amplifier circuit to be variable in capacity.

Moreover, the amplifier circuit 18 of the reading circuit 17 is composed, for example, as shown in FIG. 20, whereby it is made possible to adopt a configuration so that the capacity of the capacitor 18b of the amplifier circuit 18 can be varied.

Specifically, as the capacitor to be connected in parallel to the operational amplifier 18a of the amplifier circuit 18 composed of the charge amplifier circuit, the respective capacitors C1 to C4 are connected in parallel to one another in place of using one capacitor 18b as shown in FIG. 8. Then, a configuration is adopted so as to connect switches Sw1 to Sw3 in series to the respective capacitors C2 to C4, respectively. Note that it is also possible to adopt a configuration so as to connect a switch also to the capacitor C1.

Then, ON/OFF of the switches Sw1 to Sw3 are switched, whereby it is made possible to adopt a configuration so that the capacity of the capacitor 18b of the amplifier circuit 18 can be varied. Note that, in this case, the capacity of the capacitor 18b becomes a total value of a capacity of the capacitor C1 and the respective capacities of the capacitors C2 to C4 connected in series to the switches turned to an ON state among the switches Sw1 to Sw3.

Note that, in a case where the image data d can be read out in a state where the S/N ratio is sufficiently favorable even if the capacity cf of the capacitor 18b of the amplifier circuit 18 is not lowered, then from a viewpoint of making much of preventing an occurrence of the adverse effect, which is caused by the fact that the capacitor 18b is saturated with the electric charges Q discharged from the respective radiation detection elements 7 as mentioned above, it is also possible to adopt a configuration as follows on the contrary to the above-described case. Specifically, in the event of the readout process for the image data d before the radiation image capturing operation, the capacity cf of the capacitor 18b is varied so as to become larger than a capacity thereof in the event of the readout process for the image data D after the radiation image capturing operation.

Also in this case, in the event of the readout process for the image data D after the radiation image capturing operation, it is necessary to accurately read out the image data D, and accordingly, the capacity cf of the capacitor 18b is returned to the usual predetermined capacity.

[Configuration 6]

Moreover, as shown in FIG. 78, in the case where the ON voltage is applied to a certain line Li of the scanning lines 5, and image data di is read out from the radiation detection element 7i, then the image data di actually becomes data equivalent to a total value of the electric charge Q discharged from the radiation detection element 7i concerned and of the electric charges q leaked through the TFTs 8 from the other radiation detection elements 7 connected to the same signal line 6.

Therefore, these electric charges q that leak from the other radiation detection elements 7 are increased, whereby it is made possible to further increase the image data d, and to thereby improve the S/N ratio of the image data d.

Figure 21:
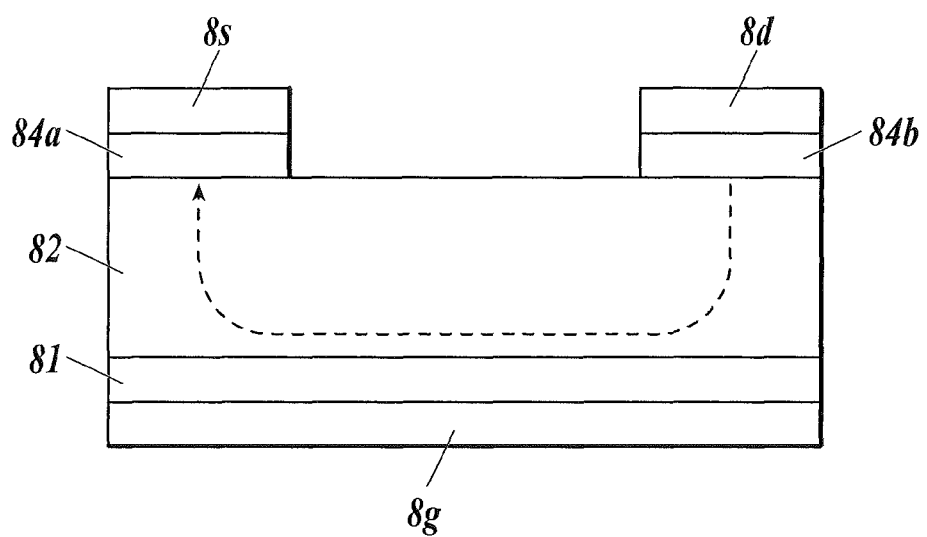
FIG. 21 is a schematic diagram explaining that a leak current flowing inside the TFT flows by passing a region on a gate electrode side having low electron density in a semiconductor layer.

As shown in FIG. 21 that schematically shows the cross-sectional structure of the TFT 8 shown in FIG. 5, with regard to the TFT 8, since the OFF voltage is applied to the gate electrode 8g thereof, the gate electrode 8g side (lower side in FIG. 21) of the semiconductor layer 82 of the TFT 8 is in a state where an electron density is small.

Then, it is conceived that, by the fact that holes flow through a region with a small electron density on the gate electrode 8g side of this semiconductor layer 82, the electric charge q leaks in the TFT 8 in the OFF state. Note that, in this case, in this embodiment, the reverse bias voltage is applied to the second electrode 78 (not shown in FIG. 21) of the radiation detection element 7 connected to the source electrode 8s, and accordingly, a leak current passes from the drain electrode 8d side, in which the potential is relatively high, through the gate electrode 8g-side region of the semiconductor layer 82, and flows through the source electrode 8s side in which the potential is relatively low.

Meanwhile, when the radiation image capturing apparatus 1 is irradiated with the radiation, and irradiated with the electromagnetic wave converted from the radiation in the scintillator 3 (not shown in FIG. 21), since the scintillator 3 is provided on an upper side in FIG. 21, the electron-hole pairs are generated mainly on the scintillator 3 side (upper side in FIG. 21) of the semiconductor layer 82 of the TFT 8.

Then, as mentioned above, the electron density is relatively high on the scintillator 3 side of the semiconductor layer 82, and accordingly, a probability that the generated holes are recombined with the electrons rises. Therefore, as mentioned above, the electromagnetic wave is emitted from the scintillator 3 by the radioactive irradiation, whereby the electron-hole pairs are generated in the semiconductor layer 82 of the TFT 8, and an amount of the leak current flowing through the TFT 8 in the OFF state is increased. However, a part of the holes as carriers are recombined with the electrons, and accordingly, an increased rate of the leak current is reduced.

Accordingly, if a region with a low electron density is formed also on the scintillator 3 side of the semiconductor layer 82 of the TFT 8, then the holes as the carriers come to flow through two channels, which are: the gate electrode 8g-side region of the semiconductor layer 82; and the scintillator 3-side region of the semiconductor layer 82, and it is made possible to further increase the amount of the electric charge q that leaks from the radiation detection element 7. Then, the amount of the leaked electric charge q is increased, whereby it is made possible to enhance the detection efficiency by improving the S/N ratio of the image data d.

Figure 22:
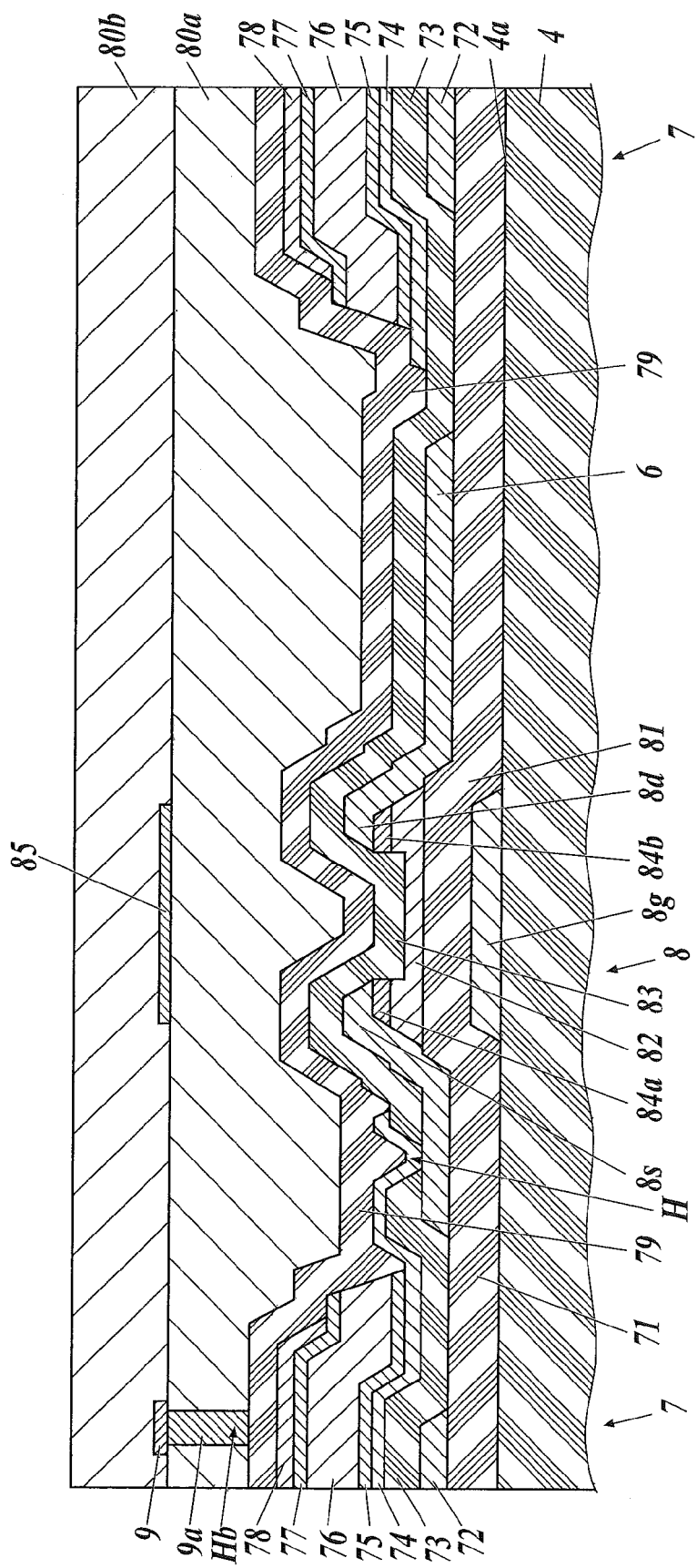
FIG. 22 is a cross-sectional view explaining wiring of the TFT arranged on the scintillator side.
Figure 23:
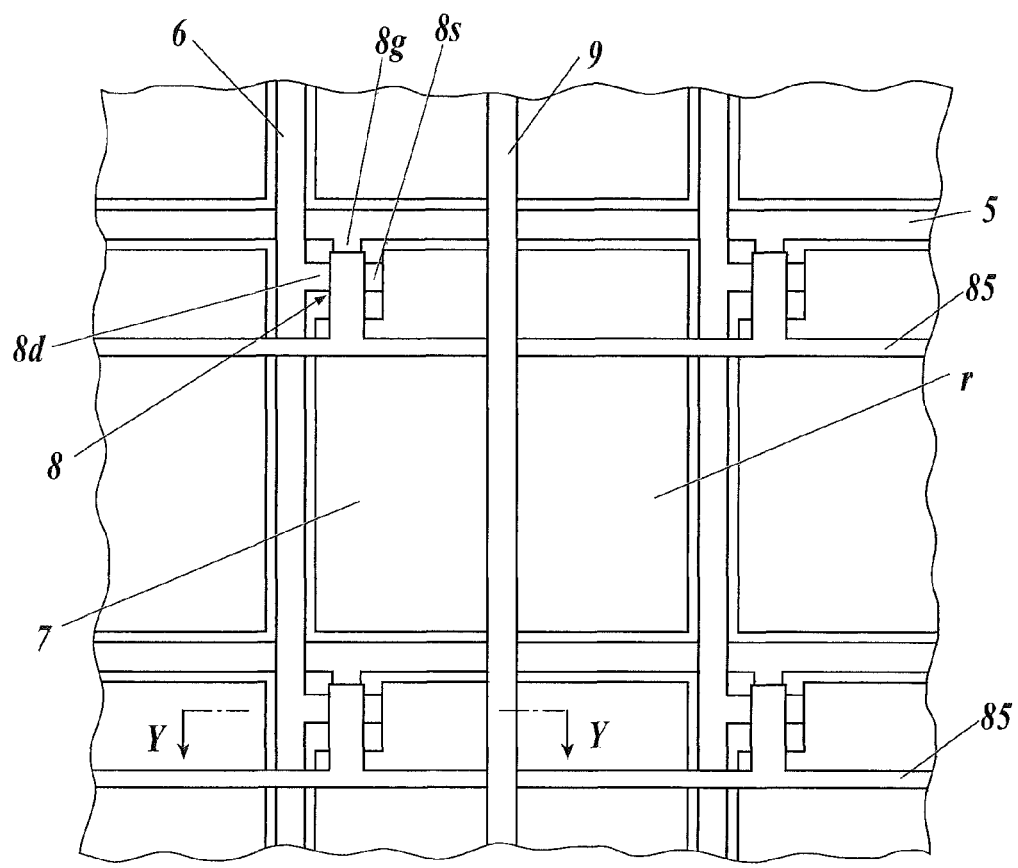
FIG. 23 is a plan view explaining the wiring of the TFT arranged on the scintillator side.

In order to form the region with a low electron density also on the scintillator 3 side of the semiconductor layer 82 of the TFT 8, it is possible to adopt a configuration as follows. For example, as shown in FIG. 22 and FIG. 23, wires 85 are arranged on the scintillator 3-side of each TFT 8. Here, the scintillator 3 is not shown in FIG. 22 and FIG. 23, and is provided above the radiation detection element 7 and the TFT 8 in FIG. 22. Moreover, a negative voltage is applied to the wires 85 in the event of the readout process to be repeatedly performed at least before the radiation image capturing operation.

Specifically, the wires 85 are formed of a conductive material such as ITO, which transmits therethrough the electromagnetic wave to be irradiated from the scintillator 3, and for example, as shown in FIG. 23, the wires 85 are provided in parallel to the respective scanning lines 5 by the same number as that of the scanning lines 5. Then, a configuration is adopted so that, in the event of the readout process to be repeatedly performed at least before the radiation image capturing operation, for example, the wires 85 can be applied with the same negative voltage as the OFF voltage to be applied from the scanning drive unit 15 to the respective scanning lines 5.

Note that it is not always necessary that the negative voltage to be applied to the respective wires 85 be a negative voltage with the same value as that of the OFF voltage, and the negative voltage concerned is set at a voltage at which the region with a low electron density can be surely formed on the scintillator 3 side of the semiconductor layer 82 of the TFT 8 as described above. Moreover, it is also possible to adopt a configuration so as to apply the OFF voltage to the respective wires 85 from the power source circuit 15a of the scanning drive unit 15, and further, it is also possible to adopt a configuration so as to apply a negative voltage from another power source circuit.

Moreover, measures to increase the amount of the electric charges q leaked from the other radiation detection elements 7 as described above are measures for using the image data d, which are to be read out in the readout process before the radiation image capturing operation, for detecting the initiation of the radioactive irradiation, and in the event of reading out the image data D as the final image in the readout process after the radiation image capturing operation, it is favorable that the component of the electric charges q, which are superimposed on the image data D to be read out and leak from the other radiation detection elements 7, be less.

Therefore, in the event of the readout process for the image data d, which is to be performed at least after the radioactive irradiation onto the radiation image capturing apparatus 1, in order that the readout of the image data D from the respective radiation detection elements 7 cannot be adversely affected, the application of the negative voltage to the respective wires 85 is stopped (that is, the wires 85 are turned to a floating state), or a predetermined voltage such as 0 [V] is applied thereto.

Moreover, in FIG. 22, illustrated is the case where each of the wires 85 and each of the bias lines 9 are formed on an upper surface (that is, the unillustrated scintillator 3-side surface) of a first planarizing layer 80a formed by being stacked above the radiation detection elements 7 and the TFTs 8, and further, a second planarizing layer 80b is formed above the first planarizing layer 80a. However, a mode of forming the wire 85 is not limited to this mode, and it is possible to arrange the wire 85 at an appropriate position as long as the wire 85 can form the region with a low electron density on the scintillator 3 side of the semiconductor layer 82 of the TFT 8.

[Configuration 7]

Moreover, in accordance with the researches of the inventors of the present invention, it is understood that, for example, in the case where the bias power source 14 is configured so as to be capable of varying a resistance value of a resistor (not shown) provided in an inside thereof, then the noise derived from the bias power source 14 is reduced when the resistance value of the resistor is varied so as to be increased.

When the resistance value of the resistor of the bias power source 14 is increased, the resistor functions like a so-called low-pass filter, and in particular, can reduce noise with a high frequency. Accordingly, for example, in the event of the readout process for the image data d before the radiation image capturing operation, it is possible to configure the bias power source 14 so as to vary the resistance value of the resistor in the bias power source 14 so that the resistance value can be increased.

Then, if the configuration is adopted as described above, it is made possible to remove noise as a high frequency component of at least the noise derived from the bias power source 14 among the noises to be superimposed on the image data d, and the S/N ratio of the image data d is improved by that amount. Therefore, it is made possible to enhance the detection efficiency by improving the S/N ratio of the image data d.

Note that, also in this case, the resistance value of the resistor in the bias power source 14 is returned to the usual resistance value that is original at least in the event of the readout process for the image data D after the radiation image capturing operation.

Note that it is also possible to adopt a configuration by appropriately combining Configuration 1 to Configuration 7, which are described above, with one another.

[Regarding Prevention of Continuous Appearance of Line Defects on Plurality of Adjacent Scanning Lines, and the Like]

As mentioned above, in the event of the readout process for the image data d before the radiation image capturing operation, a part of the electric charges (that is, the image data D to be readout as the final image) generated by the radioactive irradiation flows out from the radiation detection elements 7 subjected to the readout process while the radiation image capturing apparatus 1 is irradiated with the radiation, and then the part concerned is read out as the image data d.

Therefore, with regard to the respective radiation detection elements 7, the image data D read out in the readout process after the radiation image capturing operation is data in which a part of the data to be originally read out is already read out and lost as the image data d in the readout process before the radiation image capturing operation. Accordingly, there is a case where a configuration is adopted so as to regard the image data D as unreliable data, and to invalidate and resign the image data D concerned. In this case, the respective scanning lines 5 to which the radiation detection elements 7 concerned are connected are determined to have the line defects.

With regard to the above-described model configuration, as shown in FIG. 12, for example, though the radioactive irradiation onto the radiation image capturing apparatus is already initiated in actual at the point of time when the ON voltage is applied to the line Ln of the scanning lines 5 and the readout process is executed, since the detection efficiency is low, it is determined that it is detected that the radioactive irradiation is initiated at the point of time when the ON voltage is applied to the line Ln+2 of the scanning lines 5 and the readout process is executed.

Figure 24:
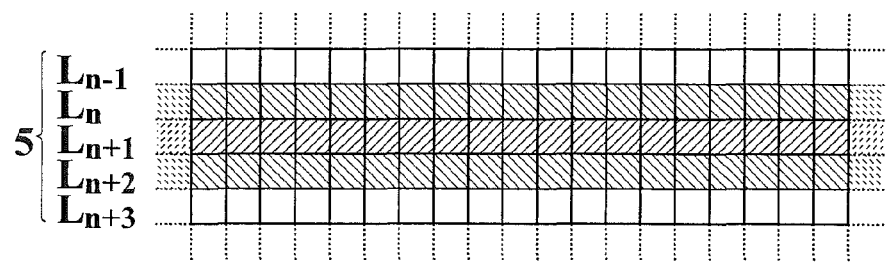
FIG. 24 is a view explaining a state in which line defects successively occur in the plurality of adjacent scanning lines.

Then, the lines Ln to Ln+2 of the scanning lines 5 come to have the line defects, and in this case, as shown in FIG. 24, the line defect comes to continuously appear on the plurality of adjacent lines Ln to Ln+2 of the scanning lines 5. Then, for these continuous line defects, for example, if the image data D concerned is restored by performing interpolation therefor by the image data D of the respective radiation detection elements 7 connected to the line Ln−1 and line Ln−1 of the scanning lines 5, then as mentioned above, it is apprehended that the information of the lesion portion of the patient, which is imaged on the portions of the respective scanning lines 5, which are determined to have the line defects, may be lost by the correction such as the interpolation.

For the above-described fact, for example, as described in [Configuration 1] described above, if the configuration is adopted so that the ON time of the TFT 8 in the event of the readout process for the image data d before the radiation image capturing operation can become longer than the ON time in the event of the readout process for the image data D after the radiation image capturing operation, then the detection efficiency in the event of detecting that the radioactive irradiation is initiated is enhanced.

Figure 25:
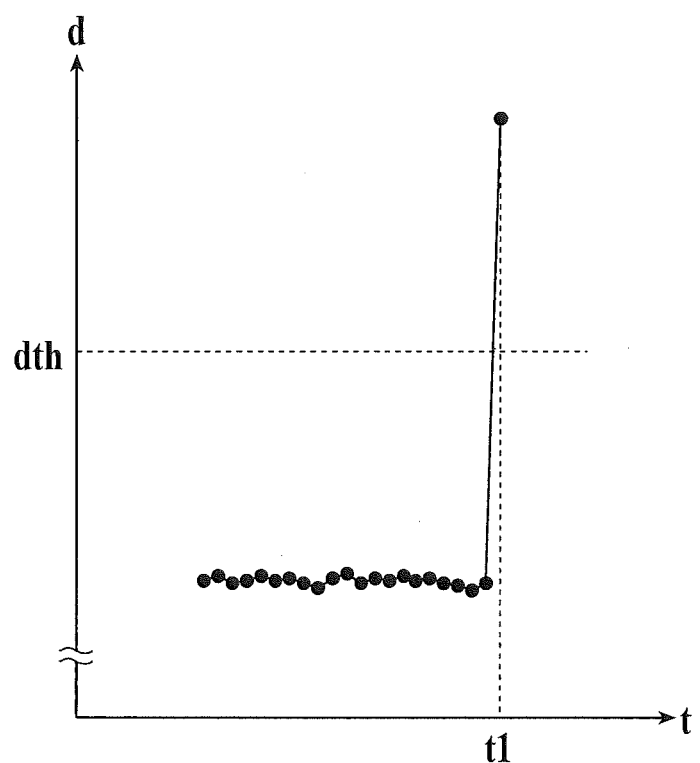
FIG. 25 is a graph in which the image data is plotted, the image data being read out in the readout process before initiating the radiation image capturing operation in a case of Configuration 1.
Figure 79:
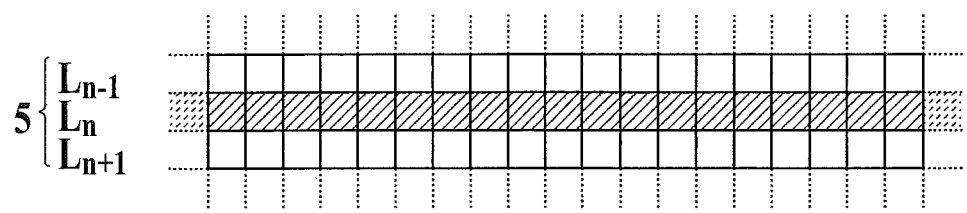
FIG. 79 is a view explaining that a line defect occurs by the image data in one scanning line being abandoned.

Therefore, as shown in FIG. 25, at the point of time t1 when the actual radioactive irradiation onto the radiation image capturing apparatus is initiated, that is, at the point of time t1 when the ON voltage is applied to the line Ln of the scanning lines 5 and the readout process is executed as shown in FIG. 13, the value of the image data d to be read out is suddenly increased, and exceeds the threshold value dth, and accordingly, it is made possible to detect that the radioactive irradiation is initiated at this point of time t1. Therefore, in this case, only the line Ln of the scanning lines 5 comes to have the line defect as shown in FIG. 79.

As described above, the detection efficiency in the event of detecting that the radioactive irradiation is initiated is enhanced, whereby the image data d read out in the readout process executed at the point of time when the actual radioactive irradiation onto the radiation image capturing apparatus is initiated comes to exceed the preset threshold value dth. Therefore, it is made possible to prevent the line defects from continuously appearing on the plurality of adjacent scanning lines 5.

Moreover, even if it cannot be detected that the radioactive irradiation is initiated at the point of time when the actual radioactive irradiation is initiated, since the detection efficiency is enhanced, it is surely detected that the radioactive irradiation is initiated based on the image data d read out in the readout process executed immediately thereafter. Therefore, it is made possible to surely reduce the number of scanning lines 5 in which the line defects occur.

Moreover, not only in the case of adopting a configuration like [Configuration 1], but also in the case of adopting configurations like [Configuration 2] to [Configuration 7] described above, and in configurations in which these configurations are combined with one another, it is made possible to prevent the line defects from continuously appearing on the plurality of adjacent scanning lines 5 in a similar way, or to surely reduce the number of scanning lines 5 in which the line defects occur in a similar way.

Moreover, also by adopting the respective configurations to be mentioned below, it is made possible to prevent the line defects from continuously appearing on the plurality of adjacent scanning lines 5, or to surely reduce the number of scanning lines 5 in which the line defects occur.

[Configuration 8]

Figure 26:
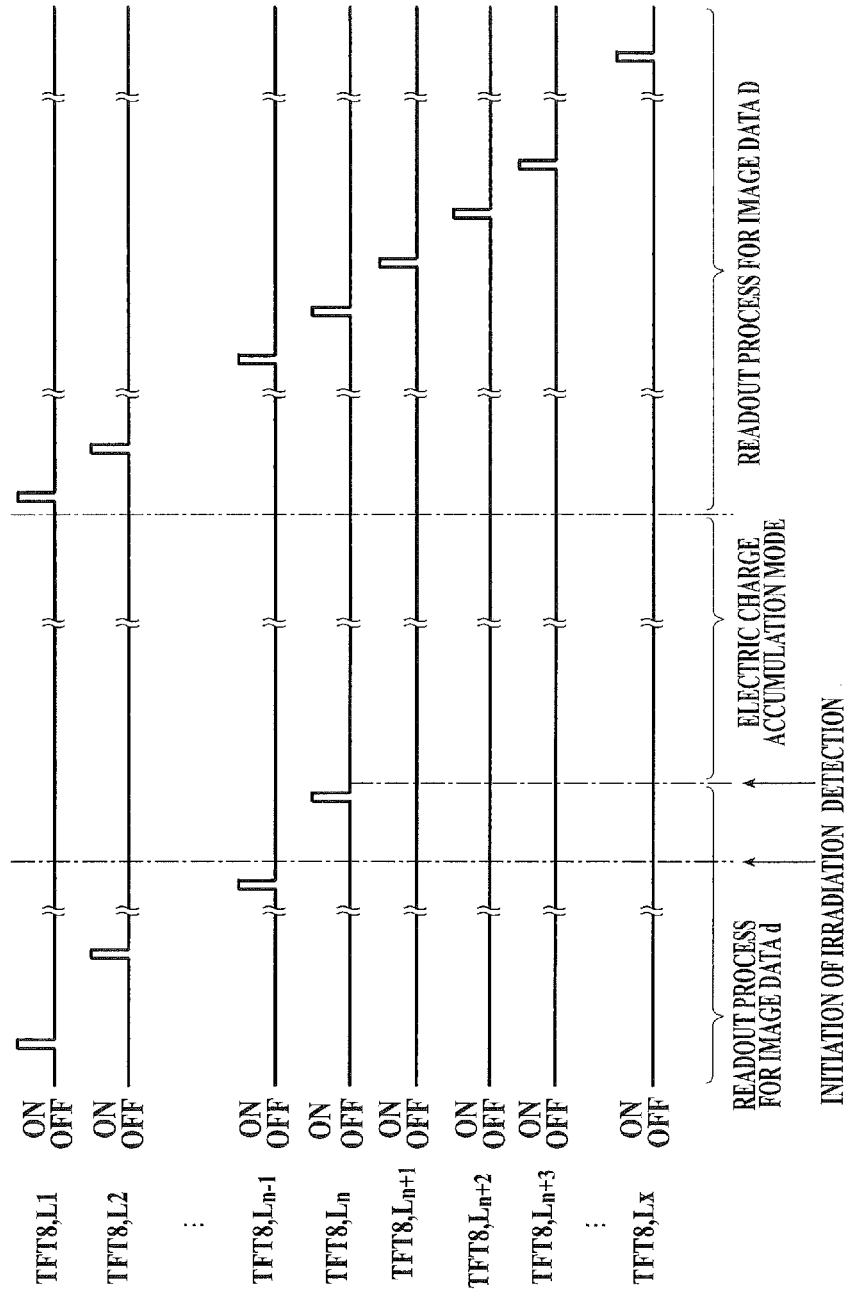
FIG. 26 is a timing chart showing application timing of the ON voltage to each scanning line in Configuration 8, in which a gate cycle is lengthened in the readout process before initiating the radiation image capturing operation.

When a description is made based on the model configuration shown in FIG. 12, though the same is also applied to [Configuration 1] to [Configuration 7], which are described above, it is possible to adopt a configuration as follows. For example, as shown in FIG. 26, in the event of the readout process for the image data d before the radiation image capturing operation, a cycle after the ON voltage is applied to a certain scanning line 5 from the scan driving 15 until the ON voltage is applied to the next scanning line 5 (hereinafter, this cycle is abbreviated as a gate cycle) is made longer then a gate cycle in the event of the readout process for the image data F after the radioactive irradiation.

If the configuration is adopted as described above, in the case where the radiation image capturing apparatus 1 is irradiated with the radiation in the readout process for the image data d before the radiation image capturing operation, then the amount of the electric charges generated and accumulated in the respective radiation detection elements 7 by the radioactive irradiation is increased, for example, more than in the case of the model configuration shown in FIG. 12.

Therefore, the value of the image data d to be read out at the point of time when the actual radioactive irradiation onto the radiation image capturing apparatus is initiated or immediately thereafter is increased, and a possibility that the value concerned may exceed the threshold value dth is enhanced. Therefore, it is made possible to prevent the line defects from continuously appearing on the plurality of adjacent scanning lines 5, or to surely reduce the number of scanning lines 5 in which the line defects occur.

Note that, in this case, the gate cycle is returned to a usual gate cycle, which is original, in the event of the readout process for the image data D at least after the radiation image capturing operation.

[Configuration 9]

In the above, the description has been made of the case of enhancing the detection efficiency of the radiation image device 1, and so on, thereby preventing the line defects from continuously appearing on the plurality of adjacent scanning lines 5, and reducing the number of scanning lines 5 in which the line defects occur. However, meanwhile, among radiation generating devices (not shown), each of which irradiates the radiation image capturing apparatus 1 with the radiation, there is a radiation generating device in which, at the time when the radioactive irradiation is initiated, rise of the dose of the radiation to be emitted is slow, and the dose of the radiation with which the radiation image capturing apparatus 1 to be irradiated is increased so-called sluggishly.

In the case of irradiating the radiation image capturing apparatus with the radiation from the radiation generating device as described above onto the radiation image capturing apparatus 1, even if the detection efficiency on the radiation image capturing apparatus 1 side is enhanced, the image data d to be read out in the readout process before the radiation image capturing operation is increased, for example, as shown in FIG. 11, and the point of time when the radioactive irradiation is actually initiated and the point of time when, in the radiation image capturing apparatus 1, it is detected that the radioactive irradiation is initiated are shifted from each other. Therefore, even if the detection efficiency on the radiation image capturing apparatus 1 is enhanced, there is a case where a state is brought where the line defects continuously appear on the plurality of adjacent scanning lines 5.

In the case as described above, for example, in the readout process for the image data d before the radiation image capturing operation, it is possible to adopt a configuration as follows. At the next timing to the timing when the ON voltage is applied to a certain line Ln of the scanning lines 5 from the gate driver 15b of the scanning drive unit 15, the ON voltage is applied to the scanning lines 5 other than the line Ln−1 and line Ln+1 of the scanning lines, which are adjacent to the line Ln of the scanning lines 5 on the detecting section P, then the ON voltage is sequentially applied to the respective lines L1 to Lx of the scanning lines 5, and the readout process for the image data d from the radiation detection elements 7 is executed.

Figure 27:
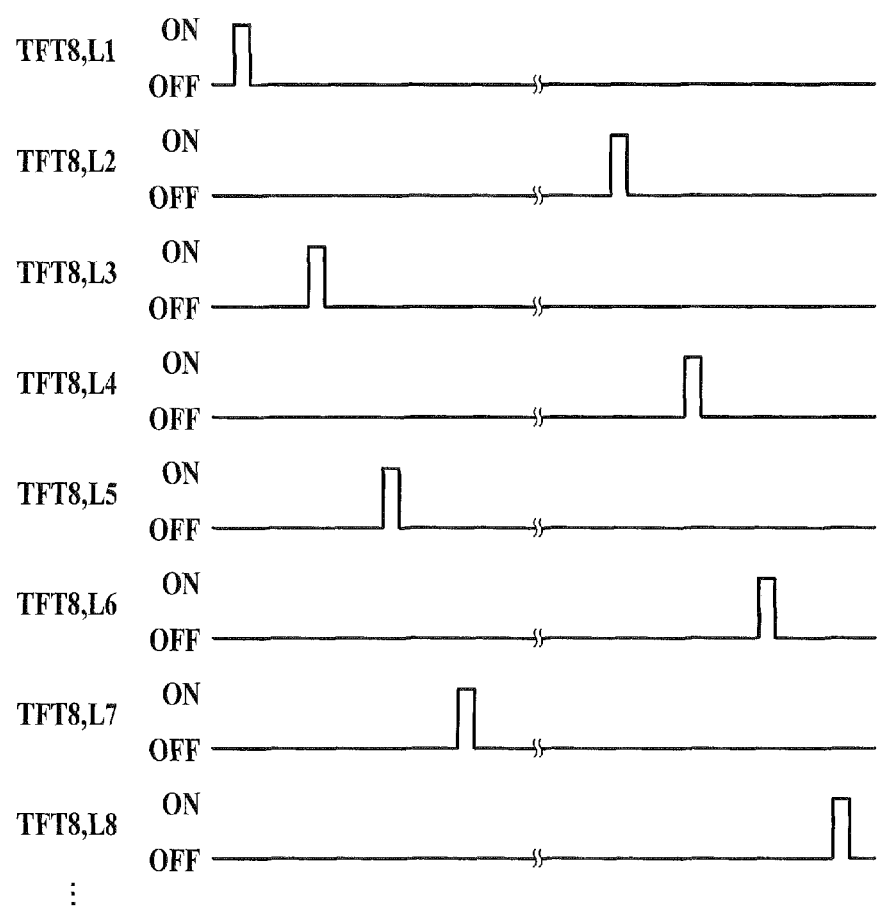
FIG. 27 is a timing chart showing application timing of the ON voltage to each scanning line in Configuration 9, in which the ON voltage is configured not to be applied successively to the adjacent scanning lines.

Specifically, for example, as shown in FIG. 27, it is possible to adopt a configuration so as to sequentially apply the ON voltage to the odd number-th lines L1, L3, L5, L7 . . . of the scanning lines 5 from the scanning drive unit 15, and thereafter, subsequently to sequentially apply the ON voltage to the even number-th lines L2, L4, L6, L8 . . . of the scanning lines 5 therefrom.

Moreover, though not shown, in the case where, for example, 128 lines of the scanning lines 5 are connected to the gate IC 12a (refer to FIG. 6), which compose the gate driver 15b of the scanning drive unit 15, for example, at the next timing to the timing when the ON voltage is applied to the line L1 of the scanning lines 5, which is connected to a first terminal of a first gate IC 12a, the ON voltage is applied to a line L129 of the scanning lines connected to a first terminal of a second gate IC 12a, and thereafter, the ON voltage is applied to lines L257, L385 . . . of the scanning lines 5, which are connected to first terminals of the respective gate ICs 12a.

Subsequently, the ON voltage is sequentially applied to the lines L2, L130 . . . of the scanning lines 5 individually connected to second terminals of the respective gate ICs 12a, and subsequently, the ON voltage is sequentially applied to the lines L3, L131 . . . of the scanning lines 5 individually connected to third terminals of the respective gate ICs 12a. With regard to this operation, it is also possible to adopt a configuration so as to sequentially apply the ON voltage to all the lines L1 to Lx of the scanning lines 5 while shifting the terminals of the respective gate ICs 12a, to which the ON voltage is to be applied, one by one, and to execute the readout process for the image data d from the respective radiation detection elements 7.

As described above, unless the configuration is adopted so as to apply the ON voltage to the line Ln−1 and line Ln+1 of the scanning lines 5, which are adjacent to a certain line Ln of the scanning lines 5, at the next timing to the timing when the ON voltage is applied to the line Ln of the scanning lines 5, it is also possible to adopt a configuration so as to sequentially apply the ON voltage to the respective lines L1 to Lx of the scanning lines 5 at any timing.

Figure 28:
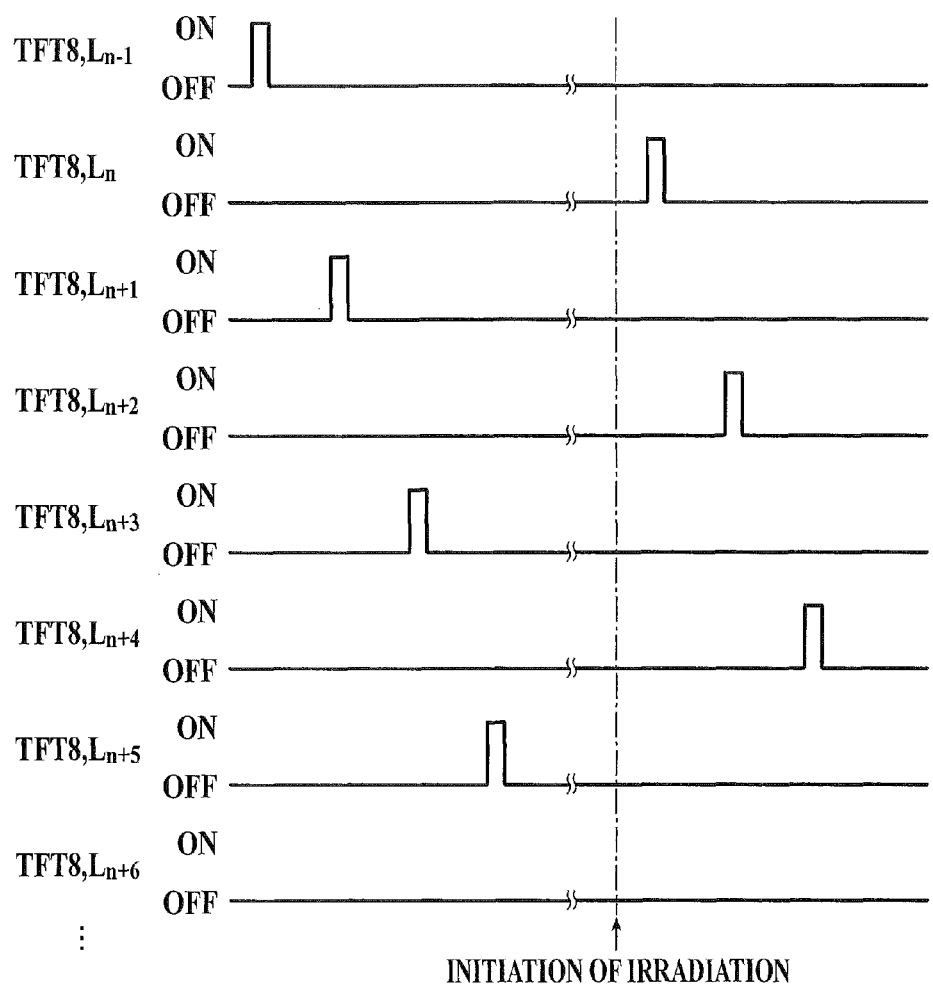
FIG. 28 is a timing chart explaining an example in a case when a time of detecting the initiation of the radioactive irradiation is shifted from the actual time of initiating the radioactive irradiation.
Figure 29:
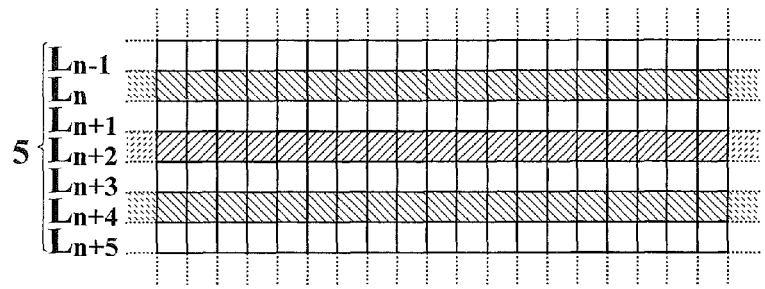
FIG. 29 is a view showing a state where the scanning lines in which the line defects occur in a manner of being separated with each other.

If the configuration is adopted as described above, even if the rise of the dose of the radiation to be emitted from the radiation generating device is slow as described above, as shown in FIG. 28, the initiation of the radioactive irradiation cannot be detected in the line Ln of the scanning lines 5, to which the ON voltage is applied at the point of time when the radioactive irradiation is actually initiated, and in the line Ln+2 of the scanning lines 5, to which the ON voltage is applied next thereto, and it is first detected that the radioactive irradiation is initiated at the point of time when the ON voltage is applied to the next line Ln+4 of the scanning lines 5, then as shown in FIG. 29, the scanning lines 5 in which the line defects occur appear as the lines Ln, Ln+2 and Ln+4 of the scanning lines 5, and the scanning lines 5 in which the line defects occur come to appear in a state of being spaced apart from one another (that is, are turned to a state of appearing in a so-called discrete manner).

Therefore, it is made possible to surely prevent the line defects from continuously appearing on the plurality of adjacent scanning lines 5.

Moreover, as shown in FIG. 28, the lines Ln−1, Ln+1, Ln+3 and Ln+5 of the scanning lines on the peripheries of the line defects applied with the ON voltage at the timing before the timing when the Lines Ln, Ln+2, Ln+4 of the scanning lines applied with the ON voltage, and the lines Ln−1, Ln+1, Ln+3 and Ln+5 are certainly applied with the OFF voltage at the time when the radioactive irradiation is initiated, and accordingly, the electric charges do not flow out from the respective radiation detection elements 7 thereof.

Therefore, from the respective radiation detection elements 7 connected to the lines Ln−1, Ln+1, Ln+3 and Ln+5 on the peripheries of the line defects, the electric charges are read out without being lost in the readout process for the image data D after the radiation image capturing operation, and accordingly, the image data D read out from these respective radiation detection elements 7 certainly have a normal value.

Therefore, it is made possible to appropriately restore, by using these image data D with the normal value, the image data D of the respective radiation detection elements 7 connected to the respective lines Ln, Ln+2 and Ln+4 of the scanning lines 5 determined to be invalided, resigned and have the line defects.

Note that, as described above, in the case of adopting the configuration so as to sequentially apply the ON voltage to each of the scanning lines 5 for each of the gate ICs 12a that composes the gate driver 15b, a state is brought where the line defects appear in a ratio of one line with respect to 128 lines of the scanning lines 5.

[Regarding Configuration for Speeding Up Detection Period of Initiation of Radioactive Irradiation, and the Like]

Figure 30:
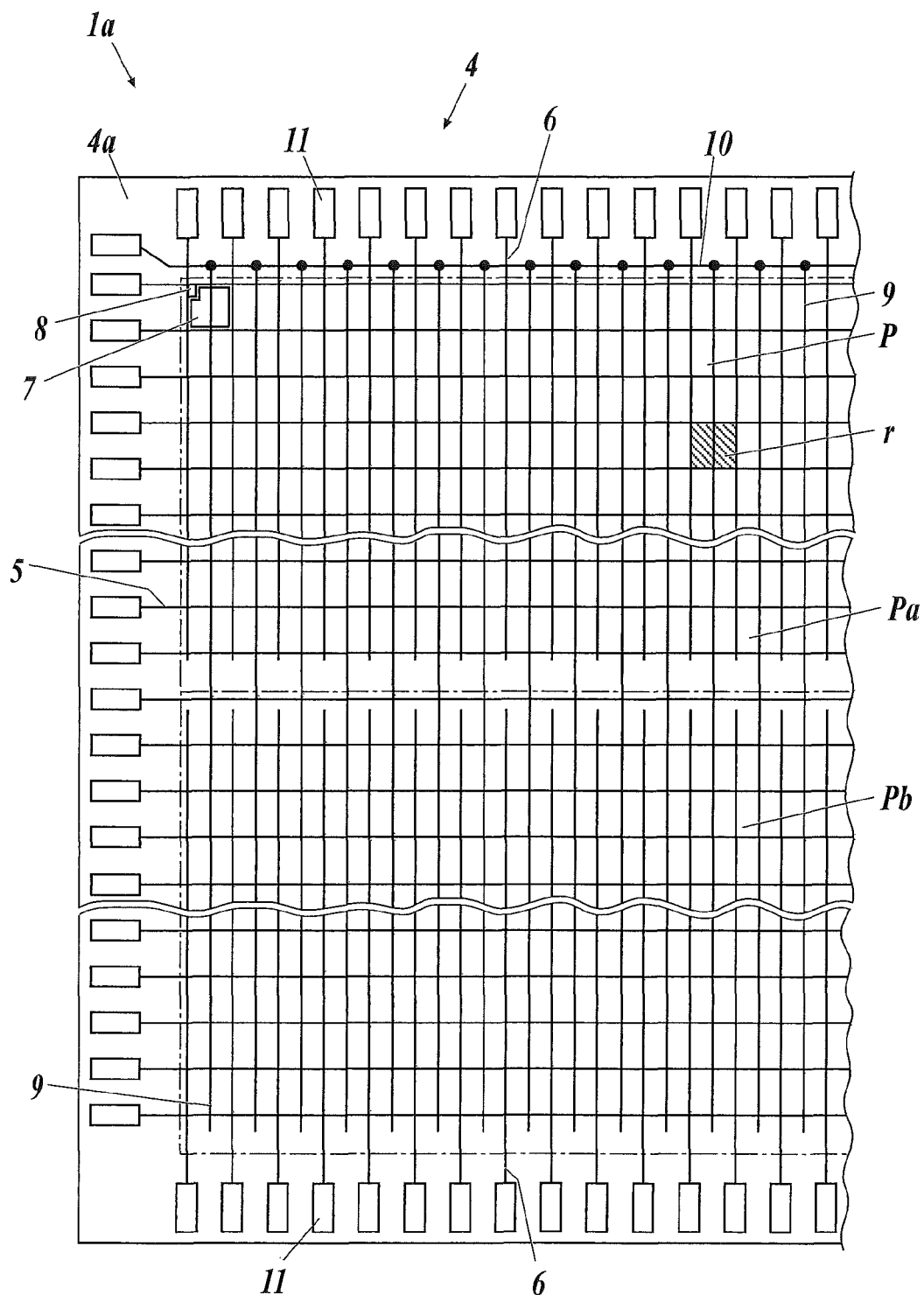
FIG. 30 is a plan view showing a configuration of the substrate of the radiation image capturing apparatus in which each signal line is decoupled halfway in an extending direction.
Figure 31:
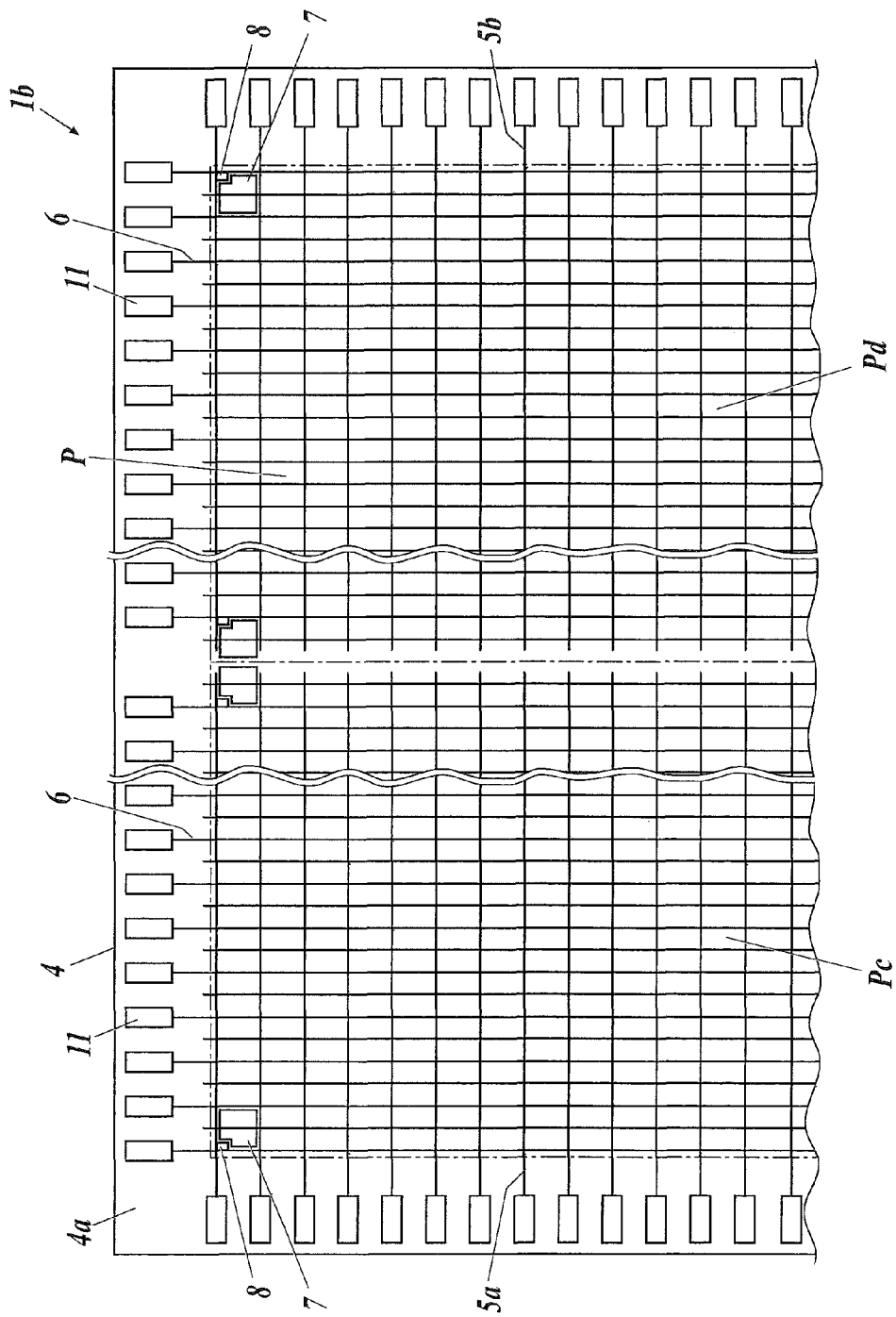
FIG. 31 is a plan view showing a configuration of the substrate of the radiation image capturing apparatus in which each scanning line is decoupled halfway in an extending direction.

Note that, among the radiation image capturing apparatus, for example, as shown in FIG. 30 and FIG. 31, there is a device in which the detecting section P is configured to be divided into a plurality of regions.

For example, in a radiation image capturing apparatus 1a shown in FIG. 30, the respective signal lines 6 are decoupled halfway in an extended direction thereof on the detecting section P, and the detecting section P is divided into two regions Pa and Pb. Moreover, for example, in a radiation image capturing apparatus 1b shown in FIG. 31, the respective scanning lines 5 are decoupled halfway in an extended direction thereof on the detecting section P, and the detecting section P is divided into two regions Pc and Pd. Note that, though not shown, it is also possible to adopt a configuration so as to decouple, for example, both of the respective scanning lines 5 and the respective signal lines halfway in the extended directions thereof on the detecting section P, and to divide the detecting section P, for example, into four regions.

A description is made below of the case of FIG. 30, which is taken as an example. In the case where the configuration is adopted as described above, the respective scanning lines 5 of the respective regions Pa and Pb are individually connected to separate gate drivers 15b through the respective input/output terminals 11, and there is a case in which a configuration is adopted so as to be capable of applying the ON voltage from the respective gate drivers 15b to the respective scanning lines 5 of the respective regions Pa and Pb at pieces of timing, which are independent of each other.

Accordingly, in the above case, it is possible to adopt a configuration as follows. In the event of the readout process for the image data d before the radiation image capturing operation, timing of applying the ON voltage from the gate driver 15b, which corresponds to one region Pa, to the respective scanning lines 5 of the region Pa concerned, is not made simultaneous with timing of applying the ON voltage from the gate driver 15b, which corresponds to the other region Pb, to the respective scanning lines 5 of the region Pb concerned, so that the ON voltage is sequentially applied to the respective scanning lines 5, whereby the readout process is executed.

Specifically, it is assumed that a configuration is adopted as follows. For example, as shown in FIG. 31, the detecting section P is divided into two regions Pa and Pb, the ON voltage is sequentially applied from the gate driver 15b, which corresponds to the region Pa, to the respective lines L of the scanning lines 5 in order of the lines L1, L2, L3 ..., and the ON voltage is sequentially applied from the gate driver 15b, which corresponds to the region Pb, to the respective lines L of the scanning lines 5 in order of the lines Lx, Lx−1, Lx−2 ..., whereby the readout process is executed.

In the above case, it is possible to adopt a configuration as follows. For example, as shown in FIG. 32, in the event of the readout process for the image data d before the radiation image capturing operation, timing of applying the ON voltage from the gate driver 15b, which corresponds to one region Pa, to the respective lines L1, L2, L3 ... of the respective scanning lines 5, is not made simultaneous with timing of applying the ON voltage from the gate driver 15b, which corresponds to the other region Pb, to the respective lines Lx, Lx−1, Lx−2 ... of the scanning lines 5, so that the ON voltage is applied to the respective scanning lines 5, whereby the readout process is executed.

In the case applying the ON voltage to the respective lines L1, L2 ..., Lx−1 and Lx of the scanning lines 5 in this order as in the case of such a model configuration as described above, for example, in the case where the initiation of the radioactive irradiation is not detected at the timing when the ON voltage is applied to the line L1 of the scanning lines 5, it cannot be determined whether or not the radioactive irradiation is initiated until the readout process to be executed by applying the ON voltage to the next line L2 of the scanning lines 5. This is similarly applied to such a case of applying the ON voltage as shown in FIG. 27.

Figure 32:
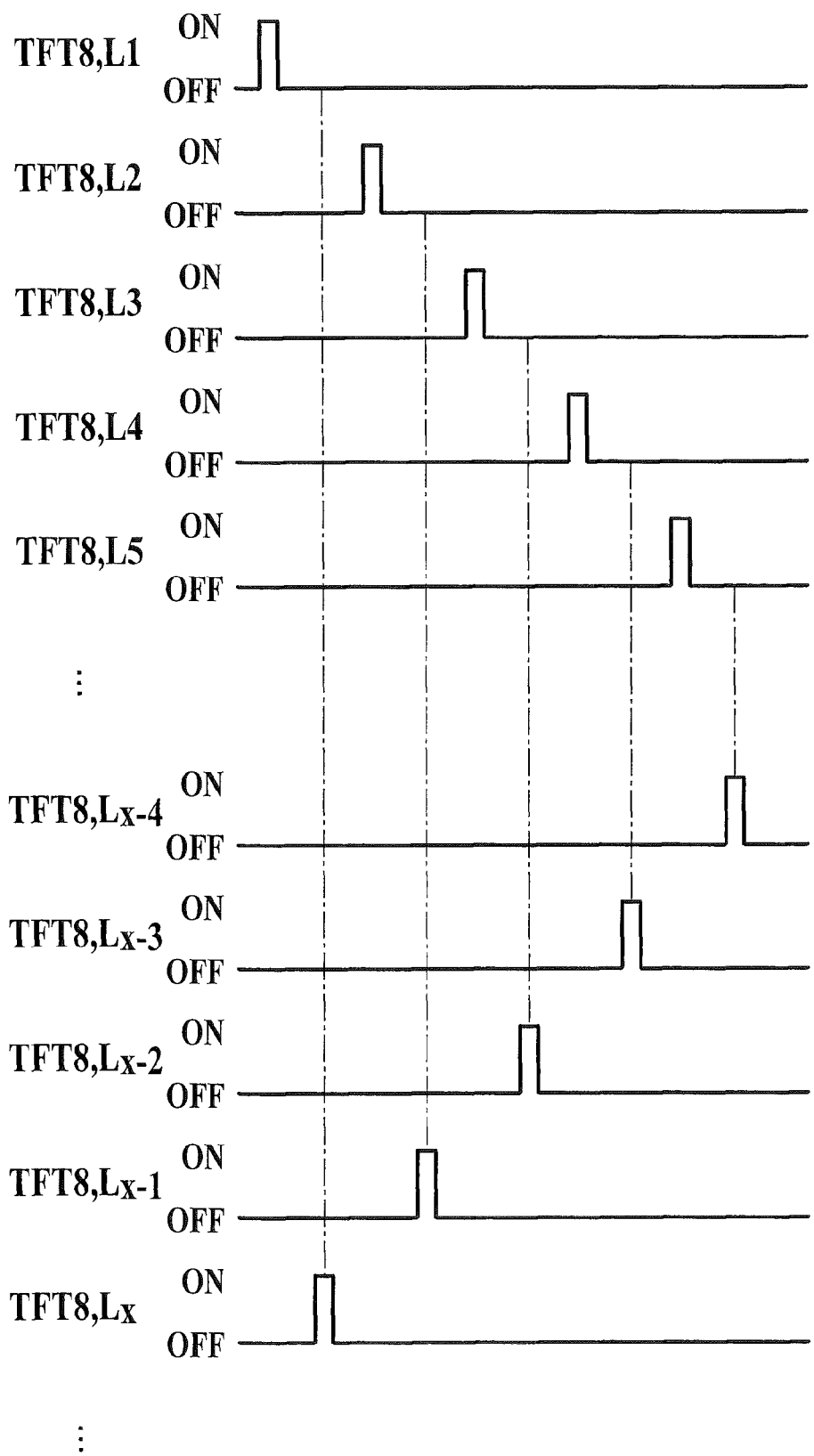
FIG. 32 is a timing chart explaining an example in a case in which a configuration is made so that in a case of FIGS. 30 and 31, one region and the other region do not have the same application timing of the ON voltage to each scanning line.

However, if a configuration is adopted as shown in FIG. 32, for example, in the case where the initiation of the radioactive irradiation is not detected at the timing when the ON voltage is applied to the line L1 of the scanning lines 5 of the region Pa, then it is made possible to determine whether or not the radioactive irradiation is initiated in the readout process, which is to be executed by applying the ON voltage to the line Lx of the scanning lines 5 of the region Pb, without waiting for the readout process to be executed by applying the ON voltage to the line L2 of the scanning lines 5 of the same region Pa.

As described above, the configuration is adopted so as to execute the readout process in the respective regions Pa and Pb of the detecting section P by sequentially applying the ON voltage to the respective scanning lines 5 so that the points of the timing of applying the ON voltage from the respective gate drivers 15b, which correspond to the respective regions Pa and Pb, to the respective scanning lines 5 of the respective regions Pa and Pb, cannot be made simultaneous with each other. In such a way, it is made possible to speedup the period of detecting that the radioactive irradiation is initiated, and when the radioactive irradiation onto the radiation image capturing apparatus 1 is initiated, it is made possible to rapidly detect the initiation concerned.

[Regarding Processes after Detecting Initiation of Radioactive Irradiation]

Next, a description is made of the respective processes after the controller 22 detects that the radioactive irradiation is initiated based on the image data d read out in the readout process to be repeatedly executed before the radiation image capturing operation, that is, by determining that the image data d exceeds the threshold value dth.

Note that a description is made below of, as a process before the radiation image capturing operation, the case of sequentially applying the ON voltage to the respective lines L1 to Lx of the scanning lines 5 as described in [Configuration 1] (refer to FIG. 13); however, needless to say, it is possible to have the above-described respective configurations and to execute the above-described respective processes.

[Shift to Electric Charge Accumulation Mode and Process in Electric Charge Accumulation Mode]

Upon detecting as described above that the radioactive irradiation is initiated, as shown in FIG. 13, the controller 22 stops such readout operations for the image data d before the radiation image capturing operation, applies the OFF voltage to the scanning drive unit 15 to all the lines L1 to Lx of the scanning lines 5, maintains a state where the respective TFTs 8 are turned to the OFF state, and shifts to the electric charge accumulation mode. As shown in FIG. 13, for example, in the case where the initiation of the radioactive irradiation is detected based on the image data d read out by applying the ON voltage to the line Ln of the scanning lines 5, the controller 22 shifts to the electric charge accumulation mode at that point of time.

Then, in the electric charge accumulation mode, for example, it is possible to adopt a configuration so that, after being held in a standby state for a predetermined time preset to be a longer time than an irradiation time of the radiation, the process can be shifted to the readout process for the image data D after the radiation image capturing operation.

Moreover, for example, a configuration is adopted as follows, whereby it is also possible to detect the end of the radioactive irradiation.

As described by using FIG. 78, from the respective radiation detection elements 7, the electric charges q are leaked little by little through the TFTs 8. Then, when the radiation image capturing apparatus 1 is irradiated with the radiation, the radiation concerned is converted into the electromagnetic wave in the scintillator 3, and the respective TFTs 8 is irradiated with this electromagnetic wave, then the electric charges q thus leaked increase. Then, when the radioactive irradiation onto the radiation image capturing apparatus 1 is ended, the leaked electric charges q turn to an original small value.

By using this, it can be detected that the radioactive irradiation onto the radiation image capturing apparatus 1 is ended.

Figure 33:
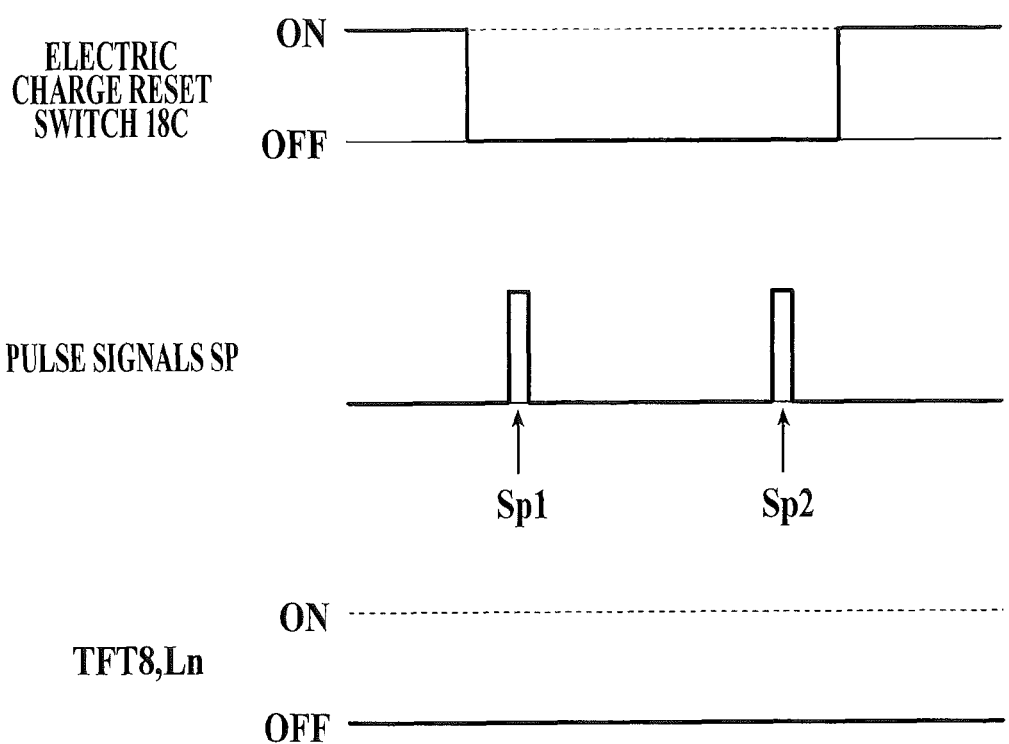
FIG. 33 is a timing chart showing ON/OFF timing of the electric charge reset switch, pulse signals, and the TFTs in the readout process for leaked data.

Specifically, in the electric charge accumulation mode, in a state where the OFF voltage is applied to all the lines L1 to Lx of the scanning lines 5, as shown in FIG. 33, the respective reading circuits 17 are operated. That is to say, in a similar way to the case of the readout process for the image data d, a state where the electric charges are accumulated in the capacitors 18b is brought by turning, to the OFF state, the electric charge reset switches 18c (refer to FIG. 8) of the amplifier circuits 18 of the reading circuits 17, and the controller 22 transmits the pulse signals Sp1 and Sp2 and causes the correlated double sampling circuits (CDSs) 19 are to perform sampling. During a period of this sampling, the ON/OFF operations for the respective TFTs 8 are not performed.

When the respective reading circuits 17 are operated as described above, then as shown in FIG. 34, the respective electric charges q leaked from the respective radiation detection elements 7 through the respective TFTs 8 turned to the OFF state are accumulated in each of the capacitors 18b of the amplifier circuits 18. Therefore, from each of the amplifier circuits 18, a voltage value equivalent to a total value of the electric charges thus accumulated, that is, of the electric charges q leaked from the respective radiation detection elements 7 is outputted, and is sampled in each of the correlated double sampling circuits (CDSs) 19 which are not shown in FIG. 34, whereby data is outputted.

Hereinafter, this data is referred as leaked data Dleak in the meaning that the data is one based on the electric charges q leaked from the respective radiation detection elements 7.

As described above, after it is detected that the radioactive irradiation is initiated in the readout process for the image data d before the radiation image capturing operation, and the voltage to be applied to all the lines L1 to Lx of the scanning lines 5 is switched to the OFF voltage, the readout operations by the respective reading circuits 17 are continued, whereby a readout process for the leaked data Dleak is executed.

Figure 35:
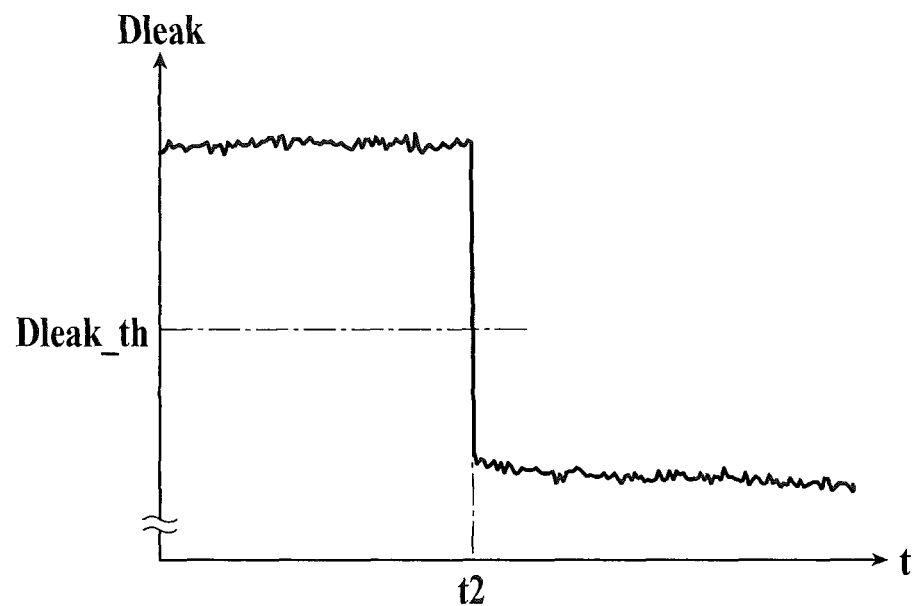
FIG. 35 is a graph showing that the leaked data reduces after finishing the radiation image capturing operation.

Then, at the point of time when the readout process for the leaked data Dleak is started, the radiation image capturing apparatus 1 is irradiated with the radiation, and the radiation image capturing apparatus 1 is in a state where the electric charges q leaked from the respective radiation detection elements 7 through the TFTs 8 increase, and accordingly, as shown in FIG. 35, a value of the leaked data Dleak to be read out is in a large state.

Then, when the readout process for the leaked data Dleak is continued, at the point of time (refer to a time t2 in FIG. 35) when the radioactive irradiation onto the radiation image capturing apparatus 1 is ended, the electric charges q leaked from the respective radiation detection elements 7 through the TFTs 8 are lowered and are returned to the original small value, and accordingly, as shown in FIG. 35, the value of the leaked data Dleak to be read out reduce.

Accordingly, for example, it is possible to configure the controller 22 so as to monitor the value of this leaked data Dleak, and to determine that the radioactive irradiation is ended at the point of time when the value of the leaked data Dleak becomes a preset threshold value Dleak_th or less.

As described above, if the radiation image capturing apparatus 1 is configured so as to detect by itself that the radioactive irradiation is ended, then it is made possible to start the readout process for the image data D immediately after the end of the radioactive irradiation is detected, and it is made possible to rapidly execute the processes on and after the readout process for the image data D.

In particular, in the radiation image capturing operation using the radiation image capturing apparatus 1, in many cases, a configuration is adopted so as to create and display a preview image before generating a diagnostic radiation image by performing a full-scale image process for the image data D by an external computer and the like, to allow a radiation engineer or the like to see the preview image, and to allow the radiation engineer to confirm whether or not the subject is imaged on the radiation image, whether or not the subject is imaged at an appropriate position on the radiation image, and so on.

In that case, it is rapidly determined whether or not re-imaging is necessary, and the re-imaging is performed if the re-imaging is necessary, whereby it is made possible to reduce the load to be applied to an examinee as the subject. As described above, it is made possible to rapidly start the readout process for the image data D after the end of the radioactive irradiation, whereby there are advantages that it is made possible to rapidly display the preview image, and that it is made possible for the radiation engineer or the like to rapidly determine whether or not the re-imaging is necessary.

Moreover, as shown in FIG. 13, if a configuration is adopted so as to stop the readout operations by the reading circuit 17 and the process is held in a standby state in a similar way to the case of the usual radiation image capturing operation in the electric charge accumulation mode after the initiation of the radioactive irradiation, then there are advantages that it becomes unnecessary to execute the readout process for the leaked data Dleak in the electric charge accumulation mode, and that it is made possible to suppress power consumption of the radiation image capturing apparatus 1. Moreover, operations in this case only involves the application of the OFF voltage to all the lines L1 to Lx of the scanning lines 5, and stopping of differential operations of the respective reading circuits 17, and accordingly, there is also an advantage that the control configuration becomes simple.

Note that, in FIG. 35, the case where, also after the end of the radioactive irradiation is detected at the time t2, the leaked data readout process is subsequently executed to read out the leaked data Dleak is shown. However, this is merely an experimental example for showing how the leaked data Dleak is changed following the radioactive irradiation, and in actual, the leaked data readout process is stopped when the end of the radioactive irradiation is detected at the time t2, and immediately, the readout process for the image data D is started.

[Regarding Readout Process for Image Data D]

At the point of time when a predetermined time elapses in the case shown in FIG. 13, or at the point of time when the end of the radioactive irradiation is detected in the case of performing the readout process for the leaked data Dleak in the electric charge accumulation mode as shown in FIG. 33 and the like, as shown in FIG. 13, subsequently, the controller 22 sequentially causes the scanning drive unit 15 to apply the ON voltage therefrom to the respective lines L1 to Lx of the scanning lines 5, causes the reading circuits 17 to sequentially perform the readout operations, and causes the reading circuits 17 to execute the readout process for the image data D, which is of reading out the image data individually from the respective radiation detection elements 7.

In the readout process for the image data d, the scanning drive unit 15, the reading circuits 17 and the like are operated as shown in FIG. 9 and FIG. 10, and the image data thus read out are sequentially stored in the storage section 40 (refer to FIG. 7 and the like).

Figure 36:
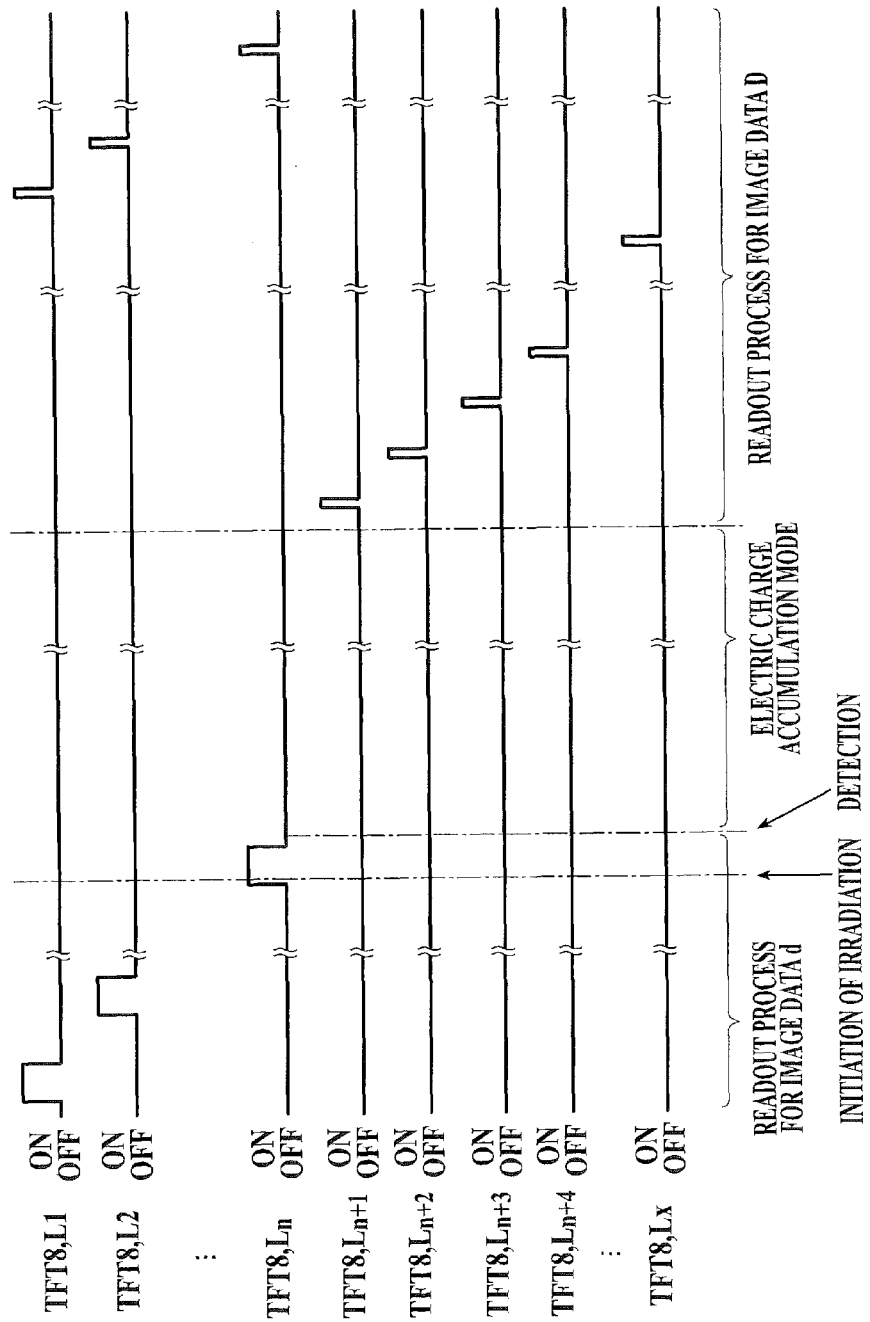
FIG. 36 is a timing chart explaining a case in Configuration 1 in which the readout process for the image data is executed after finishing the radiation image capturing operation by sequentially applying the ON voltage starting from a scanning line to which the ON voltage is to be applied after the scanning line which detected the initiation of the radioactive irradiation.

Note that, in FIG. 13, there is shown the case where, in the readout process for the image data D, the readout process is executed by sequentially applying the ON voltage to the lines of the scanning lines 5 in order from the first line L1 thereof; however, for example, as shown in FIG. 36, in the readout process for the image data D, it is also possible to adopt a configuration so as to apply the ON voltage to the lines of the scanning lines 5 sequentially from the scanning line 5 (line Ln+1 of the scanning lines 5 in the case of FIG. 36) to which the ON voltage is applied next to the scanning line 5 (line Ln of the scanning lines 5 in the case of FIG. 36) from which it is detected that the radioactive irradiation is initiated in the readout process for the image data d before the radiation image capturing operation.

If the configuration is adopted as described above, there is an advantage that it is made possible to perform the readout process for the image data d before the radiation image capturing operation and the readout process for the image data D after the radiation image capturing operation in the same process sequence. There are excellent advantages in other points, and a description is made of these points in a fourth embodiment.

As described above, in accordance with the radiation image capturing apparatus 1 according to this embodiment, the ON voltage is sequentially applied from before the radiation image capturing operation, whereby the readout process for the image data d is executed, and based on the value of the image data thus read out, it is detected that the radioactive irradiation is initiated onto the radiation image capturing apparatus 1. Therefore, it is made possible to detect the initiation of the radioactive irradiation by the radiation image capturing apparatus 1 itself.

Then, in that event, a configuration is adopted so as to control to lengthen the ON time in the event of the readout process for the image data d before the radiation image capturing operation more than the ON time in the event of the readout process for the image data D as the final image after the radiation image capturing operation, whereby it is made possible to appropriately enhance the detection efficiency in the event of detecting that the radioactive irradiation is initiated.

Then, since it is made possible to enhance the detection efficiency in the event of detecting that the radioactive irradiation is initiated as described above, it is made possible to detect that the radioactive irradiation is initiated at the point of time when the radioactive irradiation onto the radiation image capturing apparatus 1 is actually initiated, and accordingly, the line defect comes to occur only on one scanning line 5, whereby it is made possible to appropriately prevent the line defects from continuously appearing on the plurality of adjacent scanning lines 5.

Moreover, even in the case where it cannot be detected that the radioactive irradiation is initiated at the point of time when the radioactive irradiation is actually initiated, since the detection efficiency is enhanced as described above, it is accurately detected that the radioactive irradiation is initiated based on the image data d read out in the readout process executed immediately thereafter. Therefore, it is made possible to appropriately reduce the number of scanning lines 5 in which the line defects occur.

Then, the number of scanning lines 5 which come to have the line defects is restricted to one, or the number of scanning lines 5 in which the line defects occur is appropriately reduced. Accordingly, even if the image data D determined to have the line defects are restored, for example, by using the image data D on the periphery thereof, then for example, the matter that the information of the lesion portion of the patient, which is imaged on the portions of the line defects, is lost is appropriately avoided. Then, the information of the lesion portion comes to appear also in the radiation image to be created based on the above-described image data D, and accordingly, it is made possible to appropriately use the created radiation image for the medical diagnosis and the like.

[Regarding Restore Process for Image Data D]

Here, a description is made of the restore process for the image data D read out as the final image in the readout process after the radiation image capturing operation.

In that event, as described above, the radiation image capturing apparatus 1 is a device that detects that the radioactive irradiation is initiated at the point of time when the image data d read out in a manner that the ON voltage is applied to a certain line Ln of the scanning lines 5 exceeds the threshold value dth. For example, as shown in FIG. 11, even if the radioactive irradiation is actually initiated onto the radiation image capturing apparatus 1 from the external radiation generating device (not shown), and the value of the image data d to be readout rises, unless the value of the image data d exceeds the threshold value dth, the radiation image capturing apparatus 1 cannot recognize that the radioactive irradiation is actually initiated.

Therefore, it is necessary to focus on the point that the radiation image capturing apparatus 1 itself cannot detect when the radioactive irradiation is actually initiated. Then, the radiation image capturing apparatus 1 itself cannot grasp how many lines of the scanning lines 5 the ON voltage is applied to, to perform the readout process for the image data d during the period from when the radioactive irradiation is actually initiated to when it is detected that the radioactive irradiation is initiated, that is, which of the scanning lines 5 should be determined to have the line defects.

Accordingly, for example, it is possible to adopt a configuration so as to preset the number of scanning lines 5 which should be determined to have the line defects. In this embodiment, since the detection efficiency is enhanced as described above, problem does not arise in terms of practical use even if a configuration is adopted so as to preset, at one, the number of scanning lines 5 which should be determined to have the line defects, and to determine only the scanning line 5 to have the line defect, the scanning line being applied with the ON voltage at the point of time when it is detected that the radioactive irradiation is initiated.

Moreover, in the case of performing the image process more strictly, it is possible to adopt a configuration as follows.

For example, information of the rise of the dose of the radiation to be emitted from the radiation generating device that irradiates the radiation image capturing apparatus 1 with the radiation (that is, information as to how quickly the dose rises), the time span from when the ON voltage is applied to a certain line L of the scanning lines 5 in the radiation image capturing apparatus 1, that is, the above mentioned gate cycle, and the like are taken into consideration, and in response to these imaging conditions, the scanning line 5 that should be determined to have the line defect is determined.

Moreover, it is also possible to adopt a configuration as follows. For example, after the radiation image capturing operation is ended, in the event of performing the image process by an external device such as a computer for the image process (alternatively, by the radiation image capturing apparatus 1 in the case of performing the image process by the radiation image capturing apparatus 1), and creating the radiation image based on the obtained image data d and the like, it is determined how many lines of the scanning lines 5 including the line Ln of the scanning lines 5, from which the radiation image capturing apparatus 1 detects the initiation of the radioactive irradiation, should be determined to have the line defects.

In this event, it is also possible to adopt a configuration as follows. For example, in the readout process for the image data d before the radiation image capturing operation, a transition (for example, refer to FIG. 11, FIG. 25 and the like) of the value of the image data d sequentially readout from the respective radiation detection elements 7 connected to the respective lines L1 to Lx of the scanning lines is analyzed, and the point of time when the radioactive irradiation is actually initiated from the radiation generating device is determined, whereby the scanning lines 5 which should be determined to have the line defects are determined.

Specifically, as mentioned above, when the radioactive irradiation onto the radiation image capturing apparatus 1 is initiated, the value of the image data d to be read out is increased, and accordingly, when the image data d that makes a transition, for example, as shown in FIG. 11 is analyzed, three scanning lines 5, which include the scanning line 5 from which the start of the radioactive irradiation is detected at the time t1, are determined to have the line defects. Moreover, when the image data d that makes a transition as shown in FIG. 25 is analyzed, only the scanning line 5 from which the initiation of the radioactive irradiation is detected at the time t1 is determined to have the line defect.

Moreover, it is also possible to adopt a configuration as follows. In place of analyzing the image data d readout in the readout process before the radiation image capturing operation as described above, or alternatively, in combination therewith, the image data D as the final image read out in the readout process after the radiation image capturing operation is analyzed, and the number of scanning lines 5 which should be determined to have the line defects is determined.

Figure 37:
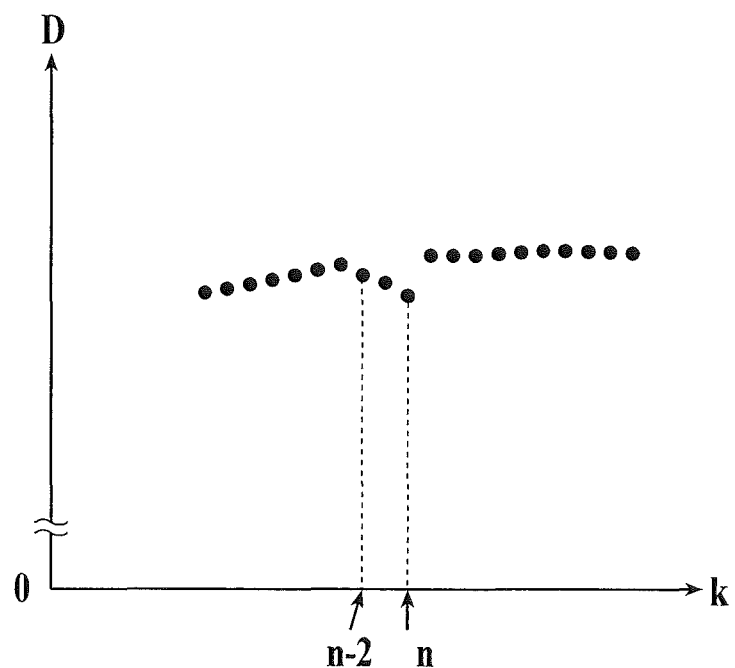
FIG. 37 is a graph in which the image data is plotted for each scanning line, the image data being read out in the readout process after finishing the radiation image capturing operation.

For example, in the case where the image data D in the case of plotting the image data D read out in the readout process after the radiation image capturing operation (correctly speaking, the image data D has a value obtained by subtracting an offset correction value O to be described later from the image data D) for each of the lines L1 to Lx of the scanning lines makes a transition, for example, as shown in FIG. 37, when the transition of the value of this image data D is analyzed, it is understood that the respective lines Ln−2 to Ln of the scanning lines 5 should be determined to have the line defects.

As described above, first, the scanning lines 5 which should be determined to have the line defects are determined, for example, in a manner that the scanning lines 5 concerned are restricted only to the scanning line 5 applied with the ON voltage at the point of time when it is detected that the radioactive irradiation is initiated, that the scanning lines 5 concerned are determined in response to the imaging conditions, or that the image data d and the image data D are analyzed.

Next, the restore process is executed for the image data D read out from the respective radiation detection elements 7 connected to the scanning lines 5, which are determined to have the line defects and are determined as described above. In that event, as mentioned above, it is possible to adopt a configuration so as to regard the image data D in such a line defect portion as data with low reliability, and to invalidate and abandon the image data D concerned.

In this embodiment, as mentioned above, the line defects come to occur in one or two scanning lines 5, and appear in a state as shown in FIG. 79 or FIG. 80. Moreover, in the case where the ON voltage is applied to the respective scanning lines 5, for example, as shown in FIG. 27 and the like in the readout process for the image data d before the radiation image capturing operation, a state where the line defects appear in a so-called discrete manner is brought as shown in FIG. 29.

Accordingly, in the case of adopting the configuration as described above so as to abandon the image data D in the line defect portion, for example, a configuration can be adopted so as to restore the abandoned image data D by a method such as linear interpolation by using the image data on the periphery thereof.

That is to say, the abandoned image data D is restored by individually using the image data D of the respective radiation detection elements 7 connected to the lines Ln−1 and Ln+1 of the scanning lines 5, for example, in the case of FIG. 79, and connected to the lines Ln−1 and Ln+2 of the scanning lines 5, for example, in the case of FIG. 80. Moreover, with regard to the line defects of the scanning lines 5 in the case of FIG. 29, a configuration can be adopted so as to restore the line defect of the line Ln of the scanning lines 5, for example, by using the lines Ln−1 and Ln+1 of the scanning lines 5, to restore the line defect of the line Ln+2 of the scanning lines 5, for example, by using the lines Ln+1 and Ln+3 of the scanning lines 5, and to restore the line defect of the line Ln+4 of the scanning lines 5, for example, by using the lines Ln+3 and Ln+5 of the scanning lines 5.

Meanwhile, in this embodiment, the image data d is read out in the readout process before the radiation image capturing operation as described above, and accordingly, it is also possible to adopt a configuration so as to restore the image data D as the final image by using this image data d. Note that, in this case, the image data D read out from the respective radiation detection elements 7 connected to the scanning lines 5 determined to have the line defects are not abandoned.

Then, with regard to these respective radiation detection elements 7, it can be regarded that a part of the image data D to be read out as the final image in the readout process after the radiation image capturing operation is read out as the image data d before the radiation image capturing operation. Therefore, as a method of restoring the image data D, it is conceived to restore the image data D by simply adding the image data D and the image data d to each other.

Note that, in this case, the amounts of offsets caused by the dark electric charges are individually superimposed on both of the image data D and the image data d, and accordingly, both of the image data D and image data d are added to each other while subtracting values of the amounts concerned therefrom. The amount of offset to be superimposed on the image data D is also referred to as the offset correction value O, and is described in detail in a second embodiment to be described later.

Then, if data, which is contained in the image data D, and is caused only by the electric charges generated in the respective radiation detection elements 7 by the radioactive irradiation, that is, data that does not contain an amount of the dark electric charges is referred to as true image data D*, then the true image data D* is calculated by performing the following arithmetic operation (1) for each of the radiation detection elements 7:

$$D^* = D - O \quad (1)$$

Moreover, it is difficult to use the above-described offset correction value O as each of the amounts of offsets superimposed on the image data d; however, as described above, among the image data d to be readout in the readout process repeatedly executed before the radiation image capturing operation, the image data d read out before the radioactive irradiation is initiated does not contain the amount of electric charges generated by the radioactive irradiation, and is data caused only by the dark electric charges, and accordingly, can be used as the amount of offsets for the image data d.

If this is referred to as an offset correction value o for the image data d, then true image data d* as data, which is contained in the image data d read out in the readout process before the radiation image capturing operation during the period from when the radioactive irradiation is initiated to when the initiation of the radioactive irradiation is detected, and is caused only by the electric charges generated in the respective radiation detection elements 7 by the radioactive irradiation, that is, data that does not contain the amount of dark electric charges, is calculated by performing the following arithmetic operation (2) for each of the radiation detection elements 7:

$$d^* = d - o \quad (2)$$

Note that it is also possible to adopt a configuration so as to prepare the offset correction value o for the image data d in advance by an experiment and the like.

Then, with regard to the respective radiation detection elements 7 connected to the scanning lines 5 determined to have the line defects, the true image data D* and the true image data d*, which are described above, are added to each other, whereby it is made possible to restore the true image data D* which should be originally read out from the respective radiation detection elements 7 concerned.

However, as described by using FIG. 78 mentioned above, in the image data d read out during the period from when the radioactive irradiation is initiated to when the initiation of the radioactive irradiation is detected, there is also contained an increment of the electric charges q leaked by the radioactive irradiation from other radiation detection elements 7 connected to the signal line 6 to which each of the radiation detection elements 7 is connected, as well as the above-described data caused only by the electric charges generated in each of the radiation detection elements 7 concerned by the radioactive irradiation, and the above-described data cause by the dark electric charges.

Therefore, if the true image data d* is calculated by subtracting the offset correction value o from the image data d in accordance with the above-described Expression (2), the true image data d* does not directly become a value of a part of the above-mentioned true image data D*, and becomes a value added with the above-described increment of the electric charges q leaked from the other radiation detection elements 7, the increment being caused by the radioactive irradiation.

As described above, the configuration of simply adding the true image data D* and the true image data d* to each other is a configuration that ignores the above-described increment of the electric charges q leaked from the other radiation detection elements 7, the increment being caused by the radioactive irradiation. However, originally in this embodiment, the number of line defects which occur can be suppressed to an extremely small number, and accordingly, also by this method, the true image data D* can be restored relatively favorably.

Moreover, it is also possible to adopt a configuration so as to correct and add the increment of these electric charges q leaked from the other radiation detection elements 7, the increment being caused by the radioactive irradiation. In this case, for example, it is possible to adopt a configuration so as to preset a coefficient to be multiplied to the true image data d* calculated in accordance with the above-described Expression (2), and to add the true image data d*, which is multiplied by this coefficient, to the true image data D*.

Then, in this case, it is possible to set the above-described coefficient, for example, at the one in which a value is changed in response to a dose per unit time of the radioactive irradiation onto the radiation image capturing apparatus 1, that is, a dose rate and the like. Moreover, it is also possible to set the coefficient at a constant value, and the coefficient is set as appropriate. If the configuration is adopted as described above, it is made possible to eliminate the influence of the phenomenon that occurs during the period while the above-described radioactive irradiation, and to appropriately restore the true image data D* of the respective radiation detection elements 7.

Second Embodiment

In the above-described first embodiment, the description has been made of the respective processes included in the readout process for the image data d before the radiation image capturing operation, the shift to the electric charge accumulation mode after the initiation of the radioactive irradiation is detected, and the readout process for the image data D after the radiation image capturing operation.

In a second embodiment, a description is made of a process for obtaining the offset correction value O, which is to be executed after the readout process for the image data D after the radiation image capturing operation.

The offset correction value O is also referred to as a dark reading value. The offset correction value O is equivalent to data, in which the dark electric charges generated by thermal excitation and the like by heat (temperature) of the radiation detection elements 7 themselves separately from the electric charges generated and accumulated in the respective radiation detection elements 7 by the radioactive irradiation, and the like are accumulated in the respective radiation detection elements 7 during the period while the process mode is being shifted to the electric charge accumulation mode and the respective TFTs 8 are being turned to the OFF state. The offset correction value O is equivalent to the amount of offset of the image data D.

The value of the offset correction value O, that is, to which extent the amount of offset is contained in the image data D cannot be understood only by seeing the value of the image data D. Accordingly, separately, the process for obtaining the offset correction value O becomes necessary. Therefore, in usual, before or after the radiation image capturing operation, the radiation image capturing apparatus 1 is left standing in a state where the respective TFTs 8 are turned to the OFF state without irradiating the radiation image capturing apparatus 1 with the radiation, and thereafter, the accumulated dark electric charges and the like are read out from the respective radiation detection elements 7 in a similar way to the readout process for the image data D, whereby the offset correction value O is obtained for each of the radiation detection elements 7.

Then, in a creation process for the radiation image, which is to be executed by the external computer and the like, the offset correction value O is subtracted individually from each piece of the image data D as shown in the above-described Expression (1), then the true image data D* derived only from the electric charges generated by the radioactive irradiation is calculated, and the radiation image is created based on this true image data D*.

Hence, if this offset correction value O cannot be accurately obtained, then the true image data D* to be obtained by subtracting the offset correction value O from each piece of the image data D does not have a normal value, and the radiation image to be created based on the offset correction value O becomes an abnormal one, or image quality thereof is deteriorated.

Accordingly, in this embodiment, a description is made of a process for surely obtaining the offset correction value O in the radiation image capturing apparatus 1.

Note that, in this embodiment, a description is made of the case of obtaining the offset correction value O after the radiation image capturing operation. Moreover, as described above, the process for reading out the offset correction value O from each of the radiation detection elements 7 is executed in a similar way to the readout process for the image data D, which is shown in FIG. 9 and FIG. 10, and hereinafter, is referred to as an offset correction value readout process as distinguished therefrom.

Here, a description is made of things serving as premises in the event of obtaining the offset correction value O.

[Premise 1]

As described above, the offset correction value O is equivalent to the electric charges (dark electric charges) generated and accumulated in the radiation detection elements 7 during the period while the respective TFTs 8 are being turned to the OFF state. More accurately speaking, in this embodiment or the first embodiment, the offset correction value is equivalent to the electric charges generated and accumulated in the radiation detection elements 7 during the period after switching, to the OFF voltage, the ON voltage applied to a certain line Ln of the scanning lines 5 in the event of the readout process for the image data d before the radiation image capturing operation until switching, to the OFF voltage, the ON voltage applied to the line Ln concerned of the scanning lines 5 in the readout process for the image data D after the radiation image capturing operation.

Note that, as described above, a time span after switching, to the OFF voltage, the ON voltage applied to a certain line Ln of the scanning lines 5 in the event of the readout process for the image data d before the radiation image capturing operation until switching, to the OFF voltage, the ON voltage applied to the line Ln concerned of the scanning lines 5 in the readout process for the image data D after the radiation image capturing operation is hereinafter referred to as an effective accumulation time.

[Premise 2]

Depending on the process sequence in the readout process for the image data d before the radiation image capturing operation, and on the process sequence in the readout process for the image data D after the radiation image capturing operation, this effective accumulation time sometimes becomes the same time spans among the respective lines L1 to Lx of the scanning lines 5, and sometimes become different time spans thereamong.

Specifically, for example, as in the case of the model configuration shown in FIG. 12, when, in the readout process for the image data d before the radiation image capturing operation, the ON voltage is applied to the respective lines L1 to Lx at the same ON time in the same gate cycle as those in the case of the readout process for the image data D after the radiation image capturing operation, then the effective accumulate time becomes the same at least among the lines L1 to Ln+2 of the scanning lines 5, and becomes an effective accumulation time with another length in the respective lines Ln+3 to Lx; however, among the respective lines Ln+3 to Lx of the scanning lines 5, the effective accumulation time becomes the same.

Meanwhile, for example, as shown in FIG. 13, in the case of setting the longer ON time in the readout process for the image data d before the radiation image capturing operation than in the case of the readout process for the image data D after the radiation image capturing operation, or alternatively, as shown in FIG. 26, in the case of setting the longer gate cycle in the readout process for the image data d before the radiation image capturing operation than in the case of the readout process for the image data D after the radiation image capturing operation, the effective accumulation time in each of the lines L1 to Lx of the scanning lines becomes a different time span from others.

Figure 38:
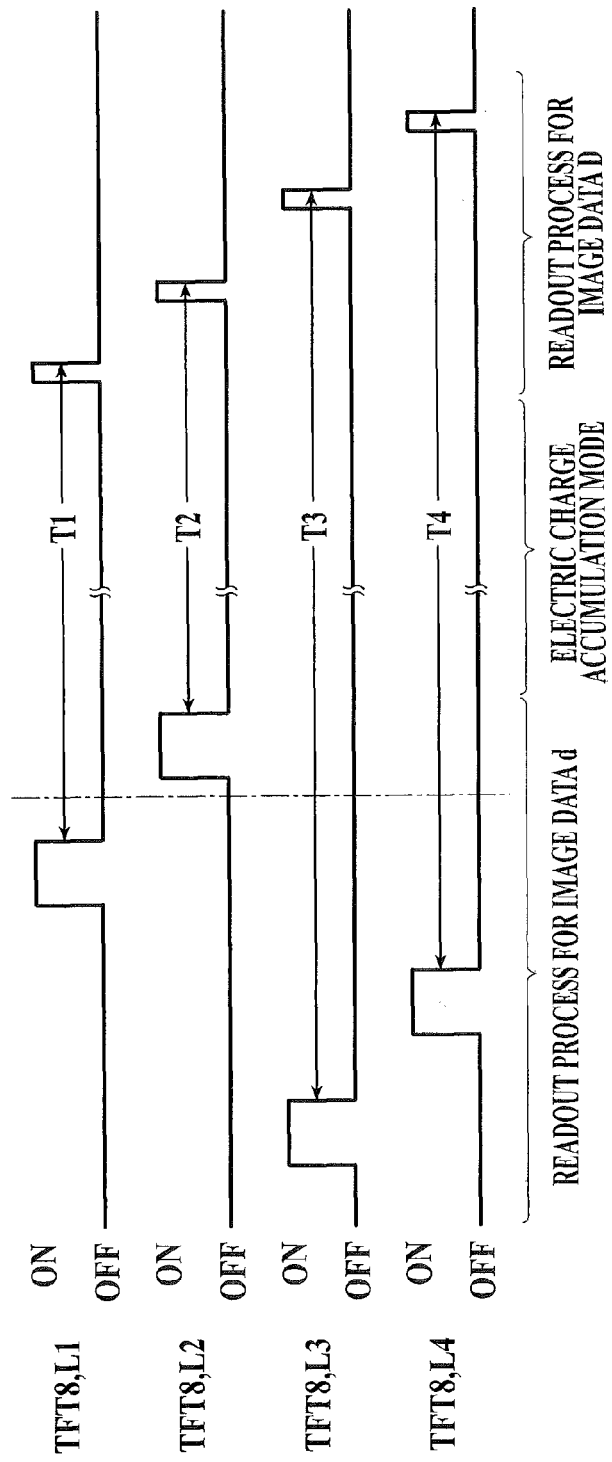
FIG. 38 is a timing chart, which is a simplified view of a case in FIG. 13, showing that an effective accumulation time becomes different in time span for each scanning line.

Specifically, for example, in the case of FIG. 13, as shown in FIG. 38 drawn by simplifying FIG. 13, time spans of the effective accumulation time T1 to T4 of the TFTs 8 in the respective lines L1 to L4 of the scanning lines 5 become different among the respective scanning lines 5.

Figure 39:
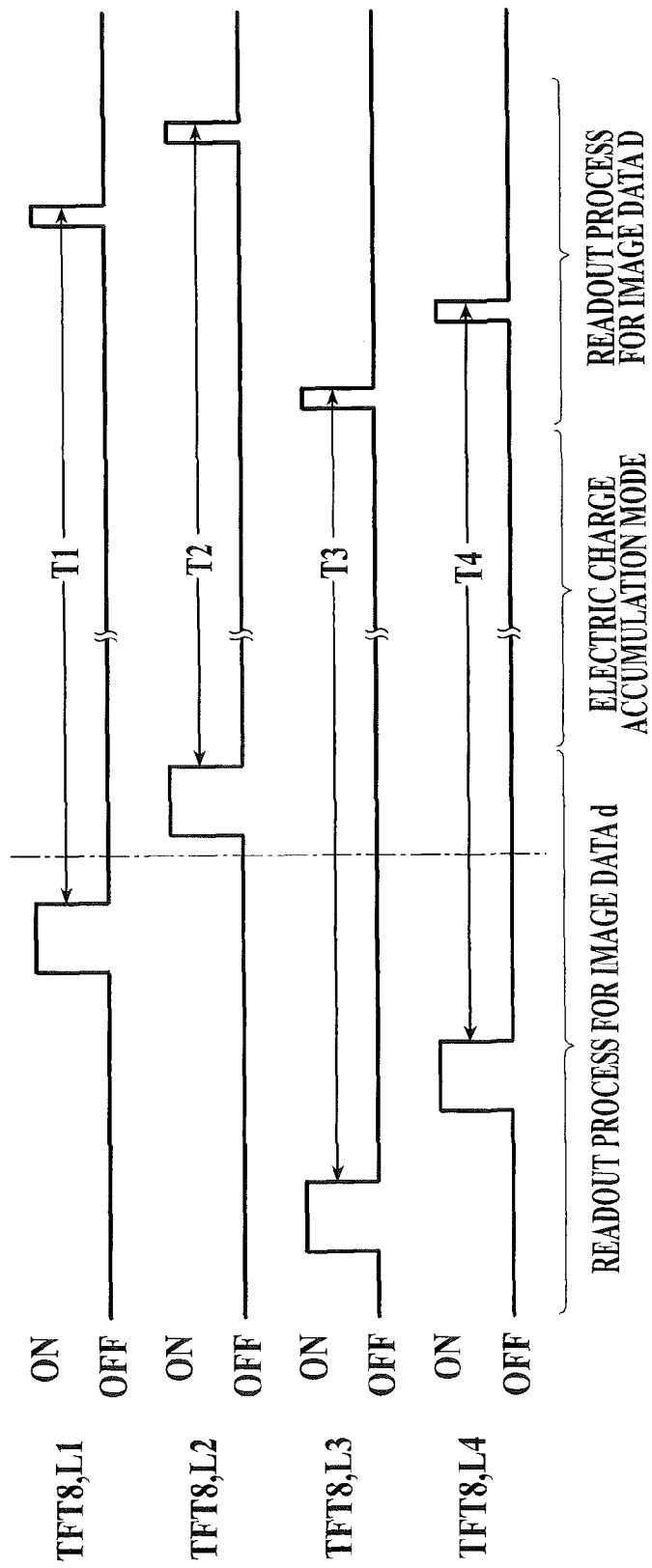
FIG. 39 is a timing chart, which is a simplified view of a case in FIG. 36, showing that an effective accumulation time becomes different in time span for each scanning line.

Moreover, even in the case of FIG. 36 showing the case of changing the readout order in the image data D after the radiation image capturing operation in FIG. 13, as shown in FIG. 39 drawn by simplifying FIG. 36, the spans of the effective accumulation time T1 to T4 of the TFTs 8 in the respective lines L1 to L4 of the scanning lines 5 become different among the respective scanning lines 5.

[Premise 3]

In the experiment conducted by the inventors of the present invention, it is understood that the offset correction value O is not always increased linearly (that is, proportionally) with respect to the effective accumulation time of the TFT 8. This is conceived to be because, in the case where the radiation image capturing apparatus 1 is left standing in a state of not being irradiated with the radiation as described above, a generation speed of the dark electric charges to be generated in each of the radiation detection elements 7 is nonlinear with respect to the time change. Note that such offset correction values O become the same value if the pieces of the effective accumulation time of the TFTs 8 are the same.

While taking the above respective things as premises, it is possible to configure the process for obtaining the offset correction values O as in the following respective configuration examples.

[Process for Obtaining Offset Correction Value O]

[Configuration A]

As mentioned in Premise 3 described above, each of the offset correction values O is not increased in a form of being proportional to the effective accumulation time of the TFT 8; however, the offset correction values O becomes the same value if the effective accumulation time of the TFT 8 is the same. Accordingly, for example, in the manner as below, a configuration can be adopted so that the time spans of the effective accumulation time of the TFTs 8 for each of the lines L of the scanning lines 5 can become the same effective accumulation time between the readout process for the image data D and the offset correction value readout process.

Note that a description is made below of the case of sequentially applying the ON voltage to the respective lines L1 to L4 of the scanning lines 5 as shown in FIG. 39, thereby performing the readout process for the image data d before the radiation image capturing operation and the readout process for the image data D after the radiation image capturing operation; however, a similar description is also made of the case of another configuration.

Moreover, a description is made below of the case where the scanning lines 5 are composed of the respective lines L1 to L4; however, needless to say, the following description can be generalized for the case as shown in FIG. 7 and the like, where the respective lines L1 to Lx of the scanning lines 5 are provided by thousands to tens of thousands on the detecting section P.

For example, it is possible to adopt a configuration as follows. As shown in FIG. 39, executed are: the readout process for the image data d before the radiation image capturing operation; the shift to the electric charge accumulation mode; and the readout process for the image data D after the radiation image capturing operation. Thereafter, as shown in FIG. 40, voltages to be applied to the respective lines L1 to L4 of the scanning lines 5 from the scanning drive unit 15 are switched between the ON voltage and the OFF voltage at the same timing as those of these respective processes, and the reading circuit 17 is allowed to sequentially perform the readout operation, whereby executed are: the readout process for the image data d; the shift to the electric charge accumulation mode (however, the radiation is not irradiated); and the offset correction value readout process.

That is to say, briefly speaking, the same process sequence as the process sequence until reading out the image data D (that is, the readout process for the image data d, the shift to the electric charge accumulation mode, and the readout process for the image data d) is repeated after the readout process for the image data D, and the offset correction value O is read out.

However, in this case, in the readout process for the image data d after the readout process for the image data D, it is not necessary to detect the initiation of the radioactive irradiation onto the radiation image capturing apparatus 1, and the like, and accordingly, the controller 22 does not perform the monitoring for the image data d, which is as described in the first embodiment. Moreover, a configuration may be adopted so as to perform a reset process for the respective radiation detection elements 7 in place of the readout process for the image data d after the readout process for the image data D. Then, in the case of adopting the configuration so as to perform the reset process for the respective radiation detection elements 7, the above-described ON time and gate cycle are set at the same time and cycle as those in the case of the readout process for the image data d.

Figure 40:
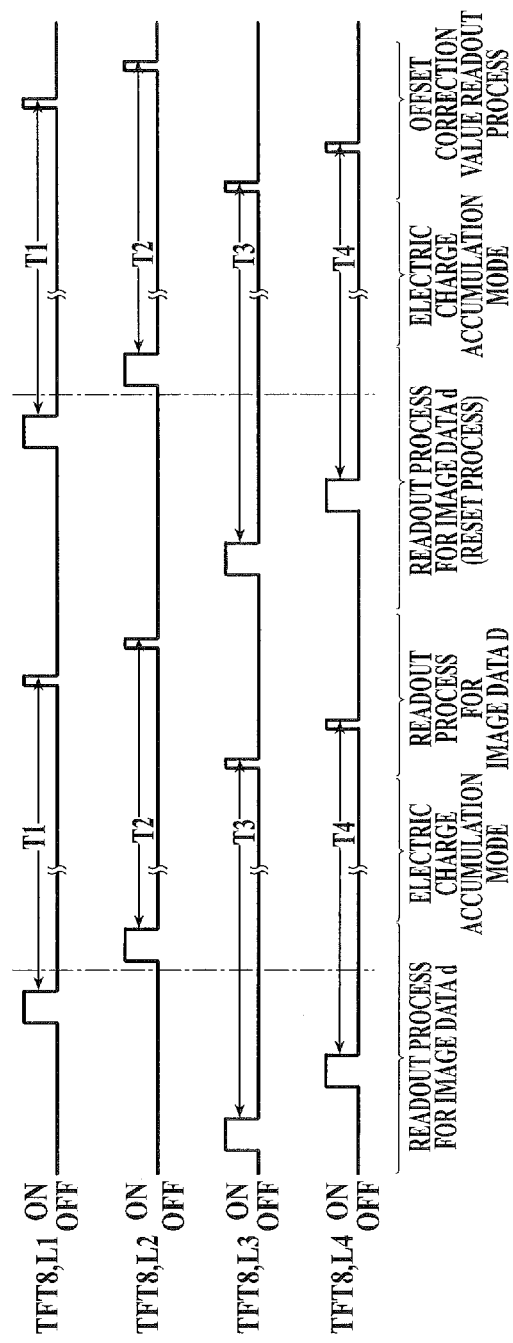
FIG. 40 is a timing chart in a case of reading out an offset correction value by repeating the same sequence as in a process sequence of reading out the image data, after the readout process for the image data.

If the configuration is adopted as shown in FIG. 40, then the offset correction value O is read out in the same process sequence as the process sequence in the event of reading out the image data D. Accordingly, even in the case where the time spans of the effective accumulation time T1 to T4 of the TFTs 8 for each of the lines L1 to L4 of the scanning lines are different from one another, in the case of viewing the time spans of the effective accumulation time T1 to T4 for each of the lines L1 to L4 of the scanning lines, the effective accumulation time of the TFT 8 in the event of reading out the image data D, and the effective accumulation time of the TFT 8 in the subsequent event of reading out the offset correction value O become the same time span.

Therefore, the respective offset correction values O themselves become values different from one another among the respective lines L1 to L4, in the case of viewing the offset correction values O for each of the lines L1 to L4 of the scanning lines, the amounts of the offsets contained in the read out image data D and the offset correction values O read out in the offset correction value readout process become the same values.

Then, also in the case of viewing the offset correction values O for each of the respective radiation detection elements 7, the amounts of the offsets contained in the read out image data D read out from the radiation detection elements 7 in the readout process for the image data D and the offset correction values O read out from the radiation detection elements 7 concerned in the subsequent offset correction value readout process become the same values.

Hence, in the event of the creation process for the radiation image, each of the offset correction values O read out in the offset correction value readout process is subtracted from each of the read out image data D, whereby it is made possible to accurately calculate the true image data D* derived only from the electric charges generated by the radioactive irradiation for each of the radiation detection elements 7. Then, it is made possible to accurately create the radiation image based on this true image data D*.

Note that it is also possible to adopt a configuration as follows. After the readout process for the image data D after the radiation image capturing operation is ended, as described above, before repeating the same process sequence as the process sequence until reading out the image data D, that is, before the second readout process for the image data d in FIG. 40 (or alternatively, the reset process for the respective radiation detection elements 7), the reset process for the respective radiation detection elements 7 is executed a predetermined number of times.

It is not necessary that the reset process in this case be executed at the same ON time in the same cycle as those in the case of the readout process for the image data d, and for example, it is also possible to adopt a configuration so as to repeat, at a high speed, the reset process at a shorter ON time in a shorter gate cycle. Then, in this case, after the reset process is executed a predetermined number of times, the second readout process for the image data d is executed, or alternatively, the reset process for the respective radiation detection elements 7, which is to be executed at the same ON time in the same gate cycle as those in the case of the second readout process for the image data d, is executed, then the electric charge accumulation mode is conducted, and thereafter, the offset correction value readout process is executed.

That is to say, the process sequence immediately before the offset correction value readout process just needs to be the same process sequence as the process sequence until reading out the image data D, and it is possible to adopt a configuration during the execution of the process sequence, so as to execute an appropriate process such as the reset process for the respective radiation detection elements 7.

When the configuration is adopted as described above, in the case where the controller 22 causes the storage section 40 (refer to FIG. 7 and the like) to sequentially store the image data D read out from the respective radiation detection elements 7 in the readout process for the image data D, and thereafter, does not perform another imaging subsequently, then the controller 22 automatically repeats the same process sequence, executes the offset correction value readout process, and causes the storage section 40 to sequentially store the read out offset correction values O.

Then, a configuration is adopted so as to sequentially read out the respective image data D and the respective offset correction values O sequentially from the storage section 40 at appropriate timing, and to transmit these image data through the antenna device 39 (refer to FIG. 1, FIG. 7 and the like) to the external computer or the like, which performs the image process. Moreover, it is also possible to adopt a configuration so as to cause the controller 22 itself to perform a subtraction process for subtracting the offset correction values O from the respective image data D.

[Configuration B]

Figure 41:
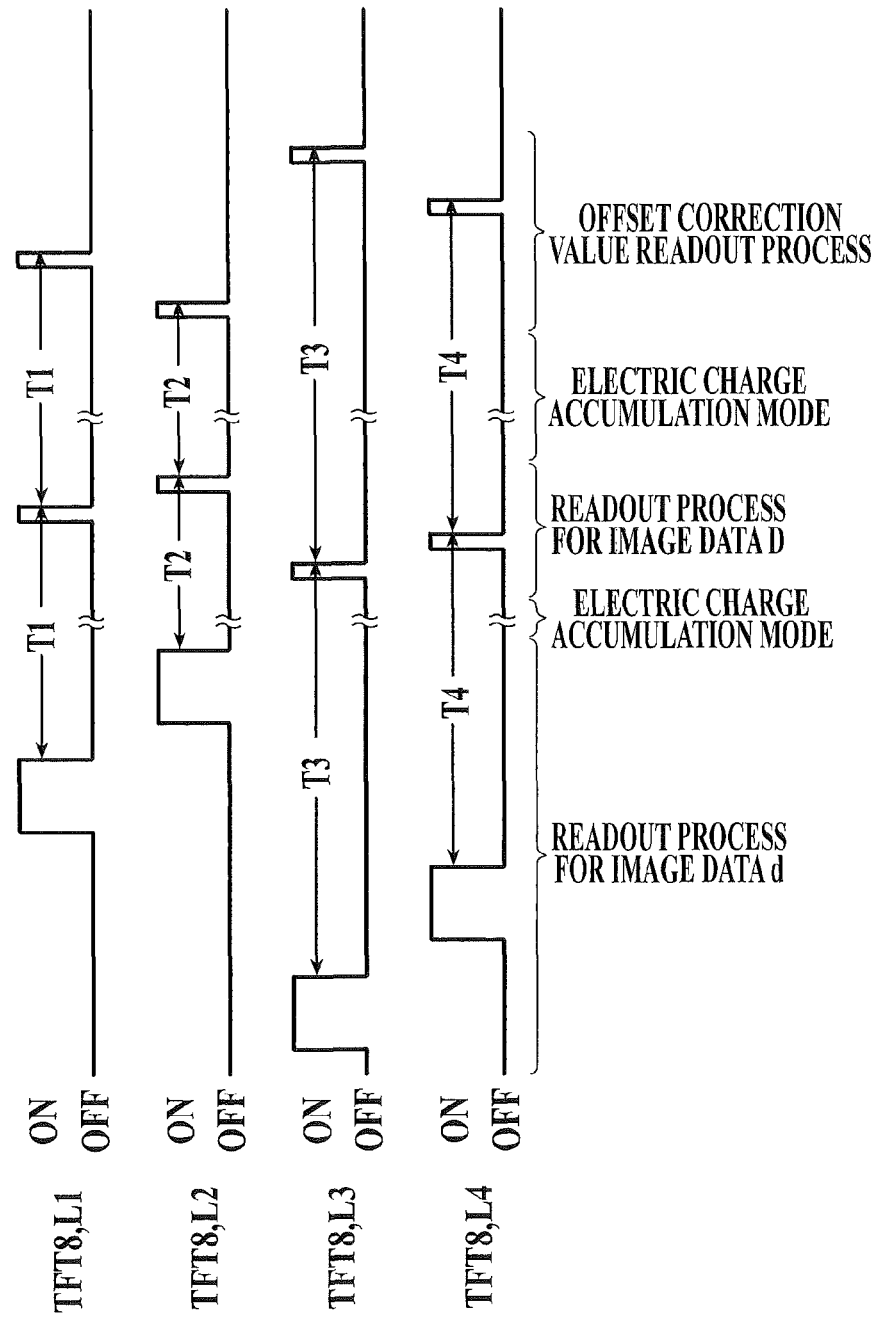
FIG. 41 is a timing chart in a case of executing an offset correction value readout process, so that the effective accumulation time of the TFT between the image data readout process and the offset correction value readout process becomes equal to the effective accumulation time of the TFT before initiating the radiation initiation.

Moreover, it is possible to adopt a configuration as follows. For example, as schematically shown in FIG. 41, the offset correction value readout process is executed at a timing in which the time spans of the effective accumulation time of the TFT 8 from when the ON voltage applied to the scanning lines 5 in the readout process for the image data D is switched to the OFF voltage for each of the lines L1 to L4 of the scanning lines 5 in a state where the radiation is not irradiated after the readout process for the image data D is ended to when the ON voltage applied to the scanning lines 5 in the offset correction value readout process is switched to the OFF voltage becomes individually the same as the time spans of the effective accumulation time T1 to T4 of the TFTs 8, which are shown in FIG. 39.

That is to say, briefly speaking, the offset correction value readout process is individually executed so that, for each of the lines L1 to L4 of the scanning lines 5, the time spans from the readout process for the image data d before the radiation image capturing operation to the readout process for the image data D after the radiation image capturing operation (that is, the time spans of the effective accumulation time T1 to T4 of the TFTs 8) and the time spans (the time spans of the effective accumulation time) from the readout process for the image data D to the offset correction value readout process can become the same.

Moreover, it is also possible to adopt configuration as follows. Though not shown, after the readout process for the image data D is ended, the reset process for the respective radiation detection elements 7 is once executed, and thereafter, the offset correction value readout process is executed so that the time spans from the reset process for the respective radiation detection elements 7 to the offset correction value readout process can become the same as the time spans from the readout process for the image data d before the radiation image capturing operation to the readout process for the image data D after the radiation image capturing operation.

When the configuration is adopted as described above, then the time spans of the effective accumulation times T1 to T4 of the TFTs 8 until the readout process for the image data D and the time spans of the effective accumulation time T1 to T4 of the TFTs 8 until the offset correction value readout process becomes equal. Accordingly, in a similar way to the above, for each of the radiation detection elements 7, the amounts of offsets contained in the image data D and the offset correction values O read out in the offset correction value readout process become the same values.

Therefore, in the event of the creation process for the radiation image, each of the offset correction values O is subtracted from each of the read out image data D, whereby it is made possible to accurately calculate the true image data D*, which is derived only from the electric charges generated by the radioactive irradiation, for each of the radiation detection elements 7. Then, it is made possible to accurately create the radiation image based on this true image data D*.

[Configuration C]

Figure 42:
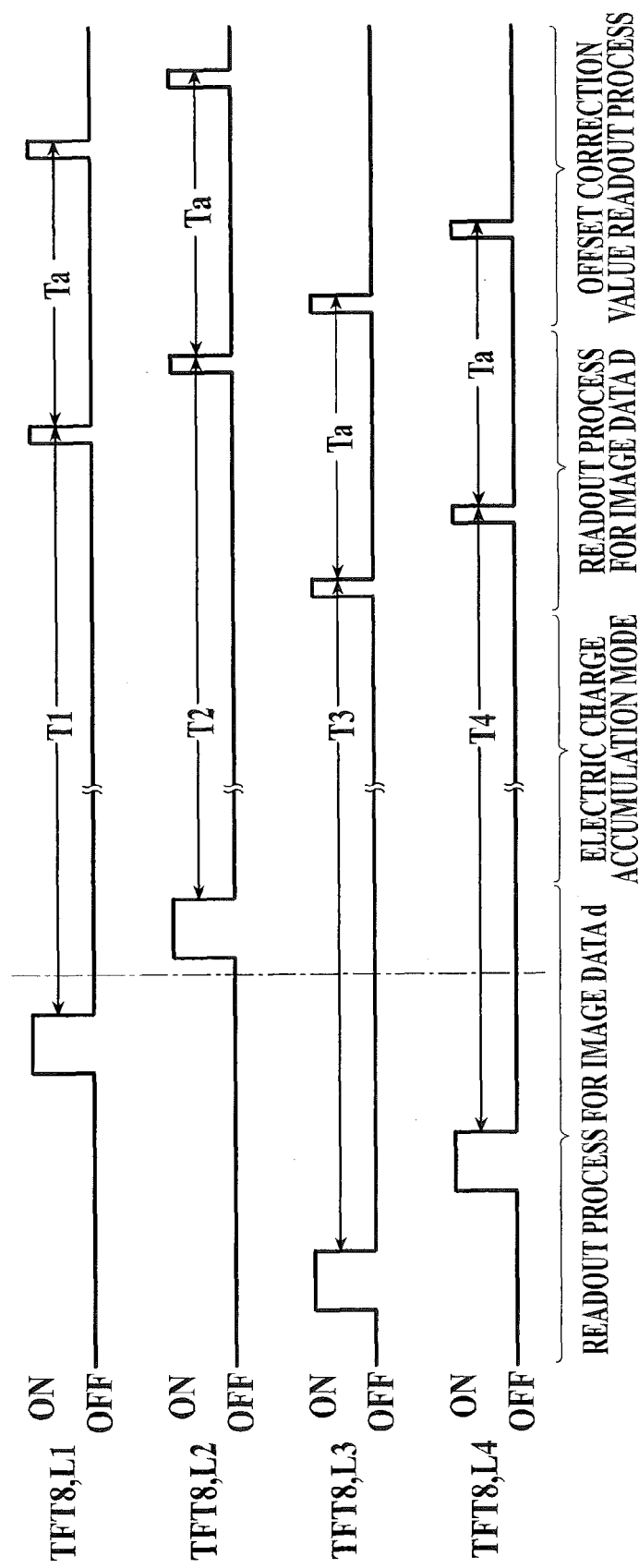
FIG. 42 is a timing chart in a case of executing the offset correction value readout process immediately after the readout process for the image data, and after a predetermined time has elapsed from the readout process for the image data.

Meanwhile, it is also possible to adopt a configuration as follows. As shown in FIG. 42, soon after the readout process for the image data D is ended or after an elapse of a predetermined time thereafter, in a state where the radioactive irradiation is not performed, the ON voltage is sequentially applied from the scanning drive unit 15 to the respective lines L1 to L4 of the scanning lines 5 at the same timing as that of the readout process for the image data D, whereby the offset correction value readout process is executed. Note that, also in this case, it is also possible to adopt a configuration so as to once execute the reset process for the respective radiation detection elements 7 after the readout process for the image data D is ended, and to thereafter execute the offset correction value readout process.

In this case, the time spans from the readout process for the image data D to the offset correction value readout process (that is, the time spans of the effective accumulation time of the TFTs 8) become the same time span Ta in all the lines L1 to L4 of the scanning lines. Therefore, in this case, the time spans of the effective accumulation time T1 to T4 of the TFTs 8 in the respective lines L1 to L4 of the scanning lines from the readout process for the image data d before the radiation image capturing operation to the readout process for the image data D after the radiation image capturing operation and the time span Ta from the readout process for the image data Da to the offset correction value readout process do not become the same.

Therefore, in the case of viewing each of the lines L1 to L4 of the scanning lines, each amount of the offset contained in the read out image data D and each of the offset correction values O read out in the offset correction value readout process do not become the same value, and even if the offset correction value O is subtracted from the image data D, the true image data D* cannot be accurately calculated. That is to say, the true image data D* has a value different from an intrinsic one.

Figure 43:
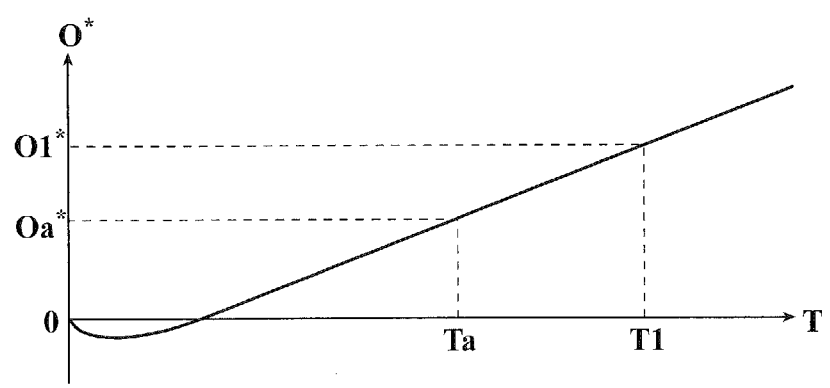
FIG. 43 is a table showing a relation between the effective accumulation time of the TFT and an offset correction value as a reference, or a graph showing a relational expression therebetween.

Accordingly, in the case of this Configuration C, for example, a table as shown in FIG. 43, which represents a relationship between the effective accumulation time T of the TFT 8 and an offset correction value O* serving as a reference, or a relational expression, is experimentally obtained in advance, and the table or the relational expression is held in advance in the external computer or the like, which performs the image process based on the image data D transmitted from the radiation image capturing apparatus 1 and on the offset correction value O. Note that, in this case, the experiment is performed in a state where temperatures and the like in the respective functional units, which include the reading circuits 17 of the radiation image capturing apparatus 1, in the substrate 4 and in the like are stabilized by energizing the respective functional units for a long time, and so on.

Then, for example, in the case of calculating the amount of offset (hereinafter, written as an offset amount O1) contained in the image data D read out from the respective radiation detection elements 7 connected to the line L1 of the scanning lines 5 in the readout process for the image data D, then the computer or the like first reads out or calculates an offset correction value O1* (refer to FIG. 43), which serves as a reference corresponding to the effective accumulation time T1, with reference to the above-described table, or in accordance with the above-described relational expression.

However, imaging conditions such as the temperature of the reading circuits 17 in the event of obtaining the table shown in FIG. 43 or obtaining the relational expression and the imaging conditions when the radiation image capturing operation is actually performed differ from each other.

Accordingly, the offset correction value O1* serving as a reference, which is thus read out or calculated, cannot be directly used as the above-described offset amount O1.

Therefore, for example, based on the above-described table or relational expression, an offset correction value Oa*, which serves as a reference at the effective accumulation time Ta, is obtained, and subsequently, the following fact is used. A ratio of the offset correction value O1* serving as a reference and the above-described offset amount O1 is equal to a ratio of the offset correction value Oa* serving as a reference, and the offset correction value O read out in the offset correction value readout process. In other words, the following Expression (3) is established:

$$O1^*:O1=Oa^*:O \qquad (3)$$

By using this relationship, the above-described offset amount O1 is calculated from the read out offset correction value O in accordance with the following Expression (4) derived from the above-described Expression (3):

$$O1=O\times O1^*/Oa^* \qquad (4)$$

Then, the offset amount O1 calculated in accordance with the above-described Expression (4) is subtracted from each piece of the image data D, whereby it is made possible to accurately calculate the true image data D* derived only from the electric charges generated by the radioactive irradiation for each of the radiation detection elements 7.

Moreover, a similar process is also executed for the lines L2 to L4 of the scanning lines 5, offset amounts (that is, offset amounts O2 to O4) contained in the image data D read out from the respective radiation detection elements 7 connected to the lines L2 to L4 of the scanning lines 5 in the readout process for the image data D are calculated, and the calculated offset amounts O2 to O4 are individually subtracted from the respective image data D, whereby it is made possible to accurately calculate the true image data D* derived only from the electric charges generated by the radioactive irradiation.

Then, the configuration is adopted as described above, whereby, also in the case of Configuration C, it is made possible to accurately create the radiation image based on the calculated true image data D*.

Note that the description has been made of the case where, in each of the above-described Configurations A to C, the process for obtaining the offset correction value O, which includes the offset correction value readout process, is executed only once after the readout process for the image data D; however, it is also possible to adopt a configuration, for example, so as to execute the process for obtaining the offset correction value O plural times, and to adopt a configuration so as to average, for each of the radiation detection elements 7, the respective offset correction values O obtained in the respective processes, and to use each of average values thus obtained as the offset correction value O for each of the radiation detection elements 7.

Third Embodiment

In the above-described second embodiment, the description has been made of the case of performing the offset correction value readout process mainly after the readout process for the image data D after the radiation image capturing operation in order to obtain the offset correction value O.

Meanwhile, it is also possible to adopt a configuration so as to prepare offset correction values O for each of the radiation detection elements 7 in advance in place of obtaining the offset correction values O for each radiation image capturing operation as described above, and to determine the offset correction values O with reference to these.

In the case where the configuration is adopted as described above, then it must be considered that the time spans of the effective accumulation time of the TFTs 8 of the respective scanning lines 5 will be changed as described above depending on the positions of the scanning lines 5 to which the ON voltage is applied at the point of time when it is detected that the radioactive irradiation is initiated.

That is to say, for example, as shown in FIG. 39 thus simplified, in the case where it is detected that the radioactive irradiation is initiated, for example, based on the image data d, which is read out in a manner that the ON voltage is applied to the line L2 of the scanning lines 5, in the readout process for the image data d before the radiation image capturing operation, then among the time spans of the effective accumulation time T1 to T4 of the TFTs 8 of the respective lines L1 to L4 of the scanning lines 5, the effective accumulation time T2 becomes the shortest, and the effective accumulation time T3 becomes the longest.

However, when it is detected that the radioactive irradiation is initiated based on the image data d read out in a manner that the ON voltage is applied to the line L3 of the scanning lines 5, then among the time spans of the effective accumulation time T1 to T4 of the TFTs 8 of the respective lines L1 to L4 of the scanning lines 5, the effective accumulation time T3 becomes the shortest, and the effective accumulation time T4 becomes the longest.

As understood by generalizing this matter, the time spans of the effective accumulation time T1 to Tx of the TFTs 8 in the respective lines L1 to Lx of the scanning lines 5 change depending on which scanning line 5 is the scanning line 5 to which the ON voltage is applied at the point of time when it is detected that the radioactive irradiation is initiated. Then, if the time spans of the effective accumulation time T1 to Tx change, then as shown in FIG. 43, the values of the offset correction values O of the respective radiation detection elements 7 also change.

Figure 44:
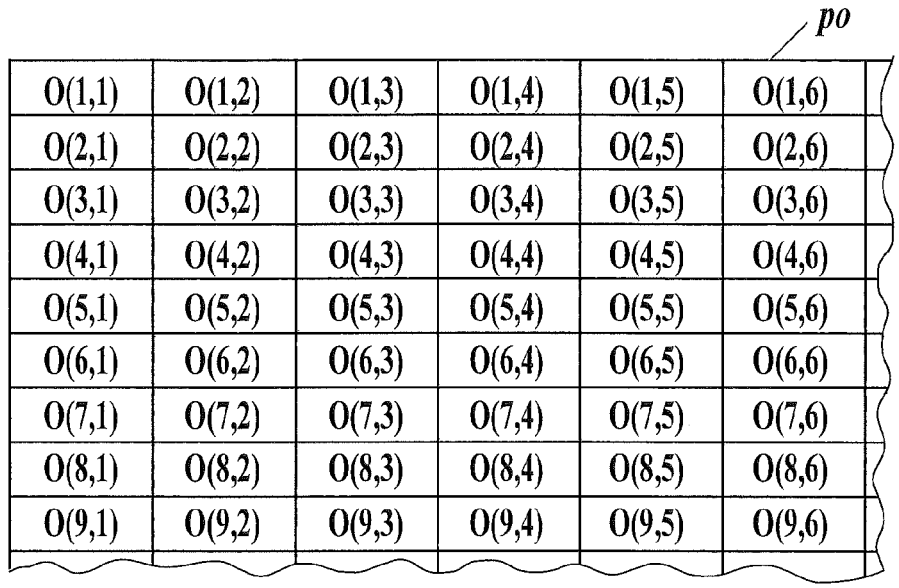
FIG. 44 is a view explaining an offset image created by offset correction values are allocated for the respective radiation detection elements.

Therefore, as described above, in the case of adopting the configuration so as to prepare the offset correction values O for each of the radiation detection elements 7 in advance, then for example as shown in FIG. 44, the offset correction values O(m, n) in the case where it is detected that the radioactive irradiation is initiated in the event where the ON voltage is applied to a certain scanning line 5 are obtained experimentally in advance, and these are individually assigned to the respective radiation detection elements (m, n), whereby an offset image po is created.

In this case, it is not preferable to execute the process for obtaining the respective offset correction values O(m, n) only once, since noise is contained in the respective offset correction values O(m, n) thus obtained. Accordingly, it is preferable to adopt a configuration so as to obtain the offset correction values O(m, n) plural times in the case where the initiation of the radioactive irradiation is detected in the event where the ON voltage is applied to the same scanning line 5, and for example, to use average values of these offset correction values O(m, n) for each of the radiation detection elements as the offset correction values O(m, n) of the radiation detection elements (m, n) concerned.

Figure 45:
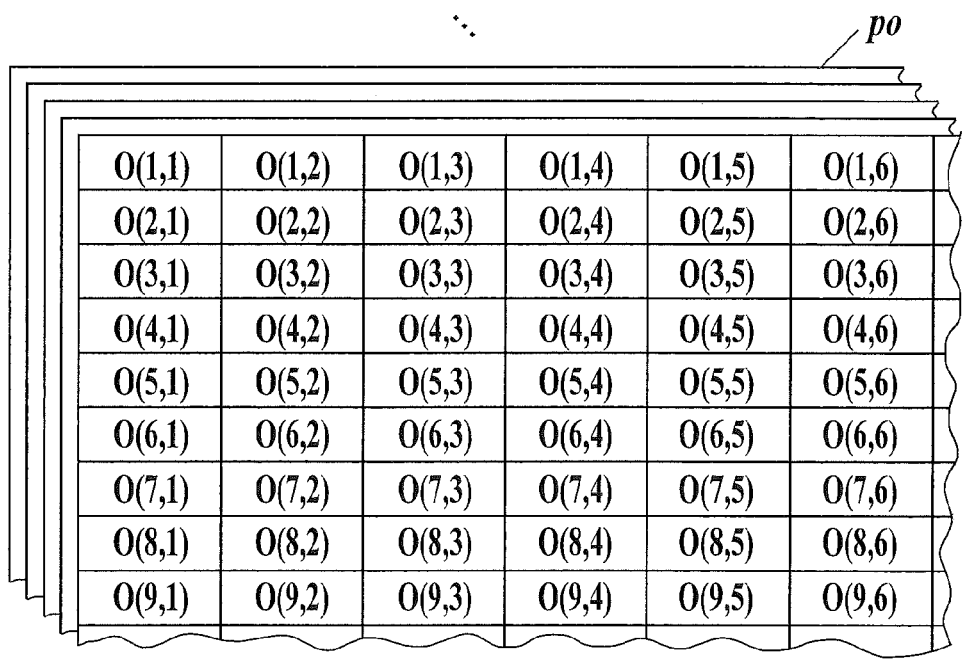
FIG. 45 is a view explaining a group of the offset images created for each scanning line.

Then, this process is executed while changing the scanning line 5 to which the ON voltage is applied in the event where the initiation of the radioactive irradiation is detected, whereby the offset images po are created individually for all the scanning lines 5. Then, as shown in FIG. 45, a group of the offset images po created for each of the scanning lines 5 is prepared in advance by being stored in the storage section 40 (refer to FIG. 7 and the like).

Then, in the event of the actual radiation image capturing operation, the controller 22 detects the line Ln of the scanning lines 5, to which the ON voltage is applied at the point of time when it is detected as described above that the radioactive irradiation onto the radiation image capturing apparatus 1 is initiated based on the value of the image data d read out in the readout process before the radiation image capturing operation. Then, the controller 22 stores a line number (n in this case) of the detected line Ln.

Then, it is possible to adopt a configuration as follows. At the stage where the offset correction values O become necessary in each process after the radiation image capturing operation, the offset image po corresponding to the scanning line 5 (that is, the line Ln of the scanning lines 5) corresponding to that line number n is referred to, the respective offset correction values O(m, n) individually assigned to the respective radiation detection elements (m, n) on the offset image po are determined, and these respective offset correction values O(m, n) are individually determined as the respective correction values O(m, n) for the respective radiation detection elements (m, n).

Here, in the case of adopting the configuration as described above, it is necessary to focus on the point that the offset correction values O can be changed by the temperature of the substrate 4 (refer to FIG. 3 and the like) of the radiation image capturing apparatus 1, and the like.

For example, in the case where the radiation image capturing apparatus 1 is a radiation image capturing apparatus of a so-called dedicated machine type, which is formed integrally with a support stage (not shown) or the like, for example, a configuration is adopted so as to always supply electric power to the radiation image capturing apparatus 1, whereby the radiation image capturing apparatus 1 can be set in a state of being always capable of the imaging. In that case, a state where the temperature of the substrate 4 of the radiation image capturing apparatus 1 is substantially constant is maintained. Accordingly, if the offset images po are created under the same temperature condition in the event of creating the offset images po concerned in advance, then the offset correction values O(m, n) assigned to the offset images po as described above can be directly used as the offset correction values O(m, n) for each of the radiation detection elements (m, n).

However, in the case of the portable radiation image capturing apparatus 1 as shown in the first embodiment, if a configuration is adopted so as to always supply electric power from the battery 41 (refer to FIG. 7), then a consumption of the electric power of the battery 41 becomes intense, continuous charging becomes inevitable, causing a decrease in imaging efficiency.

Therefore, in the case of the radiation image capturing apparatus 1 of such a battery built-in type, frequently, a configuration is adopted so as to be capable of switching to a power saving mode (also referred to as a sleep mode) of supplying electric power only to necessary functional units in the case other than the radiation image capturing operation. Then, the electric power mode is often set at the power saving mode immediately before the radiation image capturing operation for the purpose of suppressing the electric power consumption as much as possible.

However, if the radiation image capturing apparatus 1 of the battery built-in type is operated as described above, a temperature of the substrate 4 in the event of the actual radiation image capturing operation does not become the same as the temperature of the substrate 4 when the offset images po are created. Accordingly, in some case, the offset correction values O assigned to the offset images po cannot be directly used.

Therefore, for example, in the case where the scintillator 3 is formed to be smaller than the detecting section P provided on the substrate 4 as shown FIG. 19 with regard to the radiation image capturing apparatus 1, a configuration can be adopted so as to correct and use the offset correction values O, which are assigned to the offset images po, based on the image data d read out from the respective radiation detection elements 7 connected to the signal line 6 at a position C1 in FIG. 19 among the positions C on the detecting section P, which are other than the positions immediately under the scintillator 3, that is, the positions C on the detecting section P, into which the electromagnetic wave from the scintillator 3 does not enter.

The electromagnetic wave from the scintillator 3 does not enter the respective radiation detection elements 7 connected to the signal line 6 at the position C1 in FIG. 19, and accordingly, even if the radiation image capturing apparatus 1 is irradiated with the radiation, these radiation detection elements 7 are in a state where the electric charges are not generated by the radioactive irradiation. Then, from these radiation detection elements 7, the image data d caused by the dark electric charges is always read out. Therefore, by using the image data d to be read out from these respective radiation detection elements 7, it is known to which extent the temperature of the substrate 4 of the radiation image capturing apparatus 1 becomes at this point of time.

However, it is not necessary to determine the temperature of the substrate 4 of the radiation image capturing apparatus 1 at this point of time based on the image data d read out from these respective radiation detection elements 7, but it is necessary just to know to which extent the size of the image data d caused by the dark electric charges is changed between this imaging time and the time of creating the offset images po. Then, in response to the change in size, the offset correction values O assigned to the offset images po can be corrected.

Accordingly, in this case, for example, at the time of creating the offset images po, average values (or total values, the same applies below) of the respective image data d read out from the respective radiation detection elements 7 connected to the signal line 6 at the position C1 are calculated in advance as information of the image data d, and are stored together with the group of offset images po.

Moreover, also in the event of the actual radiation image capturing operation, average values of the respective image data d read out from the respective radiation detection elements 7 connected to the signal lines 6 are calculated.

Then, as described above, it is possible to adopt a configuration as follows. In the event of the actual radiation image capturing operation, the offset image po corresponding to the scanning lines 5 to which the ON voltage is applied at the point of time when it is detected that the radioactive irradiation is initiated is referred to, and the respective offset correction values O(m, n) for each of the radiation detection elements (m, n) are determined. Thereafter, a ratio calculated by dividing each of the average values of the respective image data, which is calculated in the event of the actual radiation image capturing operation, by each of the average values of the respective image data at the time of creating the offset images po is individually multiplied to the respective offset correction values O(m, n) thus determined, whereby the offset correction values O(m, n) of the respective radiation detection elements 7 in the radiation image capturing operation at this time are calculated and determined.

Moreover, it is also possible to adopt a configuration as follows. In place of multiplying the ratio, which is calculated as described above, to the respective determined offset correction values O(m, n), for example, a difference calculated by subtracting each of the average values of the respective image data at the time of creating the offset images po from each of the average values of the respective image data calculated in the event of the actual radiation image capturing operation is added individually to the respective determined offset correction values O(m, n), whereby the offset correction values O(m, n) of the respective radiation detection elements 7 in the radiation image capturing operation at this time are calculated and determined.

As described above, it is made possible to correct the respective offset correction values O(m, n), which are individually assigned to the respective radiation detection elements (m, n) in the offset images po, based on the information of the image data d at the time of creating the offset image po and on the information of the image data d read out at the current imaging time, and to individually determine the respective corrected offset correction values O(m, n) as the respective offset correction values O(m, n) for the respective radiation detection elements (m, n).

Moreover, with regard to the radiation image capturing apparatus 1, in the case where the scintillator 3 is not formed to be smaller than the detecting section P provided on the substrate 4 as shown in FIG. 19, for example, a configuration is adopted so as to interpose a light shield plate (not shown) between the scintillator 3 and the respective radiation detection elements 7 connected to one or plural signal lines 6 among the signal lines 6 on the detecting section P. In such a way, even if the radiation image capturing apparatus 1 is irradiated with the radiation, the respective radiation detection elements 7 can be turned to a state where the electric charges are not generated by the radioactive irradiation.

Then, it is also possible to adopt a configuration so as, by using the respective radiation detection elements 7 turned to such a state, to correct the respective offset correction values O(m, n), which are individually assigned to the respective radiation detection elements (m, n) in the offset images po, in a similar way to the above.

Meanwhile, as described in the above respective embodiments, in the present invention, the readout process for the image data d is repeatedly executed from before the radiation image capturing operation, and the image data d read out before the radioactive irradiation onto the radiation image capturing apparatus 1 is initiated is the data caused by the dark electric charges.

Accordingly, it is also possible to adopt a configuration so as to correct the respective offset correction values O(m, n), which are individually assigned to the respective radiation detection elements (m, n) in the offset images po, by using the image data d caused by the dark electric charges.

That is to say, in this case, for example, at the time of creating the offset images po, the readout process for the image data d before the radiation image capturing operation is repeatedly executed, and for example, average values (or total values, the same applies below) of the respective image data d read out from all the respective radiation detection elements 7 on the detecting section P or from the respective radiation detection elements 7 in a predetermined range thereon are calculated in advance as information of the image data d.

Then, also in the event of the actual radiation image capturing operation, average values of the respective image data d read out from the respective radiation detection elements 7 in the same range as that at the time of creating the offset images po are calculated in the readout process for the image data d before the radioactive irradiation onto the radiation image capturing apparatus 1 is initiated. Then, in a similar way to the above, a configuration can be adopted so as to calculate a ratio of either the average values or a difference therebetween, and to calculate and determine the offset correction values O(m, n) of the respective radiation detection elements 7 in the radiation image capturing operation at this time.

As described above, the configuration is adopted so as to correct the respective offset correction values O(m, n), which are individually assigned to the respective radiation detection elements (m, n) in the offset images po, based on the information of the image data d at the time of creating the offset images po and on the information of the image data d read out at this imaging time, and to determine the corrected offset correction values O(m, n) as the respective offset correction values O(m, n) for the respective radiation detection elements (m, n). In such a way, it becomes unnecessary to perform the offset correction value readout process before and after the radiation image capturing operation.

Therefore, it is made possible to suppress the consumption of the electric power by the amount that the offset correction value readout process is not executed, and in addition, as mentioned above, it is made possible to more rapidly execute the process for creating the diagnostic radiation image by transmitting the image data D as the final image and the like to the external computer and the like, and the processing for creating and displaying the preview image.

Incidentally, if a configuration is adopted as follows, then the offset correction values O for each of the radiation detection elements 7 can be obtained without performing the offset correction value readout process after the radiation image capturing operation or preparing the offset images po in advance as described above.

In the case of the model configuration shown in FIG. 12, in the readout process for the image data d before the radiation image capturing operation, the ON voltage is applied to the respective lines L1 to Lx of the scanning lines 5 at the same ON time in the same gate cycle as those of the case of the readout process for the image data D after the radiation image capturing operation. Accordingly, as mentioned in [Premise 2] of the second embodiment, at least among the lines L1 to Ln+2 of the scanning lines 5, the pieces of the effective accumulation time become the same, and in the respective lines Ln+3 to Lx of the scanning lines 5, the pieces of the effective accumulation time become different therefrom; however, among the respective lines Ln+3 to Lx of the scanning lines 5, the time spans of the effective accumulation time become the same.

Figure 46:
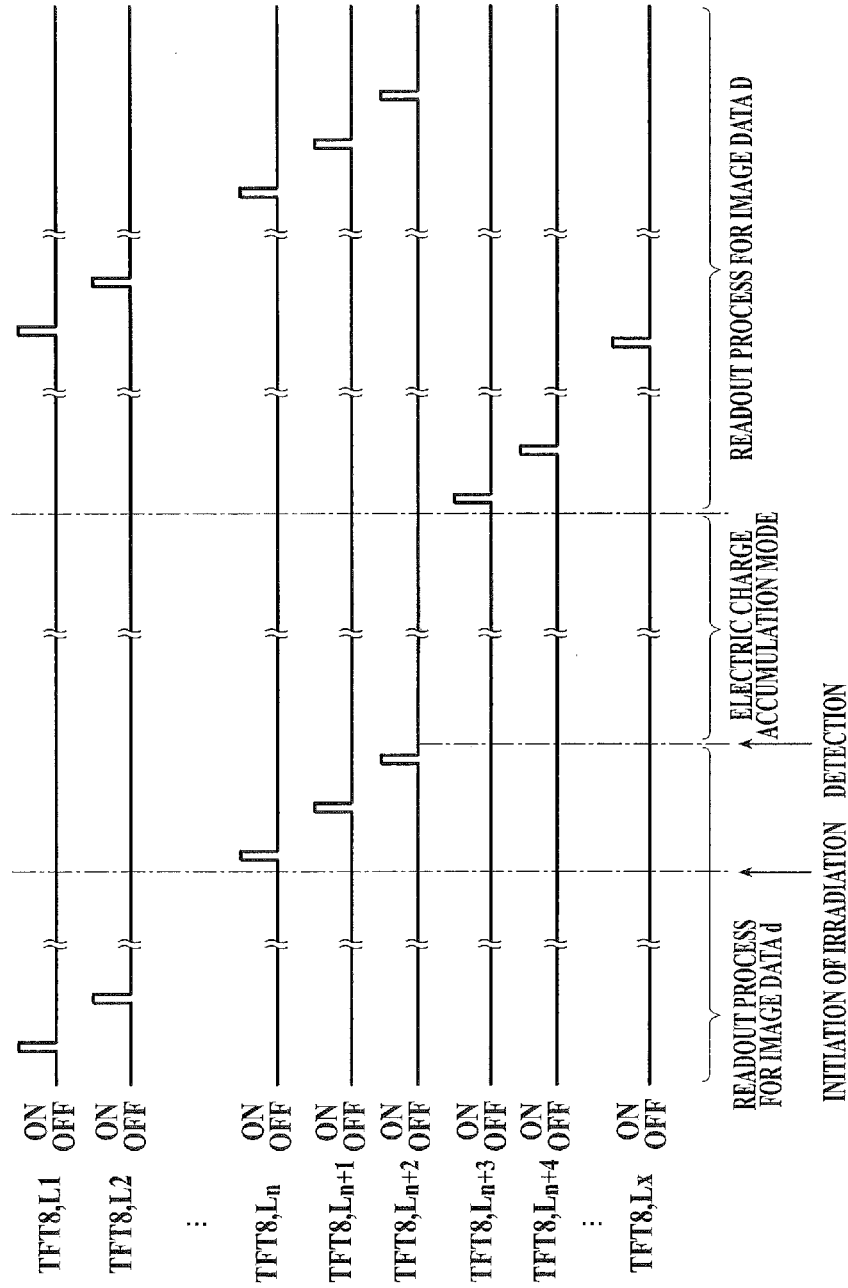
FIG. 46 is a timing chart showing application timing of the ON voltage to each scanning line in a case of applying the configuration of FIG. 36 to the model configuration of FIG. 12.

Then, it is supposed that this model configuration is applied with the configuration shown in FIG. 36, in which, in the readout process for the image data D, the ON voltage is sequentially applied to the lines of the scanning lines 5 in order from the line Ln+1 of the scanning lines 5, to which the ON voltage should be applied next to the line Ln of the scanning lines 5, from which it is detected that the radioactive irradiation is initiated in the readout process for the image data d before the radiation image capturing operation, whereby the readout process for the image data D is executed. Then, as shown in FIG. 46, the ON voltage the respective lines L1 to Lx of the scanning lines 5 are in the state of the ON voltage being applied thereto. Then, if a configuration is adopted as described above, the time spans of the effective accumulation time become the same among all the lines L1 to Lx of the scanning lines 5.

Figure 74:
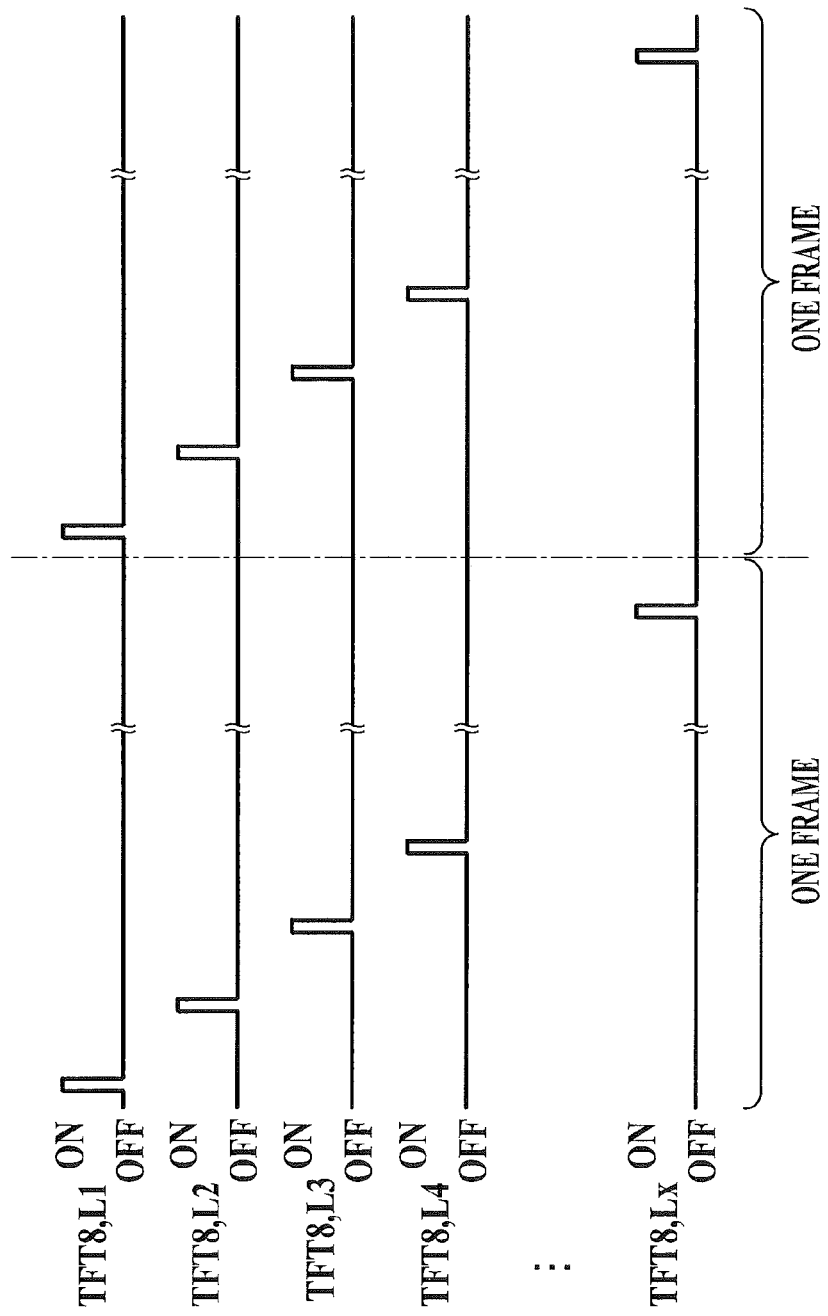
FIG. 74 is a timing chart explaining that the image data readout process is repeated for each frame.
Figure 75:
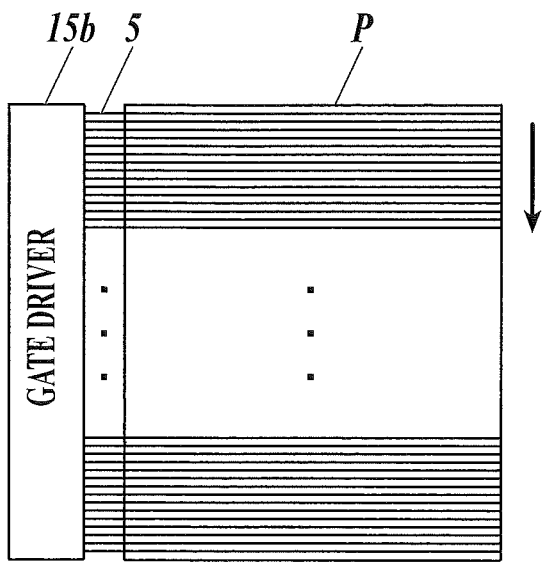
FIG. 75 is a view explaining the readout process for data from each of the radiation detecting devices for each frame.
Figure 76:
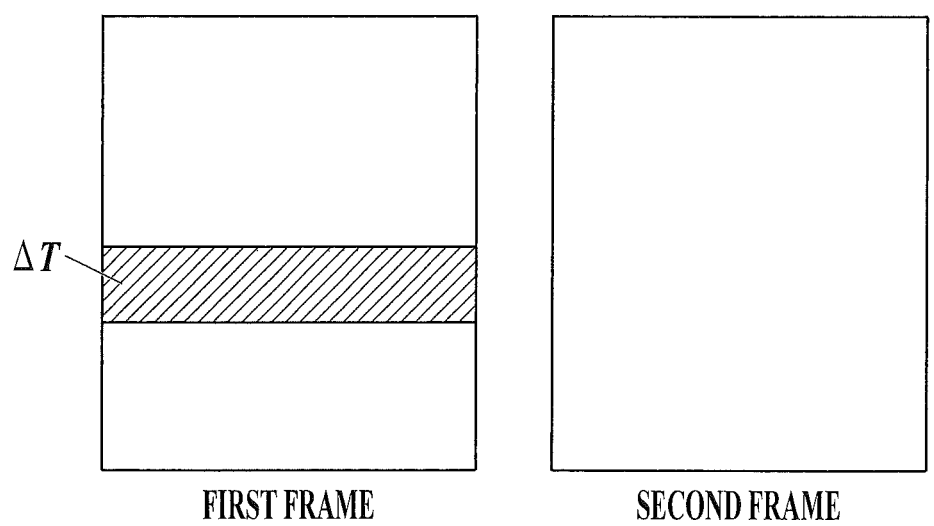
FIG. 76 is a view showing that the radioactive irradiation is performed while the ON voltage being sequentially applied to the scanning lines in a portion ΔT, and the radioactive irradiation is finished.
Figure 77A:
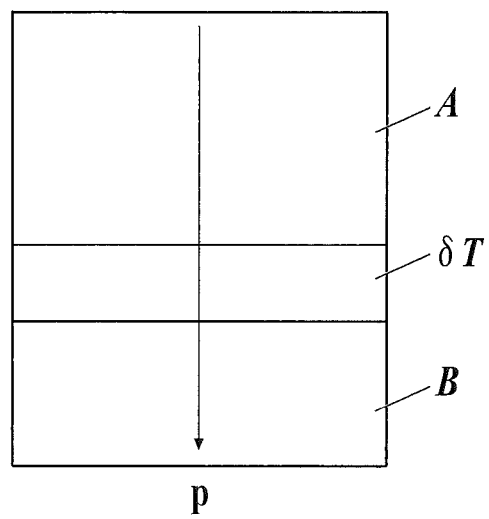
FIG. 77A is a view showing a radiation image generated based on a reconstructed image data.
Figure 77B:
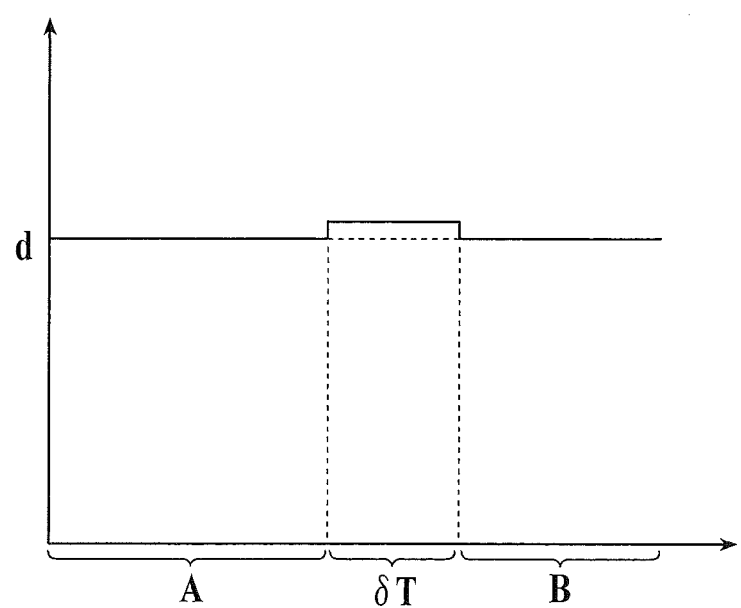
FIG. 77B is a graph showing that image data in an image region δT becomes larger than image data in image regions A and B.

Meanwhile, the description has been made above on the premise that, in the readout process for the image data d before the radiation image capturing operation, as shown in FIG. 74, the ON voltage is sequentially applied to the respective lines L1 to Lx of the scanning lines 5, and the ON voltage is applied to the first line L1 of the scanning lines 5 at the timing immediately after the timing when the ON voltage is applied to the last line Lx of the scanning lines 5, and in such a way, the readout process for each of the frames is repeated.

Then, also in this case, the time spans of the effective accumulation time of the TFTs 8 become the same among all the lines L1 to Lx of the scanning lines 5, become shorter than the pieces of the effective accumulation time of the TFTs 8 in the case shown in FIG. 46 by the time span of the electric charge accumulation mode.

Figure 47:
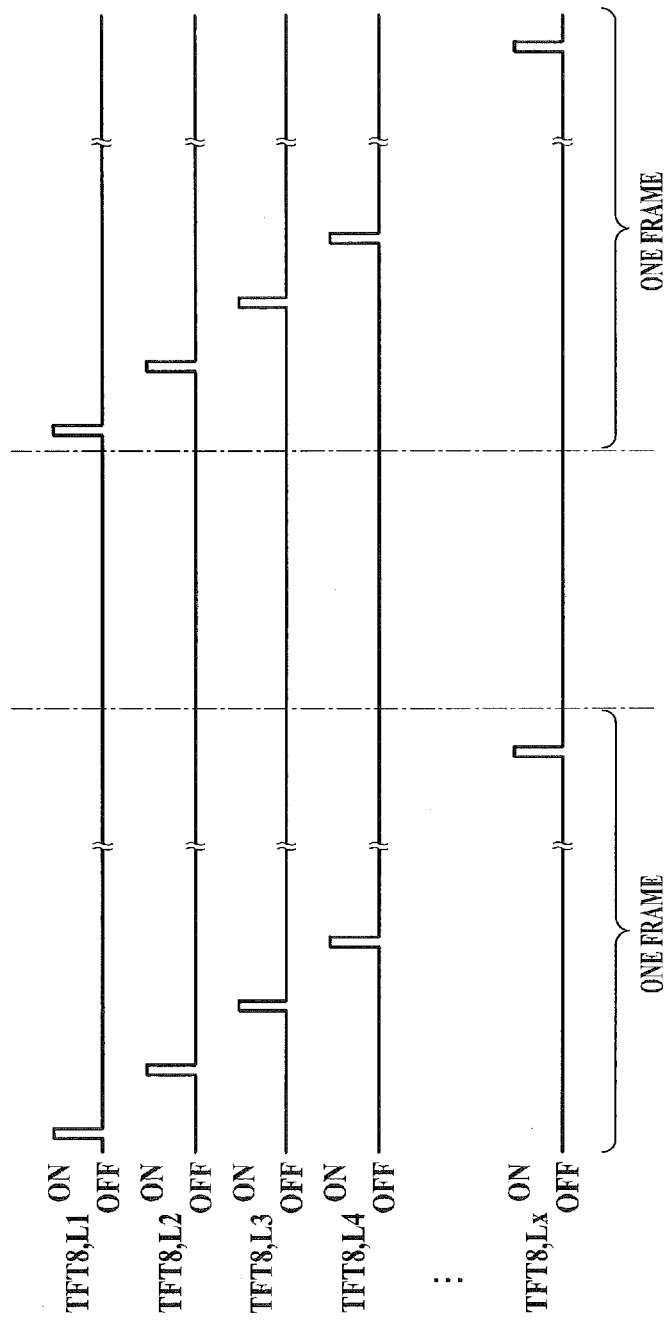
FIG. 47 is a timing chart explaining that during the readout process for the image data for each frame, a time period in which an OFF voltage is applied to the scanning lines becomes equal to a time period in which the OFF voltage is applied to all of the scanning lines in an electric charge accumulation mode.

Accordingly, in the readout process for the image data d before the radiation image capturing operation, in place of applying the ON voltage to the first line L1 of the scanning lines 5 at the timing immediately after the timing when the ON voltage is applied to the last line Lx of the scanning lines 5 as shown in FIG. 74, for example, as shown in FIG. 47, a configuration is adopted so as, after a readout process for the image data d for an amount of one frame is ended, to apply the OFF voltage to all the lines L1 to Lx of the scanning lines 5 for the same period as the period of applying the OFF voltage to all the lines L1 to Lx of the scanning lines 5 in the electric charge accumulation mode, and thereafter, to start a readout process for the image data d for the next frame, and to thereby repeatedly execute the readout process for the image data d for each of the frames. Then, in this case, the time spans of the effective accumulation time of the TFTs 8 in the readout process for the image data d before the radiation image capturing operation and the time spans of the effective accumulation time of the TFTs 8 at the radiation image capturing operation time shown in FIG. 46 can be made the same.

Then, in the readout process before the radiation image capturing operation, which is to be executed as described above, the image data d caused by the dark electric charges is read out as the image data d read out in the frame before the radioactive irradiation is initiated, and accordingly, it is made possible to use this image data d as the offset correction values O for each of the radiation detection elements 7.

In this case, it is also possible to adopt a configuration so as to obtain in advance the image data d of an amount of several frames before the radioactive irradiation is initiated, that is, the offset correction values O, to calculate, for example, an average value of the plurality of the offset correction values O, and to use the calculated average value of the offset correction values O as the offset correction values O for each of the radiation detection elements 7.

If the configuration is adopted as described above, then it becomes unnecessary to execute the offset correction value readout process after the radiation image capturing operation, and moreover, becomes unnecessary to prepare the offset images po in advance as described above. Moreover, the readout process for the image data d before the radiation image capturing operation just needs to be executed only for the above-described period in the electric charge accumulation mode for each of the frames, and accordingly, the process configuration for obtaining the offset correction values O becomes extremely simple.

Note that, the description has been made of this embodiment on the premise that the above-described respective processes are executed by the controller 22 of the radiation image capturing apparatus 1; however, it is also possible to adopt a configuration so as to transmit necessary data such as the image data D and the imaging data d from the radiation image capturing apparatus 1 to an external radiation image process device (not shown) that executes the image process for the image data D, and to execute the image process in the radiation image process device.

In this case, in the case of adopting a configuration so as to calculate and correct the offset correction values O of the respective radiation detection elements 7 by using the offset images po, then a configuration is adopted so as to prestore the information of a group of the offset images po, which is related to the radiation image capturing apparatus 1, in storage section (not shown) of the radiation image process device.

Moreover, in the radiation image capturing operation in which the image data D to be treated as the object of the image process is obtained, necessary information such as information of the line Ln of the scanning lines 5, to which the ON voltage is applied at the point of time when it is detected that the radioactive irradiation onto the radiation image capturing apparatus 1 is initiated, (that is, information such as the line number n of the scanning line 5 concerned) is appropriately transmitted from the radiation image capturing apparatus 1 to the radiation image process device.

Fourth Embodiment

In the aforementioned second embodiment, the description is given of various configurations for acquiring the offset correction value O due to dark electric charges, which are generated by thermal excitation due to heat (temperature) of the radiation detection element 7 itself, and the like and are accumulated within the respective radiation detection elements 7 while the respective TFTs 8 are turned off.

By the way, the study of the inventors has revealed that, in the case where the radiation image capturing apparatus 1 is irradiated with strong radiation, when the offset correction value O is read out in the aforementioned manner after the readout process for the image data D from the respective radiation detection elements 7, in addition to the offset component due to dark electric charges generated by thermal excitation due to heat (temperature) of the radiation detection element 7 itself, another offset component due to a so-called lag is read out in some cases.

The offset due to dark electric charges and the like is comparatively easily removed by repeating the reset process of each of the radiation detection elements 7, for example. However, the offset due to lag is not easily removed by repeating the reset process of each of the radiation detection elements 7.

To be specific, if the reset process of each of the radiation detection elements 7 is repeated, the offset due to dark electric charges and the like is reduced to a value close to 0 comparatively promptly. However, even if the reset process of each of the radiation detection elements 7 is repeated, the offset, due to lag can be hardly removed. Even if the reset process is repeatedly executed, when the offset correction value readout process is executed after the radiation image capturing apparatus 1 is left without being exposed to the radiation, the read out offset correction value O is larger than that read in the case involving only the offset due to dark electric charges and the like.

The reason why the offset due to lag cannot be easily removed by repetition of the reset process of each of the radiation detection elements is considered to be because some of electrons and holes generated within the radiation detection element 7 by irradiation with the strong radiation transit to a metastable energy level of a kind (a metastable state) and the mobility thereof within the radiation detection element 7 remains lost for a comparatively long time. Accordingly, the offset due to lag can be hardly removed even if the reset process of each of the radiation detection elements 7 is repeated, for example, after the radiation image capturing operation.

The electrons and holes which are in the metastable state transit by heat energy to a conduction band having an energy level which is thought to be higher than the above-described metastable state at a certain probability, and the mobility thereof is restored. The electrons and holes having the mobility again gradually appear in such a manner. Accordingly, in the offset correction value readout process after the radiation image capturing operation, it is considered that the offset due to lag is added to the offset due to dark electric charges and the like and is read out as the offset correction value O. Hereinafter, the offset due to lag is indicated by Olag.

The offset Olag due to lag is produced not only by irradiation with the strong radiation but also by irradiation with a normal dose of radiation including weak radiation. However, if the radiation image capturing apparatus 1 is irradiated with moderate radiation, the proportion of the offset Olag due to lag in the offset correction value O is negligibly small in many cases.

The degree of radiation which can increase the offset Olag to a considerable proportion depends on the performance of the radiation detection elements 7 such as photodiodes included in the radiation image capturing apparatus 1. Accordingly, it is properly determined for each radiation image capturing apparatus 1 whether to use the method of the fourth embodiment described below depending on the degree of radiation. Moreover, it can be configured so that the readout process for the image data D and the offset correction value readout process are always executed by the methods of the fourth embodiment.

Figure 48:
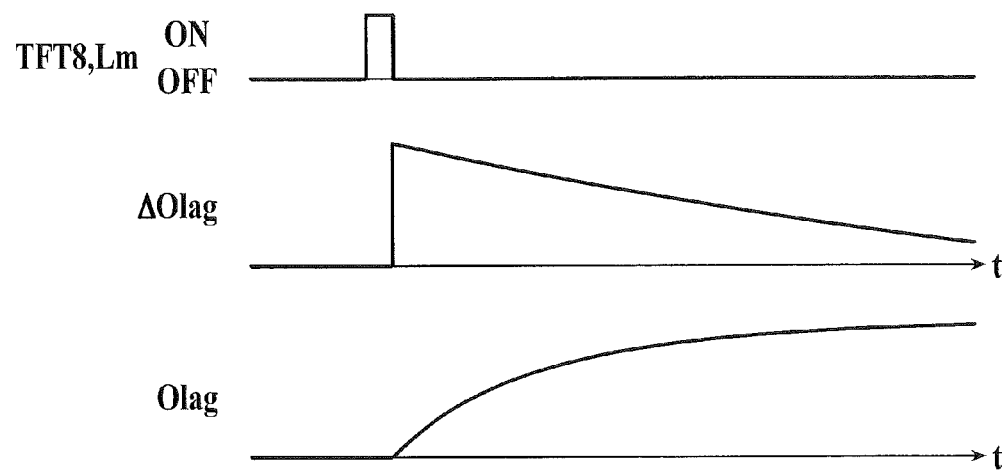
FIG. 48 is a timing chart showing ON/OFF timing of the TFT, and a graph showing that an offset portion due to a lag per unit time and an offset portion due to a lag which is an integral value of the offsets increase over time.

On the other hand, according to the study of the inventors, in the readout process for the image data D after the radiation image capturing apparatus 1 is irradiated with the radiation, as shown in FIG. 48, when the image data d is read out by sequentially applying ON voltage to respective lines Ln of the scanning lines 5, the offset Olag due to lag is produced immediately after the voltage applied to the respective lines Ln of the scanning lines 5 change from ON voltage to OFF voltage.

Herein, the offset Olag due to lag occurring per unit time is indicated by ΔOlag. As shown in FIG. 48, it is known that the offset ΔOlag due to lag per unit time is maximized when the voltage applied to the respective lines Ln of the scanning line 5 changes from ON voltage to OFF voltage and then gradually degreases. Accordingly, the offset Olag due to lag, which is represented as an integral of the offset ΔOlag per unit time over time, is a value increasing with time as shown in FIG. 48.

Since the offset Olag due to lag increases with time, the following problems arise.

As previously described, the image data D read out at the readout process for the image data d after the radiation image capturing operation includes true image data D* derived from electric charges generated within the respective radiation detection elements 7 by the radioactive irradiation and the offset due to dark electric charges (hereinafter, indicated as Od).

Accordingly, the following relationship is established.

$$D = D^* + Od \quad (5)$$

Moreover, the offset correction value O read out at the offset correction value readout process includes the offset Od due to dark electric charges and the like and the offset Olag due to lag. Accordingly, the following relationship is established.

$$O = Od + Olag \quad (6)$$

If the offset correction value O is subtracted from the image data D in accordance with the way of normal image processing, therefore, the offset Od due to dark electric charges and the like is canceled, but the offset Olag due to lag is not canceled as follows.

$$D - O = (D^* + Od) - (Od + Olag)$$

$$\therefore D - O = D^* - Olag \quad (7)$$

Next, consideration is given to the case where the radiation image capturing apparatus 1 is uniformly irradiated with the strong radiation, that is, the front surface of the radiation entrance face R (see FIG. 1 and the like) is irradiated with a uniform dose of the strong radiation, for example. In this case, the image data which is finally obtained for the respective radiation detection elements 7 should have the same value. Herein, fault of the radiation detection elements 7, the offset component of each reading circuit 17, and the like are not considered.

Figure 49:
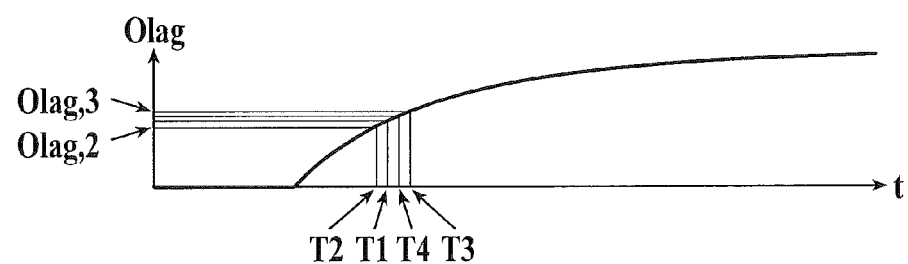
FIG. 49 is a graph explaining offset portions due to lags in the respective scanning lines when the processes in FIG. 40 and the like are executed.

In this case, the true image data D* derived from electric charges generated within the respective radiation detection elements 7 by the radioactive irradiation have the same value. However, if the processes are executed in a manner shown in FIG. 40, for example, the TFTs 8 have the effective accumulation times T1 to T4, which are different depending on the respective lines L1 to L4 of the scanning lines 5, and as shown in FIG. 49, offsets Olag(1) to Olag(4) due to lag of the respective lines L1 to L4 of the scanning lines 5 are therefore different from each other.

Accordingly, when the process of subtracting the offset correction value O from the image data D is performed as described above, the value D−O, which is calculated by subtracting the offset correction value O from the image data D, varies depending on the respective lines L1 to L4 of the scanning lines 5 since the Olag varies on the respective lines L1 to L4 of the scanning lines 5 while the D* in the above equation (7) does not vary.

Accordingly, for the radiation image capturing apparatus 1 is uniformly irradiated with the strong radiation, if the radiation image is generated based on the calculated value D−O, the lightness (brightness) of the radiation image slightly varies depending on a region of the image although the radiation image should have the same brightness over the entire region.

Figure 50:
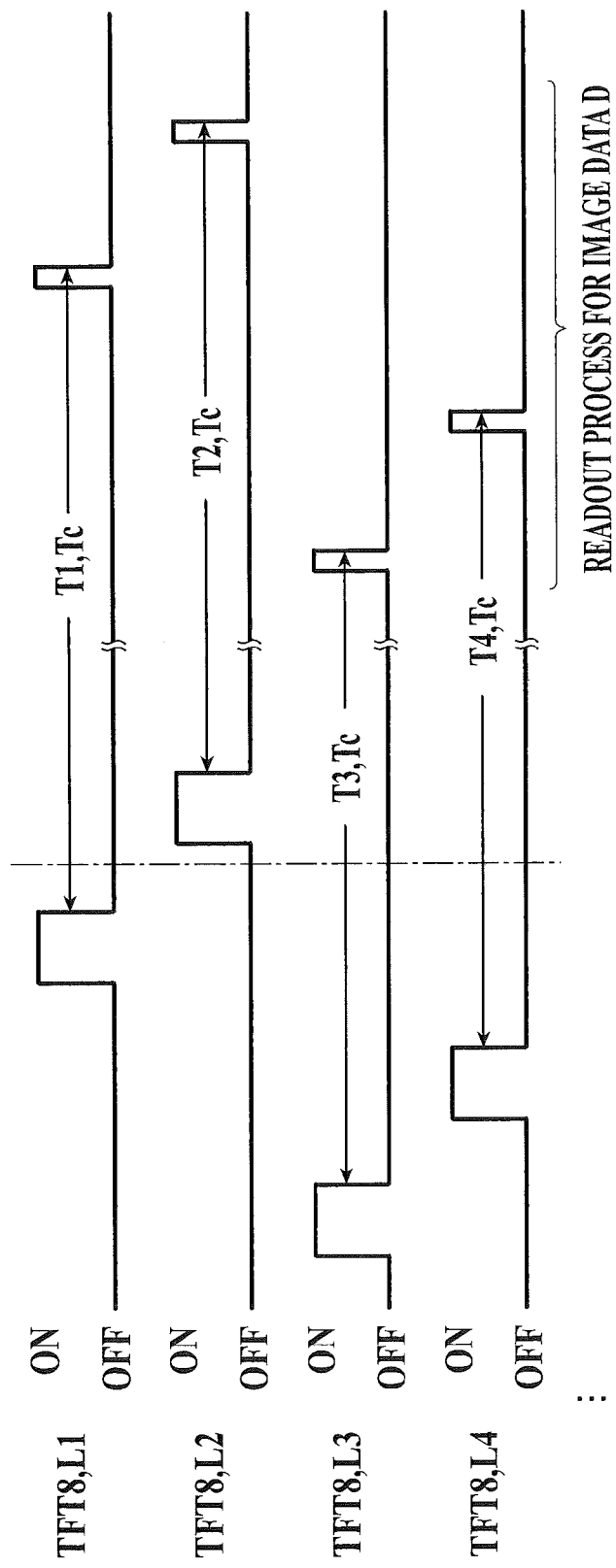
FIG. 50 is a timing chart of the readout process for the image data before initiating the radioactive irradiation, the electric charge accumulation mode and the readout process for the image data after finishing the radioactive irradiation in a fourth embodiment.

In the fourth embodiment, as a method to prevent the above problem, for example, as shown in FIG. 50, it can be configured that the times when the ON voltage is sequentially applied to the respective lines L1 to L4 of the scanning lines 5 (as described above, the same goes with the respective lines L1 to Lx of the scanning lines 5) are changed in the readout process for the image data D after the radiation image capturing operation so that the effective accumulation times T1 to T4 of the TFTs 8 are equal to the same time span Tc for all of the lines L1 to L4 of the scanning lines 5.

With the aforementioned configuration, the effective accumulation times T1 to T4 of the TFTs 8 before and after the readout process for the image data D can be set to the same time span Tc, in the case where the process sequence to read out the image data D and the process sequence to read out the offset correction value O after the readout process for the image data D are composed of the same process sequence like Configuration A of the aforementioned second embodiment; and in the case where the offset correction value readout process is executed so that the effective accumulation times T1 to T4 of the TFTs 8 before starting the readout process for the image data D are equal to the accumulation times T1 to T4 of the TFTs 8 before starting the offset correction readout process for each of the L1 to L4 scanning lines 5 like Configuration B.

When the radiation image capturing apparatus 1 is uniformly irradiated by the strong radiation like the aforementioned example, therefore, as known from FIGS. 48 and 49, all the offsets Olag(1) to Olag(4) due to lag have the same value. Since the true image data D* derived from the electric charges generated within the respective radiation detection elements 7 by radioactive irradiation have the same value, the value D–O calculated by the above equation (7) is equal for all of the lines L1 to L4 of the scanning lines 5.

If the radiation image is generated based on the calculated values D–O, therefore, the radiation image has the same brightness over the whole region when being imaged by uniformly irradiating the radiation image capturing apparatus 1 with the strong radiation. In such a way, it is possible to prevent production of differences in brightness in the radiation image as described above.

Also in the case of Configuration C of the above second embodiment, the same effect as described above can be provided by setting the time span Ta from the readout process for the image data D to the offset correction value readout process (see FIG. 42) equal to the above-described time span Tc. In this case, since all the effective accumulation times T1 to T4 of the TFTs 8 before and after the readout process for the image data D are equal to the same time span Tc, it is unnecessary to calculate the offset Od (O1 in the equation) due to dark electric charges in accordance with the above-described equation (4) based on the above-described table and relationships.

Moreover, as previously described, the offset Olag due to lag becomes a problem in the case of the irradiation with the strong radiation and does not become a problem in the case of the irradiation with weak or a normal dose of radiation in many cases.

Accordingly, it can be configured so that the times when ON and OFF voltages are applied to the respective lines L1 to Lx of the scanning lines 5 in the readout process for the image data D after the radiation image capturing operation is changed between the normal timing mode (in the case of the second embodiment) and the variable timing mode (in the case of the fourth embodiment) according to the dose of radiation delivered to the radiation image capturing apparatus 1, for example.

With the above configuration, when the times when the ON voltage is sequentially applied to the respective lines L1 to Lx of the scanning lines 5 are changed in the readout process for the image data D after the radiation image capturing operation like the fourth embodiment, the time taken to execute each process at the radiation image capturing apparatus 1 are a little longer than that of the case of normal timing. However, when the radiation image capturing apparatus 1 is irradiated with weak or a normal dose of radiation, the increase in time taken to execute each process can be prevented by executing the readout process for the image data d with the normal timing.

Fifth Embodiment

As described above, in the readout process to read out the image data d from the respective radiation detection elements 7 before the radiation image capturing operation, the image data d is read out from the radiation detection elements 7 one after another by sequentially applying the ON voltage to the lines L1 to Lx of the scanning lines 5 from the gate driver 15*b* in a manner that the scanning line 5 to which the on voltage is applied is shifted to sequentially change the TFTs 8 which are turned on.

Figure 51:
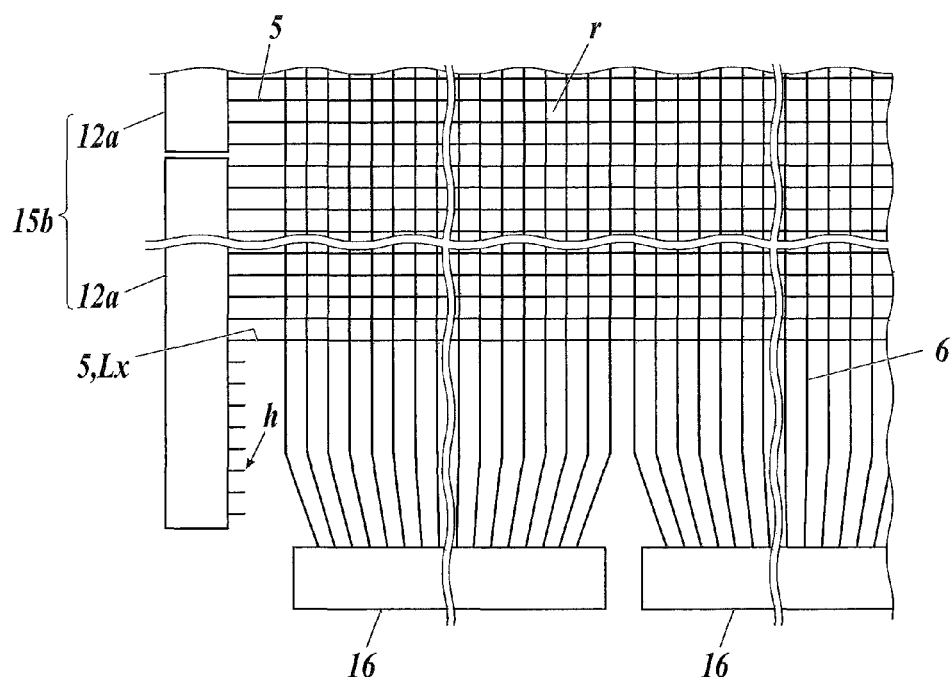
FIG. 51 is a view explaining the gate driver configured by arranging gate ICs in parallel and non-connecting terminals.

As shown in FIG. 51, the gate driver 15*b* of the scanning drive unit 15 or the plurality of gate ICs 12*a* constituting the same include so-called non-connecting terminals h, which are not connected to the scanning lines 5, in some cases. If the terminal to which the ON voltage is applied is sequentially changed to sequentially apply the ON voltage to the lines L1 to Lx of the scanning lines 5 from the gate driver 15*b*, the ON voltage is eventually applied to the non-connecting terminals h.

Figure 52:
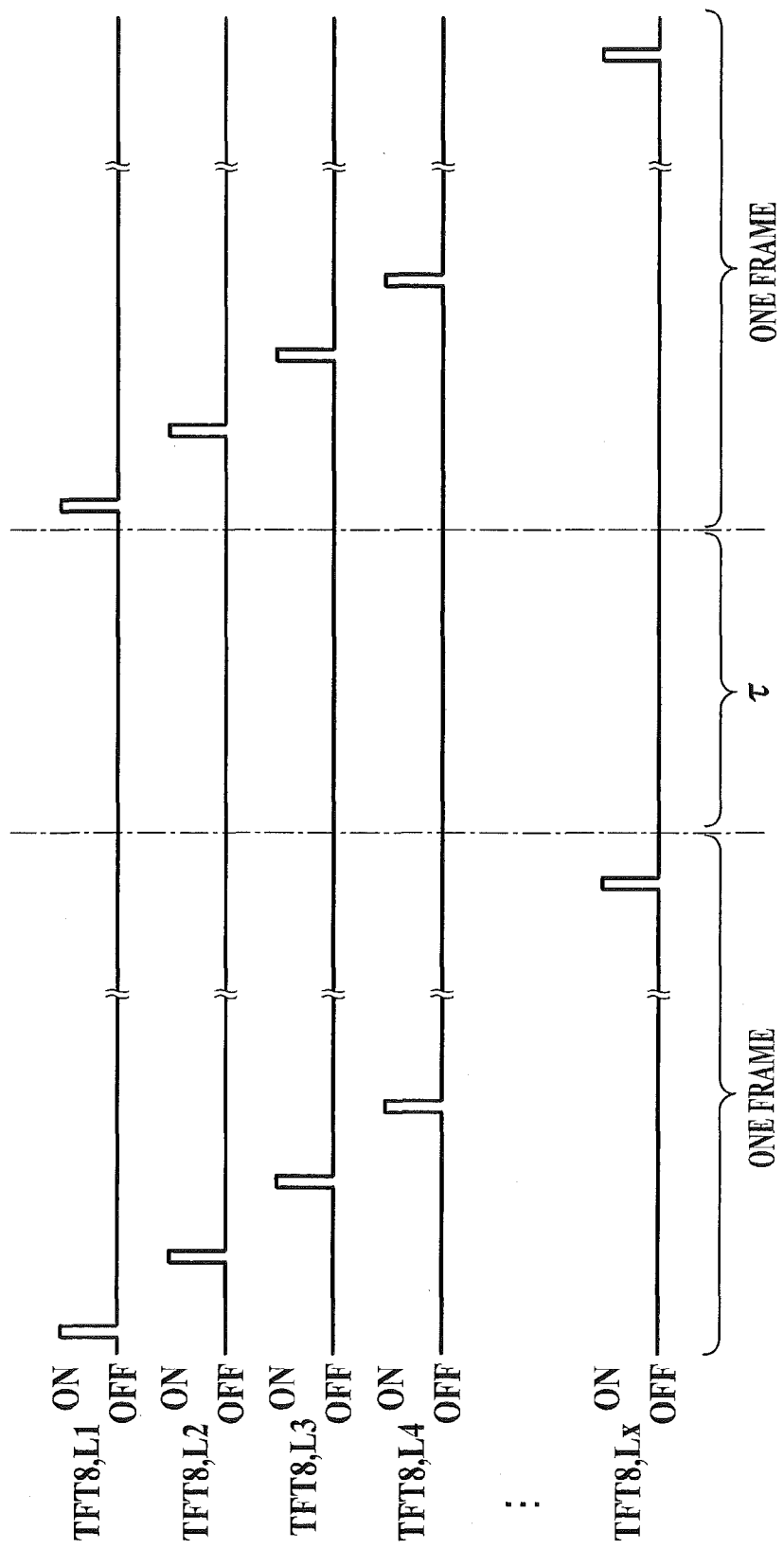
FIG. 52 is a timing chart explaining that a period τ is generated which is a period with no image data being read out from any of the radiation detection elements with a procedure of the conventional readout process for the image data.

However, for the non-connecting terminals h are not connected to the scanning lines 5, as shown in FIG. 52, while the ON voltage is applied to the non-connecting terminals h (see τ in the drawing), the ON voltage is not applied to any one of the lines L1 to Lx of the scanning lines 5, and the image data d is not read out from any of the radiation detection elements 7. In FIG. 52, as previously described, one frame refers to a period when the ON voltage is sequentially applied to all the scanning lines 5 on the detecting section P (see FIGS. 3 and 7) for reading out the image data d from the respective radiation detection elements 7.

When the period τ during which the ON voltage is applied to the non-connecting terminals h of the gate driver 15*b* or gate ICs 12*a*, that is, the period τ during which image data is not read out from any of the radiation detection elements 7 is produced between the frames of the readout process for the image data d, if the radiation image capturing apparatus 1 is irradiated with radiation during the period τ, irradiation of the radiation image capturing apparatus 1 is detected for the first time when the readout process is started in the frame after a lapse of the period τ.

In other words, the radioactive irradiation cannot be detected until the readout process is started at the frame after the period τ. The initiation of the radioactive irradiation is detected later than the actual initiation of the radioactive irradiation.

If the initiation of the radioactive irradiation is detected, normally, the OFF voltage continues to be applied to all the lines L1 to Lx of the scanning lines 5 for a predetermined period of time which is set longer than the irradiation time, so that useful electric charges generated within the respective radiation detection elements 7 by the radioactive irradiation are accumulated. If the detection of the initiation of the radioactive irradiation is delayed as described above, the OFF voltage continues to be applied to all the lines L1 to Lx of the scanning lines 5 longer as a result.

Accordingly, so-called dark electric charges, which are generated by thermal excitation by heat of the radiation detection elements 7 themselves, accumulate more within the respective radiation detection elements 7. This can cause a problem of degradation of the S/N ratio of the image data D as the final image read out. The degradation of the S/N ratio of the image data D as the final image read out results in deterioration in image quality of the radiation image p generated based on the image data D.

Accordingly, it is desirable that the radiation image capturing apparatus 1 can prevent production of the period τ or minimize the period τ, during which the image data d or the like is not read out, in the readout process for the image data d and the like before the radiation image capturing operation and can accurately detect the radioactive irradiation.

In the fifth embodiment, a description is given of the radiation image capturing apparatus 1 capable of solving the aforementioned problem. Hereinafter, a description is given of a radiation image capturing apparatus according to the fifth embodiment with reference to the drawings.

In the fifth embodiment, the basic configuration and operations of each functional section of the radiation image capturing apparatus 1 are the same as those of the above described embodiments. However, in the fifth embodiment, as shown in FIG. 53, the gate driver 15b of the scanning drive unit 15 or the gate ICs 12a constituting the same include the above-described non-connecting terminals h which are not connected to the scanning lines 5.

Herein, a description is given of the configuration of the gate driver 15b of the scanning drive unit 15 of the fifth embodiment and the way of driving the same. FIG. 53 is a view showing the configuration of the scanning drive unit 15 according to the fifth embodiment, wirings concerning the gate driver 15b, and the like.

As described above, in the fifth embodiment, the gate driver 15b of the scanning drive unit 15 is composed of the aforementioned plurality of gate ICs 12a which are arranged side by side. Each gate IC 12a is supplied with the ON voltage from the power source circuit 15a through the wiring Lon supplying the ON voltage. Moreover, each gate IC 12a is supplied with the OFF voltage from the power source circuit 15a though a not-shown another wiring. The wiring Lon and the wiring supplying the OFF voltage constitute the above-described wiring 15c (see FIG. 7).

Figure 53:
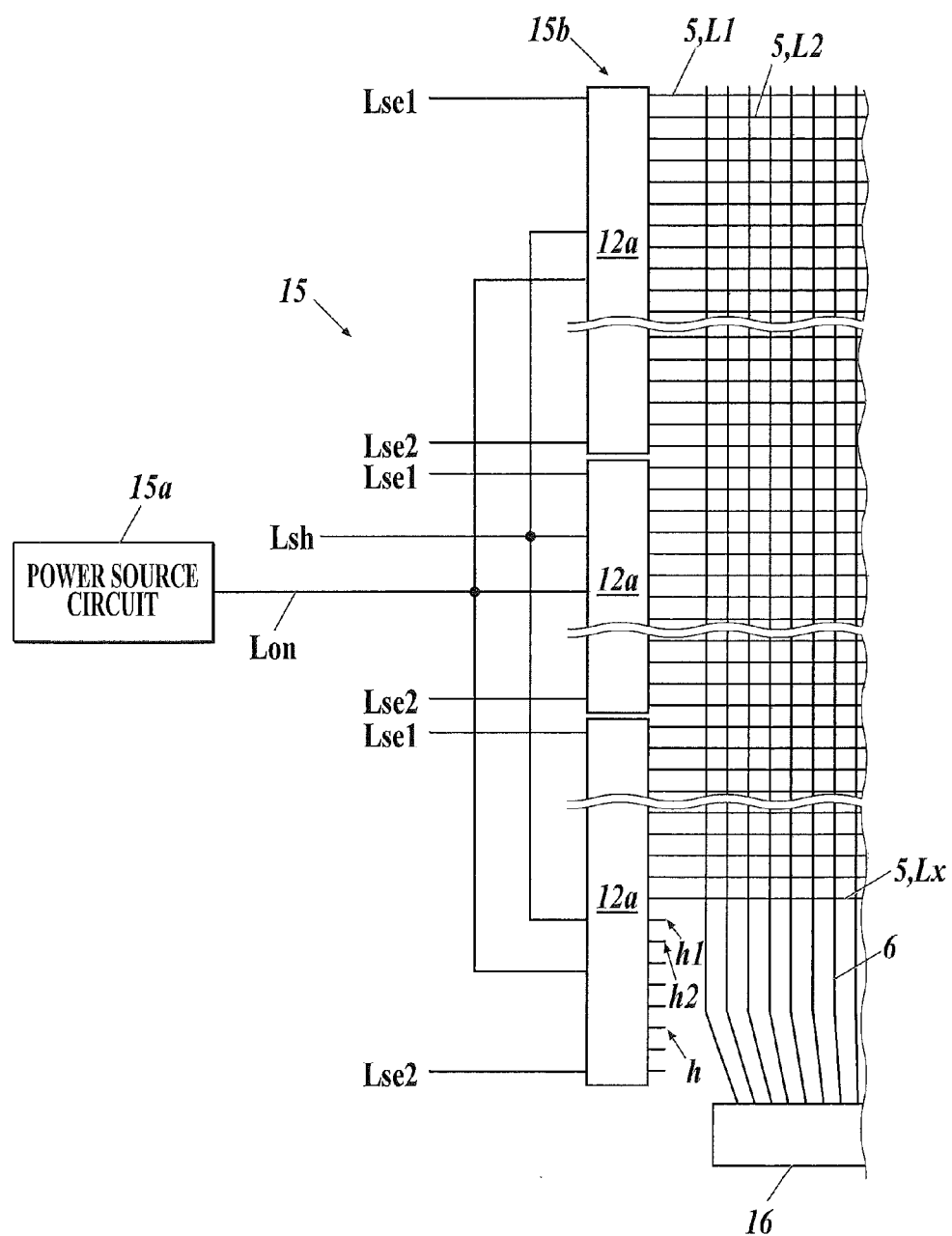
FIG. 53 is a view showing a configuration of scanning drive unit and wirings and the like connected to the gate driver according to a fifth embodiment.

As shown in FIG. 53, in the fifth embodiment, the both ends of each gate IC 12a are connected to wirings Lse1 and Lse2, which are individually connected to the controller 22. Each gate IC 12a is connected to a wiring Lsh from the controller 22.

When the seed signal is inputted through the wiring Lse1 of each gate IC 12a, the terminal of the gate IC 12a at the top in the drawing is activated. When the ON voltage is then supplied from the power source circuit 15a through the wiring Lon as described above, the ON voltage is applied to the scanning line 5 connected to the terminal at the top, which is active.

When a shift signal is inputted through the wiring Lsh, the terminal which is activated (hereinafter, referred to as an active terminal) is shifted to the next terminal below in the drawing. When the ON voltage is then supplied from the power source circuit 15a through the wiring Lon in that state, the ON voltage is applied to the active terminal. When the terminal is connected to any of the scanning lines 5, the ON voltage is applied to the connected scanning line 5.

In the above manner, each gate IC 12a is configured to shift the active terminal one by one when the seed signal is inputted to the gate IC 12a through the wiring Lse1 and the shift signals are inputted to the same through the wiring Lsh one after another. Moreover, by supplying the ON voltage to the IC 12 from the power source circuit 15a through the wiring Lon when that each terminal is activated, the ON voltage is sequentially applied to the terminals to sequentially apply the ON voltage to the scanning line 5 connected to each terminal.

In the fifth embodiment, when the seed signal is inputted to each gate IC 12a from the wiring Lse1 as described above, a seed signal is outputted from the wiring Lse2 at the timing subsequent to the timing when the terminal of each gate IC 12a at the bottom in the drawing is activated.

For example, the seed signal is inputted through the wiring Lse1 to the gate IC 12a which is at the top in the drawing, and the shift signals are inputted through the wiring Lsh one after another to shift the active terminal. The ON voltage is therefore sequentially applied to the scanning lines 5, and at the same time as the seed signal is outputted through the wiring Lse2, the seed signal is then inputted to the second gate IC 12a through the wiring Lse1.

The shift signals are inputted to the second gate IC 12a through the wiring Lsh one after another to shift the active terminal. The ON voltage is therefore sequentially applied to the scanning lines 5, and at the same time as the seed signal is outputted through the wiring Lse2, the seed signal is then inputted to the third gate IC 12a through the wiring Lse1. By repeating the aforementioned control, the ON voltage can be sequentially applied to the lines L1 to Lx of the scanning lines 5 connected to the terminals at the bottom of each gate IC 12a.

In the fifth embodiment, when the seed signal is inputted to each gate IC 12a through the wiring Lse2 and the shift signals are inputted through the wiring Lsh one after another contrary to the above description, the active terminal is shifted up starting from the terminal at the bottom of each gate IC 12a in the drawing.

For example, the seed signal is inputted through the wiring Lse2 to the gate IC 12a which is at the bottom in FIG. 53, and the shift signals are inputted through the wiring Lsh one after another to shift the active terminal upward. The ON voltage is sequentially applied to the scanning lines 5, and at the same time as the seed signal is outputted through the wiring Lse1, the seed signal is inputted to the next gate IC 12a above in the drawing, through the wiring Lse2.

By repeating the above control, the radiation image capturing apparatus 1 can be configured so that the ON voltage is sequentially applied to the lines L1 to Lx of the scanning lines 5 starting from the Lx scanning line toward the L1 scanning line.

Moreover, the radiation image capturing apparatus 1 can be configured as follows. The wiring Lse2 of a certain one of the gate ICs 12a is connected to the wiring Lse1 of the gate IC 12a adjacent thereto. The seed signal outputted from the wiring Lse2 or Lse1 of one of the connected gate ICs 12a is automatically inputted to the next gate IC 12a through the wiring Lse1 or Lse2, respectively.

In the fifth embodiment, in the aforementioned configuration, the radiation image capturing apparatus 1 itself detects the initiation of the radioactive irradiation onto the radiation image capturing apparatus 1 based on the image data d read out before the radiation image capturing operation in a similar manner to each of the above-described embodiments.

In the case where one (or some) of the gate ICs 12a constituting the gate driver 15b includes so-called non-connecting terminals h, which are not connected to the scanning lines 5 as shown in FIG. 53, the problem described above arises (see FIG. 52) when the active terminal is shifted one by one upward or downward in FIG. 53 to sequentially apply the ON voltage to the scanning lines 5 as described above.

While the ON voltage is applied to the non-connecting terminals (see τ in the drawing), the ON voltage is not applied to any one of the lines L1 to Lx of the scanning lines 5, and the image data d is not read out from any of the radiation detection elements 7. This produces the period τ during which the image data d is not read out (see FIG. 52).

Accordingly, as described above, the radiation image capturing apparatus 1 cannot detect the initiation of the radioactive irradiation at the same time as being actually irradiated with radiation. The radioactive irradiation is detected later than the actual initiation of the radioactive irradiation. This can cause a problem that the initiation of the radioactive irradiation cannot be detected in real time.

Moreover, since the detection of the initiation of the radioactive irradiation is delayed, the amount of dark electric charges accumulated in the respective radiation detection elements 7 increases, thus degrading the S/N ratio of the image data D as the final image read out.

Accordingly, in the fifth embodiment, the aforementioned problem is prevented by employing any one of the following methods, and the initiation of the radioactive irradiation to at least the radiation image capturing apparatus 1 can be accurately detected.

[Method 1]

The scanning drive unit 15 is configured as follows. In the case where one of the gate ICs 12a constituting the gate driver 15b includes non-connecting terminals h, which are not connected to the scanning lines 5 (see FIG. 53), in the process of sequentially applying the ON voltage to the scanning lines 5 from the gate driver 15b in the readout process for the image data d before the radiation image capturing operation, the ON voltage is always applied to any one of the terminals connected to the scanning lines 5 and is not applied to the non-connecting terminals h of the gate IC 12a to sequentially apply the ON voltage to the lines L1 to Lx of the scanning lines from the gate driver 15b.

In the gate driver 15b shown in FIG. 53, for example, as previously described, when the seed signal is inputted to each gate IC 12a through the wiring Lse1 and the shift signals are inputted through the wiring Lsh one after another, the active terminal is shifted one by one from the top in the drawing, and the ON voltage is supplied from the power source circuit 15a through the wiring Lon at each timing. The lines L1 to Lx of the scanning lines 5 to which the ON voltage is applied are therefore sequentially changed, so that the ON voltage is sequentially applied to the lines L1 to Lx of the scanning lines 5.

When the terminal connected to the last Lx scanning line 5 is activated while the ON voltage is applied to the Lx scanning line 5, at the subsequent timing, the seed signal is outputted from the gate IC 12a (the gate IC 12a at the bottom in FIG. 53) through the wiring Lse2. Alternatively, the seed signal within the gate IC 12a is forcibly removed from the gate IC 12a by grounding or the like.

At the same timing, the seed signal is inputted to the gate IC 12a at the top in FIG. 53 through the wiring Lse1. With this configuration, the ON voltage is applied to the first L1 scanning line 5 at the subsequent timing after the ON voltage is applied to the last Lx scanning line 5.

After the ON voltage is applied to the first L1 scanning line 5, the scanning line 5 to which the ON voltage is applied can be sequentially shifted down in the drawing by sequentially inputting the shift signals to the corresponding gate IC 12a (the gate IC 12a at the top in FIG. 53). As described above, the radiation image capturing apparatus 1 can be configured so that the ON voltage is sequentially applied to the lines L1 to Lx of the scanning lines from the gate driver 15b in a manner that the ON voltage is always applied to any of the terminals connected to the scanning lines 5 and is not applied to the non-connecting terminals h of the gate IC 12a.

Figure 54:
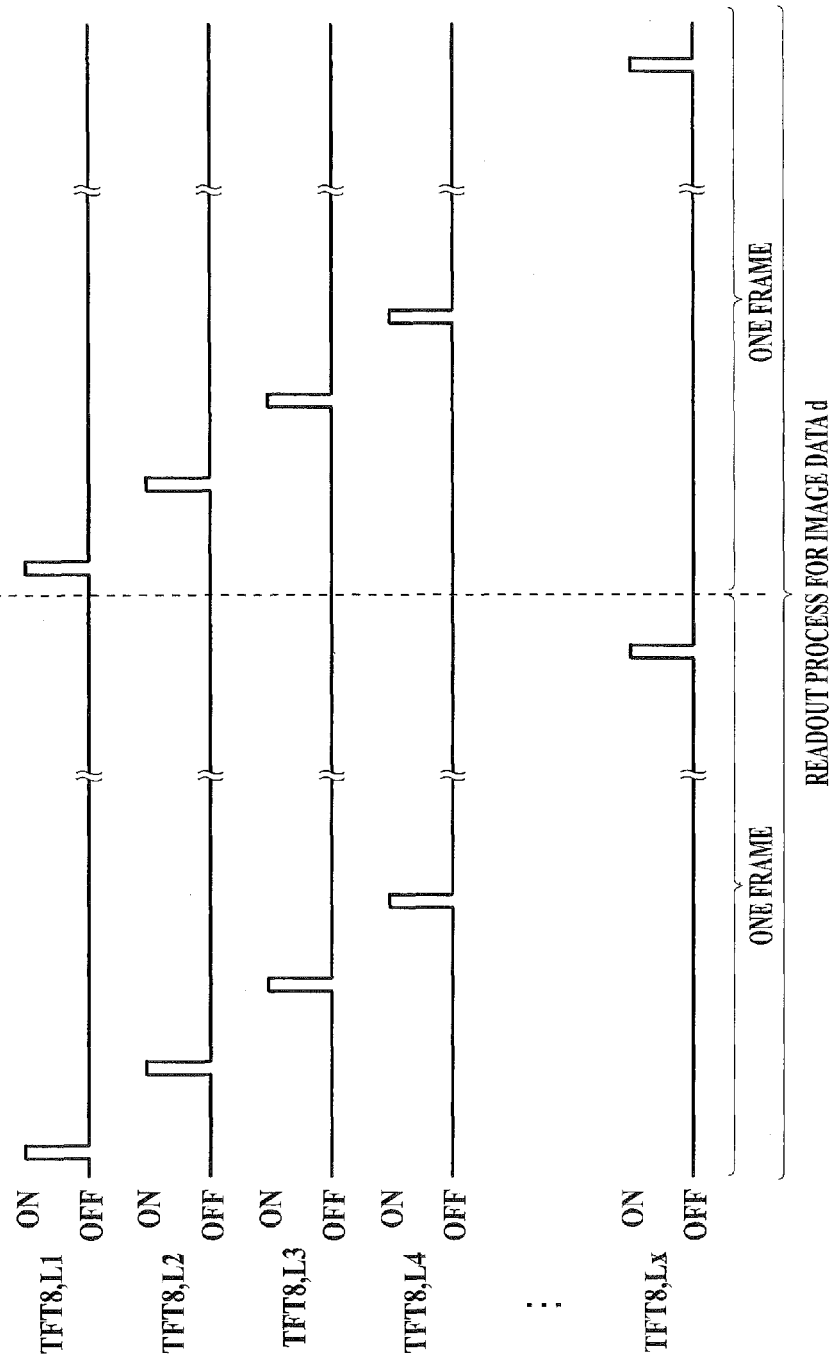
FIG. 54 is a timing chart explaining that in Procedure 1, the readout process for the image data d for each frame is executed successively in terms of time.

With the above configuration, in the readout process for the image data d before the radiation image capturing operation, the period τ, when the ON voltage is not applied to any of the lines L1 to Lx of the scanning lines 5, is not produced between the frames like FIG. 52. As shown in FIG. 54, after the readout process for the image data d of a certain frame is finished, the image data d of the next frame is subsequently started. The image data d is therefore temporarily continuously read out.

The radiation image capturing apparatus 1 can be therefore configured so as not to produce the period the period τ, during which the ON voltage is not applied to any of the lines L1 to Lx of the scanning lines 5 and the image data d is not readout. This can appropriately prevent the problem including the delay in detecting the initiation of the radioactive irradiation as described above. The radiation image capturing apparatus 1 itself can therefore accurately detect the radioactive irradiation.

The same applies to the case where the ON voltage is sequentially applied to the Lx to L1 scanning lines 5 so that the scanning line 5 to which the ON voltage is applied (or the corresponding terminal of each gate IC 12a) is shifted up sequentially starting from the last Lx scanning line 5 toward the L1 scanning line 5.

In that case, the radiation image capturing apparatus 1 is configured so that, at the timing subsequent to the timing when the ON voltage is applied to the L1 scanning line 5 and the terminal connected thereto, the seed signal is inputted to the gate IC 12a at the bottom in FIG. 53 and the ON voltage is applied to the terminal connected to the last Lx scanning line 5. By sequentially shifting the terminal to which the ON voltage is applied, similarly to the above, the radiation image capturing apparatus 1 can be configured so that the ON voltage is sequentially applied to the Lx to L1 scanning lines 5 without producing the period τ.

In each method below, the scanning line 5 to which the ON voltage is applied is sequentially shifted to the next scanning line 5 above starting from the last Lx scanning line 5 in some cases. The description about such a case is omitted but is the same as the case where the scanning line 5 to which the ON voltage is applied is sequentially shifted to the next scanning line 5 below starting from the first L1 scanning line 5.

[Method 2]

On the other hand, as described above, some of the gate ICs 12a are configured so that the seed signal once inputted cannot be outputted through the wiring Lse2 during the process of shifting the terminal or forcibly removed from the gate IC 12a by grounding within the gate IC 12a.

Figure 55:
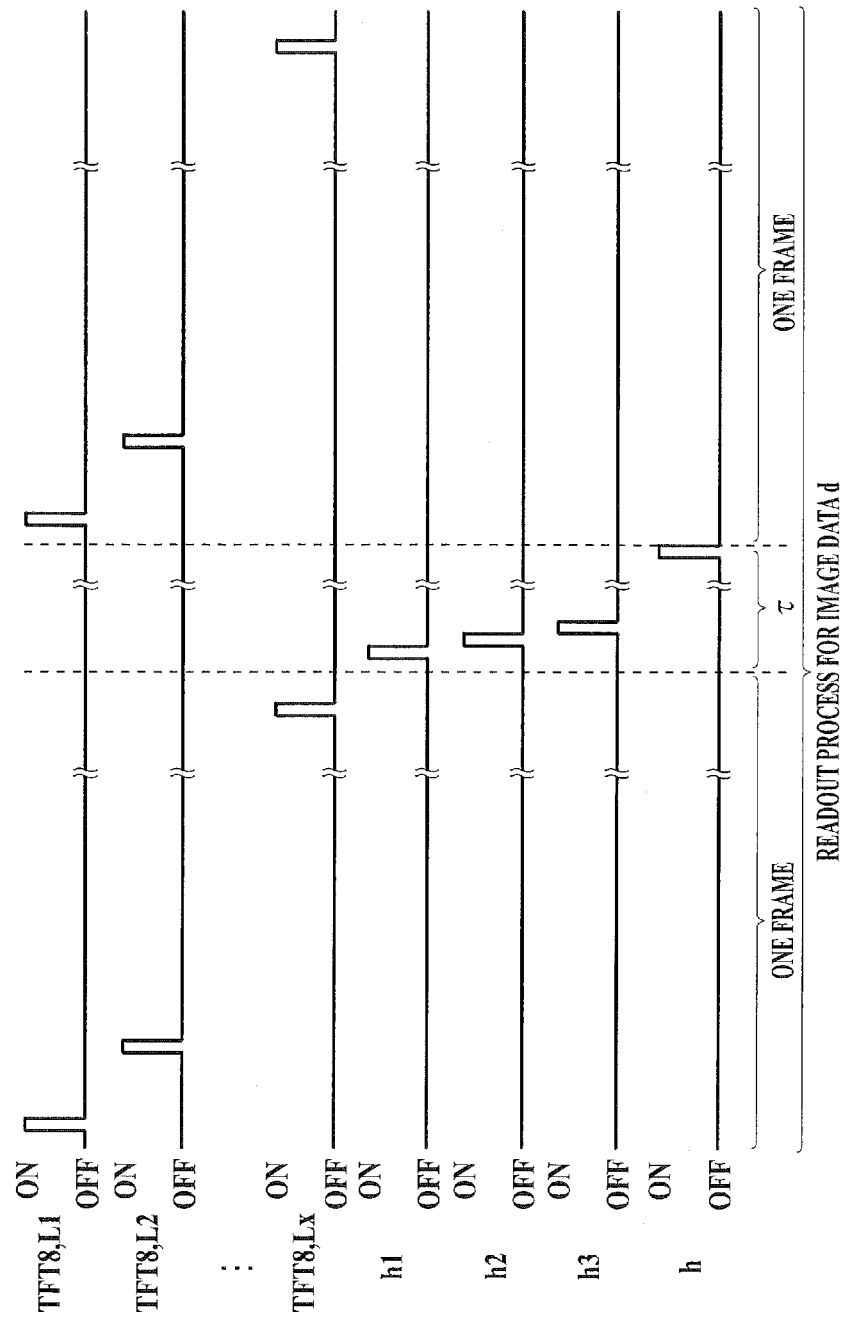
FIG. 55 is a timing chart explaining application timing of the ON voltage to terminals of the respective scanning lines and non-connecting terminals using Procedure 2.

In this case, for example, as shown in FIG. 55, the radiation image capturing apparatus 1 can be configured as follows. In the process of applying the ON voltage to the terminals of each gate IC 12a, the ON voltage is sequentially applied to the terminals of each gate IC 12a constituting the gate driver 15b in a manner that the ON voltage is sequentially applied to the non-connecting terminals h1, h2, . . . (see FIG. 53) of the gate IC 12a at shorter time intervals than the time intervals at which the ON voltage is sequentially applied to the terminals connected to the scanning lines 5.

Figure 56:
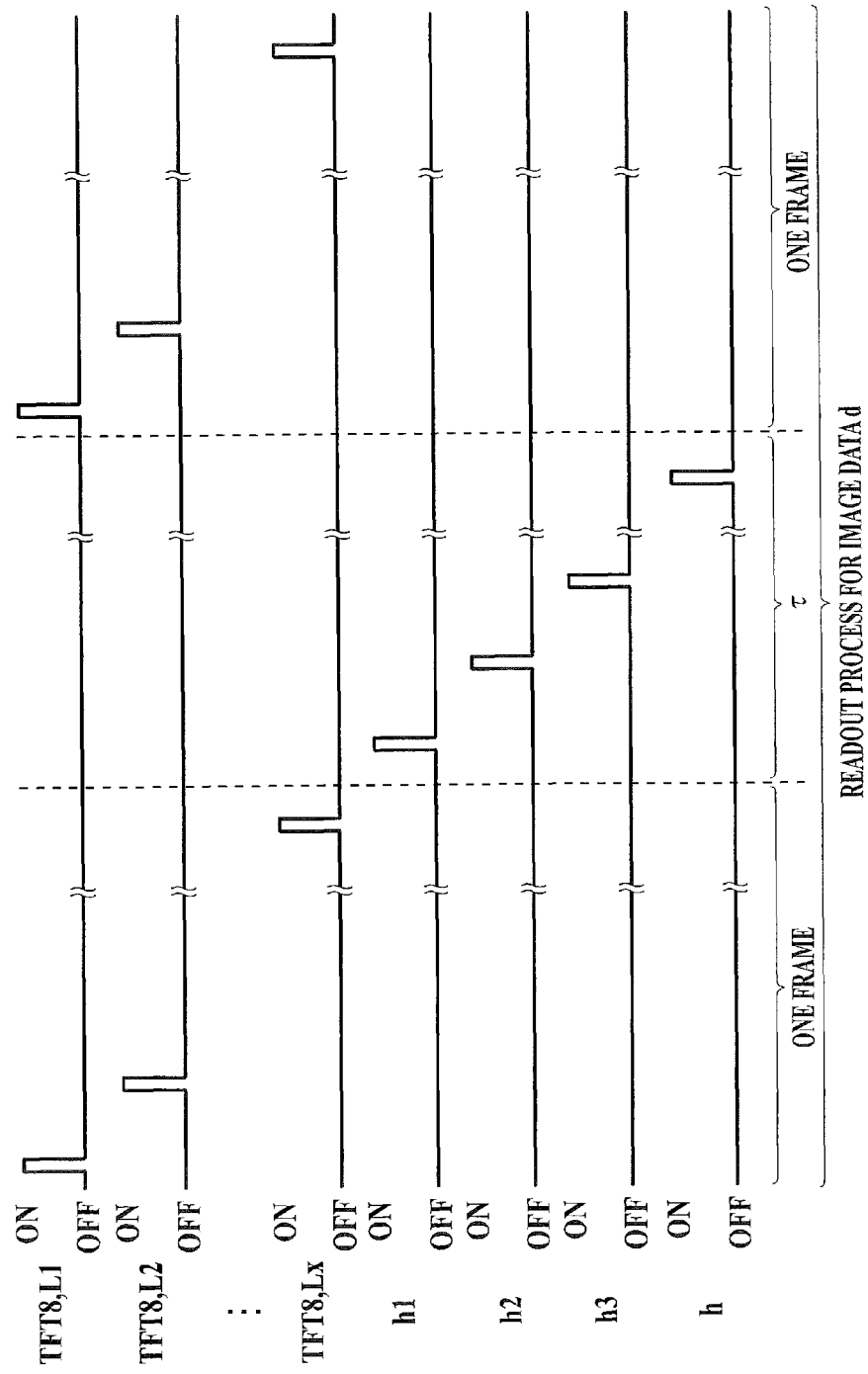
FIG. 56 is a timing chart explaining application timing of the ON voltage to terminals of the respective scanning lines and non-connecting terminals using the conventional procedure.

In a conventional normal way, as shown in FIG. 56, the ON voltage is sequentially applied to the terminals of each gate IC 12a in a manner that the ON voltage is sequentially applied to the non-connecting terminals h1, h2, . . . of the gate IC 12a at the same time intervals as the time intervals at which the ON voltage is sequentially applied to the terminals connected to the scanning lines 5.

Accordingly, in the readout process for the image data d before the radiation image capturing operation, the period τ, during which the ON voltage is applied to the non-connecting terminals h of the gate IC 12a and the image data d is not read out from any of the radiation detection elements 7, is long between the frames.

By contrast, as shown in FIG. 55, with a configuration, in which the ON voltage is sequentially applied to the non-connecting terminals h1, h2, . . . of the gate IC 12a at shorter time intervals than the time intervals at which the ON voltage is sequentially applied to the terminals connected to the scanning lines 5, the period τ, during which the ON voltage is applied to the non-connecting terminals h of the gate IC 12a and the image data d is not read out from any of the radiation detection elements 7, between the frames can be made shorter than that of the conventional case shown in FIG. 56.

Accordingly, since the period τ, during which the ON voltage is not applied to any one of the lines L1 to Lx of the scanning lines 5 and the image data d is not read out from any of the radiation detection elements 7, is shortened, even if the detection of the initiation of the radioactive irradiation is delayed as described above, the delay can be minimized. In addition, virtually, immediately after the readout process for the image data d of a frame is finished, the image d readout process for the next frame can be started. Accordingly, if the radioactive irradiation is started during the period τ, the radioactive irradiation can be then detected promptly.

Moreover, if the initiation of the radioactive irradiation is detected later than the actual initiation of the radioactive irradiation, the delay is very small, and the amount of dark electric charges accumulated within respective radiation detection elements is not greatly increased. The S/N ratio of the image data D as the final image read out is hardly reduced practically. In this manner, by employing the above Method 2, it is possible to prevent degradation of image data D as the final image read out and keep high the S/N ratio of the image data D.

FIG. 55 shows the case where the ON voltage is actually applied to the non-connecting terminals h1, h2, . . . of the gate IC 12a. As described above, the active terminal is shifted each time the shift signal is inputted to the gate IC 12a. However, it is unnecessary to apply the ON voltage to the non-connecting terminals h.

The radiation image capturing apparatus 1 can be therefore configured as follows in the case where the gate IC 12a is configured to shift the active terminal even if the ON voltage is not applied to the active terminal. If any one of the non-connecting terminals h is activated, the ON voltage is not applied, and only the active state thereof is shifted. When the terminal connected to any one of the scanning lines 5 is activated, the ON voltage is applied.

With this configuration, it is possible to prevent the power from being wasted by applying the ON voltage to the non-connecting terminals h. Also in Methods 3 to 6 below, the radiation image capturing apparatus 1 can be configured so that the ON voltage is not applied to an active non-connecting terminal h.

FIG. 55 shows a case where the time period when each non-connecting terminal h is activated (represented as a time period when the ON voltage is applied in FIG. 55) is set equal to the time period when the terminal connected to each scanning line 5 is activated. As described above, as for the non-connecting terminals h, the active state is just shifted among the terminals. It is therefore unnecessary to set as described above.

Accordingly, the time period when each non-connecting terminal h is activated is minimized by inputting the shift signals to the gate IC 12a at the shortest possible time intervals or by another means so that the active terminal is shifted promptly, for example. This can further shorten the time period τ, during which the ON voltage is applied to the non-connecting terminals h and the image data d is not read out from any of the radiation detection elements 7. The above-described effect can be therefore appropriately exerted.

[Method 3]

In the above Methods 1 and 2, it is assumed that only one seed signal can be inputted to the gate driver 15b composed of the plurality of gate ICs 12a. However, if two or more seed signals can be inputted at different timings, the radiation image capturing apparatus 1 can be configured in the following manner so as not to produce the period τ.

Specifically, for example, as described above, the seed signal is inputted through the wiring Lse1, sequentially starting from the top gate IC 12a shown in FIG. 53, and the shift signals are inputted through the wiring Lsh one after another. The ON voltage is then applied as the active terminal is sequentially shifted one by one from the top in the drawing. The ON voltage is therefore sequentially applied to the lines L1 to Lx of the scanning lines 5.

In the gate IC 12a at the bottom in FIG. 53, when the shift signal is inputted through the wiring Lsh at the next timing after the ON voltage is applied to the last Lx scanning line 5, the non-connecting terminal h1 of the gate IC 12a, which is next to the terminal connected to the Lx last scanning line 5, is activated.

At the same time as the shift signal is inputted to activate the non-connecting terminal h1, the seed signal is inputted through the wiring Lse1 to the gate IC 12a at the top in FIG. 53. By such a control, the non-connecting terminal h1 is activated, and simultaneously, the top terminal of the gate IC 12a at the top in FIG. 53, which is connected to the first L1 scanning line 5, is activated.

At this point of time, in short, the two terminals of the gate driver 15b (terminals of two different gate ICs 12a constituting the gate driver 15b) are simultaneously activated.

When the ON voltage is then supplied from the power source circuit 15a of the scanning drive unit 15 to the gate driver 15b in this state, the ON voltage is applied to the non-connecting terminal h1, and simultaneously, the ON voltage is applied to the top terminal of the gate IC 12a at the top in FIG. 53 to apply the ON voltage to the L1 first scanning line 5.

Subsequently, when the shift signal is inputted through the wiring Lsh, the both of two activated terminals described above are simultaneously shifted down in the drawing, so that the non-connecting terminal h2 and the terminal connected to the second L2 scanning line 5 are simultaneously activated. When the ON voltage is then supplied from the power source circuit 15a, the ON voltage is applied to the non-connecting terminal h2, and simultaneously, the ON voltage is also applied to the second terminal from the top of the gate IC 12a at the top in FIG. 53 to apply the ON voltage to the second L2 scanning line 5.

By repeating the above control, the activated terminals are individually shifted. One of the non-connecting terminals h and one of the terminals connected to the scanning lines 5 are simultaneously activated until the last one of the non-connecting terminals h is activated. On voltage therefore continues to be applied to one of the non-connecting terminals h and one of the scanning lines 5.

Figure 57:
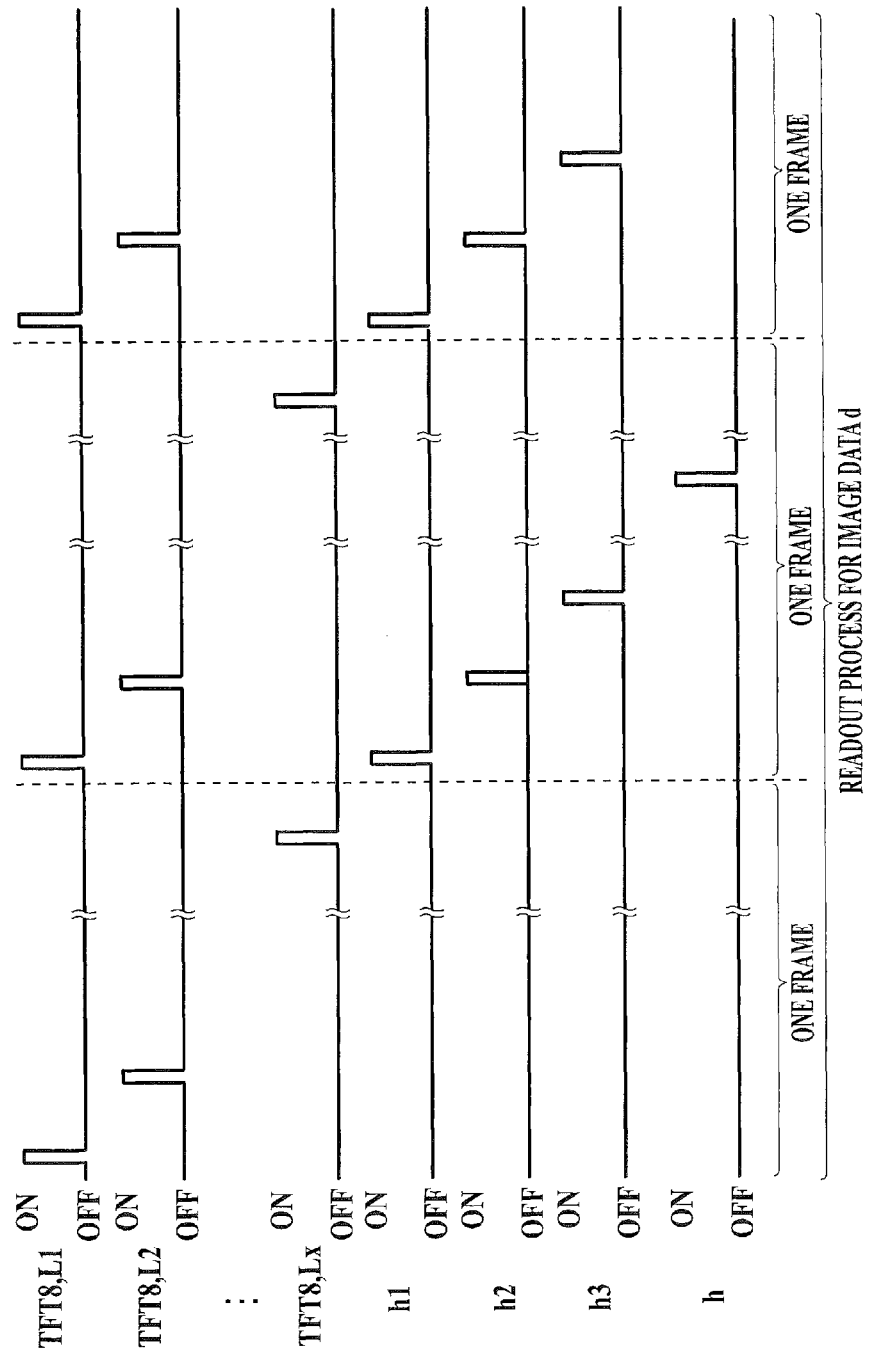
FIG. 57 is a timing chart explaining application timing of the ON voltage to terminals of the respective scanning lines and non-connecting terminals using Procedure 3.

As shown in FIG. 57, as for the lines L1 to Lx of the scanning lines 5, at the timing subsequent to the timing when the ON voltage is applied to the last Lx scanning line 5, the ON voltage is applied to the first L1 scanning line 5, restarting the readout process for the image data d for the next frame.

By employing the above Method 3, in such a manner, in the readout process for the image data d before the radiation image capturing operation, as shown in FIG. 57, when the readout process for the image data d for a certain frame is finished, the readout process for the image data d for the next frame is then continuously started, and the image data d is temporarily continuously read out. The period τ, during which the ON voltage is not applied to any one of the lines L1 to Lx of the scanning lines 5, is not produced between the frames as shown in FIG. 52.

Therefore, the radiation image capturing apparatus 1 can be configured so as not to produce the period τ, during which the ON voltage is not applied to any one of the lines L1 to Lx of the scanning lines 5 and the image data d is not read out. This can appropriately prevent the problems including the delay in detecting the initiation of the radioactive irradiation as described above. The radiation image capturing apparatus 1 itself therefore can accurately detect the radioactive irradiation.

In this case, as described above, when the ON voltage is applied to the terminals connected to the scanning lines 5 to apply the ON voltage to the scanning lines 5, the ON voltage is simultaneously applied to the non-connecting terminals h. This can waste electric power or give some kind of bad influence to the ON voltage applied to each scanning line 5 in some cases.

Figure 58:
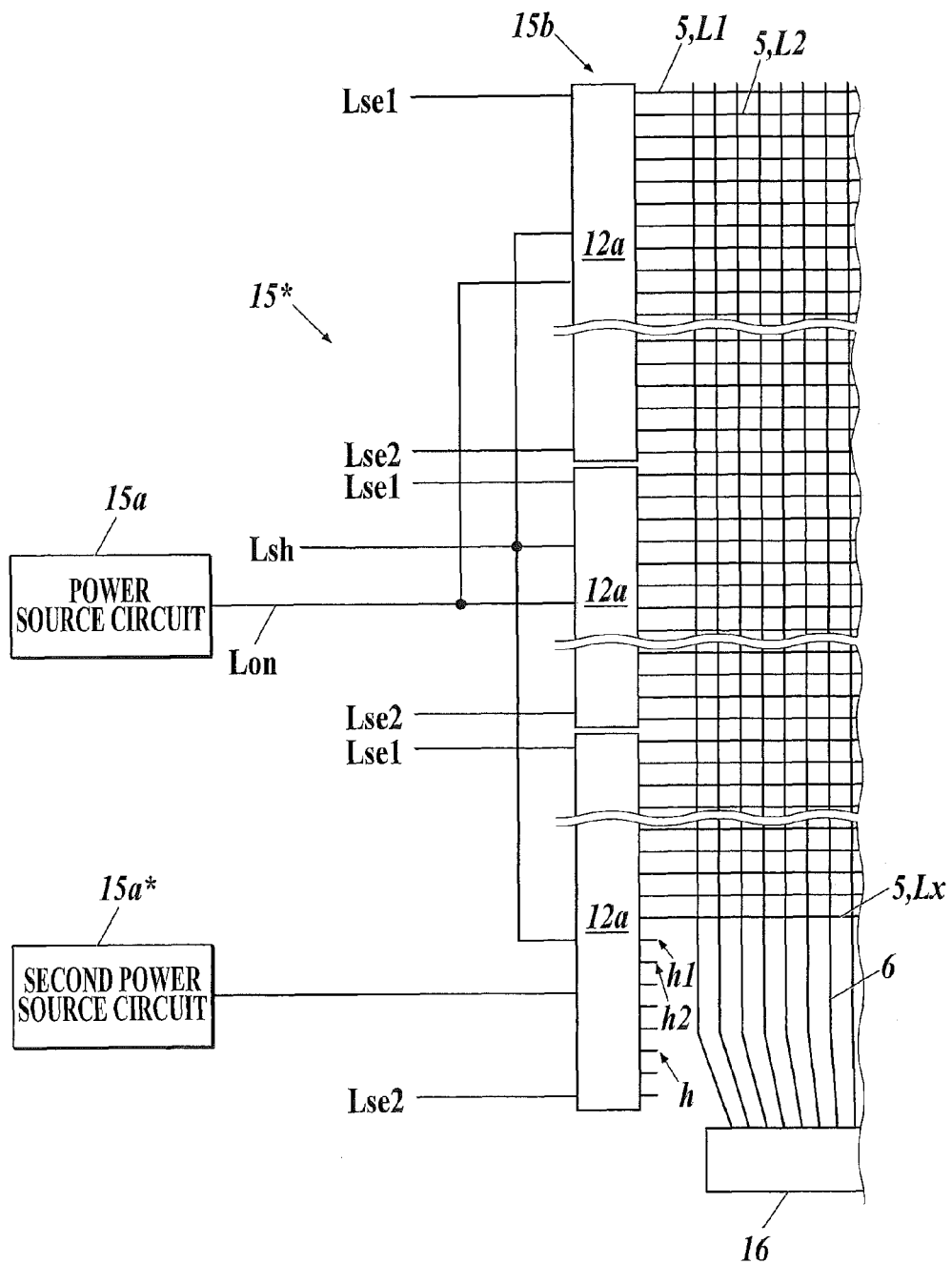
FIG. 58 is a view showing a configuration and so on of a modification of the scanning drive unit shown in FIG. 53.

In that case, like a scanning drive unit 15* shown in FIG. 58, for example, a second power source circuit 15a*, which supplies the ON voltage to the gate IC 12a including the non-connecting terminals h, can be provided separately from the power source circuit 15a, which supplies the ON voltage to each gate IC 12a whose terminals are connected to the scanning lines 5.

The radiation image capturing apparatus 1 can be configured as follows. At the timing of activating any one of the terminals connected to any scanning line 5 in the gate IC 12a including the non-connecting terminals h, the ON voltage is supplied to the gate IC 12a from the second power source circuit 15a. At the time of activating any one of the non-connecting terminals h, the ON voltage is supplied to the gate IC 12a from the second power source circuit 15a*.

The above configuration can appropriately prevent the electric power from being wasted by supplying the ON voltage to the non-connecting terminals h or the ON voltage applied to each scanning line 5 is influenced.

[Method 4]

Figure 59:
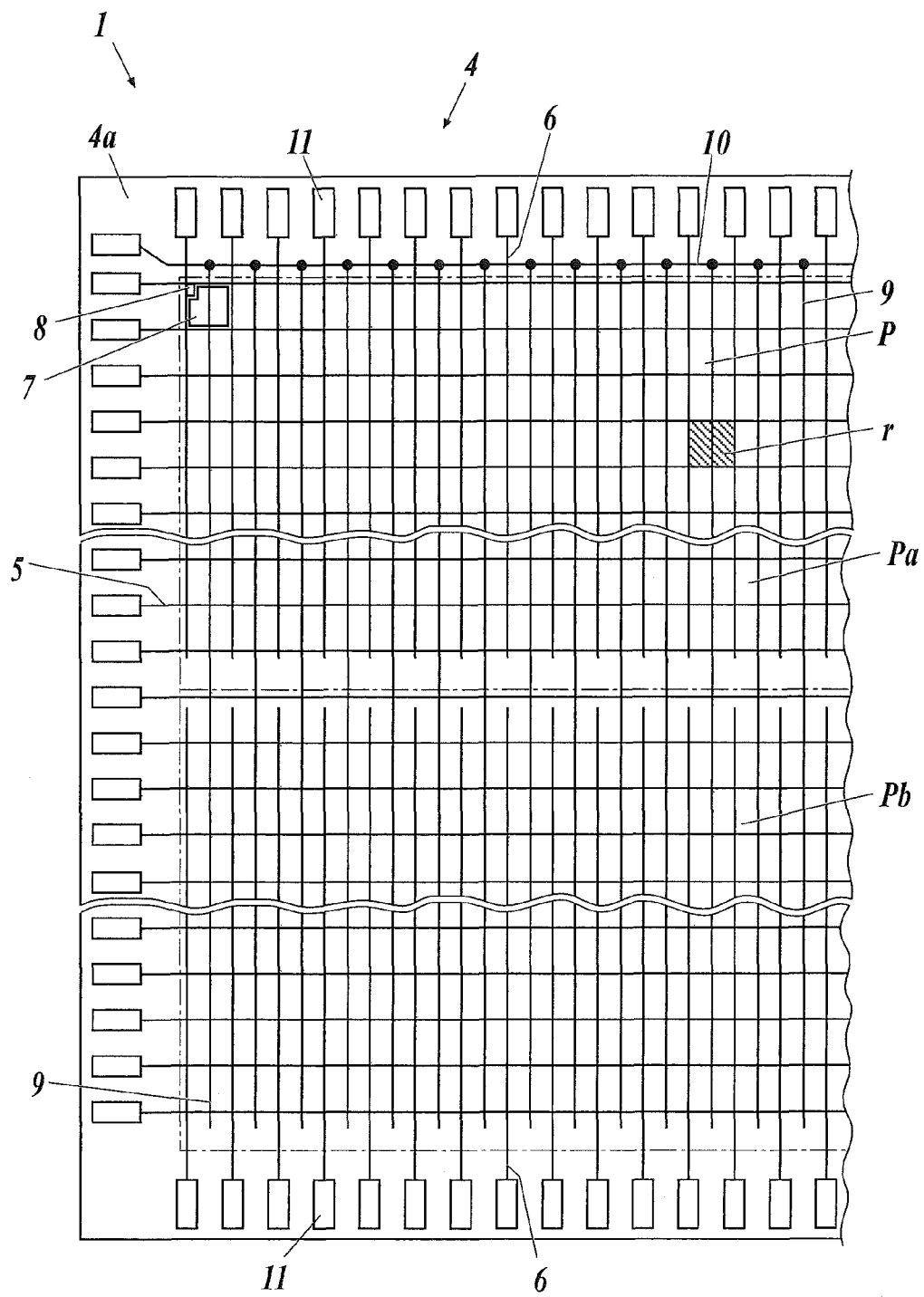
FIG. 59 is a plan view showing a configuration of the substrate of the radiation image capturing apparatus in which each signal line is decoupled halfway in an extending direction.
Figure 60:
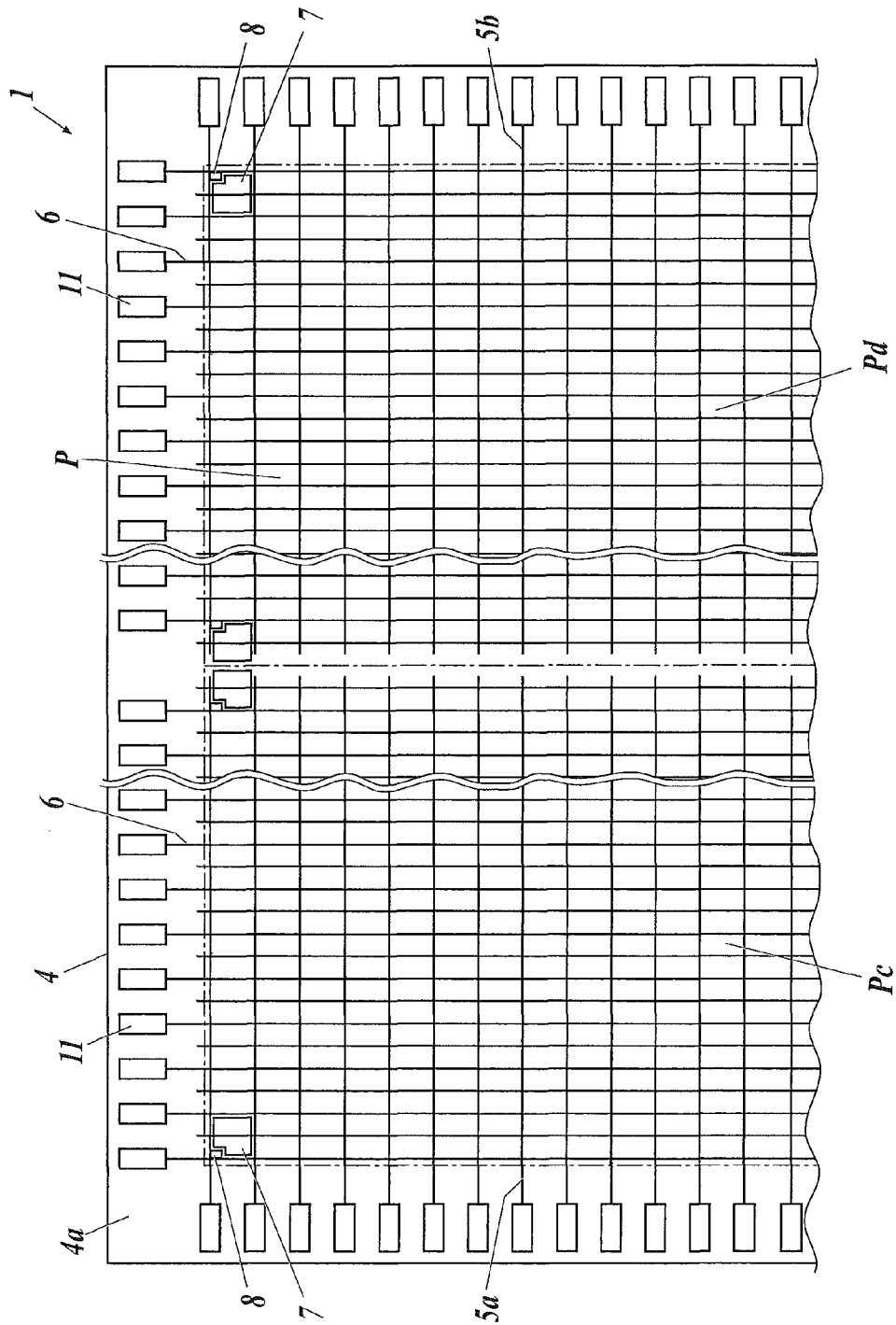
FIG. 60 is a plan view showing a configuration of the substrate of the radiation image capturing apparatus in which each scanning line is decoupled halfway in an extending direction.

On the other hand, in some radiation image capturing apparatus, the detecting section P is divided into a plurality of regions as shown in FIGS. 59 and 60, for example. For example, in the radiation image capturing apparatus 1 shown in FIG. 59, the signal lines 6 are decoupled halfway in the extending direction thereof, and the detecting section O is divided into two regions Pa and Pb.

In the radiation image capturing apparatus 1 shown in FIG. 60, for example, the scanning lines 5 are decoupled halfway in the extending direction thereof on the detecting section P, and the detecting section P is divided into two regions Pc and Pd. For example, the radiation image capturing apparatus can be also configured so that both of the scanning lines 5 and the signal lines are decoupled halfway in the extending directions thereof and the detecting section P is divided into four regions, for example.

Figure 61:
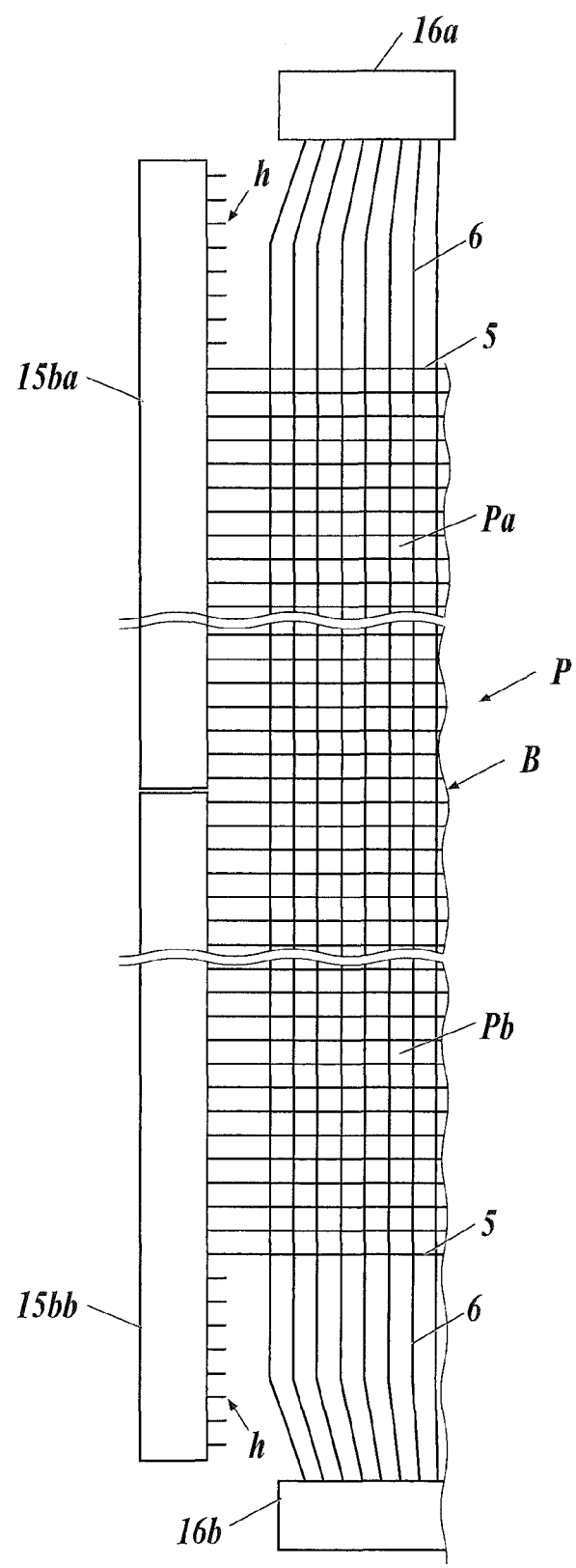
FIG. 61 is a view explaining that in a case of FIG. 59, each of the scanning lines and signal lines in different regions in the detecting section are connected to different gate drivers and different reading ICs.

In the example of FIG. 59, the scanning lines 5 of the region Pa of the detecting section P and the scanning lines 5 of the region Pb thereof are connected to different gate drivers 15ba and 15bb, respectively, as shown in FIG. 61. The signal lines 6 of the region Pa of the detecting section P and the signal lines 6 of the region Pb thereof are connected to different reading ICs 16a and 16b, respectively.

In some cases, the radiation image capturing apparatus 1 is configured so that the ON voltages are independently applied to the scanning lines 5 of the region Pa from the gate driver 15ba and to the scanning lines 5 of the region Pb from the gate driver 15bb. The gate drivers 15ba and 15bb are each composed of a plurality of gate ICs 12a arranged side by side, which are not shown. As shown in FIG. 61, the gate drivers 15ba and 15bb include non-connecting terminals ha and hb at the extremities thereof, respectively.

In this case, for example, when the readout process for the image data d before the radiation image capturing operation is executed in a manner that the scanning lines 5 to which the ON voltage is applied are shifted from the boundary B sides of the regions Pa and Pb toward the reading ICs 16a and 16b, respectively (in the region Pa, shifted up in the drawing, and in the region Pb, shifted down in the drawing), the non-connecting terminals h of the regions Pa and Pb can be activated at the same time in some cases.

If the non-connecting terminals h of the regions Pa and Pb are activated simultaneously in this manner, during that time, the period τ, during which the ON voltage is not applied to any one of the lines L1 to Lx of the scanning lines 5 and the image data d is not read out, is produced, thus causing the above-described problem.

In Method 4, as shown in FIGS. 59 and 60, in the case where the detecting section P is divided into a plurality of regions in a manner that the scanning lines 5 and/or signal lines 6 are decoupled halfway in the extending directions thereof on the detecting section P and each region is provided with the gate driver 15 which includes non-connecting terminals h, the ON voltage is applied to each L scanning line 5 in the following manner at least in the readout process for the image data d after the radiation image capturing operation.

Specifically, in the process of sequentially applying the ON voltage to the scanning lines 5 from the gate drivers 15ba and 15bb, at the timing when the ON voltage is applied to any non-connecting terminal h in one of the gate drivers 15b (for example, the gate driver 15ba), the ON voltage is applied to the terminal connected to any scanning line 5 in the other gate driver 15b (for example, the gate driver 15bb). The ON voltage is thus applied to anyone of the scanning lines 5 at each point of timing. The ON voltage is thus sequentially applied to the scanning lines 5 from the gate drivers 15ba and 15bb.

To be specific, for example, in the case where the readout process for the image data d is executed in a manner that the scanning lines 5 to which the ON voltage is applied are shifted from the boundary B sides of the regions Pa and Pb toward the reading ICs 16a and 16b, respectively, as described above, the scanning line 5 to which the ON voltage is applied, that is, the active terminal, starts to be shifted from the boundary b side in the region Pa at timing different from the timing when the active terminal starts to be shifted in the region Pb.

For example, the radiation image capturing apparatus 1 is configured as follows. When the readout process in the region Pa is started earlier than the readout process in the region Pb is started, the terminal connected to any scanning line 5 is activated in the region Pb at the timing when any non-connecting terminal h is active in the region Pa. At the timing when any non-connecting terminal h is activated later in the region Pb, the procedure is already moved to the readout process for the next frame in the region Pa to activate the terminal connected to any scanning line 5.

Moreover, for example, the radiation image capturing apparatus 1 can be configured as follows. The readout process for the image data d is executed in a manner that the scanning line 5 to which the ON voltage is applied is shifted from the non-connecting terminal h side on the reading IC 16a side in the region Pa and the scanning line 5 to which the ON voltage is applied is shifted from the boundary B side of the region Pb toward the non-connecting terminal h side on the reading IC 16a side in the region Pb. In the both regions Pa and Pb, the active terminals are shifted from the top to the bottom in the drawing.

With the aforementioned configuration, at the timing when the ON voltage is sequentially applied from the gate drivers 15ba and 15bb to the scanning lines 5, even when the non-connecting terminal h is active in one of the gate drivers 15b and the ON voltage is not applied any one of the scanning lines 5 connected to the gate driver 15b, in the other gate driver 15b, any one of the terminals connected to the scanning lines 5 is always active, and the ON voltage is applied to the scanning line 5 connected thereto.

Accordingly, by employing Method 4, in the readout process for the image data d before the radiation image capturing operation, production of the period τ, during which the ON voltage is not applied to any one of the lines L1 to Lx of the scanning lines 5, is prevented, and the readout process for the image data d is executed in at least one of the regions Pa and Pb at each timing.

Accordingly, the image data d can be read out temporarily continuously, and the problems including the delay in detecting the initiation of the radioactive irradiation as described above can be prevented. The radiation image capturing apparatus 1 itself can therefore accurately detect the radioactive irradiation.

(Method 5)

In the description of the aforementioned Methods 1 to 4, the period τ, during which the image data d is not read out, is prevented from being produced or is minimized in the following manner: the readout process for the image data d is executed using only the terminals connected to the scanning lines 5 (Method 1); the period τ, during which the non-connecting terminals h are activated, is shortened (Method 2); or the terminal connected to any scanning line 5 is activated to apply the ON voltage when any non-connecting terminal h is activated (Methods 3, 4).

As previously described, the above configurations are for the purpose of accurately detecting the initiation of the radioactive irradiation to the radiation image capturing apparatus 1 based on the read image data d by utilizing the fact that the image data d read in the readout process before the radiation image capturing operation is considerably larger at the initiation of the radiation of irradiation to the radiation image capturing apparatus 1 than the image data read before.

Figure 34:
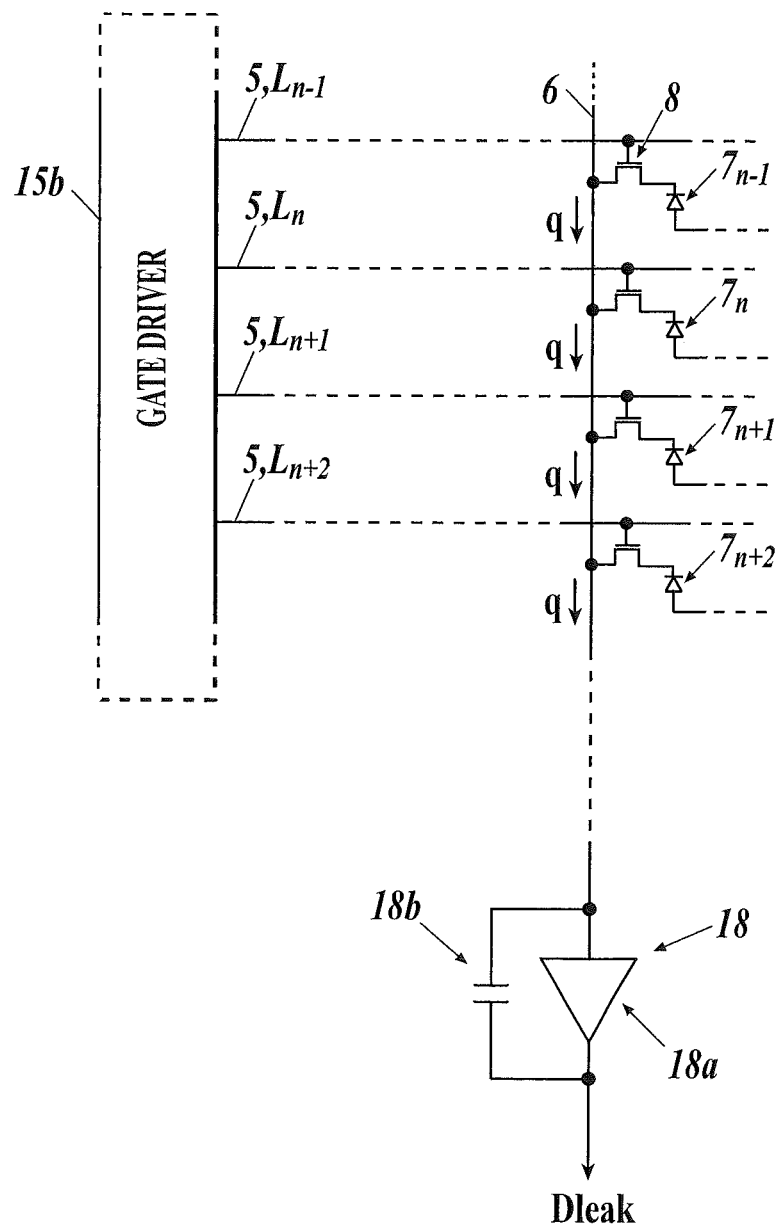
FIG. 34 is a view explaining that an electric charge, which leaks from each radiation detection element through each TFT, is read out as the leaked data.

On the other hand, as shown in FIGS. 33 and 34 previously described, according to the study of the inventors, it is known that similar to the above-described image data d, the aforementioned leaked data Dleak at the initiation of the radioactive irradiation to the radiation image capturing apparatus 1 has a value considerably larger than the leaked data Dleak obtained before. The leaked data Dleak is obtained by applying the OFF voltage to all the scanning lines 5 without applying the ON voltage to each of the scanning lines 5 to turn off each of the TFTs 8 and reading electric charges q leaking from each radiation detection element 7 through the corresponding TFT 8 by each reading circuit 17 including the amplifier circuit 18.

Accordingly, the radiation image capturing apparatus 1 can be configured so that, in the readout process for the image data d before the radiation image capturing operation, the leaked data Dleak is read out instead of the image data d during at least the period τ, that is, during the period τ during which the ON voltage is not applied to any one of the lines L1 to Lx of the scanning lines 5 and the image data d is not read out since only the non-connecting terminals h are active, and the initiation of the radioactive irradiation to the radiation image capturing apparatus 1 is detected based on the read leaked data Dleak.

In Method 5, a description is given a configuration to detect the initiation of the radioactive irradiation to the radiation image capturing apparatus 1 based on the image data d and leaked data Dleak as described above.

The process of reading out the leaked data Dleak is described in more detail. When any of the non-connecting terminals h of the gate driver 15b is active, the OFF voltage is applied to the lines L1 to Lx of the scanning lines 5.

In this state, each of the reading circuits 17 is operated as shown in FIG. 33 described above. Specifically, in a similar manner to the case of the readout process for the image data d, the electric charge reset switch 18c (see FIG. 18) of the amplifier circuit 18 of the reading circuit 17 is turned off so that the electric charge accumulate in the capacitor 18b. The pulse signals Sp1 and Sp2 are sent from the controller 22 to the correlated double sampling circuit 19 for sampling. During that time, each TFT 8 is not turned on or off.

When each reading circuit 17 is operated in the manner as shown in FIG. 34 described above, the electric charge q leaking from each radiation detection element 7 through the TFT 8, which is turned off, are accumulated in the capacitor 18b of the amplifier circuit 18. Accordingly, the amplifier circuit 18 outputs a voltage value corresponding to the sum of the accumulated electric charges, that is, the electric charges q leaking from the radiation detection elements 7. The outputted voltage value is sampled by the correlation double sampling circuit 19, which is not shown in FIG. 34, and the leaked data Dleak is read out.

With the above configuration, a very small amount of electric charge q leaks from each radiation detection element 7i through each TFT 8 before the radiation image capturing apparatus 1 is irradiated with the radiation, and the sum of the electric charges q is very small. The leaked data Dleak therefore has a small value. After the radioactive irradiation to the radiation image capturing apparatus 1 is started, the amount of electric charge q leaking from each radiation detection element 7 through each TFT 8 increases, and the sum thereof increases. Accordingly, similarly to the increase in the value of the image data d described above, the read value of the leaked data Dleak increases.

Figure 62:
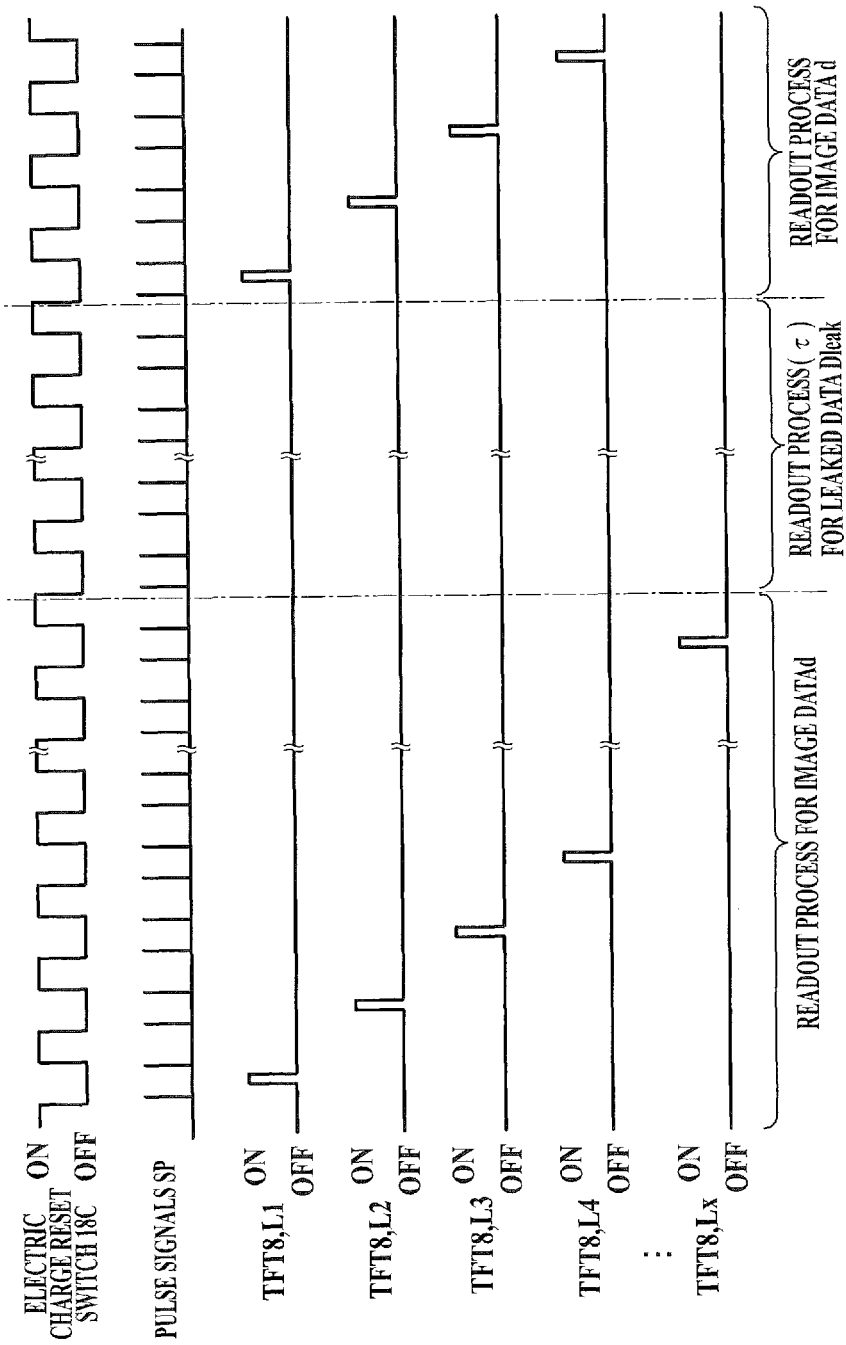
FIG. 62 is a timing chart explaining application timing to which the ON voltage is applied to each scanning line and ON/OFF operation of the electric charge reset switch and the like, in the image data readout process and the leaked data readout process.

Accordingly, as shown in FIG. 62, for example, the radiation image capturing apparatus 1 can be configured so that the leaked data Dleak is regularly read out during the above-described period τ. The initiation of the radioactive irradiation is detected in a manner that if the read leaked data Dleak greatly increases and exceeds a previously set threshold, it is determined at that time that the radioactive irradiation to the radiation image capturing apparatus 1 is initiated.

In the case shown in FIG. 62, during the readout process for the image data d before the radiation image capturing operation, the value of the image data d is monitored as described above. Moreover, during the period τ, during which any non-connecting terminal h is active (or the period τ during which the OFF voltage is applied to all the lines L1 to Lx of the scanning lines 5), the value of the leaked data Dleak which is read out in the readout process for the leaked data Dleak shown in FIG. 33 is monitored. Accordingly, the initiation of the radioactive irradiation to the radiation image capturing apparatus 1 can be detected when any one piece of the image data d or leaked data Dleak greatly increases.

As described above, by employing Method 5, in the readout process for the image data d before the radiation image capturing operation, it is possible to accurately detect the initiation of the radioactive irradiation onto the radiation image capturing apparatus 1 based on the image data d during the readout process for the image data d and based on the leaked data Dleak during the period τ during which the readout process for the image data d is not executed.

This can eliminate the period τ during which the radioactive irradiation to the radiation image capturing apparatus 1 cannot be detected, and allow detection of the radioactive irradiation to be always performed. Accordingly, it is possible to appropriately prevent the problems including the delay in detecting the initiation of the radioactive irradiation as described above. The radiation image capturing apparatus 1 itself can therefore accurately detect the radioactive irradiation.

Figure 63:
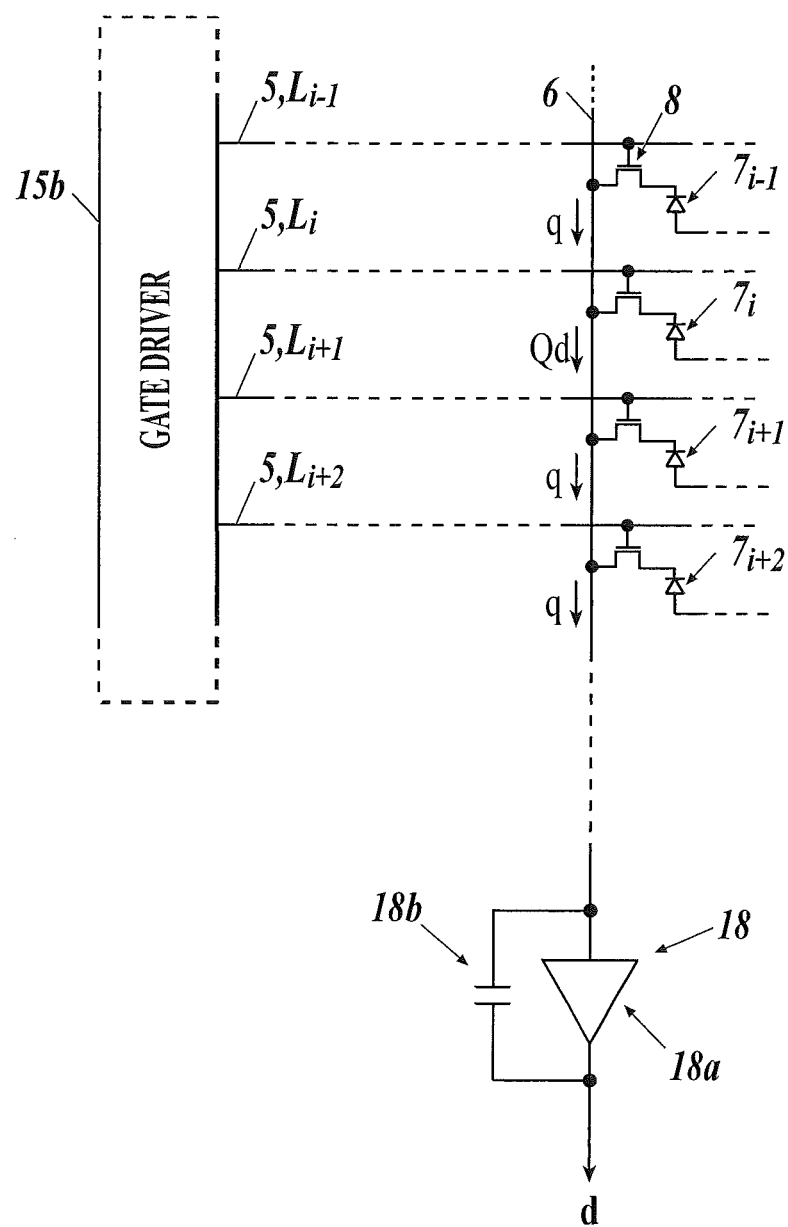
FIG. 63 is a view explaining that in the image data d, data due to dark electric charges discharged from the radiation detection elements and the leaked data corresponding to the electric charge leaked from each radiation detection elements via each TFT are included.

As shown in FIG. 63, the image data d read out before the radiation image capturing operation includes the leaked data Dleak corresponding to the sum of the electric charges q leaking from the other radiation detection elements 7 shown in FIG. 34, and further includes data due to the dark electric charge Qd discharged from the radiation detection element 7 connected to the scanning line 5 to which the ON voltage is applied (the Li scanning line 5 in FIG. 63). Accordingly, the read out value of the leaked data Dleak is normally smaller than the value of the image data d.

Concerning the threshold value used to determine whether the radiation image capturing apparatus 1 is irradiated with the radiation, preferably, the threshold value dth for the image data d (see FIG. 11) and the threshold value for the leaked data Dleak are set different from each other. The radiation image capturing apparatus 1 can be configured so that the thresholds for the both are set to the same value. The thresholds for the image data d and leaked data Dleak are set to appropriate values.

[Method 6]

In the description of the above-described Method 5, in the readout process for the image data d before the radiation image capturing operation, the readout process for the leaked data Dleak is executed only during the period τ, during which any of the non-connecting terminals his activated and the image data d is not read out, and the readout process for the image data d is executed in the other period (see FIG. 62 and the like).

However, the radiation image capturing apparatus 1 can be also configured so that the readout process for the leaked data Dleak is repeatedly executed before the radiation image capturing operation instead of the readout process for the image data d. In Method 6, a description is given of a configuration to detect the initiation of the radioactive irradiation to the radiation image capturing apparatus 1 only based on the leaked data Dleak without performing the readout process for the image data d.

Figure 64:
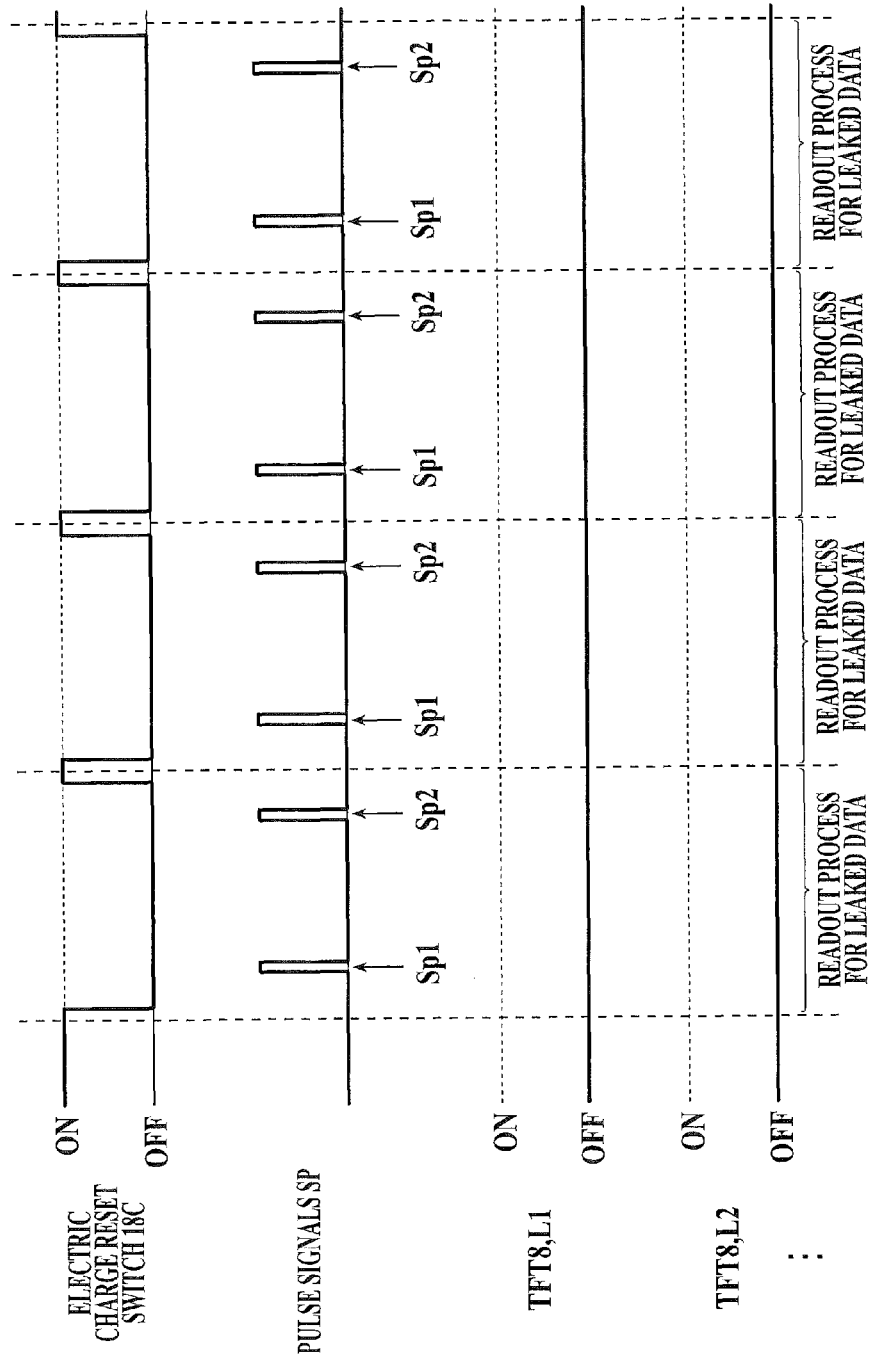
FIG. 64 is a timing chart showing ON/OFF timing of the electric charge reset switch, pulse signals, and the TFTs in a case of making a configuration in which the leaked data readout process is repeated before initiating the radiation image capturing operation.

In this case, the radiation image capturing apparatus 1 can be also configured as follows. Before the radiation image capturing operation, in a state where the OFF voltage is applied from the scanning drive unit 15 to all the lines L1 to Lx of the scanning lines 5 to turn off the TFTs 8, the control to each reading circuit 17 shown in FIG. 33 is repeated. Specifically, ON/OFF control of the electric charge reset switch 18c of the amplifier circuit 18 of the reading circuit 17, transmission of the pulse signals Sp1 and Sp2 to the correlated double sampling circuit 19, and the like are repeated. The readout process for the leaked data Dleak can be thus continuously executed as shown in FIG. 64.

However, if each TFT 8 continues to be off in the above manner, dark electric charge generated within each radiation detection element 7 are accumulated within the radiation detection element 7, and the amount of accumulated dark electric charge continues to increase. Actually, as shown in FIG. 65, preferably, the process of resetting each radiation detection element 7 is executed between the readout process for the leaked data Dleak and the subsequent readout process for the leaked data Dleak as the scanning line 5 to which the ON voltage is applied is sequentially shifted.

From the viewpoints of preventing that dark electric charge continue to accumulate within each radiation detection element 7, instead of the configuration to perform the process of resetting each radiation detection element 7 between the readout processes for the leaked data Dleak, as shown in FIG. 66, the radiation image capturing apparatus 1 can be configured so as to perform the readout process for the image data d between the readout processes for the leaked data Dleak. Moreover, in the case described below, the readout process for the leaked data Dleak is executed between the readout processes for the leaked data Dleak. However, the same explanation applies to the case where the readout process for the image data d is executed between the readout processes for the leaked data Dleak.

In the case of the configuration where the readout process for the leaked data Dleak and the process of resetting each radiation detection element 7 are alternately repeated as described above, the terminal of the gate driver 15b to which the ON voltage is sequentially applied (including the non-connecting terminals h, see FIG. 53 and the like) is sequentially shifted as previously described in the process of resetting each radiation detection element 7.

As shown in FIG. 67, at the timing when the ON voltage is sequentially applied to the terminals connected to the scanning lines 5 of the gate driver 15b, the ON voltage is sequentially applied to the lines L1 to Lx of the scanning lines 5 from the gate driver 15b through the terminals to discharge the electric charges remaining in the radiation detection elements 7 connected to the scanning lines 5 for the reset process.

Moreover, at the time when the ON voltage is applied to the non-connecting terminals of the gate driver 15b, the ON voltage is sequentially applied to the non-connecting terminals h from the gate driver 15b, but the ON voltage is not applied to any of the scanning lines 5 through these non-connecting terminals h. Accordingly, during this time, the process of resetting the radiation detection elements 7 is not executed.

FIG. 67 shows a case where the ON voltage is actually applied to the non-connecting terminals h1, h2, . . . of the gate IC 12a. However, it is not necessary to apply the ON voltage to the non-connecting terminals h. Accordingly, as previously described, the radiation image capturing apparatus 1 can be configured so as not to apply the ON voltage to the non-connecting terminals h and only shift the active state thereof.

With this configuration, similarly to the case described in the above Method 5, a very small amount of electric charge q leaks from the radiation detection element 7i through the TFT 8 before the radiation image capturing apparatus 1 is irradiated with radiation, and the sum of the electric charges q is very small. The value of the leaked data Dleak read by each readout process therefore has a small value. However, after the radioactive irradiation to the radiation image capturing apparatus 1 is started, the amount of electric charge q leaking from each radiation detection element 7 through the TFT 8 increases, and the sum thereof increases. Accordingly, similarly to the increase in the value of the image data d described above, the read value of the leaked data Dleak increases.

Accordingly, the radiation image capturing apparatus 1 can be configured as follows. A threshold value is previously provided for the leaked data Dleak. The initiation of the radioactive irradiation is detected in a manner that if the read leaked data Dleak greatly increases and exceeds the previously set threshold value, it is determined that the radioactive irradiation onto the radiation image capturing apparatus 1 is initiated.

However, the study of the inventors reveals that the following phenomenon appears in the case where the readout process for the leaked data Dleak and the process of resetting each radiation detection element 7 are alternately repeated before the radiation image capturing operation as described above.

Figure 68A:
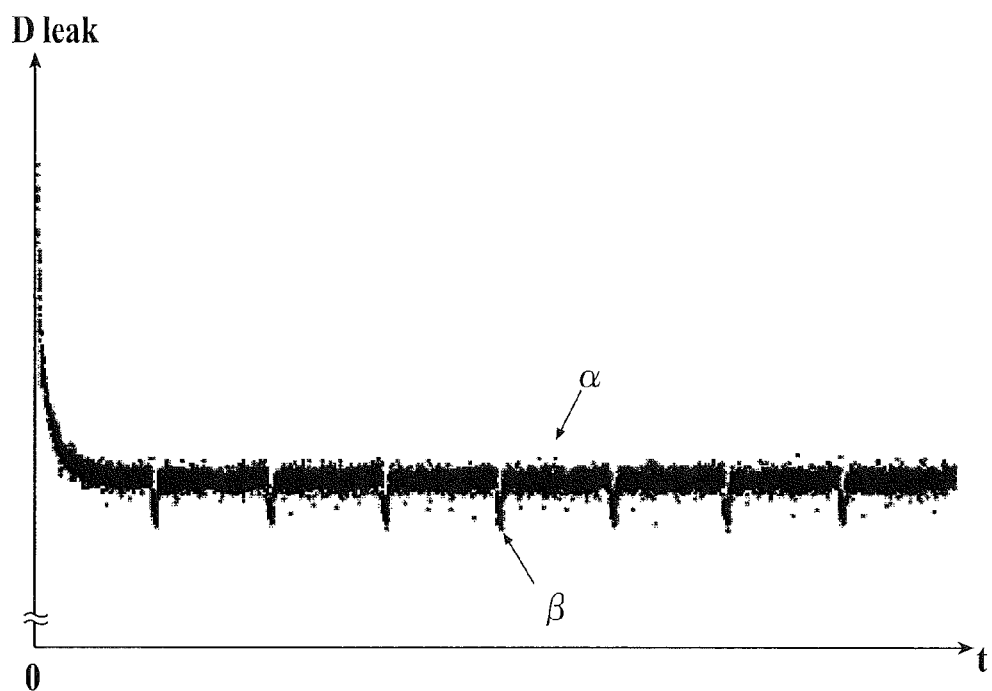
FIG. 68A is a graph showing a time shift of the leaked data read out in a case of executing the leaked data readout process and the reset process of each of the radiation detection elements are executed alternately.

Specifically, as shown in FIG. 68A, it is revealed that, with regard to the leaked data Dleak read out at each leaked data Dleak readout process, the leaked data Dleak which is read out at the readout process when the non-connecting terminals h are activated and the process of resetting each radiation detection element 7 is not executed (see data of the part indicated by β in the drawing) is smaller than the leaked data Dleak which is read out at the readout process executed after the ON voltage is applied to the scanning lines 5 for the process of resetting each radiation detection element 7 (see data of the part indicated by α in the drawing).

Figure 68B:
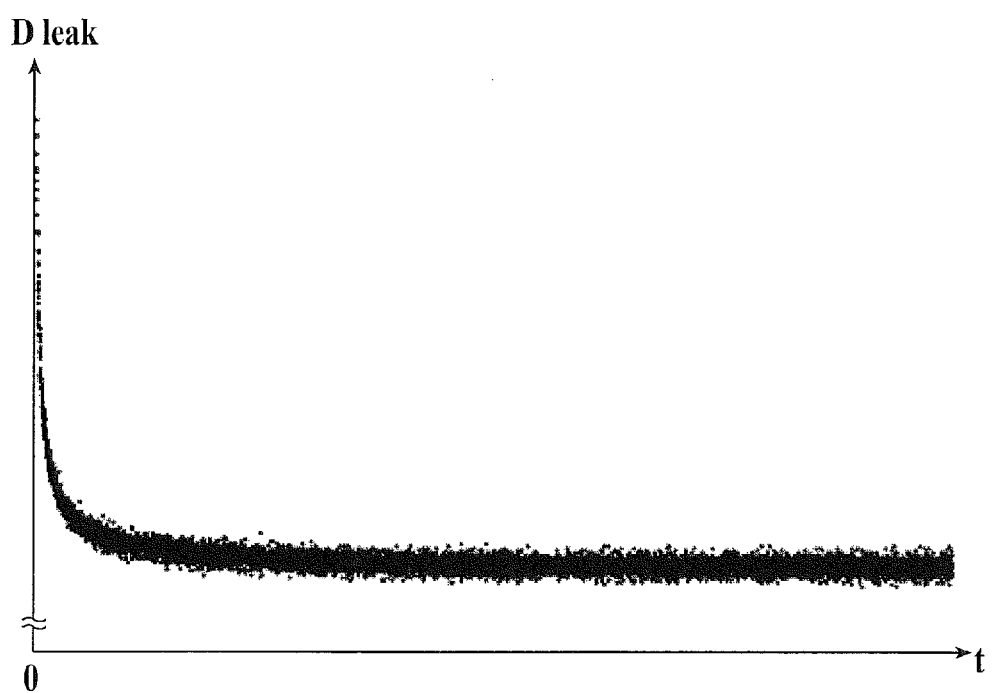
FIG. 68B is a graph showing a time shift of the leaked data read out in a case of executing only the leaked data readout process repeatedly.

As a control experiment for the above, only the readout process for the leaked data Dleak is repeated instead of alternately repeating the readout process for the leaked data Dleak and the process of resetting each radiation detection element 7 as described above. FIG. 68B shows the leaked data Dleak read out at each leaked data Dleak readout process over time.

As shown in FIG. 68B, the read out values of the leaked data Dleak in the control experiment are smaller than the values of the leaked data Dleak of the part indicated by a in FIG. 68A, that is, the values of the leaked data Dleak read out at the readout process executed after the process of resetting each radiation detection element 7. Moreover, the control experiment shows characteristics that there is no part in the leaked data Dleak having smaller values than the other leaked data unlike the leaked data Dleak of the part indicated by β in FIG. 68A.

The reason why the leaked data Dleak read out at the readout process in the state where the process of resetting each radiation detection element 7 is not executed (see data of the part indicated by α in FIG. 68A) is smaller than the leaked data Dleak read out at the readout process executed after the process of resetting each radiation detection element 7 (see the part indicated by β in FIG. 68A and FIG. 68B) is considered as follows.

Figure 69A:
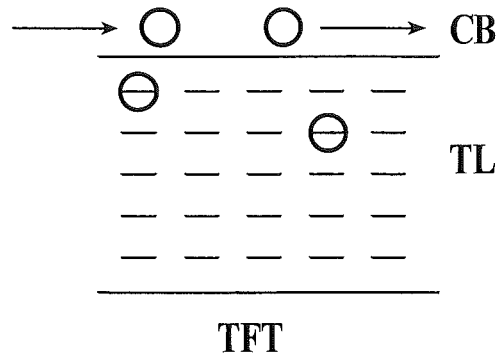
FIG. 69A is an image view explaining that an amount of the leaked electric charge is small when the reset process of each of the radiation detection elements is not executed immediately before.
Figure 69B:
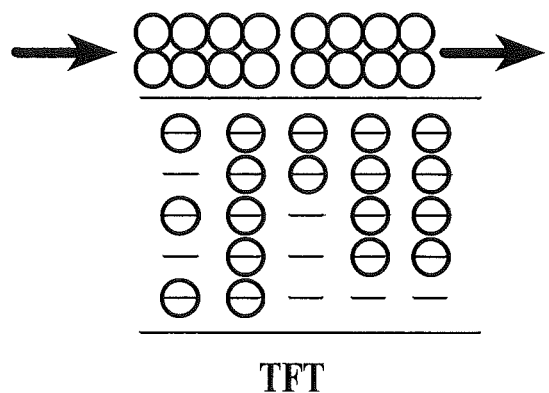
FIG. 69B is an image view explaining that in the reset process, a part of the electric charge discharged is trapped at a trap level.
Figure 69C:
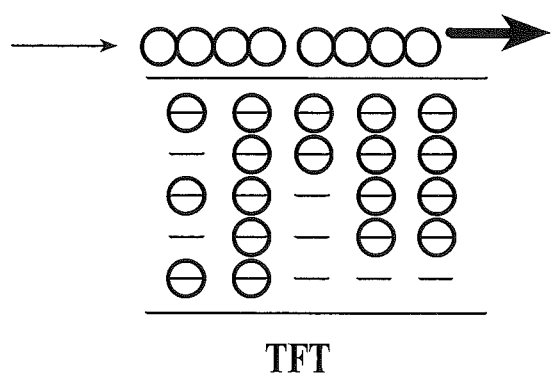
FIG. 69C is an image view explaining that after the state of FIG. 69B, the amount of the leaked electric charge via the TFT increases.

In the case where the process of resetting each radiation detection element 7 is not executed before the readout process for the leaked data Dleak, as schematically shown in FIG. 69A, electric charge particles leak from the radiation detection element 7 through a conduction band CB in the TFT 8 which has a high energy level. Each of FIGS. 69A, 69B, and 69C shows a case where the electric charge particles flow to the TFT 8 from the not-shown radiation detection element 7 (to the left of the drawing) and then flow out to a not-shown signal line 6 (to the right of the drawing). The amounts of moving electric charge particles are represented by thicknesses of arrows in the drawing.

If the process of resetting each radiation detection element 7 is executed in the state of FIG. 69A, as shown in FIG. 69B, a part of a comparatively large amount of electric charge particles discharged from the radiation detection element 7 to the signal line 6 through the conduction band CB is trapped in the trap level TL existing in a band gap of an energy level lower than the conduction band CB and remains in the TFT 8. In this case, the thick arrows represent movement of the large amount of electric charge particles.

Thereafter, as shown in FIG. 69C, as the electric charge particles leak from the radiation detection element 7 to the signal line 6 through the conduction band CB in the TFT 8 having a high energy level, part of the electric charge particles trapped by the trap energy level TL are excited to the conduction level CB having a high energy level and therefore leak together to be discharged to the signal line 6. Accordingly, the amount of electric charge leaking from each of the radiation detection element 7 to the signal line 6 increases.

This is considered to cause the phenomenon that the value of the leaked data Dleak read out at the readout process executed after the process of resetting each radiation detection element 7 (see data of part indicated by α in FIG. 68A) is larger than the value of the leaked data Dleak read out at the readout process in the state where the process of resetting each radiation detection element 7 is not executed (see data of the part indicated by β in FIG. 68A).

FIGS. 68A and 68B show the case where the process of resetting each radiation detection element 7 is repeatedly executed many times before the readout process for the leaked data Dleak is started, that is, before counting of the elapsed time t is started in each drawing (before an elapsed time t of 0 in the horizontal axis). In each drawing, the values of the leaked data Dleak read out at an elapsed time t close to 0 are large. Accordingly, it can be considered that the leaked data Dleak is large because of the aforementioned mechanism.

Moreover, it is confirmed that the aforementioned phenomenon is similarly caused when the readout process for the image data d is executed before the readout process for the leaked data Dleak (see FIG. 66) as well as when the process of resetting each radiation detection element 7 is executed.

As described above, in the configuration in which the readout process for the leaked data Dleak and the process of resetting each radiation detection element 7 are alternately repeated before the radiation image capturing operation (see FIG. 67) and in the process of resetting each radiation element 7, the reset process is executed in a manner that the ON voltage is sequentially applied or the terminals of the gate driver 15b (including the non-connecting terminals h) which are sequentially activated are sequentially shifted, the value of the leaked data Dleak read out at each leaked data. Dleak readout process change as described above.

Therefore, in this case, preferably, the threshold value for detecting the initiation of the radioactive irradiation, which is applied to the leaked data Dleak read out at the leaked data Dleak after the ON voltage is applied to the non-connecting terminals h of the gate driver 15b (or after the non-connecting terminals h are activated), is set smaller than the threshold value which is applied to the leaked data Dleak read out at the readout process for the leaked data Dleak after the ON voltage is applied from the gate driver 15b to the terminals connected to the scanning lines 5 to sequentially apply the ON voltage to the lines L1 to Lx of the scanning lines 5 for the process of resetting each radiation detection element 7.

In this case, the controller 22 is configured so as to switch the aforementioned threshold values for the timing at which the ON voltage is sequentially applied to the non-connecting terminals h of the gate driver 15b (or the timing at which the non-connecting terminals h are sequentially activated) and the timing at which the ON voltage is sequentially applied to the lines L1 to Lx of the scanning lines 5 from the gate driver 15b for the process of resetting each radiation detection element 7.

On the other hand, in this Method 6, in the case where the radiation image capturing apparatus 1 is configured so that the readout process for the leaked data Dleak and the process of resetting each radiation detection element 7 (or the readout process for the image data d, the same applies hereinafter) are alternately repeated before the radiation image capturing operation, the above described Method 1 can be applied. In the process of resetting each radiation detection element 7 executed between the readout processes for the leaked data Dleak, the reset process is executed by sequentially applying the ON voltage only to the terminals of the gate driver 15b connected to the scanning lines 5 instead of applying the ON voltage to the non-connecting terminals h of the gate driver 15b or activating the same as shown in FIG. 67 and the like.

With the above configuration, as for the above described threshold values, just one threshold value thereof should be set, thus eliminating the need to perform the control to switch the plurality of threshold values as described above.

In a similar manner, the aforementioned Methods 3 or 4 can be applied to Method 6. In such a configuration, the terminals connected to the scanning lines 5 are activated and the ON voltage is applied at the same timing as the timing at which any non-connecting terminal h is active. With this configuration, as for the above described threshold values, just one threshold value thereof should be set, thus eliminating the need to perform the control to switch the plurality of threshold values as described above.

Figure 70:
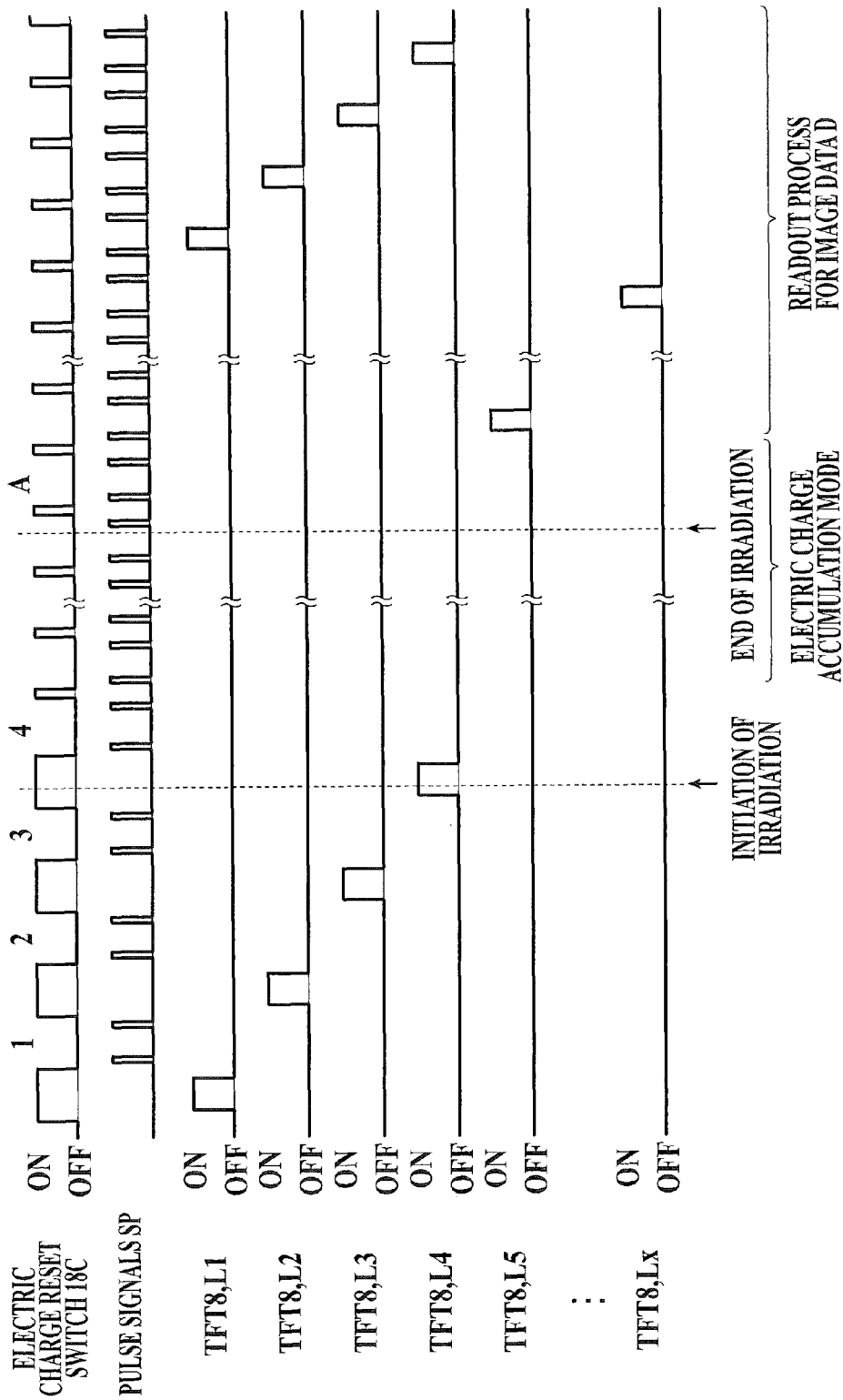
FIG. 70 is a timing chart explaining application timing of the ON voltage to each scanning line in a case of repeating the leaked data readout process in the electric charge accumulation mode.

In the aforementioned Method 6, as shown in FIG. 70, when the leaked data Dleak read out at the readout process for the leaked data Dleak (see L4 in the drawing) after the ON voltage is applied to a certain L scanning line 5 (the fourth line L4 in the scanning lines 5 in the drawing) for the process of resetting each radiation detection element 7 exceeds the threshold value, it is detected at that time the radioactive irradiation is started. The process of resetting each radiation detection element 7 is then stopped, and the OFF voltage is applied to all the lines L1 to Lx of the scanning lines 5 to shift to the electric charge accumulation mode. The same applies to the cases of Methods 1 to 5.

At that time, as shown in FIG. 70, even after the shift to the electric charge accumulation mode, the reading circuit 17 is caused to repeatedly perform the readout operation for repeating the readout process for the leaked data Dleak. If the read leaked data Dleak continues to be monitored the end of the radioactive irradiation can be detected as previously described.

Moreover, as shown in FIG. 70, the radiation image capturing apparatus 1 can be configured so that, when the end of the radioactive irradiation is detected based on the leaked data Dleak which is reduced to a value equal to or lower than the threshold value (see A in the drawing), the application of the ON voltage to the L5 to Lx scanning lines 5 is sequentially started again, and the process of reading out the image data D as the final image is started. This makes it possible to start the readout process for the image data D immediately after the end of the radioactive irradiation is detected and to quickly perform the processes after the readout process for the image data D as described above. FIG. 70 shows a case where Method 1 is applied to Method 6.

As described above, the radiation image capturing apparatus 1 according to this embodiment achieves the same advantageous effect to that of the respective aforementioned embodiments. Also, even in the case of not being able to make an interface with the radiation generation device, the radiation image capturing apparatus 1 executes the readout process for the image data d from the time before the initiation of the radiation image capturing operation, that is, the time before irradiating the radiation image capturing apparatus 1 with the radiation, based on the read out image data d, or based on the image data d and the leaked data Dleak when using the above Procedure 5, so that the radiation generation device 1 can detect by the device itself that the radiation generation device 1 is irradiated with the radiation.

Further, at that time, even when the non-connecting terminals h are present in the gate driver 15b of the scanning drive unit 15, to which the scanning lines 5 are not connected, the configurations are made so that: the non-connecting terminals h are made into the active state so that the period τ is not generated, during which the image data d is not read out (the above Procedure 1, 3 and 4); the period τ is made short (the above Procedure 2); or the leaked data Dleak is read out during the period τ (the above Procedure 5). This achieves the secure detection of the radioactive irradiation onto the radiation image capturing apparatus 1.

For this reason, the problem caused in the conventional procedure shown in FIG. 52 can be surely prevented. In the conventional procedure, the period τ becomes long to cause the detection of the irradiation initiation to be delayed, and the longer the delay is, the more the amount of dark electric charges are accumulated in the radiation detection elements 7, making the S/N ratio of the read out image data as the final image deteriorate.

In addition, in the above embodiments, although the case is described in which the gate driver 15b of the scanning drive unit 15 is configured by arranging the plurality of gate ICs 12a in parallel as illustrated in FIG. 53, the same problem may arise also in a case in which the gate driver 15a and the gate ICs 12a are differently configured, as long as the non-connecting terminals h are present to which the scanning lines 5 are not connected. Accordingly, the present invention is also applicable to the case of the gate driver 15b and the gate ICs 12a taking the different configurations.

Furthermore, even in the case of using a radiation image capturing apparatus of a so-called dedicated machine type as the radiation image capturing apparatus 1, which is integrally formed with a not-shown supporting stand or the like, and even in the case of having a configuration in which the interface with the radiation generation device is not made as above and detecting the irradiation with the radiation by the radiation image capturing apparatus itself, the present invention is applicable.

Incidentally, in the case of making a configuration using the aforementioned Procedure 6 in which the detection of the initiation and the like of irradiating the radiation image capturing apparatus 1 with the radiation based on the value of the leaked data Dleak, because usually from thousands to tens of thousands of the signal lines 6 are arranged on the detecting section P (see FIGS. 3 and 7) of the radiation image capturing apparatus 1, the number of pieces of the leaked data Dleak amounts from thousands to tens of thousands.

And, when a configuration is made to execute a process to determine whether or not the data has exceeded the threshold value for each readout process, for all of the leaked data Dleak, the process load becomes large. For this reason, for example, a configuration can be made, in which a maximum value is extracted from the leaked data Dleak read out in each readout process and the determination of whether or not the maximum value of the leaked data Dleak has exceeded the threshold value is made.

However, the respective reading circuits 17 (see FIG. 7 and so on) usually have different data readout efficiency from each other. So even if the total values of the electric charges q that leak from the respective radiation detecting device to each of the signal lines 6 (see FIG. 34) are the same for every signal line 6, some of the reading circuits 17 always read out the leaked data Dleak of larger values than the others, and some of the reading circuits 17 always read out the leaked data Dleak of smaller values than the others.

Figure 71:
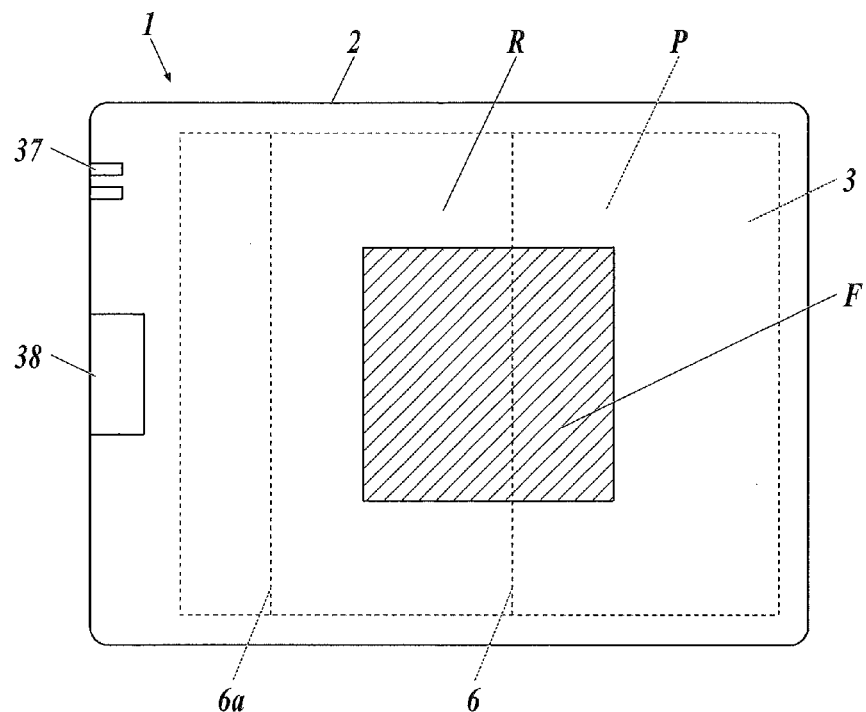
FIG. 71 is a view showing a case of irradiating the radiation image capturing apparatus with the radiation of which irradiation field is narrowed.

Under the circumstance, as illustrated in FIG. 71 for example, a case is considered in which the radiation image capturing apparatus 1 is irradiated with the radiation having the irradiation field F being narrowed, and the signal line 6a connected to the reading circuit 17, which always reads out the larger leaked data Dleak than the other reading circuits, is present outside the irradiation field F.

Figure 72:
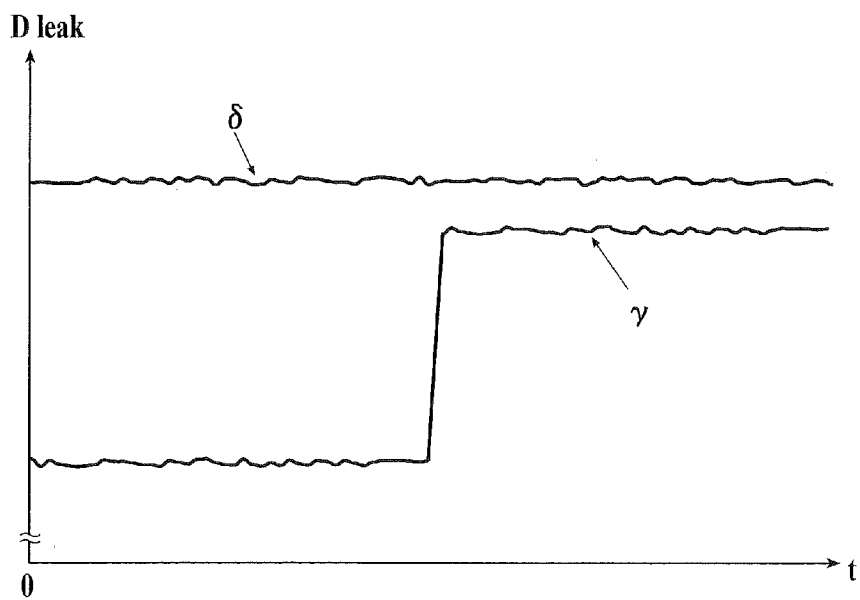
FIG. 72 is a graph showing an example of a time shift of the leaked data read out by each reading circuit.

In this case, as shown in FIG. 72, even if the value of the leaked data Dleak (see data indicated by γ in the figure) read out by the reading circuit 17, which is connected to the signal lines present inside the irradiation field F, increases by the radioactive irradiation, the value may not exceed that of the leaked data Dleak (see data indicated by δ in the figure) read out by the reading circuit 17 connected to the signal line 6a present outside the irradiation field F.

And as in the case described above in which the value of the leaked data Dleak (γ) which increases with the radioactive irradiation does not exceed that of the leaked data Dleak (δ) which is present outside the irradiation field F and does not increase by the radioactive irradiation, because the maximum value of the leaked data Dleak to be extracted is the leaked data indicated as δ in the figure, the maximum value of the extracted leaked data Dleak does not change by the radioactive irradiation and as a result, does not exceed the threshold value and the radioactive irradiation cannot be detected.

For this reason, to avoid the above problem, for example, a configuration is made to calculate the moving average of the leaked data read out for each readout process for each reading circuit 17. In other words, for every readout process for the leaked data Dleak, an average value Dleak_ave of the leaked data Dleak (moving average) read out from each of the reading circuits 17 is calculated using a predetermined number of previous readout processes including the one immediately before the current round of the readout process.

Then, the difference ΔDleak between the leaked data Dleak read out in the present readout process and the calculated average value Dleak_ave of the moving average is calculated. And a configuration can be made to detect the radioactive irradiation onto the radiation image capturing apparatus 1 when there is any reading circuit 17 in which the difference ΔDleak exceeds a threshold value previously set for the difference ΔDleak.

By the above configuration, the increase of the leaked data Dleak can be accurately detected without being affected by the readout efficiency and the like shown above of each of the reading circuit 17, and thus the initiation of the radioactive irradiation onto the radiation image capturing apparatus 1 can be accurately detected.

However, even in this case, the process load becomes very large when a configuration is made to execute the above process for each piece of the leaked data Dleak of which readout number amounts from thousands to tens of thousands for every readout process for the leaked data Dleak.

For this reason, as illustrated in FIG. 51 and so on, for example, using the fact that in the radiation image capturing apparatus 1, 128 or 256 reading circuits 17 are formed in the reading IC 16 and the plurality of reading circuits 16 are provided, the total value of respective pieces of the leaked data Dleak read out in the respective reading circuits 17 is calculated for each of the reading ICs 16, for each readout process for the leaked data Dleak. Here, in this case, a configuration may also be applied in which the average value of respective pieces of the leaked data Dleak is calculated for each of the reading ICs 16.

And likewise to the above, the moving average of the total value of respective pieces of leaked data Dleak is calculated for each of the reading ICs 16. Then the difference is calculated, which is a difference between the total value of the leaked data Dleak read out in the present readout process calculated for each of the reading ICs 16 and the average value of the moving average of the calculated total values. And the configuration can be made to detect the radiation detection of the radiation image capturing apparatus 1 when there is any reading IC 16 in which the difference exceeds a threshold value previously set for the difference.

Moreover, a configuration is made in which a maximum value is extracted from the above difference, which is calculated for each readout process for the leaked data Dleak, for each of the reading ICs 16, as described above, and the determination is made whether or not the maximum value has exceeded the threshold value. In this case, because the values of the difference for the respective reading ICs 16 becomes nearly equal to each other, the problem as indicated in FIG. 72 does not occur.

By the above configuration, as in the above case, the total value (or average value) of the leaked data Dleak increases without being influenced by the readout efficiency of each of the reading circuits 17, to accurately detect whether or not the above difference (or the maximum value thereof) has exceeded the threshold value. Accordingly, the initiation of the radioactive irradiation onto the radiation image capturing apparatus 1 can be accurately detected, and the process load reduces because the calculation of the moving average is performed for each of the reading ICs 16 instead of each of the reading circuits 17.

Now, also in the case of configuring the device to detect the initiation of the radioactive irradiation as described above, as in Procedure 6 illustrated in FIG. 67, when alternately executing the readout process for the leaked data Dleak and the reset process of each of the radiation detection elements 7 before initiating the radiation image capturing operation, as shown in FIG. 68A, the value of the leaked data Dleak read out in the readout process becomes small in a case of having the non-connecting terminal h in the active state and not executing the reset process of each of the radiation detection elements 7 (refer to data indicated by portions β). Accordingly, the value of the moving average calculated during the above period becomes small.

Then, the terminal in the active state shifts from the non-connecting terminal h to the terminal to which the scanning line 5 is connected, as shown in FIG. 68A, the value of the read out leaked data Dleak increases. Therefore, the difference (or the maximum value thereof) increases, the difference being that between the read out leaked data Dleak (or the total value or average value of the read out leaked data Dleak for each of the reading ICs 16) and the moving average (or the moving average of the total value or average value) of the leaked data Dleak until the previous round of the readout process.

For that reason, the difference exceeds the threshold value even if the radiation image capturing apparatus 1 is not irradiated with the radiation, the risk of false detection may arise that the radiation is irradiated.

Accordingly, also in this case, a configuration can be made by applying Procedure 1 for example to the above procedure, in which the non-connecting terminals h of the gate driver 15b are not applied with the ON voltage or not turned to the active state. Alternatively, by applying Procedures 3 and 4, a configuration can made in which the terminal to which the scanning line 5 is connected is turned to the active state and is applied with the ON voltage simultaneously with timing of the non-connecting terminal h being in the active state.

With the above configuration, the problem can be avoided, in which the moving average reduces in the case of having the non-connecting terminal h in the active state and not executing the reset process of each of the radiation detection elements 7.

Also, instead of applying Procedures 1, 3 and 4 to the above procedure, a configuration can be made, in which two or plurality of threshold values for the above difference are set in advance, and the threshold values are selected according to how the moving average is calculated. Here, the moving average is either calculated based on the leaked data Dleak read out in the readout process in the case of having the non-connecting terminal h in the active state and not executing the reset process of each of the radiation detection elements 7, or calculated based on the leaked data Dleak read out in the readout process after the reset process of each of the radiation detection elements 7 which is executed when the ON voltage is applied to the respective lines L1 to Lx of the scanning lines 5.

By the above configuration, by using different threshold values, the configuration can be made so that the above difference exceeds the threshold value when the radiation image capturing apparatus 1 is irradiated with the radiation. And with the difference having exceeded the threshold value, the radioactive irradiation onto the radiation image capturing apparatus 1 can be accurately detected.

INDUSTRIAL APPLICABILITY

The present invention is applicable in the fields in which the radiation image capturing operation is conducted (especially in medical fields).

DESCRIPTION OF THE NUMERALS

1 Radiation image capturing apparatus
3 Scintillator
5, L1 to Lx Scanning lines
6 Signal lines
7, (m, n) Radiation detection elements
8 TFT (Switch unit)
14 Bias power source
15 Scanning drive unit
15a Power source circuit
15b, 15ba, 15bb Gate drivers
16 Reading IC
17 Reading circuit
18 Amplifier circuit
18a Operation amplifier
18b, C1 to C4 Capacitors
22 Controller
85 Wire
C Location above the detecting section P in which electromagnetic waves do not enter
cf Capacity
D Image data
d Image data
dave Average value
Dleak Leaked data
Dleak_th Threshold value
dmax Maximum value
dmin Minimum value
dth Threshold value
h non-connecting terminal
O, O(m,n) Offset correction value
P Detecting section
Pa to Pd Regions
po Offset image
Q, q Electric charge
r Region
T1 to T4 Effective accumulation time (time spans)
Tc Same time span
Δd Difference
Δdth Threshold value

The invention claimed is:

1. A radiation image capturing apparatus comprising:
a detecting section that includes:
a plurality of scanning lines and a plurality of signal lines arranged to intersect with each other, and
a plurality of radiation detection elements that are two-dimensionally aligned with being individually aligned in respective regions partitioned by the plurality of scanning lines and the plurality of signal lines;
a scanning drive unit that applies a voltage to each of the scanning lines while switching the voltage between an ON voltage and an OFF voltage;
switch units each connected to each of the scanning lines, discharges electric charges accumulated in the radiation detection elements to the signal lines when the ON voltage is applied thereto through the scanning lines, and accumulates the electric charges in the radiation detection elements when an OFF voltage is applied thereto through the scanning lines;
reading circuits which convert the electric charges discharged to the signal lines from the radiation detection elements into image data and reads out the image data during an image data readout process in which the image data is read out from the radiation detection elements; and
a controller which controls at least the scanning drive unit and the reading circuit and causes the same to execute the readout process for the data from the radiation detection elements,
wherein the controller controls to:
before radiation image capturing operation, cause the scanning drive unit to sequentially apply the ON voltage to each of the scanning lines to execute the readout process for the image data from the radiation detection elements, and detect initiation of radioactive irradiation at a time when the read out image data exceeds a threshold value,
when the initiation of the radioactive irradiation is detected, cause the scanning drive unit to apply an OFF voltage to all of the scanning lines and turn each of the switch unit to an OFF state to shift to an electric charge accumulation mode,
after finishing the radioactive irradiation, cause the scanning drive unit to sequentially apply the ON voltage to each of the scanning lines, and cause the reading circuit to sequentially execute the readout operation to execute the readout process for the image data from each of the radiation detection elements, and
make time or period longer during the readout process for the image data before the radiation image capturing operation than the time or period during the readout process for the image data after finishing the radiation image capturing operation, where the time is one causing the scanning drive unit to apply the ON voltage to each of the scanning lines, and the period is one from causing the scanning drive unit to apply the ON voltage to one scanning line until applying the ON voltage to the next scanning line.

2. The radiation image capturing apparatus of claim 1, wherein, the controller controls to, before radiation image capturing operation, cause the scanning drive unit to apply the ON voltage to one of the scanning lines in a certain timing, and in the next timing, apply the ON voltage to the scanning lines other than the ones adjacent to the one scanning line, so that the ON voltage is sequentially applied to each of the scanning lines and the readout process for the image data from the radiation detection elements is executed.

3. The radiation image capturing apparatus of claim 1, wherein, the controller controls to, before radiation image capturing operation: cause the scanning drive unit to sequentially apply the ON voltage to each of the scanning lines to execute the readout process for the image data from the radiation detection elements; extract a maximum value and a minimum value from the image data read out for each of the reading circuits in the same readout process; calculate a difference in which the minimum value is subtracted from the maximum value; and detect that the radioactive irradiation is initiated at a time when the calculated difference exceeds a threshold value.

4. The radiation image capturing apparatus of claim 3, wherein, the controller controls to: calculate moving averages for respective pieces of the image data read out for each of the reading circuits in a predetermined number of previous readout processes including one immediately before a current round of the readout process; and extract the maximum value and the minimum value from values each calculated by subtracting the respective moving averages from the respective pieces of currently readout image data for each of the reading circuits.

5. The radiation image capturing apparatus of claim 3, further comprising:
 a plurality of reading ICs in each of which a predetermined number of the reading circuits are formed,
 wherein, the controller controls to: calculate, for each of the reading ICs, an average or total value of respective pieces of the image data read out for each of the reading circuits in the same readout process, instead of each pieces of image data read out for each of the reading circuits in the same readout process; and extract the maximum value and the minimum value from among the average values or total values of the respective pieces of the image data for each of the reading ICs, or, extract the maximum value and the minimum value from the values calculated by subtracting a moving average of the average value or total value from the average or total value of the respective pieces of the image data for each of the reading ICs.

6. The radiation image capturing apparatus of claim 1, wherein, the controller controls to cause the scanning drive unit to simultaneously apply the ON voltage to a plurality of the scanning lines which are not adjacent to each other on the detecting section to execute the readout process.

7. The radiation image capturing apparatus of claim 1, wherein, on the detecting section in which the plurality of the radiation detection elements are aligned two-dimensionally, each of the signal lines, scanning lines or both is decoupled halfway in each of extending directions thereof, the detecting section is partitioned in a plurality of regions, and the scanning drive unit is provided for each of the regions, and
 the controller controls to, during the readout process for the image data before the radiation image capturing operation, apply the ON voltage to execute the readout process so that timing to apply the ON voltage from the scanning drive unit corresponding to one of the regions to the scanning lines in the concerned region does not coincide with timing to apply the ON voltage to the scanning lines in other regions from the scanning drive unit corresponding to the other regions.

8. The radiation image capturing apparatus of claim 1, wherein, the controller controls to:
 when detecting that the radioactive irradiation is initiated, shift to the electric charge accumulation mode while maintaining each of the switch unit in the OFF state;
 cause the reading circuit to execute the readout operation in a state of applying the OFF voltage from the scanning drive unit to all of the scanning lines, and execute the readout process for leaked data corresponding to an electric charge which leaks from each of the radiation detection elements via the switch unit;
 when detecting that the radioactive irradiation is finished at a time when the read out leaked data becomes the threshold value or less, cause the scanning drive unit to sequentially apply the ON voltage to each of the scanning lines; and
 cause the reading circuit to sequentially execute the readout operation and execute the readout process for the image data from each of the radiation detection elements to which the radioactive irradiation has finished.

9. The radiation image capturing apparatus of claim 1, wherein, the controller controls to, in a state that the radiation is not irradiated after finishing the readout process after the end of the radioactive irradiation, switch the voltage applied from the scanning drive unit to each of the scanning lines between the ON voltage and the OFF voltage at the same timing as: the readout process for the image data before the radiation image capturing operation; the shift to the electric charge accumulation mode; and the readout process for the image data after finishing the radiation image capturing operation, to execute an offset correction value readout process for reading out an offset correction value from each of the radiation detection elements.

10. The radiation image capturing apparatus of claim 9, wherein, after finishing the readout process for the image data after the end of the radioactive irradiation, the controller controls to, execute a reset process of each of the radiation detection elements instead of the readout process for the image data when switching the voltage applied from the scanning drive unit to each of the scanning lines between the ON voltage and the OFF voltage, at the same timing as in the readout process for the image data before the radiation image capturing operation.

11. The radiation image capturing apparatus of claim 1, wherein,
 when a period is defined as one frame which is the period of sequentially applying the ON voltage to each of the scanning lines and reading out the pieces of the image data of the respective radiation detection elements to be read out among all of the radiation detection elements arranged on the detecting section, the controller controls to:
 during the readout process for the image data before the radiation image capturing operation and after finishing the readout process for one frame of the image data, apply the OFF voltage to all of the scanning lines for the same period as the period to apply the OFF voltage to all of the scanning lines from the scanning drive unit in the electrical charge accumulation mode, and thereafter, start the readout process for the image data in the next frame, in order to execute the readout process for the image data for each of the frames; and
 determine the image data read out in the frame before initiating the radioactive irradiation as offset correction value of each of the radiation detection elements.

12. The radiation image capturing apparatus of claim 1, wherein,
 the scanning drive unit comprises a power source circuit and a gate driver, and
 when non-connecting terminals to which none of the scanning lines are connected are present in the gate driver, at least when sequentially applying the ON voltage to each of the scanning lines by the gate driver in the readout process for the image data before the radiation image capturing operation, the scanning drive unit causes not to apply the ON voltage to the non-connecting terminals of the gate driver and to apply the ON voltage to any of the terminals to which the scanning line is always connected, in order to sequentially apply the ON voltage to each of the scanning lines by the gate driver.

13. The radiation image capturing apparatus of claim 1, wherein,
the scanning drive unit comprises a power source circuit and a gate driver, and
when non-connecting terminals to which none of the scanning lines are connected are present in the gate driver, at least when sequentially applying the ON voltage to each of the scanning lines by the gate driver in the readout process for the image data before the radiation image capturing operation, with regard to timing to apply the ON voltage to the non-connecting terminals of the gate driver, the scanning drive unit applies the ON voltage in a time span shorter than that of when applying the ON voltage to the terminal to which the scanning line is connected, in order to sequentially apply the ON voltage to each of the terminals of the gate driver.

14. The radiation image capturing apparatus of claim 1, wherein,
the scanning drive unit comprises a power source circuit and a gate driver, and
when non-connecting terminals to which none of the scanning lines are connected are present in the gate driver, at least when sequentially applying the ON voltage to each of the scanning lines by the gate driver in the readout process for the image data before the radiation image capturing operation, with regard to timing to apply the ON voltage to the non-connecting terminals of the gate driver, the scanning drive unit simultaneously applies the ON voltage to the terminals to which the scanning lines are connected so that any of the scanning lines is applied with the ON voltage in each timing, in order to sequentially apply the ON voltage to each of the scanning lines by the gate driver.

15. The radiation image capturing apparatus of claim 1, wherein,
the scanning drive unit comprises a power source circuit and gate drivers,
each of the signal lines, scanning lines or both is decoupled halfway in each of the extending directions thereof on the detecting section, the detecting section is partitioned in a plurality of the regions, and each of the gate drivers is provided in each of the regions, and
when non-connecting terminals to which none of the scanning lines are connected are respectively present in each of the gate drivers, at least when sequentially applying the ON voltage to each of the scanning lines by each of the gate drivers in the readout process for the image data before the radiation image capturing operation, with regard to timing to apply the ON voltage to the non-connecting terminals of one of the gate drivers, the scanning drive unit applies the ON voltage to the terminals of other of the gate drivers to which the scanning lines are connected, so that any of the scanning lines is applied with the ON voltage in each timing, in order to sequentially apply the ON voltage to each of the scanning lines by each of the gate drivers.

* * * * *